US010426753B2

(12) United States Patent
Roy et al.

(10) Patent No.: US 10,426,753 B2
(45) Date of Patent: Oct. 1, 2019

(54) SUPRAMOLECULAR COMBINATORIAL THERAPEUTICS

(71) Applicant: INVICTUS ONCOLOGY PVT. LTD., Delhi (IN)

(72) Inventors: Monideepa Roy, Delhi (IN); Samad Hossain, Delhi (IN); Aniruddha Sengupta, Delhi (IN); Sanghamitra Mylavarapu, Delhi (IN); Shiladitya Sengupta, Waltham, MA (US); Anubhab Mukherjee, Delhi (IN)

(73) Assignee: INVICTUS ONCOLOGY PVT. LTD., Delhi (IN)

( * ) Notice: Subject to any disclaimer, the term of this patent is extended or adjusted under 35 U.S.C. 154(b) by 58 days.

(21) Appl. No.: 15/301,570

(22) PCT Filed: Mar. 27, 2015

(86) PCT No.: PCT/US2015/023009
§ 371 (c)(1),
(2) Date: Oct. 3, 2016

(87) PCT Pub. No.: WO2015/153345
PCT Pub. Date: Oct. 8, 2015

(65) Prior Publication Data
US 2017/0112800 A1 Apr. 27, 2017

(30) Foreign Application Priority Data
Apr. 3, 2014 (IN) .............................. 975/DEL/2014

(51) Int. Cl.
| A61K 31/337 | (2006.01) |
| A61K 31/282 | (2006.01) |
| A61K 31/7068 | (2006.01) |
| A61K 39/395 | (2006.01) |
| A61K 45/06 | (2006.01) |
| A61K 9/127 | (2006.01) |
| C12Q 1/68 | (2018.01) |
| G01N 33/574 | (2006.01) |
| C12Q 1/6886 | (2018.01) |
| A61K 47/54 | (2017.01) |
| A61K 39/00 | (2006.01) |

(52) U.S. Cl.
CPC ............ *A61K 31/337* (2013.01); *A61K 9/127* (2013.01); *A61K 9/1271* (2013.01); *A61K 31/282* (2013.01); *A61K 31/7068* (2013.01); *A61K 39/3955* (2013.01); *A61K 45/06* (2013.01); *A61K 47/543* (2017.08); *A61K 47/545* (2017.08); *A61K 47/548* (2017.08); *A61K 47/554* (2017.08); *C12Q 1/6886* (2013.01); *G01N 33/57484* (2013.01); *A61K 2039/505* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| 2,816,110 A | 12/1957 | Sletzinger et al. |
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,100,274 A | 7/1978 | Dutta et al. |
| 4,235,871 A | 11/1980 | Papahadjopoulos et al. |
| 4,737,323 A | 4/1988 | Martin et al. |
| 4,897,355 A | 1/1990 | Eppstein et al. |
| 4,960,790 A | 10/1990 | Stella et al. |
| 5,013,556 A | 5/1991 | Woodle et al. |
| 5,015,744 A | 5/1991 | Holton |
| 5,059,595 A | 10/1991 | Le Grazie |
| 5,073,543 A | 12/1991 | Marshall et al. |
| 5,120,548 A | 6/1992 | McClelland et al. |
| 5,171,678 A | 12/1992 | Behr et al. |
| 5,200,534 A | 4/1993 | Rao |
| 5,354,556 A | 10/1994 | Sparks et al. |
| 5,461,076 A | 10/1995 | Stanek et al. |
| 5,534,499 A | 7/1996 | Ansell |
| 5,552,545 A | 9/1996 | Pearce et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 5,747,498 A | 5/1998 | Schnur et al. |
| 5,820,873 A | 10/1998 | Choi et al. |
| 5,843,901 A | 12/1998 | Roeske |
| 5,885,613 A | 3/1999 | Holland et al. |

(Continued)

FOREIGN PATENT DOCUMENTS

| EP | 0414610 | 2/1991 |
| EP | 0520722 | 12/1992 |

(Continued)

OTHER PUBLICATIONS

Paller, et al. (2011) "Cabazitaxel: a novel second-line treatment for metastatic castration-resistant prostate cancer", Drug Design, Development and Therapy, 5: 117-24.*

(Continued)

*Primary Examiner* — Robert M Kelly
(74) *Attorney, Agent, or Firm* — Hamre, Schumann, Mueller & Larson, P.C.

(57) ABSTRACT

The present disclosure relates generally to supramolecular combinatorial therapeutics, compositions comprising same, and uses thereof. In particular, the present disclosure provides hydrophobic taxane-lipid covalent conjugates which create supramolecular assembly, for example, within lipid bilayer, providing an extra stabilization resulting in increased intratumoral concentration and hence increased efficacy. The present disclosure also provides supramolecular combinatorial therapeutics, wherein a taxane-lipid conjugate is combined with one or more of a platinum compound, a kinase inhibitor, and an immunoregulator, each of which is optionally conjugated with a lipid.

14 Claims, 3 Drawing Sheets

(56) References Cited

U.S. PATENT DOCUMENTS

| | | | |
|---|---|---|---|
| 6,194,181 | B1 | 2/2001 | Hufmann et al. |
| 6,218,367 | B1 | 4/2001 | Jacob |
| 6,320,017 | B1 | 11/2001 | Ansell |
| 6,335,434 | B1 | 1/2002 | Guzaev et al. |
| 6,365,185 | B1 | 4/2002 | Ritschel et al. |
| 6,552,065 | B2 | 4/2003 | Remiszewski et al. |
| 7,128,893 | B2 | 10/2006 | Leamon et al. |
| 2005/0090535 | A1 | 4/2005 | Reichenbach et al. |
| 2009/0247608 | A1 | 10/2009 | Manoharan et al. |
| 2010/0331290 | A1 | 12/2010 | Ansell et al. |
| 2011/0097720 | A1 | 4/2011 | Ciufolini et al. |
| 2012/0046478 | A1 | 2/2012 | Manoharan et al. |
| 2012/0189571 | A1 | 7/2012 | Sengupta et al. |

FOREIGN PATENT DOCUMENTS

| | | |
|---|---|---|
| EP | 0522958 | 1/1993 |
| EP | 0528729 | 2/1993 |
| EP | 0564409 | 10/1993 |
| EP | 0566226 | 10/1993 |
| EP | 0787722 | 8/1997 |
| EP | 0837063 | 4/1998 |
| EP | 0912535 | 11/2001 |
| WO | 9113053 | 9/1991 |
| WO | 93/06079 | 4/1993 |
| WO | 93/10076 | 5/1993 |
| WO | 9316059 | 8/1993 |
| WO | 9503283 | 2/1995 |
| WO | 96/14057 | 5/1996 |
| WO | 96/30347 | 10/1996 |
| WO | 9633980 | 10/1996 |
| WO | 96/37194 | 11/1996 |
| WO | 97/02266 | 1/1997 |
| WO | 97/30034 | 8/1997 |
| WO | 97/38983 | 10/1997 |
| WO | 97/49688 | 12/1997 |
| WO | 98/10767 | 3/1998 |
| WO | 9808849 | 3/1998 |
| WO | 9810121 | 3/1998 |
| WO | 98/22461 | 5/1998 |
| WO | 9825929 | 6/1998 |
| WO | 98/39359 | 9/1998 |
| WO | 99/03854 | 1/1999 |
| WO | 99/43653 | 9/1999 |
| WO | 0009495 | 2/2000 |
| WO | 0031247 | 6/2000 |
| WO | 02/092599 | 11/2002 |
| WO | 03013541 | 2/2003 |
| WO | 2006014626 | 2/2006 |
| WO | 2008128169 | 10/2008 |
| WO | 2009/132131 | 10/2009 |
| WO | 2009140304 | 11/2009 |
| WO | 2010/091192 | 8/2010 |
| WO | 2011130317 | 10/2011 |
| WO | 2012166923 | 12/2012 |
| WO | 2012170711 | 12/2012 |
| WO | 2013188763 | 12/2013 |

OTHER PUBLICATIONS

International Search Report/ Written Opinion issued in PCT/US2015/023009, dated Aug. 14, 2015, 15 pages.

Hennenfent, K. L. et al., "Novel formulations of taxanes: a review. Old wine in a new bottle?" European Society for Medical Oncology. Annals of Oncology, May 2006. vol. 17, No. 5. [Published online Dec. 19, 2005] [Online] Retrieved at <http://annonc.oxfordjournals.org/>, pp. 735-749.

Ketterly, Gerald J. et al., "Pharmacokinetics of Paclitaxel-Containing Liposomes in Rats,"American Association of Pharmaceutical Scientists, 2003, vol. 5, No. 4, Article 32, 11 pages.

Sparreboom, Alex et al., "Comparative Preclinical and Clinical Pharmacokinetics of a Cremophor-Free, Nanoparticle Albumin-Bound Paclitaxel (ABI-007) and Paclitaxel Formulated in Cremophor (Taxol)" Clinical Cancer Research. Jun. 1, 2005, vol. 11, Issue 11. [Online] [Retrieved on Dec. 11, 2014 ] Retrieved at: <clincancerres.aacrjournals.org>, pp. 4136-4143, 9 pages.

Sparreboom, Alex et al., "Cremophor El-mediated Alteration of Paclitaxel Distribution in Human Blood: Clinical Pharmacokinetic Implications," Cancer Research. Apr. 1, 1999, vol. 59, pp. 1454-1457.

Yared, Jean A. et al., "Update on taxane development: new analogs and new formulations" Drug Design, Development and Therapy. 2012, vol. 6, [Online] [Retrieved on Nov. 23, 2016] retrieved at: <https://www.dovepress.com>, pp. 371-384.

Stevens, Phillip J. et al., "A Folate Receptor-Targeted Lipid Nanoparticle Formulation for a Lipophilic Paclitaxel Prodrug," Pharmaceutical Research. Dec. 2004, vol. 21, No. 12, pp. 2153-2157.

Bissery, M.-C., "Preclinical Evaluation of New Taxoids," Current Pharmaceutical Design. 2001, vol. 7, No. 13, pp. 1251-1257.

Mita, Alain C. et al., "Phase 1 and Pharmacokinetic Study of XRP6258 (RPR 116258A), a Novel Taxane, Administered as a 1-Hour Infusion Every 3 Weeks in Patients with Advanced Solid Tumors," Clinical Cancer Research. Jan. 15, 2009, vol. 15, No. 2 [Online] [Retrieved on Apr. 11, 2015] retrieved at: <http://clincancerres.aacrjounals.org/content/15/2/723>, pp. 723-730, 9 pages.

Boettler, Tobias et al., "Expression of the Interleukin-7 Receptor Alpha Chain (CD127) on Virus-Specific CD8+ T Cells dentifies Functionally and Phenotypically Defined Memory T Cells during Acute Resolving Hepatitis B Virus Infection" Journal of Virology. Apr. 2006, vol. 80, No. 7, pp. 3532-3540.

Nishimura, Hiroyuki et al., Developmentally regulated expression of the PD-1 protein on the surface of double-negative (CD4-CD8-) thymocytes, International Immunology. 1996, vol. 8, No. 5, pp. 773-780.

Keir, Mary E. et al., "PD-1 and Its Ligands in Tolerance and Immunity," The Annual Review of Immunology. 2008, vol. 26, pp. 677-704, 30 pages.

Nishimura, Hiroyuki et al., "Autoimmune Dilated Cardiomyopathy in PD-1 Receptor-Deficient Mice," Science. Jan. 12, 2001, vol. 291, 5 pages.

Nishimura, Hiroyuki et al., "Development of Lupus-like Autoimmune Diseases by Disruption of the PD-1 Gene Encoding an ITIM Motif-Carrying Immunoreceptor," Immunity. Aug. 1999, vol. 11, pp. 141-151.

Yamazaki, Tomohide et al., Expression of Programmed Death 1 Ligands by Murine T Cells and APC1,: The Journal of Immunology. 2002, vol. 169, 9 pages.

Zhong, Xuemei et al., "PD-L2 expression extends beyond dendritic cells/macrophages to B1 cells enriched for VH11/VH12 and phosphatidylcholine binding," European Journal of Immunology. 2007, vol. 37, pp. 2405-2410.

Butte, Manish J. et al., "PD-L1 interacts specifically with B7-1 to inhibit T cell proliferation," National Institute of Health, NIH Public Access, Author manuscript—Immunity. Jul. 2007, vol. 27(1), 22 pages.

Carter, Laura L. et al., " PD-1:PD-L inhibitory pathway affects both CD4+ and CD8+ T cells and is overcome by IL-2," European Journal of Immunology. 2002, vol. 32, pp. 634-643.

Freeman, Gordon J. et al., "Engagement of the PD-1 Immunoinhibitory Receptor by a Novel B7 Family Member Leads to Negative Regulation of Lymphocyte Activation," Journal of Experimental Medicine. Oct. 2, 2000, vol. 192, No. 7, pp. 1027-1034.

Kuipers, Harmjan et al., "Contribution of the PD-1 ligands/PD-1 signaling pathway to dendritic call-mediated CD4+ T cell activation," European Journal of Immunology. 2006, vol. 36, pp. 2472-2482.

Bangham, A.D. et al., "Diffusion of Univalent Ions across the Lamellae of Swollen Phospholipids," Journal of Molecular Biology. 1965, vol. 13, pp. 238-252.

Felgner, Philip L. et al. "Lipofection: A highly efficient, lipid-mediated DNA-transfection procedure," Proceedings of the National Academy of Sciences. Nov. 1987, vol. 84, pp. 7413-7417.

(56) References Cited

OTHER PUBLICATIONS

Fukunaga, Masao et al., "Liposome Entrapment Enhances the Hypocalcemic Action of Parenterally Administered Calcitonin," Endocrinology. 1984, vol. 115, No. 2, pp. 757-761.

Kim, Sinil et al., "Preparation of Multivesicular Lipsomes," Biochimica et Biophysica Acta. 1983, vol. 723, pp. 339-348.

Mayhew E. et al., "Characterization of Liposomes Prepared Using a Microemulsifier," Biochimica at Biophysica Acta. 1984, vol. 775, pp. 169-174.

Olson, F. et al., "Preparation of Liposomes of Defined Size Distribution by Extrusion Through Polycarbonate Membranes," Biochimica et Biophysica Acta. 1979, vol. 557, pp. 9-23.

Szoka, Francis Jr. et al., "Procedure for preparation of liposomes with large internal aqueous space and high capture by reverse-phase evaporation," Proceedings of the National Academy of Sciences. Sep. 1978, vol. 75, No. 9, pp. 4194-4198.

Allen, Theresa et al., "A new strategy for attachment of antibodies to sterically stabilized liposomes resulting in efficient targeting to cancer cells," Biochimica et Biophysica Acta. 1995, vol. 1237, pp. 99-108.

Blume, G. et al., "Specific targeting with poly(ethylene glycol)-modified liposomes: coupling of homing devices to the ends of the polymeric chains combines effective target binding with long circulation times," Biochimica et Biophysica Acta. 1993, vol. 1149, pp. 180-184.

Zalipsky, Samuel, "Synthesis of an End-Group Functionalized Polyethylene Glycol-Lipid Conjugate for Preparation of Polymer-Grated Liposomes," Bioconjugate Chemistry. 1993, vol. 4, pp. 296-299.

Zalipsky, Samuel et al, "Long circulating, cationic liposomes containing amino-PEG-phosphatidylethanolamine," Federation of European Biochemical Societies, Letters. 1994, vol. 353, pp. 71-74.

DeFrees, Shawn A. et al., Sialyl Lewis x Liposomes as a Multivalent Ligand and Inhibitor of E-Selectin Mediated Cellular Adhesion, Journal of the American Chemical Society. 1996, vol. 118, pp. 6101-6104.

Klibanov A. L. et al., "Long-Circulating Liposomes: Development and Perspectives," Journal of Liposome Research. 1992, vol. 2, No. 3, pp. 321-334.

Sapra, P. et al., "Ligand-targeted liposomal anticancer drugs," Progress in Lipid Research. 2003, vol. 42, pp. 439-462.

Abra, R. M. et al., The Next Generation of Liposome Delivery Systems: Recent Experience With Tumor-Targeted, Sterically-Stabilized Immunoliposomes and Active-Loading Gradients, Journal of Liposome Research. 2002, vol. 12(1 & 2), 4 pages.

* cited by examiner

SUPRAMOLECULAR COMBINATORIAL THERAPEUTICS

CROSS REFERENCE TO RELATED APPLICATIONS

This application claims benefit under one or more of 35 U.S.C. § 119(a)-119(d) of Indian Patent Application No. 975/DEL/2014, filed Apr. 3, 2014, the content of which is incorporated herein by reference in its entirety.

TECHNICAL FIELD

The present disclosure relates generally to supramolecular combinatorial therapeutics, compositions comprising same, and uses thereof. In particular, the present disclosure provides hydrophobic taxane-lipid covalent conjugates which create supramolecular assemblies within lipid bilayer and micelles, providing an extra stabilization resulting in increased intratumoral concentration and hence increased efficacy. The present disclosure also provides supramolecular combinatorial therapeutics, wherein a taxane-lipid conjugate is combined with one or more of a platinum compound, a kinase inhibitor, and an immunoregulator, each of which is optionally conjugated with a lipid.

BACKGROUND

According to the World Health Organization, mortality due to cancer is expected to increase from 7.6 million in 2008 to 12 million deaths in 2030. To address this growing problem, two emerging paradigms that are driving the evolution of newer treatment strategies are: (i) better understanding of oncogenic drivers, leading to the development of molecularly 'targeted' therapeutics; and, (ii) the use of nanotechnology to deliver drugs specifically to the tumor, thereby improving therapeutic index. However the interface between these two paradigms, which can offer unique opportunities for improving cancer chemotherapy, currently remains largely underexplored.

Paclitaxel, docetaxel and cabazitaxel are well known taxanes commonly used for the treatment of metastatic ovarian cancer and breast cancer. Their unique anti proliferative mechanism of action and broad range of activity were attracted by scientific community. Taxanes promote hyper stabilization of microtubules in dividing cell and thereby prevents the disassembly of microtubules necessary for cell division. Due to the high potency and non specificity towards cancer cell it shows serious undesired side effects like nausea, vomiting, diarrhea, dizziness, or drowsiness etc. Extreme insolubility in aqueous medium is another drawback and effective solvents like polyoxyethylated castor oil/ethanol and dilution with suitable buffer are used prior to administration which in addition provokes severe hypersensitive immune responses. To overcome the challenges of administration multiple approaches have been reported in literature. The improved formulation of paclitaxel in the form of micelles, liposome and emulsions[1,2] can overcome some pharmacokinetics profile but the drug partition out rapidly from the carrier in in vivo system. In some approaches the pharmacokinetics has been improved by synthesizing new taxane analogs with improved aqueous solubility[2]. Thus several taxane analogs[3] have been synthesized to overcome these challenges and the solubility problems remain a major issue, potency gone down sharply and selectivity is not improved remarkably.

To address the formulation challenge and improved efficacy several hydrophobic[4], lipophilic taxane[5] prodrugs have been synthesized where enhance permeability and retention (EPR) phenomenon considered as effective drug accumulation method to tumor and hence better in vivo efficacy. The lipids used in those prodrugs include phospholipids, cholesterol, fatty acids etc.

Platinum-based chemotherapeutic agents are used as first line of therapy in over 70% of all cancers. Cisplatin undergoes rapid formation of cis-[Pt(NH$_3$)$_2$Cl(OH$_2$)]$^+$ and cis-[Pt(NH$_3$)$_2$(OH$_2$)]$^{2+}$ resulting in nephrotoxicity. Further, aquation of both carboplatin and oxaliplatin are significantly slower, resulting in decreased potency. In the recent past, considerable progress has been made wherein, Dhar et al (PNAS, 2008, 105, 17356) generated a platinum (IV) complex (c,t,c-[Pt(NH$_3$)$_2$(O$_2$CCH$_2$CH$_2$CH$_2$CH$_2$CH$_3$)$_2$Cl$_2$] that is hydrophobic enough for encapsulation into PLGA-b-PEG nanoparticles. However, the prodrug in this case has to be intracellularly processed into cisplatin. Furthermore, alternative strategies based on conjugation of platinum to polymers (eg a polyamidoamine dendrimer-platinum complex) resulted in a 200-550 fold reduction in cytotoxicity than free cisplatin. This was a result of strong bonds formed between the polymer and platinum (J Pharm Sci, 2009, 98, 2299). Another example is AP5280, a N-(2-hydroxypropyl) methacrylamide copolymer-bound platinum that is less potent than carboplatin. Here, the platinum is held by an aminomalonic acid chelating agent coupled to the COOH-terminal glycine of a tetrapeptide spacer (Clin Can Res, 2004, 10, 3386; Eur J Can, 2004, 40, 291).

SUMMARY

The present invention describes prodrugs of taxane can assemble into supramolecular structure with improved pharmacokinetic profile such as long circulation time, enhance uptake and slow release of drug inside tumor. The taxane uptake to tumor can be achieved in higher amount by making supramolecular assemblies in aqueous buffer along with addition of some co-lipid to form nanoparticles with average particle size below 300 nm. Degradation of the supramolecular assembly as well as the prodrug releases effective drug inside the cell. Pharmaceutical compositions of prodrug of a taxane comprise a linker wherein taxane is coupled through ester, ether, amide, or other covalent conjugation with the linker. The lipid molecule can be cholesterol, alpha tocopherol, fatty acid or other naturally occurring lipid molecule which is conjugated to drug molecule through a suitable linker/spacer. The spacer can be composed of succinic acid, fumaric acid, propargylic acid, ethylene glycol, diethylene glycol, natural or unnatural amino acids individually or in any combinations.

The disclosure provides a supramolecular combinatorial therapeutic (SCT). The disclosure also provides compositions, e.g., pharmaceutical compositions comprising the supramolecular combinatorial therapeutic. As used herein, the term "supramolecular combinatorial therapeutic" or "SCT" refers to nano- or micro-sized structures in which, or on which, the active agents to be delivered are not covalently (or otherwise chemically) bound to the structure, but are instead physically or mechanically contained within or retained by the structure. These structures can be stabilized by van der Waals forces or other forms of noncovalent bonding. The supramolecular combinatorial therapeutic can be, but are not limited to, in the form of particles, liposomes, micelles, emulsions, In some embodiments, the superamolecular combinatorial therapeutic is in the form of a nano- or micro-particle. In some embodiments, the supramolecular combinatorial therapeutic is in the form of a particle, wherein particle has a lipid layer forming a lumen, wherein a taxane conjugate is present in or on the outer surface of the lipid layer.

Certain exemplary embodiments provide supramolecular combinatorial therapeutics, wherein a taxane-lipid conjugate is combined with one or more of a platinum compound, a kinase inhibitor, and an immunoregulator, each of which is optionally conjugated with a lipid.

In another aspect, described herein is a method of treating cancer, comprising, administering a supramolecular combinatorial therapeutic as described herein to a patient in need of treatment for cancer. In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer. In some embodiments, the method further comprises co-administering one or more additional anti-cancer therapy to the patient. In some embodiments, the additional therapy is selected from the group consisting of surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient.

The disclosure also provides a method for predicting the likehood of a cancer patient exhibiting a better response to self-assembled supramolecular particles than platinates or taxanes. Generally the method comprises assaying the expression level of one or more CAV1, CAV2, CAV3, LDLR, SMAD7, SMURF2, NEDD4 and PRKCA, and wherein increased expression level of at least one of CAV1, CAV2, CAV3, LDLR, SMAD7, SMURF2, NEDD4, PRKCA is indicative of a positive response to treatment comprising self-assembled supramolecular particles. In some embodiments, the sample can be a tumor sample. Further, the sample can be a biopsy sample or cells from ascitic fluid or cells from pleural effusion. The sample to be assayed can be a fixed, wax-embedded tissue sample.

DETAILED DESCRIPTION

Figure 1:
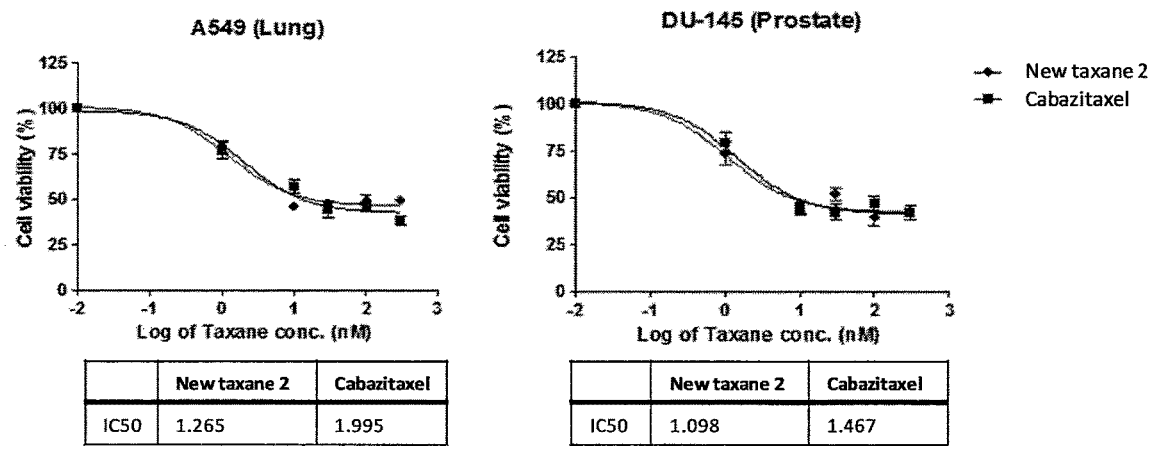
FIG. 1 shows in vitro characterization of supramolecular new taxane 2 according to an embodiment of the disclosure.

Generally the supramolecular combinatorial therapeutic comprises a taxane-lipid conjugate. It is to be recognized that the supramolecular combinatorial therapeutic can comprise only one type of taxane conjugate or two or more different types of taxane conjugates. Accordingly, in some embodiments, the supramolecular combinatorial therapeutic comprises only one type of taxane conjugate. In some other embodiments, the supramolecular combinatorial therapeutic comprises at least two (e.g., two, three, four, five, six, seven, eight, nine, ten or more) different types of taxane conjugates. By different types of taxane conjugates is meant that at least one element in the conjugates differs from each other. For example, the different types of conjugates can differ by the specific taxanes in the conjugates, the specific lipids in the conjugates, or the way the taxane and the lipid are conjugated together, i.e., the linker. In some embodiment, the taxane-lipid conjugate is a cabazitaxel-cholesterol conjugate.

In addition to the taxane conjugate supramolecular combinatorial therapeutic can further comprise a lipid conjugated kinase inhibitor. Thus, in some embodiments, the supramolecular combinatorial therapeutic comprises a taxane-lipid conjugate and a kinase inhibitor-conjugate. The supramolecular combinatorial therapeutic comprising the taxane conjugate and the kinase inhibitor conjugate can have the conjugates in any desired combination or ratio. For example, the supramolecular combinatorial therapeutic can comprise two or more (e.g. two, three, four, five, six, seven, eight, nine, ten or more) different types of taxane conjugates and one type of kinase inhibitor conjugate. In some other examples, the supramolecular combinatorial therapeutic can comprise one type of taxane conjugate and two or more (e.g. two, three, four, five, six, seven, eight, nine, ten or more) different types of kinase inhibitor conjugates. In still in some other examples, the supramolecular combinatorial therapeutic can comprise two or more (e.g. two, three, four, five, six, seven, eight, nine, ten or more) different types of taxane conjugates and two or more (e.g. two, three, four, five, six, seven, eight, nine, ten or more) different types of kinase inhibitor conjugates. In certain exemplary embodiments, the kinase inhibitor is a PI3K inhibitor. In still some other embodiments, the supramolecular combinatorial therapeutic can comprise two or more (e.g. two, three, four, five, six, seven, eight, nine, ten or more) different types of platinum conjugates, two or more (e.g. two, three, four, five, six, seven, eight, nine, ten or more) different types of taxane conjugates, and two or more (e.g. two, three, four, five, six, seven, eight, nine, ten or more) different types of kinase inhibitor conjugates. In some embodiments, the supramolecular combinatorial therapeutic further comprises an anti-PD-L1 antibody (or an antigen binding fragment thereof), optionally conjugated with a lipid.

The supramolecular combinatorial therapeutic can also comprise a platinum compound conjugated with a lipid. Thus, in some embodiments, the supramolecular combinatorial therapeutic comprises a taxane-lipid conjugate and a platinum conjugate. The supramolecular combinatorial therapeutic comprising the taxane conjugate and the platinum conjugate can have the conjugates in any desired combination or ratio. For example, the supramolecular combinatorial therapeutic can comprise two or more (e.g. two, three, four, five, six, seven, eight, nine, ten or more) different types of taxane conjugates and one type of platinum conjugate. In some other examples, the supramolecular combinatorial therapeutic can comprise one type of taxane conjugate and two or more (e.g. two, three, four, five, six, seven, eight, nine, ten or more) different types of platinum conjugates. In still in some other examples, the supramolecular combinatorial therapeutic can comprise two or more (e.g. two, three, four, five, six, seven, eight, nine, ten or more) different types of taxane conjugates and two or more (e.g. two, three, four, five, six, seven, eight, nine, ten or more) different types of platinum conjugates. In some embodiments, the supramolecular combinatorial therapeutic further comprises an anti-PD-L1 antibody (or an antigen binding fragment thereof), optionally conjugated with a lipid.

In some embodiments, the supramolecular combinatorial therapeutic further comprises an antibody (or an antigen binding fragment thereof) conjugated with a lipid. Without limitations, the antibody can be useful for therapeutic purposes (i.e., a therapeutic antibody) or for targeting the the supramolecular combinatorial therapeutic to a desired site (i.e., a targeting antibody).

In some embodiments, the supramolecular combinatorial therapeutic further comprises an immunomodulator. Immunomodulators are active agents of immunotherapy, and can either activate or suppress an immune response. In certain embodiments, the immunomodulator activates and stimulates an immune response against cancer cells, non-limiting examples of which include immune cells (e.g., natural killer cells, lymphokine-activated killer cells, cytotoxic T cells and dendritic cells), antibodies (e.g., anti-PD-L1 and anti-PD-1 antibodies, anti-CD52, anti-VEGF-A, anti-CD30, anti-EGFR, anti-CD33, anti-CD20, anti-CTLA4, and anti-HER-2 antibodies), and cytokines (e.g., interferons and interleukins). In certain exemplary embodiments, the immunomodulator is conjugated with a lipid.

An important negative co-stimulatory signal regulating T cell activation is provided by programmed death-1 receptor (PD-1)(CD279), and its ligand binding partners PD-L1 (B7-H1, CD274) and PD-L2 (B7-DC, CD273). The negative regulatory role of PD-1 was revealed by PD-1 knock outs (Pdcd1 $^{|\cdot|}$), which are prone to autoimmunity [Nishimura et al., Immunity JJ.: 141-51 (1999); Nishimura et al., Science 291: 319-22 (2001)]. PD-1 can be expressed on T cells, B cells, natural killer T cells, activated monocytes and dendritic cells (DCs). PD-1 is expressed by activated, but not by unstimulated human $CD4^+$ and $CD8^+$ T cells, B cells and myeloid cells. This stands in contrast to the more restricted expression of CD28 and CTLA-4 [Nishimura et al., Int. Immunol. 8: 773-80 (1996); Boettler et al., J. Virol. 80: 3532-40 (2006)]. PD-L1 is constitutively expressed on mouse T and B cells, CDs, macrophages, mesenchymal stem cells and bone marrow-derived mast cells [Yamazaki et al., J. Immunol. 169: 5538-45 (2002)]. PD-L1 is expressed on a wide range of nonhematopoietic cells (e.g., cornea, lung, vascular epithelium, liver nonparenchymal cells, mesenchymal stem cells, pancreatic islets, placental synctiotrophoblasts, keratinocytes, etc.) [Keir et al., Annu. Rev. Immunol. 26: 677-704 (2008)], and is unregulated on a number of cell types after activation. PD-L2 expression is more restricted than PD-L1. PD-L2 is inducibly expressed on DCs, macrophages, and bone marrow-derived mast cells. PD-L2 is also expressed on about half to two-thirds of resting peritoneal B1 cells, but not on conventional B2 B cells [Zhong et al., Eur. J. Immunol. 37: 2405-10 (2007)].

PD-1 signaling typically has a greater effect on cytokine production than on cellular proliferation, with significant effects on IFN-γ, TNF-α and IL-2 production. PD-1 mediated inhibitory signaling also depends on the strength of the TCR signaling, with greater inhibition delivered at low levels of TCR stimulation. This reduction can be overcome by co-stimulation through CD28 [Freeman et al., J. Exp. Med. 192: 1027-34 (2000)] or the presence of IL-2 [Carter et al., Eur. J. Immunol. 32: 634-43 (2002)]. Evidence is mounting that signaling through PD-L1 and PD-L2 may be bidirectional. That is, in addition to modifying TCR or BCR signaling, signaling may also be delivered back to the cells expressing PD-L1 and PD-L2. While treatment of dendritric cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-a and IL-6, and stimulated T cell proliferation [Nguyen et al, J. Exp. Med. 196: 1393-98 (2002)]. Treatment of mice with this antibody also (1) enhanced resistance to transplanted B16 melanoma and rapidly induced tumor-specific CTL [Radhakrishnan et al., J. Immunol. 170: 1830-38 (2003); Radhakrishnan et al., Cancer Res. 64: 4965-72 (2004); Heckman et al., Eur. J. Immunol. 37: 1827-35 (2007)]; (2) blocked development of airway inflammatory disease in a mouse model of allergic asthma [Radhakrishnan et al., J. Immunol. 173: 1360-65 (2004); Radhakrishnan et al, J. Allergy Clin. Immunol. UJy. 668-74 (2005)]. Further evidence of reverse signaling into dendritic cells ("DCs") results from studies of bone marrow derived DCs cultured with soluble PD-1 (PD-1 EC domain fused to Ig constant region—"s-PD-1") [Kuipers et al, Eur. J. Immunol. 36: 2472-82 (2006)]. This sPD-1 inhibited DC activation and increased IL-10 production, in a manner reversible through administration of anti-PD-1. Additionally, several studies show a receptor for PD-L1 or PD-L2 that is independent of PD-1. B7.1 has already been identified as a binding partner for PD-L1 [Butte et al, Immunity 27: 111-22 (2007)]. Chemical crosslinking studies suggest that PD-L1 and B7.1 can interact through their IgV-like domains. B7.1:PD-L1 interactions can induce an inhibitory signal into T cells.

Certain aspects of the present invention describe prodrugs of combinations of chemotherapeutic drugs with anti-PD-1 or anti-PD-L1 antibodies that can assemble into supramolecular structures with improved tumor loading and unregulated T cell-mediated immune responses, and the use of these supramolecules in the treatment of cancer.

The anti-PD-L1 antibodies according to the present invention, which have antibody dependent cell-mediated cytotoxicity (ADCC) activity, directly act on PD-L1 bearing tumor cells by inducing their lysis without showing any significant toxicity. Moreover, the antibodies block the interaction between human PD-L1 and human PD-1 and enhance T-cell function to upregulate cell-mediated immune responses for the treatment of cancer.

In another aspect, described herein is a method of treating cancer, comprising, administering a supramolecular combinatorial therapeutic as described herein to a patient in need of treatment for cancer. In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

In some embodiments, the method further comprises co-administering one or more additional anti-cancer therapy to the patient. In some embodiments, the additional therapy is selected from the group consisting of surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient. In some embodiments, the method further comprises co-administration of one or more immunomodulators to the subject. In some embodiments, the immunomodulator is an anti-PD-L1 or an anti-PD-1 antibody.

The platinum/taxane/anti-PD-L1 uptake to tumor can be achieved in higher amounts by supramolecular assembly in aqueous buffer along with addition of some co-lipid to form nanoparticles with average particle size below 300 nm. Degradation of supramolecular assembly as well as the prodrug releases effective drug inside cells. Pharmaceutical composition of prodrug of a platinum/taxane comprises a linker wherein platinum/taxane is coupled through ester, ether, amide or other covalent conjugation with the linker. The lipid molecule can be cholesterol, alpha tocopherol, fatty acid or other naturally occurring lipid molecule which is conjugated to drug molecule through a suitable linker/spacer. The spacer can be composed of succinic acid, fumaric acid, propargylic acid, ethylene glycol, diethylene glycol, natural or unnatural amino acids individually or in any combinations.

In some embodiments, the supramolecular combinatorial therapeutic is in the form of a particle, wherein the particle has a lipid layer forming a lumen, wherein a platinum/taxane/anti-PD-L1 conjugate is present in or on the outer surface of the lipid layer.

In one aspect, the disclosure provides a supramolecular combinatorial therapeutic comprising a taxane conjugate, e.g., a hydrophobic taxane-lipid conjugate. Amount of the conjugate in the supramolecular combinatorial therapeutic can range from about 1% to about 99% (w/w). For example, the amount of the conjugate in the supramolecular combinatorial therapeutic can be from about 5% to about 95%, from about 10% to about 90%, from about 15% to about 85%, from about 20% to about 75%, or from about 25% to about 50%.

In some embodiments, the composition can comprise two or more (e.g., two, three, four, five, six, seven, eight, nine, ten or more) different taxane conjugates. The different conjugates can be present in any desired ratio. For example, the different conjugates can be in a ratio ranging from about 100:1 to 1:100. In some embodiments, the different conjugates can be in a ratio ranging from about 50:1 to 1:50, 25:1 to 1:25, 10:1 to 1:10, 5:1 to 1:5, or 2.5:1 to 1:2.5. In some embodiments, the different conjugates can be in a ratio of about 1:1.

Without limitations, the supramolecular combinatorial therapeutic can be in any shape, size or form. For example, the supramolecular combinatorial therapeutic can be in the form of a nano- or micro-structure. Such structures can include, but are not limited to liposome, emulsions, and micelles. In some embodiments, the supramolecular combinatorial therapeutic can be in the form of a liposome. As used herein, the term "liposome" encompasses any compartment enclosed by a lipid layer. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

A liposome composition can be prepared by a variety of methods that are known in the art. See e.g., U.S. Pat. Nos. 4,235,871, 4,897,355 and 5,171,678; published PCT applications WO 96/14057 and WO 96/37194; Felgner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757, content of all of which is incorporated herein by reference in its entirety.

The liposomes can be prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, content of which is incorporated herein by reference in its entirety.

In some embodiments, a lipid conjugated component of the supramolecular combinatorial therapeutic is present in or on the surface of the lipid layer. In some embodiments, the supramolecular combinatorial therapeutic is in the form of a liposome, wherein the lipid non-lipid portion of a lipid conjugated component (e.g., taxane, PI3K inhibitor, platinum, antibody portion of the conjugate) is on the outer surface of the lipid layer.

The supramolecular combinatorial therapeutic can also be in the form of an emulsion. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the conjugate disclosed herein can be present as a solution in either the aqueous phase or the oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials can also be included in emulsion formulations and contribute to the properties of emulsions. These include, but are not limited to, fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The applications of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199).

The supramolecular combinatorial therapeutic can be in the form of a particle. As used herein, the term "particle" encompasses liposomes, emulsions, vesicles and lipid particles. Generally, the particle can be of any shape or form, e.g., spherical, rod, elliptical, cylindrical, capsule, or disc; and these particles can be part of a network or an aggregate. Without limitations, the particle can have any size from nm to millimeters. In some embodiments, the particle is a microparticle or a nanoparticle. As used herein, the term "microparticle" refers to a particle having a particle size of about 1 µm to about 1000 µm. As used herein, the term "nanoparticle" refers to particle having a particle size of about 0.1 nm to about 1000 nm. Generally, the particles disclosed herein are nanoparticles and have an average diameter of from about 5 nm to about 500 nm. In some embodiments, the particles have an average diameter of from about 75 nm to about 500 nm, from about 25 nm to about 250 nm, from about 50 nm to about 150 nm, from about 75 nm to about 125 nm, from about 50 nm to about 500 nm, from about 75 nm to about 200 nm, from about 100 to about 175 nm, from about 125 nm to about 175 nm, from about 40 nm to about 90 nm, or from about 50 nm to about 80 nm.

In some embodiments a nanoparticle can be less than about 1 um in diameter, e.g., about 1 um or less in diameter, about 500 nm or less in diameter, about 400 nm or less in diameter, about 300 nm or less in diameter, about 200 nm or less in diameter, about 100 nm or less in diameter, about 50 nm or less in diameter, or about 10 nm or less in diameter. In some embodiments a nanoparticle can be less than 1 um in diameter, e.g., 1 um or less in diameter, 500 nm or less in diameter, 400 nm or less in diameter, 300 nm or less in diameter, 200 nm or less in diameter, 100 nm or less in diameter, 50 nm or less in diameter, or 10 nm or less in diameter. In some embodiments, the nanoparticles in a composition can be from about 1 nm to about 1 um in diameter, e.g. from about 1 nm to about 500 nm in diameter, from about 1 nm to about 200 nm in diameter, from about 10 nm to about 200 nm in diameter, from about 100 nm to about 200 nm in diameter, or from about 10 nm to about 100 nm in diameter. In some embodiments, the nanoparticles in a composition can be from 1 nm to 1 um in diameter, e.g. from 1 nm to 500 nm in diameter, from 1 nm to 200 nm in diameter, from 10 nm to 200 nm in diameter, from 100 nm to 200 nm in diameter, or from 10 nm to 100 nm in diameter.

In some embodiments, nanoparticles can be selected to be of specific sizes, e.g. less than about 200 nm in diameter. Methods of selecting nanoparticles of a particular size and/or range of sizes are known in the art and can include, by way of non-limiting example, filtration, sedimentation, centrifugation, and/or chromatographic methods, e.g. SEC.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axis of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30 less than or equal to about 1.25 less than or equal to about 1.20 less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The particles can be, e.g., monodispersed or polydispersed and the variation in diameter of the particles of a given dispersion can vary. In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In addition to a taxane conjugate, the supramolecular combinatorial therapeutic can further include one or more additional lipids and/or other components. Without wishing to be bound by a theory, other lipids can be included in the supramolecular combinatorial therapeutic for a variety of purposes, such as to prevent lipid oxidation, to stabilize bilayer, to reduce aggregation during formation or to attach ligands onto the particle surface. Any of a number of lipids can be present, including but not limited to, amphipathic, neutral, cationic, anionic lipids, sterols, and phospholipids. Further, such lipids can be used alone or in any combination with each other. In some embodiments, the supramolecular combinatorial therapeutic further comprises a lipoprotein particle, e.g., HDL or LDL. The supramolecular combinatorial therapeutic can comprise from about 1% to about 99% (w/w) of the additional lipid or component. Further the additional lipid or component can be present in 10:1 to 1:10 ratio with the conjugate. If two or more different additional lipids are present in the supramolecular combinatorial therapeutic, each lipid can be independently in 10:1 to 1:10 ratio with the conjugate. Further, if two or more different additional lipids are present in the supramolecular combinatorial therapeutic, the two lipids can be in 10:1 to 1:10 ratio. Without limitations, two different components (conjugate and lipid or two different lipids) of the supramolecular combinatorial therapeutic can be in ratio 10:1 to 1:10, 5:1 to 1:5, or 2.5:1 to 1:2.5. In some embodiments, two different components in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. If the supramolecular combinatorial therapeutic comprises more than two components ratio between any two components can be independent of ratio between any other two components.

In some embodiments, the composition further comprises a first lipid in addition to the conjugate.

The term "lipid" as used herein means a substance that is soluble in organic solvents and includes, but is not limited to, oils, fats, sterols, triglycerides, fatty acids, phospholipids, and the like. Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of cholesterol; 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Gly ceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; and γ-Linolenic acid.

In some embodiments, the first lipid is a phospholipid.

Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyloleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof, and the like. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and β-acyloxyacids, can also be used In some embodiments, the phospholipid in the supramolecular combinatorial therapeutic is selected from the group consisting of 1,2-Didecanoyl-sn-glycero-3-phosphocholine; 1,2-Dierucoyl-sn-glycero-3-phosphate (Sodium Salt); 1,2-Dierucoyl-sn-glycero-3-phosphocholine; 1,2-Dierucoyl-sn-glycero-3-phosphoethanolamine; 1,2-Dierucoyl-sn-glycero-3[Phospho-rac-(1-glycerol) (S odium Salt); 1,2-Dilinoleoyl-sn-glycero-3-phosphocholine; 1,2-Dilauroyl-sn-glycero-3-phosphate (Sodium Salt); 1,2-Dilauroyl-sn-glycero-3-phosphocholine; 1,2-Dilauroyl-sn-glycero-3-phosphoethanolamine; 1,2-Dilauroyl-sn-glycero-3[Phospho-rac-(1-glycerol) (S odium Salt); 1,2-Dilauroyl-sn-glycero-3[Phospho-rac-(1-glycerol) (Ammonium Salt); 1,2-Dilauroyl-sn-glycero-3-phosphoserine (Sodium Salt); 1,2-Dimyristoyl-sn-glycero-3-phosphate (Sodium Salt); 1,2-Dimyristoyl-sn-glycero-3-phosphocholine; 1,2-Dimyristoyl-sn-glycero-3-phosphoethanolamine; 1,2-Dimyristoyl-sn-glycero-3[Phospho-rac-(1-glycerol) (Sodium Salt); 1,2-Dimyristoyl-sn-glycero-3[Phospho-rac-(1-glycerol) (Ammonium Salt); 1,2-Dimyristoyl-sn-glycero-3[Phospho-rac-(1-glycerol) (Sodium/Ammonium Salt); 1,2-Dimyristoyl-sn-glycero-3-phosphoserine (Sodium Salt); 1,2-Dioleoyl-sn-glycero-3-phosphate (Sodium Salt);

1,2-Dioleoyl-sn-glycero-3-phosphocholine; 1,2-Dioleoyl-sn-glycero-3-phosphoethanolamine; 1,2-Dioleoyl-sn-glycero-3[Phospho-rac-(1-glycerol) (Sodium Salt); 1,2-Dioleoyl-sn-glycero-3-phosphoserine (Sodium Salt); 1,2-Dipalmitoyl-sn-glycero-3-phosphate (Sodium Salt); 1,2-Dipalmitoyl-sn-glycero-3-phosphocholine; 1,2-Dipalmitoyl-sn-glycero-3-phosphoethanolamine; 1,2-Dipalmitoyl-sn-glycero-3[Phospho-rac-(1-glycerol) (Sodium Salt); 1,2-Dipalmitoyl-sn-glycero-3[Phospho-rac-(1-glycerol) (Ammonium Salt); 1,2-Dipalmitoyl-sn-glycero-3-phosphoserine (Sodium Salt); 1,2-Distearoyl-sn-glycero-3-phosphate (Sodium Salt); 1,2-Distearoyl-sn-glycero-3-phosphocholine; 1,2-Distearoyl-sn-glycero-3-phosphoethanolamine; 1,2-Distearoyl-sn-glycero-3 [Phospho-rac-(1-glycerol) (Sodium Salt); 1,2-Distearoyl-sn-glycero-3[Phospho-rac-(1-glycerol) (Ammonium Salt); 1,2-Distearoyl-sn-glycero-3-phosphoserine (Sodium Salt); Egg-PC; Hydrogenated Egg PC; Hydrogenated Soy PC; 1-Myristoyl-sn-glycero-3-phosphocholine; 1-Palmitoyl-sn-glycero-3-phosphocholine; 1-Stearoyl-sn-glycero-3-phosphocholine; 1-Myristoyl-2-palmitoyl-sn-glycero 3-phosphocholine; 1-Myristoyl-2-stearoyl-sn-glycero-3-phosphocholine; 1-Palmitoyl-2-myristoyl-sn-glycero-3-phosphocholine; 1-Palmitoyl-2-oleoyl-sn-glycero-3-phosphocholine; 1-Palmitoyl-2-oleoyl-sn-glycero-3-phosphoethanolamine; 1-Palmitoyl-2-oleoyl-sn-glycero-3 [Phospho-rac-(1-glycerol)] (Sodium Salt); 1-Palmitoyl-2-stearoyl-sn-glycero-3-phosphocholine; 1-Stearoyl-2-myristoyl-sn-glycero-3-phosphocholine; 1-Stearoyl-2-oleoyl-sn-glycero-3-phosphocholine; and 1-Stearoyl-2-palmitoyl-sn-glycero-3-phosphocholine.

In some embodiments, the phospholipid is SPOC, egg PC, or Hydrogenated Soy PC (HSPC). In one, the phospholipid in the composition is SOPC.

In some embodiments, the supramolecular combinatorial therapeutic further comprises a second lipid in addition to the conjugate and the first lipid. In some further embodiments, the second lipid is a phospholipid.

In some embodiments, the supramolecular combinatorial therapeutic further comprises a polyethylene glycol (PEG). The PEG can be included in the composition by itself or conjugated with a component of the supramolecular combinatorial therapeutic. For example, the PEG can be conjugated with the conjugate or a lipid component of the supramolecular combinatorial therapeutic. In some embodiments, the PEG is conjugated with a lipid component of the supramolecular combinatorial therapeutic. Without limitations, the PEG can be conjugated with any lipid or phospholipids. For example, the PEG conjugated lipid can be selected from the group consisting of PEG conjugated diacylglycerols and dialkylglycerols, PEG-conjugated phosphatidylethanolamine, PEG conjugated to phosphatidic acid, PEG conjugated ceramides (see, U.S. Pat. No. 5,885,613), PEG conjugated dialkylamines, PEG conjugated 1,2-diacyloxypropan-3-amines, and PEG conjugated to 1,2-distearoyl-sn-glycem-3-phosphoethanolamine (DSPE), and any combinations thereof. In some embodiments, the PEG conjugated lipid is 1,2-distearoyl-sn-glycem-3-phosphoethanolamine-N-[amino(polyethylene glycol)-2000] (DSPE-PEG2000).

In some embodiments, the supramolecular combinatorial therapeutic further comprises a targeting ligand. As used herein the term "targeting moiety" or "targeting ligand" refers to any molecule that provides an enhanced affinity for a selected target, e.g., a cell, cell type, tissue, organ, region of the body, or a compartment, e.g., a cellular, tissue or organ compartment. The targeting moiety or ligand can comprise a wide variety of entities. Such ligands can include naturally occurring molecules, or recombinant or synthetic molecules. Exemplary targeting ligands include, but are not limited to, antibodies (polyclonal or monoclonal), antigen binding fragments of antibodies, antigens, folates, EGFR, albumin, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Additional exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (e.g., PEG-2K, PEG-5K, PEG-10K, PEG-12K, PEG-15K, PEG-20K, PEG-40K), MPEG, $[MPEG]_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic)

is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,552,545; 6,335,434 and 7,128,893, contents of all of which are herein incorporated in their entireties by reference.

Targeting of particles with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton, Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the liposome in such a manner that the targeting moiety is available for interaction with the target, for example, a cell surface receptor.

In some embodiments, the targeting ligand binds a protein, receptor, or marker expressed on the surface of a cancer cell. Targeting ligands that preferentially bind to and/or cross the membrane of cancer cells are known in the art, e.g. iRGD, RGD, Lyp-1 peptide (CGNKRTRGC), NGR peptide, iNGR, RGR peptide, CAR peptide, tCAR peptide (CARSKNK); FSH-33, Allatostatin 1, the pentapeptide CREKA, Hepatocarcinoma targeting peptide, Peptide GFE, anti-EGFR antibodies and/or antibody fragments, in particular Cetuximab, CendR, iRGD peptide (RGD-CendR hybrid peptide), small molecules, antibodies and/or antibody fragments binding to cancer-specific epitopes like e.g. CEA, Gastrin-releasing peptide receptors, Somatostatin receptors, Galanin receptors, Follicle-stimulating hormone receptors, p32 protein, Fibroblast growth factor receptors, HepG2, Epidermal growth factor receptors, Integrin $\alpha v \beta 6$, Neuropilin-1 receptor and VEGF receptors and variants or combinations thereof. In some embodiments, a targeting agent can be iRGD, e.g. a peptide having the sequence CRGDKGPDC. In some embodiments, the targeting ligand binds EGFR.

In some embodiments, the targeting ligand is a polyclonal or monoclonal antibody or a fragment thereof retaining epitope binding activity or an antibody-based binding moiety.

In some embodiments, the targeting ligand is a polyclonal or monoclonal antibody, antibody fragments, a peptide, or a molecule that is capable of binding protein receptors expressed on the surface of cancer cells.

In some embodiments, the targeting ligand is an antibody selected from the group consisting of C242 antibody (CanAg), Rituximab (CD20), Trastuzumab (Her2), Cetuximab (EGFR), Bevacizumab (VEGF), Panitumumab, Alemtuzumab, Ofatumumab, Gemtuzumab (CD33), Inotuzumab (CD22), Lorvotuzumab (CD56), Brentuximab (CD30), Glembatumumab (GPNMB), epitope bind fragments thereof and any combinations thereof.

The targeting ligand can be present, e.g. on the surface of a supramolecular combinatorial therapeutic described herein and/or partially embedded in the membrane or lipid layer of a supramolecular combinatorial therapeutic described herein. Methods of incorporating a targeting agent are known in the art and non-limiting examples are described elsewhere herein. In some embodiments, a supramolecular combinatorial therapeutic described herein can comprise a two or more targeting agents, e.g. a supramolecular combinatorial therapeutic can comprise a combination of nanoparticles, each comprising a different targeting agent and/or a composition can comprise nanoparticles which each comprise multiple targeting agents. In some embodiments, a supramolecular combinatorial therapeutic described herein can comprise one targeting agent, two targeting agents, three targeting agents, or more targeting agents.

In one approach, the targeting ligand can be linked to a component (e.g., a lipid) of the supramolecular combinatorial therapeutic. In some embodiments, the targeting ligand can be conjugated with a lipid. A variety of different targeting ligands and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002). Other lipids conjugated with targeting moieties are described in U.S. Patent Application Publication No. US2009/0247608 and No. US2012/0046478, content of both of which is incorporated herein by reference in its entirety.

In some embodiments, the composition can further comprise a therapeutic agent in addition to the taxane conjugate. Without limitations, when present in the supramolecular combinatorial therapeutic, the therapeutic agent can be encapsulated in the supramolecular combinatorial therapeutic; present in a lipid layer of the supramolecular combinatorial therapeutic; or present on the surface of the supramolecular combinatorial therapeutic.

As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agricultural, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof, including, for example, DNAnanoplexes.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies (polyconal and monoclonal) and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine,* 13th Edition, Eds. T. R. Harrison et al. McGraw-Hill N.Y., N.Y.; Physicians' Desk Reference, 50th Edition, 1997, Oradell, N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

The therapeutic agent can be linked to a component of the supramolecular combinatorial therapeutic. For example, the therapeutic agent can be linked to a lipid or phospholipid component of the supramolecular combinatorial therapeutic. The therapeutic agent and the component of the supramolecular combinatorial therapeutic can be linked together by a bond or via a linker. This linker can be cleavable or non-cleavable, depending on the application. In certain embodiments, a cleavable linker can be used to release the therapeutic agent after transport to the desired target. The intended nature of the conjugation or coupling interaction, or the desired biological effect, will determine the choice of linker group. In some embodiments, the lipid in the lipid conjugated therapeutic agent is cholesterol.

The supramolecular combinatorial therapeutic can comprise from about 1% to about 99% (w/w) of the therapeutic agent or a conjugate thereof. Further the therapeutioc agent or a conjugate thereof can be present in 10:1 to 1:10 ratio with the taxane conjugate. Without limitations, taxane conjugate and therapeutic agent (or a conjugate thereof) in the supramolecular combinatorial therapeutic can be in ratio 10:1 to 1:10, 5:1 to 1:5, or 2.5:1 to 1:2.5. In some embodiments, taxane conjugate and therapeutic agent (or a conjugate thereof) in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10.

In some embodiments, the therapeutic agent is an antibody (e.g., polyclonal or monoclonal antibody) or an antigen binding fragment thereof. In one embodiment, the therapeutic agent is an antibody (e.g., polyclonal or monoclonal antibody), or an antigen binding fragment thereof, conjugated with a lipid, e.g., cholesterol. In some embodiments, the antibody is an immunomodulator comprising an anti-PD-1 antibody, an anti-PD-L1 antibody and combinations thereof. In some embodiments, the immunomodulator is conjugated with lipid, e.g. cholesterol or other lipids disclosed herein.

In some embodiments, the therapeutic agent is a chemotherapeutic or anti-cancer agent. As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

The term chemotherapeutic agent is a broad one covering many chemotherapeutic agents having different mechanisms of action. Generally, chemotherapeutic agents are classified according to the mechanism of action. Many of the available agents are anti-metabolites of development pathways of various tumors, or react with the DNA of the tumor cells. There are also agents which inhibit enzymes, such as topoisomerase I and topoisomerase II, or which are antimiotic agents.

Chemotherapeutic agents include, but are not limited to, an aromatase inhibitor; an antiestrogen, an anti-androgen (especially in the case of prostate cancer) or a gonadorelin agonist; a topoisomerase I inhibitor or a topoisomerase II inhibitor; a microtubule active agent, an alkylating agent, an anti-neoplastic anti-metabolite or a platin compound; a compound targeting/decreasing a protein or lipid kinase activity or a protein or lipid phosphatase activity, a further anti-angiogenic compound or a compound which induces cell differentiation processes; a bradykinin 1 receptor or an angiotensin II antagonist; a cyclooxygenase inhibitor, a bisphosphonate, a heparanase inhibitor (prevents heparan sulphate degradation), e.g., PI-88, a biological response modifier, preferably a lymphokine or interferons, e.g. interferon γ, an ubiquitination inhibitor or an inhibitor which blocks anti-apoptotic pathways; an inhibitor of Ras oncogenic isoforms or a farnesyl transferase inhibitor; a telomerase inhibitor, e.g., telomestatin; a protease inhibitor, a matrix metalloproteinase inhibitor, a methionine aminopeptidase inhibitor, e.g., bengamide or a derivative thereof; a proteasome inhibitor, e.g., PS-341 (bortezomib/Velcade); agents used in the treatment of hematologic malignancies or FMS-like tyrosine kinase inhibitors; an HSP90 inhibitors; histone deacetylase (HDAC) inhibitors; mTOR inhibitors; somatostatin receptor antagonists; integrin antagonists; anti-leukemic compounds; tumor cell damaging approaches, such as ionizing radiation; EDG binders; anthranilic acid amide class of kinase inhibitors; ribonucleotide reductase inhibitors; S-adenosylmethionine decarboxylase inhibitors; antibodies against VEGF or VEGFR; photodynamic therapy; angiostatic steroids; AT1 receptor antagonists; ACE inhibitors; and the like.

Other chemotherapeutic agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

The chemotherapeutic agent can be linked to a component of the supramolecular combinatorial therapeutic. For example, the chemotherapeutic agent can be linked to a lipid or phospholipid component of the supramolecular combinatorial therapeutic. The chemotherapeutic agent and the component of the supramolecular combinatorial therapeutic can be linked together by a bond or via a linker. This linker can be cleavable or non-cleavable, depending on the application. In certain embodiments, a cleavable linker can be used to release the chemotherapeutic agent after transport to the desired target. The intended nature of the conjugation or coupling interaction, or the desired biological effect, will determine the choice of linker group. In some embodiments, the lipid in the lipid conjugated chemotherapeutic agent is cholesterol.

The supramolecular combinatorial therapeutic can comprise from about 1% to about 99% (w/w) of the chemtherapeutic agent or a conjugate thereof. Further the chemotherapeutic agent or a conjugate thereof can be present in 10:1 to 1:10 ratio with the taxane conjugate. Without limitations, taxane conjugate and chemotherapeutic agent (or a conjugate thereof) in the supramolecular combinatorial therapeutic can be in ratio 10:1 to 1:10, 5:1 to 1:5, or 2.5:1 to 1:2.5. In some embodiments, taxane conjugate and chemotherapeutic agent (or a conjugate thereof) in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10.

In some embodiments, the chemotherapeutic agent can be a kinase inhibitor, e.g. a Phosphoinositide 3-kinase (PI 3-kinase or PI3K) inhibitor. Phosphoinositide 3-kinases are a family of related enzymes that are capable of phosphorylating the 3 position hydroxyl group of the inositol ring of phosphatidylinositol. They are also known as phosphatidylinositol-3-kinases. PI3Ks interact with the IRS (Insulin receptor substrate) in order to regulate glucose uptake through a series of phosphorylation events. The phosphoinositol-3-kinase family is composed of Class I, II and Class III, with Class I the only ones able to convert PI(4,5)P2 to PI(3,4,5)P3 on the inner leaflet of the plasma membrane.

Class I PI3K are heterodimeric molecules composed of a regulatory and a catalytic subunit; they are further divided between IA and IB subsets on sequence similarity. Class IA PI3K are composed of one of five regulatory p85α, p55α, p50α, p85β or p55γ subunit attached to a p110α, β or δ catalytic subunit. The first three regulatory subunits are all splice variants of the same gene (Pik3r1), the other two being expressed by other genes (Pik3r2 and Pik3r3, p85β and p55γ, respectively). The most highly expressed regulatory subunit is p85α, all three catalytic subunits are expressed by separate genes (Pik3ca, Pik3cb and Pik3cd for p110α, p110β and p110δ, respectively). The first two p110 isoforms (α and β) are expressed in all cells, but p110δ is primarily expressed in leukocytes and it has been suggested it evolved in parallel with the adaptive immune system. The regulatory p101 and catalytic p110γ subunits comprise the type IB PI3K and are encoded by a single gene each.

Class II comprises three catalytic isoforms (C2α, C2β, and C2γ), but unlike Classes I and III, no regulatory proteins. These enzymes catalyse the production of PI(3)P from PI (may also produce PI(3,4)P2 from PI(4)P). C2α and C2β are expressed throughout the body, however expression of C2γ is limited to hepatocytes. The distinct feature of Class II PI3Ks is the C-terminal C2 domain. This domain lacks critical Asp residues to coordinate binding of $Ca^{2+}$, which suggests class II PI3Ks bind lipids in a $Ca^{2+}$ independent manner. Class III are similar to II in that they bias the production of PI(3)P from PI, but are more similar to Class I in structure, as they exist as a heterodimers of a catalytic (Vps34) and a regulatory (p150) subunits. Class III seems to be primarily involved in the trafficking of proteins and vesicles.

As used herein, a "PI3K inhibitor" refers to an agent that inhibits the activity of PI3K, as measured by the level of phosphorylation of the 3 position hydroxyl group of the inositol ring of phosphatidylinositol, or as measured by the activity and/or phosphorylation (where increased phosphorylation indicates PI3K activity) of molecules downstream of PI3K. Examples of such downstream molecules are known in the art and can include, but are not limited to AKT, SGK, mTOR, GSK3β, PSD-95, S6, and 4EBP1. Methods of measuring the activity of PI3K, directly or indirectly are well known in the art, and include, by way of non-limiting example determining the level of phosphorylation of a molecule downstream of PI3K using phospho-isoform specific antibodies, which are commercially available (e.g. anti-phospho-AKT antibody, Cat No. ab66138 Abcam, Cambridge, Mass.).

In some embodiments, a PI3K inhibitor can be LY294002, PI103, and/or PI828. Further non-limiting examples of PI3K inhibitors can include wortmannin, demethoxyviridin, IC486068, IC87114, GDC-0941, perifosine, CAL101, PX-866, IPI-145, BAY 80-6946, BEZ235, P6503, TGR1202, SF1126, INK1117, BKM120, IL147, XL765, Palomid 529, GSK1059615, ZSTK474, PWT33597, TG100-115, CAL263, GNE-447, CUDC-907, and AEZS-136.

In some embodiments, the conjugate comprises a PI3K inhibitor covalently linked with a lipid. In some embodiments, the lipid conjugated PI3K inhibitor is dently in 10:1 to 1:10 ratio with the conjugate. Further, if two or more different PI3K inhibitor conjugates are present in the composition, the two PI3K inhibitor conjugates can be in 10:1 to 1:10 ratio. Without limitations, two different components (conjugate and PI3K inhibitor conjugate) of the supramolecular combinatorial therapeutic can be in ratio 10:1 to 1:10, 5:1 to 1:5, or 2.5:1 to 1:2.5. In some embodi-

FORMULA I

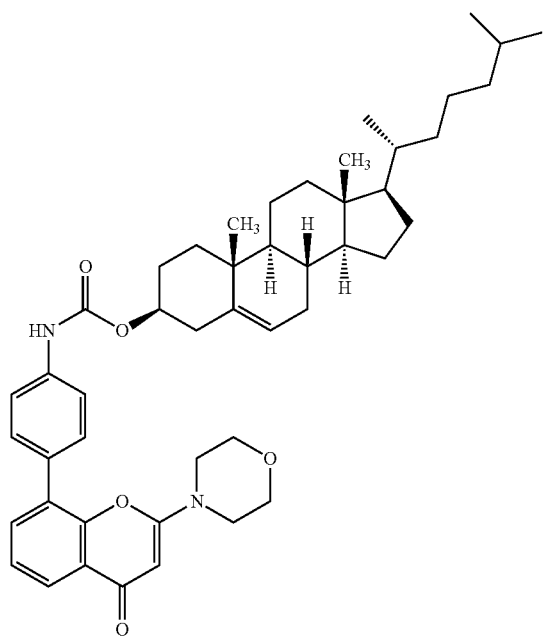

or

FORMULA II

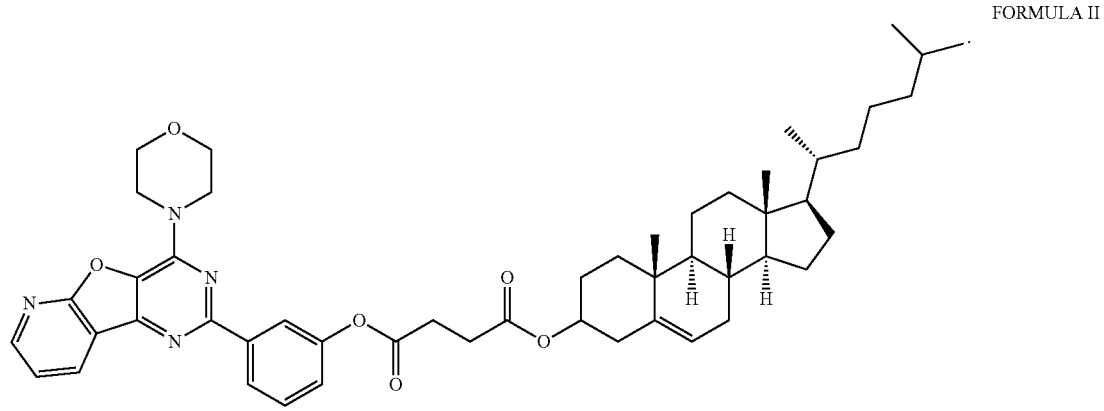

Additional PI3K inhibitors covalently linked with a lipid are described, for example, in PCT Patent Publication No. WO2013188763, the content of which is incorporated herein by reference in its entirety.

In some embodiments, the supramolecular combinatorial therapeutic comprises at least one (e.g., one two, three, four, five six, seven, eight, nine, ten or more different types of) taxane conjugate and at least one taxane conjugate (e.g., one two, three, four, five six, seven, eight, nine, ten or more different types of) lipid conjugated PI3K inhibitor). The supramolecular combinatorial therapeutic can comprise from about 1% to about 99% (w/w) of the PI3K inhibitor conjugate. Further the PI3K inhibitor conjugatecan be present in 10:1 to 1:10 ratio with the taxane conjugate. If two or more different PI3K inhibitor conjugates are present in the composition, each PI3K inhibitor conjugate can be indepenments, two different components in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. If the supramolecular combinatorial therapeutic comprises more than two components ratio between any two components can be independent of ratio between any other two components.

In some embodiments, the chemotherapeutic agent is a platinate. Any platinum compound can be used in the methods and compositions described herein. In some embodiments, the platinum compound is a platinum (II) or platinum (IV) compound. In some embodiments, the platinum (II) compound is selected from the group consisting of cisplatin, oxaliplatin, carboplatin, paraplatin, sartraplatin, and combinations thereof. In a preferred embodiment, the platinate is cisplatin or oxalipaltin. Cisplatin [cis-dichlorodiammineplatinum(II)] (CDDP) has emerged as an important class of antitumor agents, and is widely used for the treatment of many malignancies including testicular, ovarian, cervical, head and neck, and non-small cell lung cancer (Jamieson, et al, Chem. Rev. (1999), 99(9): 2467-2498). It was also shown to be active in triple negative breast cancer (Leong, et al., J. Clin. Invest. (2007), 117(5): 1370-80). Its use is however dose-limited mainly because of nephrotoxicity or toxicity to the kidney (Madias, N E and Harrington, J T, Am. J. (1978), 65(2): 307-14).

In some embodiments, the platinum can be dissociably linked to a lipid via at least one coordination bond. In some embodiments, the coordination bond is Pt→O. In some other embodiments, the coordination bond is Pt→N. In some embodiments, the conjugate comprises a platinum dissociably linked with a cholesterol via at least one coordination bond. In some embodiments, the lipid conjugated platinum compound is e.g., US Patent Publication 2012/0189571, and International Patent Publication WO 2010/091192; each of which is incorporated by reference herein in its entirety.

In some embodiments, the supramolecular combinatorial therapeutic comprises at least one (e.g., one two, three, four, five six, seven, eight, nine, ten or more different types of) taxane conjugate and at least one platinum conjugate (e.g., one two, three, four, five six, seven, eight, nine, ten or more different types of) lipid conjugated platinum). The supramolecular combinatorial therapeutic can comprise from about 1% to about 99% (w/w) of the platinum conjugate. Further the platinum conjugatecan be present in 10:1 to 1:10 ratio with the taxane conjugate. If two or more different platinum conjugates are present in the composition, each platinum conjugate can be independently in 10:1 to 1:10 ratio with the taxane conjugate. Further, if two or more different platinum conjugates are present in the composition, the two platinum conjugates can be in 10:1 to 1:10 ratio. Without limitations, two different components (taxane conjugate and platinum conjugate) of the supramolecular com-

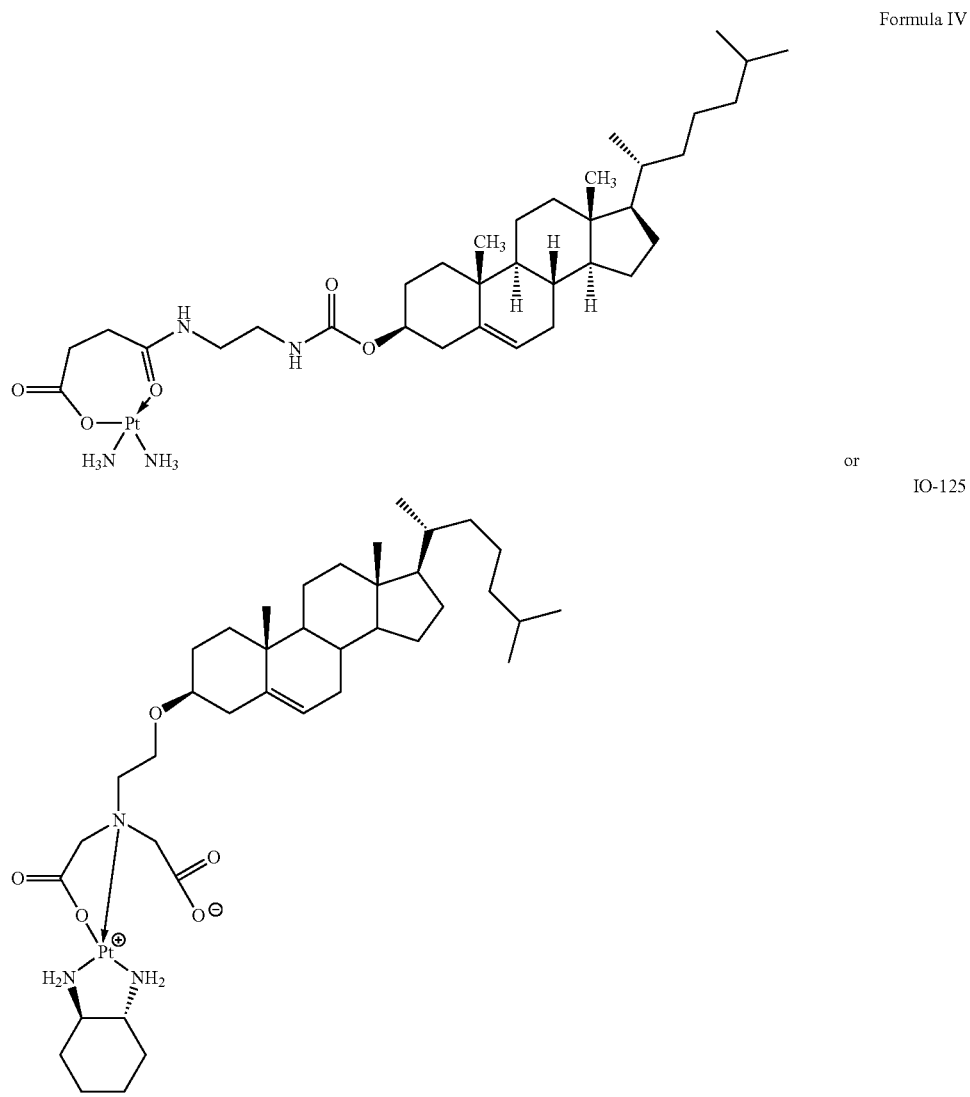

Formula IV or

IO-125

Additional conjugates comprising a platinate (or platinum-containing chemotherapeutic agent) are described in binatorial therapeutic can be in ratio 10:1 to 1:10, 5:1 to 1:5, or 2.5:1 to 1:2.5. In some embodiments, two different components in the supramolecular combinatorial therapeutic can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. If the supramolecular combinatorial therapeutic comprises more than two components ratio between any two components can be independent of ratio between any other two components.

The supramolecular combinatorial therapeutic can also include components selected to reduce aggregation of particles during formation, which can result from steric stabilization of particles which prevents charge-induced aggregation during formation. Suitable components that reduce aggregation include, but are not limited to, polyethylene glycol (PEG)-modified lipids (i.e., PEG conjugated lipids), monosialoganglioside Gm1, and polyamide oligomers ("PAO") such as (described in U.S. Pat. No. 6,320,017). Exemplary suitable PEG-modified lipids include, but are not limited to, PEG-modified diacylglycerols and dialkylglycerols, PEG-modified phosphatidylethanolamine and phosphatidic acid, PEG-ceramide conjugates (e.g., PEG-CerC14 or PEG-CerC20), PEG-modified dialkylamines, PEG-modified 1,2-diacyloxypropan-3-amines, and PEG conjugated DSPE (e.g., DSPE-PEG2000). Other compounds with uncharged, hydrophilic, steric-barrier moieties, which prevent aggregation during formation, like PEG, Gm1, or ATTA, can also be coupled to lipids to reduce aggregation during formation. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 0.1 to 15% (by mole percent of lipids). It should be noted that aggregation preventing compounds do not necessarily require lipid conjugation to function properly. Free PEG or free ATTA in solution can be sufficient to prevent aggregation. If the liposomes are stable after formulation, the PEG or ATTA can be dialyzed away before administration to a subject.

Neutral lipids, when present in the composition, can be any of a number of lipid species which exist either in an uncharged or neutral zwitterionic form at physiological pH. Such lipids include, but are not limited to, diacylphosphatidylcholine, diacylphosphatidylethanolamine, ceramide, sphingomyelin, dihydrosphingomyelin, cephalin, and cerebrosides. The selection of neutral lipids for use in liposomes described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or can be isolated or synthesized by well-known techniques. In one group of embodiments, lipids containing saturated or unsaturated fatty acids with carbon chain lengths in the range of $C_6$ to $C_{22}$ (e.g., $C_6$, $C_8$, $C_{10}$, $C_{12}$, $C_{14}$, $C_{16}$, $C_{18}$, $C_{22}$, or $C_{22}$) are preferred. Additionally, lipids having mixtures of saturated and unsaturated fatty acid chains can be used. In some embodiments, the neutral lipids can be phosphatidylcholine, DOPE, DSPC, POPC, DMPC, DPPC or any related phosphatidylcholine. The neutral lipids useful in the present invention can also be composed of sphingomyelin, dihydrosphingomyeline, or phospholipids with other head groups, such as serine and inositol.

When present in the supramolecular combinatorial therapeutic, the sterol component can be any of those sterols conventionally used in the field of liposome, lipid vesicle or lipid particle preparation. A preferred sterol is cholesterol.

When present in the supramolecular combinatorial therapeutic, the cationic lipids can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 1,2-Dioleyloxy-3-trimethylaminopropane chloride salt ("DOTAP.Cl"); 3β-(N—(N'—N'-dimethylaminoethane)-carbamoyl)cholesterol ("DC-Chol"), N-(1-(2,3-dioleyloxy) propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermyl-amide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/37194. Other suitable cationic lipids are described, for example in U.S. Patent Application Publication No. 2011/0997720 and PCT Patent Application Publication No. WO 2009/132131 and No. WO 2009/132131, content of all of which is incorporated herein by reference in its entirety.

When present in the supramolecular combinatorial therapeutic, the anionic lipid can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

As used herein, the term "amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids.

Also suitable for inclusion in the supramolecular combinatorial therapeutic described herein are programmable fusion lipids. Particles containing programmable fusion lipids have little tendency to fuse with cell membranes and deliver their payload until a given signal event occurs. This allows the supramolecular combinatorial therapeutic to distribute more evenly after administration into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the particle membrane over time. By the time the particle is suitably distributed in the body, it has lost sufficient cloaking agent so as to be fusogenic. With other signal events, it is desirable to choose a signal that is associated with the disease site or target cell, such as lower pH at a site of tumor.

One or more complementary surface active agent can be added to the supramolecular combinatorial therapeutics, for example as complements to the characteristics of an amphiphilic agent or to improve particle stabilizing capacity or enable an improved solubilization. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable non-ionic surfactants, include, but are not limited to various grades of PLURONIC®, POLOXAMER®, SPAN®, TWEEN®, POLYSORBATE®, TYLOXAPOL®, EMULPHOR® or CREMOPHOR® and the like. The complementary surface active agents can also be of an ionic nature, such as bile duct agents, cholic acid or deoxycholic their salts and derivatives or free fatty acids, such as oleic acid, linoleic acid and others. Other ionic surface active agents are found among cationic lipids like $C_6$-$C_{24}$ alkylamines or alkanolamine and cationic cholesterol esters.

In some embodiments, the supramolecular combinatorial therapeutic comprises a PEG conjugated lipid and a phospholipid.

In some embodiments, the supramolecular combinatorial therapeutic comprises a taxane-lipid conjugate and a PI3K inhibitor-lipid conjugate.

In some embodiments, the supramolecular combinatorial therapeutic comprises a taxane-lipid conjugate and a platinum-lipid conjugate.

In some embodiments, the supramolecular combinatorial therapeutic comprises a taxane-lipid conjugate and an antibody (or an antigen binding fragment thereof) lipid conjugate. I The antibody, or the antigen binding fragment thereof, can be a therapeutic agent or a targeting ligand.

In one aspect, the disclosure provides a conjugate comprising a taxane conjugated to with a lipid. The term "Taxane" is generally referred to diterpene-containing compounds produced by the plants of the genus *Taxus* (e.g., yews, such as, but not limited to, *Taxus baccata, Taxus brevifolia, Taxus canadensis, Taxus chinensis, Taxus cuspidata, Taxus floridana, Taxus globosa, Taxus sumatrana, Taxus walUchiana*), and synthetic and semisynthetic forms thereof. The term denotes a compound containing the core structure

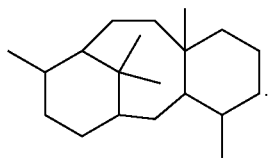 [SMILES: CC1CCCC2(C)CCC3C(C)CCC(CC12)C3(C)C]

The basic taxane core structure may further be substituted or may contain unsaturations in the ring to yield a number of compounds, generically known as taxanes. Generally, such compounds may block cell growth by stopping mitosis by interfering with microtubules. The term "diterpene," as used herein, means chemical compounds having a carbon skeleton derived from four isoprene units. The taxane group of compounds includes paclitaxel, docetaxel, and cabazitaxel.

Taxanes can be isolated from natural sources, and can also be prepared synthetically from naturally occurring precursors. Paclitaxel (TAXOL®, Bristol-Myers Squibb), for example, can be prepared from baccatin by attachment of protecting groups to the hydroxyl groups of baccatin that are to become the hydroxyl groups of paclitaxel, converting the precursor baccatin to paclitaxel, and then removing the protecting groups from the hydroxyl groups to obtain paclitaxel (see, e.g., WO93/10076. int. pub. date May 27, 1993; K. V. Rao, U.S. Pat. No. 5,200,534; R. A. Holton, U.S. Pat. No. 5,015,744; PCT US92/07990; V. J. Stella and A. E. Mathew, U.S. Pat. No. 4,960,790; K. C. Nicolau, Nature 3j54 (1993), pp. 464-466; Nicolau, K. C. et al. Nature 367 (1994) pp. 630-634; Holton, R. A., et al. J. Am. Chem. Soc. H6 (1994) pp. 1597-1600; WO93/16059, int. pub. date Aug. 19, 1993; EP 528.729, published Feb. 24, 1993; EP 522,958, published Jan. 13, 1993; WO91/13053, int. pub. date Sep. 5, 1991; EP 414,610, int. pub. date Feb. 27, 1991; the contents of these documents are incorporated herein by reference). Non-limiting examples of taxanes can include paclitaxel and docetaxel, derivatives thereof, and mixtures thereof.

Taxanes can be used effectively to treat a variety of cancers. Paclitaxel, for example, has been found to have activity against ovarian and breast cancers, as well as against malignant melanoma, colon cancer, leukemias and lung cancer (see, e.g., Bormana, Chemical & Engineering News, Sep. 2, 1991, pp. 11-18; The Pharmacological Basis of Therapeutics (Goodman Gilman et al., eds.), Pergamon Press, New York (1990), p. 1239; Suffness, Antitumor Alkaloids, in: "The Alkaloids, Vol. XXV," Academic Press, Inc. (1985), Chapter 1, pp. 6-18; Rizzo et al., J. Pharm. & Biomed. Anal. § (2):159-164 (1990); and Biotechnology 9:933-938 (October. 1991). Paclitaxel acts against cancer cells by binding to tubulin in the cells nuclei, thereby blocking the disassembly of microtubules and consequently, inhibiting cell division (Schiff et al., Nature 277:665 (1979)

The term taxane also include bactins and bactin derivatives. The term "baccatin" or "baccatin derivatives" refers to the taxane derivatives in which the side chain at the 13-position of the taxane skeleton is a hydroxy group. These are often referred to in the literature as a baccatin or "baccatin I-VII" or the like depending, on the nature of the substituents on the tricyclic rings of the taxane skeleton. As used herein the, term taxane also include abeo-taxanes. Abeo-taxanes have a 5-membered A ring. The taxanes can be derived from natural sources, can be prepared synthetically or can be obtained from semi-synthetic methods or a combination thereof. Exemplary taxanes include, but are not limited to paclitaxel (TAXOL™), docetaxel (taxotere), cabazitaxel, abretaxane, taxoprexin, xyotax, cephalomannine, 10-deacetylcephalomannine, baccatin, taxine, brevifoliol, 10-deacetylbaccatin, hongdoushan A, hongdoushan B, hongdoushan C, 7-epitaxol, 7-epibaccatin III, and 10-desacetyl-7-epitaxol.

In some embodiments, the taxane in the conjugate is cabazitaxel.

In some embodiments, the taxane and the lipid can be covalently conjugated via a linker. The term "linker" means an organic moiety that connects two parts of a compound. Linkers typically comprise a direct bond or an atom such as oxygen or sulfur, a unit such as NR[1], C(O), C(O)O, C(O)NR[1], SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherereoaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker can be a branched linker. The branch-point of the branched linker can be at least trivalent, but can be a tetravalent, pentavalent or hexavalent atom, or a group presenting such multiple valencies. In certain embodiments, the branch-point can be, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branch-point can be glycerol or a glycerol derivative.

In some embodiments, the linker comprises at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, the linker comprises an acid labile group. Generally, an acid cleavable linking group is cleavable in an acidic environment with a pH of about 6.5 or lower (e.g., about 6.5, 6.0, 5.5, 5.0, 4.5, 4.0, 3.5, 3.0, or lower), or by agents such as enzymes that can act as a general acid.

In some embodiments, the linker comprises one or more of succinic acid, fumaric acid, propargylic acid, ethylene glycol, diethylene glycol, and natural or unnatural amino acids.

In some embodiments, the linker comprises oxalic acid, malonic acid, succinic acid, glutaric acid, succinic acid, ethylene diamine, natural or unnatural amino acid, ethylene glycol, diethylene glycol, acetic acid, propionic acid, butyric acid, valeric acid, acrylic acid, but-2-enoic acid, pent-2-enoic acid, hex-2-enoic acid, 2-propynoic acid, but-2-ynoic acid, pent-2-ynoic acid, hex-2-ynoic acid, ethylene, propylene, 1-butene, 1-pentene, 1-hexene, acetylene, propyne, but-1-yne, pent-1-yne, or any combinations thereof.

In some embodiments, the linker comprises succinic acid and ethylene diamine; succinic acid and natural or unnatural amino acid; ethylene glycol and acetic acid; ethylene glycol and acrylic acid; diethylene glycol and acetic acid; hydrophobic amino acid and glycolic acid; hydrophobic amino acid and malonic acid; hydrophobic amino acid and succininc acid; hydrophobic amino acid and glutaric acid; and any combinations thereof.

In some embodiments, the linker is selected from the group consisting of —C(O)$CH_2CH_2$C(O)NH$CH_2CH_2$NHC(O)—; —C(O)$CH_2CH_2$C(O)NH$CH_2$NHC(O)—; —C(O)$CH_2$O$CH_2CH_2$—; —C(O)$CH_2CH_2$O$CH_2CH_2$—; —C(O)

CH$_2$OCH$_2$CH$_2$OCH$_2$CH$_2$—; —C(O)CH(R)NHC(O)CH$_2$—, wherein R is H, CH$_3$, CH(CH$_3$)$_2$, CH$_2$CH(CH$_3$)$_2$, C(CH$_3$)CH$_2$CH$_3$, or CH$_2$-Phenyl; —C(O)CH(R)NHC(O)CH$_2$CH$_2$—, wherein R is H, CH$_3$, CH(CH$_3$)$_2$, CH$_2$CH(CH$_3$)$_2$, C(CH$_3$)CH$_2$CH$_3$, or CH$_2$-Phenyl; —C(O)CH(R)NHC(O)(CH$_2$)$_n$C(O)—, wherein R is H, CH$_3$, CH(CH$_3$)$_2$, CH$_2$CH(CH$_3$)$_2$, C(CH$_3$)CH$_2$CH$_3$, or CH$_2$-Phenyl, and n is 1, 2, or 3; —C(O)CH(R)NHC(O)CH$_2$OCH$_2$CH$_2$—, wherein R is H, CH$_3$, CH(CH$_3$)$_2$, CH$_2$CH(CH$_3$)$_2$, C(CH$_3$)CH$_2$CH$_3$, or CH$_2$-Phenyl; —C(O)C≡C(CH$_2$)$_n$—C(O)—, wherein n is 1, 2 or 3; —C(O)C≡C(CH$_2$)$_n$—, wherein n is 0, 1, or 2; —C(O)CH=CH(CH$_2$)$_n$C(O)—, wherein n is 0, 1, 2, or 3; —C(O)CH=CH(CH$_2$)$_n$—, wherein n is 1, 2, or 3; and —C(O)CH$_2$CH$_2$C(O)NHCH$_2$C(O)—.

In some embodiments, the lipid in the taxane-lipid conjugate is cholesterol, alpha-tocopherol, or a fatty acid. In one embodiment, the lipid in the taxane-lipid conjugate is cholesterol.

The taxane and the lipid can be covalently conjugated with each other (or the linker) using a reactive functional group present in their respective structures. The term "reactive functional group" refers to a functional group that is capable of reacting with another functional group. Exemplary reactive functional groups include, but are not limited to, hydroxyls, amines, thiols, thials, sulfinos, carboxylic acids, amides, and the like. The reactive functional group on the lipid, the taxane, and the linker can be the same or different. In some embodiments, the reactive group on the lipid is a hydroxyl, an amine, a thiol, or a carboxylic acid. In some embodiments, the reactive group on the taxane is a hydroxyl, an amine, a thiol, or a carboxylic acid.

In some embodiments, the taxane-lipid conjugate can be selected from the group consisting of taxane conjugates 1-33, structures of which are shown in the Examples section.

In some embodiments, the methods described herein relate to treating a subject having or diagnosed as having cancer. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) can also aid in determining if a subject is likely to have cancer or in making a diagnosis of cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chromic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS1arcoma, and osteosarcoma; pancreatic cancer; skin cancer including melanoma, stromal cells, germ cells and mesenchymal cells; pROS1tate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors.

The compositions and methods described herein can be administered to a subject having or diagnosed as having cancer. In some embodiments, the methods described herein comprise administering an effective amount of compositions described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition described herein needed to alleviate at least one or more symptom of the disease or disorder, and relates to a sufficient amount of pharmacological composition to provide the desired effect. The term "therapeutically effective amount" therefore refers to an amount of a composition described herein that is sufficient to provide a particular anti-tumor effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition described herein, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size and/or growth, among others. The dosage can be determined by a physician and adjusted, as necessary, to suit observed effects of the treatment.

In some embodiments, the technology described herein relates to a pharmaceutical composition comprising a supramolecular combinatorial therapeutic and a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a composition as described herein.

In some embodiments, the pharmaceutical composition comprising a supramolecular combinatorial therapeutic can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, a composition as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the method of treatment disclosed herein comprises co-administering one or more additional anti-cancer therapies to the patient in addition to administering the conjugate or composition comprising the conjugate. Exemplary anti-cancer therapies include, but are not limited to, surgery, chemotherapy, radiation therapy, thermotherapy, immunotherapy, hormone therapy, laser therapy, anti-angiogenic therapy, and any combinations thereof.

In some embodiments, the method comprises co-administering the conjugate and an anti-cancer agent or chemotherapeutic agent to the subject. As used herein, the term "co-administering" refers to the administration of two or more therapeutic agents to a subject, wherein the two or more therapeutic agents may be administered in the same or different pharmaceutical compositions, using the same or different dosage forms (e.g., oral, parenteral, intravenous, intramuscular, subcutaneous, transdermal, airway (aerosol), pulmonary, cutaneous, topical, injection, or intratumoral administration), and wherein the two or more therapeutic agents may be administered at the same time or different times over the course of treatment (e.g., different times within the same hour, different times within the same day, different times within the same week, different times within the same month). As used herein, the term "anti-cancer agent" refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

In some embodiments, the anti-cancer agent is a platinate selected from the group consisting of cisplatin, oxaliplatin, carboplatin, paraplatin, sartraplatin, and any combinations thereof.

In some embodiments, the anti-cancer agent is an immunomodulator. The methods of these embodiments comprise co-administering the conjugate and the immunomodulator to the subject. In some embodiments, the conjugate and the immunomodulator are co-administered in separate pharmaceutical compositions and at different times. In some embodiments, the conjugate and the immunomodulator are co-administered at the same time in the same pharmaceutical composition. In some embodiments, the immunomodulator activates and stimulates an immune response against cancer cells. An immunomodulator may increase immune response by greater than 5%, 10%, 25%, 50%, 75%, 90%, 100% or more. An immunomodulator may reduce cancer cell numbers and/or growth by greater than 5%, 10%, 25%, 50%, 75%, 90%, 100% or more. Exemplary immunomodulators include, but are not limited to, immune cells (e.g., natural killer cells, lymphokine-activated killer cells, cytotoxic T cells and dendritic cells), antibodies (e.g., anti-PD-L1 and anti-PD-1 antibodies, anti-CD52, anti-VEGF-A, anti-CD30, anti-EGFR, anti-CD33, anti-CD20, anti-CTLA4, and anti-HER-2 antibodies), and cytokines (e.g., interferons and interleukins). In some embodiments, the immunomodulator is an anti-PD-L1, an anti-PD-1 antibody, or a mixture thereof. In certain exemplary embodiments, the immunomodulator is conjugated with a lipid.

In addition, the methods of treatment can further include the use of radiation or radiation therapy. Further, the methods of treatment can further include the use of surgical treatments.

In certain embodiments, an effective dose of a composition as described herein can be administered to a patient once. In certain embodiments, an effective dose of a composition as described herein can be administered to a patient repeatedly. For systemic administration, subjects can be administered a therapeutic amount of a composition as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size and/or growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity a composition as described herein. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition as described herein can be administered over a period of time, such as over a 5 minute, 10 minute, 15 minute, 20 minute, or 25 minute period.

The dosage ranges for the administration of a composition as described herein, according to the methods described herein depend upon, for example, the form of a composition as described herein, its potency, and the extent to which symptoms, markers, or indicators of a condition described herein are desired to be reduced, for example the percentage reduction desired for tumor growth. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition as described herein in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size and/or growth). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. a decreased in tumor size and/or growth.

In vitro and animal model assays are provided herein which allow the assessment of a given dose of a composition as described herein. By way of non-limiting example, the effects of a dose of a composition can be assessed by an in vitro cell viability assay. A non-limiting example of a protocol for such an assay is as follows: cells, e.g. cancer cell lines, are contacted with compositions described herein and viability determined at one or more timepoints using a cell viability reagent, e.g. CellTiter 96 Aqueous One Solution reagents (PROMEGA, Wis.).

The efficacy of a given dosage can also be assessed in an animal model, e.g. the murine model of ovarian cancer described in the Examples herein. Briefly, ovarian adenocarcinomas can be induced in K-Ras $^{LSL/+}$/Pten$^{fl/fl}$ mice via intrabursal delivery of adenovirus-carrying Cre recombinase. Once mice develop medium to large tumors, they can be administered a composition as described herein, e.g. via tail vein injection. Tumor imaging can be performed and/or mice can be sacrificed.

Cellular uptake of molecules into cells is often through endocytosis, which is mediated either by clathrin-coated pits or caveolae. Caveolae are specialized invaginations of the plasma membrane, consisting primarily of proteins called caveolins, with key roles in numerous biochemical and cellular processes. Caveolin-1 (CAV1) is an important constituent of caveolae, involved in endocytotic trafficking. Caveolae have also been associated with uptake of drugs into cells. Association of self-assembled supramolecular particles with caveolae may assist in their uptake into cells, facilitating therapeutic intervention in cancer cells. The current invention provides methods for predicting the likelihood of a cancer patient exhibiting a better response to self-assembled supramolecular particles than platinates or taxanes. The methods involve determining the expression levels of a gene product that correlates with responsiveness to treatment with self-assembled supramolecular particles, predictive of higher internalization of the payload drug and better therapeutic efficacy for self-assembled supramolecular particles.

Accordingly, the disclosure also provides a method of predicting the likelihood of a cancer patient exhibiting a better response to self-assembled supramolecular particles than platinates or taxanes. Generally the method comprises: (a) assaying the expression level of EEA1, SRSF5, SMAD2, SNX3, PLCD1, OSBP, DNM1, DNM2, DNM3, SGK3, FAPP1, SMAD7, SMURF2, NEDD4, PRKCA, CDH-1, LDLR, CP, CD36, LYN, FLOT-1, FLOT-2, CA4, APOE, CAV1, CAV2, CAV3, LMAN2, LAT and STOM in tumor samples obtained from patients; and (b) predicting a likelihood that the patient will exhibit a positive response, wherein: increased expression level of the one or more genes selected from CAV1, CAV2, CAV3, LDLR, SMAD7, SMURF2, NEDD4, PRKCA is positively correlated with a likelihood of a positive response to treatment comprising self-assembled supramolecular particles. The increased expression level of one or more genes can be relative to a reference or control. For example, expression level in a non-cancer cell.

The terms "assay" or "assaying" as used herein refer to performing a quantitative or qualitative analysis of a component in a sample. The terms include laboratory or clinical observations, and/or measuring the level of the component in the sample.

The term "expression level" as used herein refers to qualitative or quantitative determination of an expression product or gene product. Expression level can be determined for the RNA expression level of a gene or for the polypeptide expression level of a gene. The term "normalized" expression level as used herein refers to an expression level of a response indicator gene relative to the level of an expression product of a reference gene(s), which might be all measured expression products in the sample, a single reference expression product, or a particular set of expression products. A gene exhibits an "increased expression level" when the expression level of an expression product is higher in a first sample, such as in a tumor cell, than in a second sample, such as a normal cell or non-tumor cell. Similarly, a gene exhibits an "increased normalized expression level" when the normalized expression level of an expression product is higher in a first sample than in a second sample.

The term "reference gene" as used herein refers to a gene whose expression level can be used to compare the expression level of a gene product in a test sample. In an embodiment of the invention, reference genes include housekeeping genes, such as beta-globin, alcohol dehydrogenase, or any other gene, the expression of which does not vary depending on the disease status of the cell containing the gene. In another embodiment, all of the assayed genes or a large subset thereof may serve as reference genes.

The term "expression product" or "gene product" are used herein to refer to the RNA transcription products (transcripts) of a gene, including mRNA, and the polypeptide translation products of such RNA transcripts. An expression product can be, for example, an unspliced RNA, an mRNA, a splice variant mRNA, a microRNA, a fragmented RNA, a polypeptide, a post-translationally modified polypeptide, a splice variant polypeptide, etc.

The term "measuring" as used herein refers to performing a physical act of determining the dimension, quantity, or capacity of a component in a sample.

The term "microarray" as used herein refers to an ordered arrangement of hybridizable array elements, e.g., oligonucleotide or polynucleotide probes, on a substrate.

The term "polynucleotide" generally refers to any polyribonucleotide or polydeoxribonucleotide, which can be unmodified RNA or DNA or modified RNA or DNA. Thus, for instance, polynucleotides as used herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" also includes DNAs (including cDNAs) and RNAs and those that contain one or more modified bases. Thus, DNAs or RNAs with backbones modified for stability or for other reasons, are "polynucleotides" as that term is used herein. Moreover, DNAs or RNAs comprising unusual bases, such as inosine, or modified bases, such as tritiated bases, are included within the term "polynucleotides" as used herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA/DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "primer" or "oligonucleotide primer" as used herein, refers to an oligonucleotide that acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with their use in synthesis of primer extension products, and can be in the range of between about 8 nucleotides and about 100 nucleotides (nt) in length, such as about 10 nt to about 75 nt, about 15 nt to about 60 nt, about 15 nt to about 40 nt, about 18 nt to about 30 nt, about 20 nt to about 40 nt, about 21 nt to about 50 nt, about 22 nt to about 45 nt, about 25 nt to about 40 nt, and so on, e.g., in the range of between about 18 nt and about 40 nt, between about 20 nt and about 35 nt, between about 21 and about 30 nt in length, inclusive, and any length between the stated ranges. Primers can be in the range of between about 10-50 nucleotides long, such as about 15-45, about 18-40, about 20-30, about 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

Primers are in many embodiments single-stranded for maximum efficiency in amplification, but can alternatively be double-stranded. If double-stranded, the primer is in many embodiments first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the covalent addition of bases at its 3' end.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeably herein, refers to a structure comprised of a polynucleotide, as defined above, that contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with their use in specific detection of all or a portion of a target sequence of a target nucleic acid, and are in many embodiments in the range of between about 8 nt and about 100 nt in length, such as about 8 to about 75 nt, about 10 to about 74 nt, about 12 to about 72 nt, about 15 to about 60 nt, about 15 to about 40 nt, about 18 to about 30 nt, about 20 to about 40 nt, about 21 to about 50 nt, about 22 to about 45 nt, about 25 to about 40 nt in length, and so on, e.g., in the range of between about 18-40 nt, about 20-35 nt, or about 21-30 nt in length, and any length between the stated ranges. In some embodiments, a probe is in the range of between about 10-50 nucleotides long, such as about 15-45, about 18-40, about 20-30, about 21-28, about 22-25 and so on, and any length between the stated ranges. In some embodiments, the probes are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

In some embodiments, one can assay a gene product for measuring the expression level of the gene. In some embodiments, the expression level of one or more genes is a level of RNA transcript of the corresponding gene(s). The term "RNA transcript" as used herein refers to the RNA transcription product of a gene, including, for example, mRNA, an unspliced RNA, a splice variant mRNA, a microRNA, and a fragmented RNA.

The sample for assaying the gene expression level can be any desired biological sample from a subject. The term "biological sample" as used herein denotes a sample taken or isolated from a biological organism, e.g., cell lysate, a homogenate of a tissue sample from a subject. The term "biological sample" also includes untreated or pre-treated (or pre-processed) biological samples. In some embodiments, the biological sample can be a tissue sample, a biological fluid, including, but not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In other embodiments, the biological sample can include cell lysate and fractions thereof. For example, cells can be harvested and lysed to obtain a cell lysate. In some embodiments, the sample is from a resection, biopsy, or core needle biopsy. In addition, fine needle aspirate samples can be used. Samples can be either paraffin-embedded or frozen tissue. In some embodiments, the sample is a fixed, wax-embedded tissue sample.

In some embodiments, the sample can be a tumor sample. For example, the tumor sample can be a biopsy sample or cells from ascitic fluid or cells from pleural effusion.

The term "tumor" as used herein, refers to all neoplastic cell growth and proliferation, whether malignant or benign, and all pre-cancerous and cancerous cells and tissues. The term "tumor cell" as used herein refers to a cancerous cell obtained from a cancer cell line or a cancer patient. The term encompasses a tumor cell obtained from tumor tissue samples, for example, tissue obtained by surgical resection and tissue obtained by biopsy, such as for example, a core biopsy or a fine needle biopsy. The term "tumor cell" also encompasses tumor cells obtained from sites other than the primary tumor, e.g., circulating tumor cells. The term further encompasses cells that are the progeny of the patient's tumor cells, e.g. cell culture samples derived from primary tumor cells or circulating tumor cells. The term further encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

The biological sample can be a clinical sample. A "clinical sample" is a sample derived from a human subject. A biological sample can also be referred to as a "subject sample." A test biological sample is the biological sample that has been the object of analysis, monitoring, or observation. A control biological sample can be either a positive or a negative control for the test biological sample. Often, the control biological sample contains the same types of tissues, cells and biological fluids as that of the test biological sample. The sample can be obtained by removing a sample of cells from a subject, but can also be accomplished by using previously isolated cells. In addition, the biological sample can be freshly collected or a previously collected sample.

In some embodiments, the test sample or the biological sample can be a frozen biological sample, e.g., a frozen tissue or cells. The frozen sample can be thawed before employing methods, assays and systems of the invention. After thawing, a frozen sample can be centrifuged before being subjected to the assays disclosed herein.

In some embodiments, a biological sample can be a nucleic acid product amplified after polymerase chain reaction (PCR). The nucleic acid product, such as DNA, RNA and mRNA, can be isolated from a particular biological sample using any of a number of procedures, which are well-known in the art, the particular isolation procedure chosen being appropriate for the particular biological sample. Methods of isolating and analyzing nucleic acid variants as described above are well known to one skilled in the art and can be found, for example in the Molecular Cloning: A Laboratory Manual, 3rd Ed., Sambrook and Russel, Cold Spring Harbor Laboratory Press, 2001.

In some embodiments, the test sample or the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample.

In some embodiments, tumor cells or a tumor sample is assayed or measured for an expression level of an indicator gene product(s). The tumor sample can be obtained from a solid tumor, e.g., via biopsy, or from a surgical procedure carried out to remove a tumor; or from a tissue or bodily fluid that contains cancer cells. In an embodiment of the invention, the tumor cell or tumor sample is obtained from a tumor of epithelial origin. In another embodiment of the invention, the tumor cell is a breast, colon, non-small cell lung, renal, ovarian, prostate, or melanoma tumor cell. In another embodiment, the tumor sample is obtained from a patient with breast cancer, colon cancer, non-small cell lung cancer, renal cancer, ovarian cancer, prostate cancer, or melanoma.

Methods of gene expression profiling include methods based on hybridization analysis of polynucleotides, methods based on sequencing of polynucleotides, and proteomics-based methods. Exemplary methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and PCR-based methods, such as reverse transcription PCT (RT-PCR) (Weis et al., *Trends in Genetics* 8:263-264 (1992)). Antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

In some embodiments, the level of RNA transcript of one or more genes is assayed using a quantitative reverse transcription polymerase chain reaction (RT-PCR or qPCR). One of the most sensitive and most flexible quantitative PCR-based gene expression profiling methods is RT-PCR, which can be used to compare mRNA levels in different sample populations, in normal and tumor tissues, to characterize patterns of gene expression, to discriminate between closely related mRNAs, and to analyze RNA structure.

The first step is the isolation of mRNA from a target sample. The starting material is typically total RNA isolated from tumors or tumor cell lines, and corresponding normal tissues or cell lines, respectively. Thus RNA can be isolated from a variety of primary tumors, including breast, lung, colorectal, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et ah, Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al, BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$). To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al, Genome Research 6:986-994 (1996). b. Mass ARRAY System In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization tinie-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sd. USA 100:3059-3064 (2003). c. Other PCR-based Methods Further PCR-based techniques include, for example, differential display (Liang and Pardee, Science 257:967-971 (1992)); amplified fragment length polymorphism (iAFLP) (Kawamoto et al., Genome Res. 12:1305-1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex[100] LabMAP system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl Acids. Res. 31(16) e94 (2003)).

Differential gene expression can also be identified, or confirmed using the microarray technique. Thus, the expression profile of breast cancer-associated genes can be measured in either fresh or paraffin-embedded tumor tissue, using microarray technology, hi this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of niRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al, Proc. Natl. Acad. ScL USA 93(2): 106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types. 4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al, Science 270:484-487 (1995); and Velculescu et al, Cell 88:243-51 (1997).

Gene Expression Analysis by Massively Parallel Signature Sequencing (MPSS) is described in Brenner et al, Nature Biotechnology 18:630-634 (2000). This method is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3\times10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Immunohistochemistry methods are also suitable for detecting the expression levels of genes. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

In order to minimize expression measurement variations due to non-biological variations in samples, e.g., the amount and quality of expression product to be measured, raw expression level data measured for a gene product (e.g., cycle threshold (Ct) measurements obtained by qRT-PCR) can be normalized relative to the mean expression level data obtained for one or more reference genes. Examples of reference genes include housekeeping genes, such as GAPDH. Alternatively, all of the assayed genes or a large subset thereof may also concurrently serve as reference genes and normalization can be based on the mean or median signal (Ct) of all of the assayed genes or a subset thereof (often referred to as "global normalization" approach). On a gene-by-gene basis, measured normalized amount of a patient tumor mRNA can be compared to the amount found in a cancer tissue reference set. See e.g., Cronin, M. et al., *Am. Soc. Investigative Pathology* 164:35-42 (2004). The normalization can be carried out such that a one unit increase in normalized expression level of a gene product generally reflects a 2-fold increase in quantity of expression product present in the sample. For further information on normalization techniques applicable to qRT-PCR data from tumor tissue, see e.g., Silva, S. et al. (2006) *BMC Cancer* 6, 200; deKok, J. et al. (2005) *Laboratory Investigation* 85, 154-159.

The materials for use in the methods of disclosed herein are suited for preparation of kits produced in accordance with well known procedures. The disclosure thus provides kits comprising agents, which can include gene-specific or gene-selective probes and/or primers, for quantitating the expression of the disclosed genes. Such kits can optionally contain reagents for the extraction of RNA from tumor samples, in particular, fixed paraffin-embedded tissue samples and/or reagents for RNA amplification. In addition, the kits can optionally comprise the reagent(s) with an identifying description or label or instructions relating to their use in the methods of the present invention. The kits can comprise containers (including microliter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase). Mathematical algorithms used to estimate or quantify prognostic or predictive information are also properly potential components of kits.

The methods and systems described herein can be implemented in numerous ways. In one embodiment, the methods involve use of a communications infrastructure, for example, the internet. Several embodiments of the invention are discussed below. The present invention may also be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

In an embodiment of the invention, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a result and/or generate a report in the reviewer's computing environment. The score can be a numerical score (representative of a numerical value) or a non-numerical score representative of a numerical value or range of numerical values (e.g., "A": representative of a 90-95% likelihood of sensitivity to a PI3K inhibitor; "High": representative of a greater than 50% chance of sensitivity to (or some other selected threshold of likelihood); "Low": representative of a less than 50% chance of sensitivity to (or some other selected threshold of likelihood), and the like.

As a computer system, the system generally includes a processor unit. The processor unit operates to receive information, which can include test data (e.g., level of a predictive gene product(s); level of a reference gene product(s); normalized level of a predictive gene product(s); and may also include other data such as patient data. This information received can be stored at least temporarily in a database, and data analyzed to generate a report as described above.

Part or all of the input and output data can also be sent electronically. Certain output data (e.g., reports) can be sent electronically or telephonically (e.g., by facsimile, using devices such as fax back). Exemplary output receiving devices can include a display element, a printer, a facsimile device and the like. Electronic forms of transmission and/or display can include email, interactive television, and the like. In an embodiment of the invention, all or a portion of the input data and/or output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record that may exist in a confidential database as the healthcare facility.

The disclosure also provides a computer-readable storage medium (e.g., CD-ROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium includes a program that provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out a response likelihood assessment (e.g., primers, probes, arrays, or such other kit components).

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, PI3K, e.g. its ability to decrease the level and/or activity of PI3K can be determined, e.g. by measuring the level of a PI3K polypeptide (and/or mRNA encoding such a polypeptide) and/or the activity of PI3K. Methods for measuring the level of a given mRNA and/or polypeptide are known to one of skill in the art, e.g. RTPCR with primers can be used to determine the level of RNA and Western blotting with an antibody can be used to determine the level of a polypeptide. The activity of, e.g. PI3K can be determined using methods known in the art and described above herein.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the term "amphiphilic" refers to a molecule that has both a hydrophobic portion and a lipophobic portion, i.e. at least one a polar, water-soluble group and at least one a nonpolar, water-insoluble group. Typically, in a two phase system having a polar, aqueous phase and a non-polar, non-aqueous phase, an amphiphilic molecule will partition to the interface of the two phases. In simpler non limiting terms, an amphiphile is a molecule that is soluble in both an aqueous environment and a non-aqueous environment. The term "amphiphile" refers to an amphiphilic molecule.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketokonazole, vorozole, fadrozole, anastrozole and letrozole.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride.

The term "anti-androgen", as used herein, relates to any substance which is capable of inhibiting the biological effects of androgenic hormones and includes, but is not limited to, bicalutamide.

The term "gonadorelin agonist", as used herein, includes, but is not limited to, abarelix, goserelin and goserelin acetate. Goserelin is disclosed in U.S. Pat. No. 4,100,274 and is marketed as ZOLADEX. Abarelix can be formulated, e.g., as disclosed in U.S. Pat. No. 5,843,901. The term "topoisomerase I inhibitor", as used herein, includes, but is not limited to, topotecan, irinotecan, gimatecan, camptothecin and its analogues, 9-nitrocamptotecin and the macromolecular camptothecin conjugate PNU-166148 (compound A1 in WO 99/17804).

The term "topoisomerase II inhibitor", as used herein, includes, but is not limited to, the anthracyclines, such as doxorubicin, daunorubicin, epirubicin, idarubicin and nemorubicin; the anthraquinones mitoxantrone and losoxantrone; and the podophillotoxines etoposide and teniposide.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; colchicines; and epothilones and derivatives thereof, e.g., epothilone B or D or a derivative thereof. Also included are Epotholine derivatives which are disclosed in U.S. Pat. No. 6,194,181, WO 98/10121, WO 98/25929, WO 98/08849, WO 99/43653, WO 98/22461 and WO 00/31247. Especially preferred are Epotholine A and/or B.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin, BCNU, Gliadel), temozolomide, nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death.

The terms "anti-neoplastic" and "anti-metabolite" agents refers to the group of compounds that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, 5-fluorouracil (5-FU); asparaginase; capecitabine; cladribine (2-CDA); cytarabine; DNA de-methylating agents, such as 5-azacytidine and decitabine; edatrexate; floxuridine (5-FUdR); fludarabine phosphate; folic acid antagonists such as pemetrexed; gemcitabine; hydroxyurea; leucovorin; mercaptopurine (6-MP); methotrexate; pentostatin; and thioguanine (6-TG).

The term "compound targeting/decreasing a protein or lipid kinase activity", as used herein, includes, but is not limited to: protein tyrosine kinase and/or serine and/or threonine kinase inhibitors or lipid kinase inhibitors, e.g., i) compounds targeting, decreasing or inhibiting the activity of the platelet-derived growth factor-receptors (PDGFR), especially compounds which inhibit the PDGF receptor, e.g., a /V-phenyl-2-pyrimidine-amine derivative, e.g., imatinib, SU101, SU6668 and GFB-111; ii) compounds targeting, decreasing or inhibiting the activity of the fibroblast growth factor-receptors (FGFR); iii) compounds targeting, decreasing or inhibiting the activity of the insulin-like growth factor I receptor (IGF-IR), especially compounds which inhibit the IGF-IR, such as those compounds disclosed in WO 02/092599, in particular trans-5-(3-benzyloxy-phenyl)-7-(3-pyrrolidin-1-ylmethyl-cyclobutyl)-7H-pyrrolo[2,3-d]pyrimidin-4-ylamine and cis-7-(3-azetidin-1-ylmethyl-cyclobutyl)-5-(3-benzyloxy-phenyl)-7H-pyrrolo[2,3-d]pyrimidin-4-ylamine or pharmaceutically acceptable salts of these compounds; iv) compounds targeting, decreasing or inhibiting the activity of the Trk receptor tyrosine kinase family; v) compounds targeting, decreasing or inhibiting the activity of the Axl receptor tyrosine kinase family; vi) compounds targeting, decreasing or inhibiting the activity of the RET receptor tyrosine kinase; vii) compounds targeting, decreasing or inhibiting the activity of the c-kit receptor tyrosine kinases, especially compounds which inhibit the c-Kit receptor, e.g., imatinib; viii) compounds targeting, decreasing or inhibiting the activity of members of the c-Abl family and their gene-fusion products, e.g., Bcr-Abl kinase, such as especially compounds which inhibit the activity of c-Abl family members and their gene fusion products, e.g., a /V-phenyl-2-pyrimidine-amine derivative, e.g., imatinib, PD180970, AG957, NSC 680410 or PD173955 from Parke-Davis; ix) compounds targeting, decreasing or inhibiting the activity of members of the protein kinase C (PKC) and Raf family of serine/threonine kinases, members of the MEK, SRC, JAK, FAK, PDK and Ras/MAPK family members, or PI3 kinase (PI3K) family, or of the PI3-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; llmofosine; RO 318220 and RO 320432; GO 6976; Isis 3521; LY333531/LY379196; isochinoline compounds, such as those disclosed in WO 00/09495; FTIs; PD184352 or QAN697 (a PI3K inhibitor); x) compounds targeting, decreasing or inhibiting the activity of protein tyrosine kinase inhibitors include imatinib mesylate (GLEEVEC/GLIVEC) or a tyrphostin. A tyrphostin is preferably a low molecular weight ($M_r$<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556 and AG957 and adaphostin (4-{[(2,5-dihydroxyphenyl)methyl]amino}-benzoic acid adamantyl ester, NSC 680410); and xi) compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF-related ligands, and are in particular those compounds, proteins or antibodies generically and specifically disclosed in WO 97/02266, e.g., the compound of Example 39, or in EP 0 564409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347, e.g., compound known as CP 358774, WO 96/33980, e.g., compound ZD 1839; and WO 95/03283, e.g., compound ZM105180, e.g., trastuzumab (Herceptin®), cetuximab, gefitinib (Iressa), erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID) and TNP-470.

The term "cyclooxygenase inhibitor" as used herein includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib (BEXTRA) or a 5-alkyl-2-arylaminophenylacetic acid, e.g., 5-methyl-2-(2'-chloro-6'-fluoroanilino) phenyl acetic acid (lumiracoxib, PREXIGE).

The term "bisphosphonate", as used herein, includes, but is not limited to, etridonic, clodronic, tiludronic, pamidronic, alendronic, ibandronic, risedronic and zoledronic acid.

The term "heparanase inhibitor", as used herein, refers to compounds which target, decrease or inhibit heparin sulphate degradation. The term includes, but is not limited to, PI-88.

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and non-peptidomimetic inhibitors; tetracycline derivatives, e.g., hydroxamate peptidomimetic inhibitor batimastat; and its orally-bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of Flt-3; interferons; cytosine arabinoside (Ara-C); bisulfan; and ALK inhibitors, i.e. compounds which target, decrease or especially inhibit anaplastic lymphoma kinase (ALK).

The term "FMS-like tyrosine kinase inhibitors", as used herein, includes, but is not limited to, compounds which target, decrease or inhibit the activity of FMS-like tyrosine kinase receptors such as especially compounds, proteins or antibodies which inhibit Flt-3, e.g., PKC412, midostaurin, a staurosporine derivative, SU 11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino,17-demethoxygeldanamycin (17-AAG), a geldanamycin derivative; other geldanamycin-related compounds; radicicol and HDAC inhibitors.

The term "histone deacetylase inhibitors" or "HDAC inhibitors" relates to compounds which target, decrease or especially inhibit the activity of histone deacetylase (HDAC), such as sodium butyrate and suberoylanilide hydroxamic acid (SAHA). Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-7H-indol-3-yl)-ethyl]-amino]methyl]phenyl]-2E-2-propenamide, or a pharmaceutically acceptable salt thereof and /V-hydroxy-3-[4-[(2-hydroxyethyl){2-(7H-indol-3-yl) ethyl]-amino]methyl]phenyl]-2E-2-propenamide, or a pharmaceutically acceptable salt thereof, especially the lactate salt.

The term "mTOR inhibitors" relates to compounds which target, decrease or inhibit the activity/function of the serine/threonine mTOR kinase family and are especially compounds, proteins or antibodies which inhibit members of the mTOR kinase family, e.g., CCI-779, ABT578, SAR543, rapamycin and derivatives/analogs thereof, AP23573 and AP23841 from Ariad, everolimus (CERTICAN, RAD001) and sirolimus (RAPAMUNE).

"Somatostatin receptor antagonists", as used herein, refers to agents which target, treat or inhibit the somatostatin receptor, such as octreotide and SOM230. The term "integrin antagonists", as used herein, includes, but is not limited to, e.g. αvβ3 antagonists and αvβ5 antagonists.

"Tumor cell damaging approaches" refers to approaches, such as ionizing radiation. The term "ionizing radiation", referred to above and hereinafter, means ionizing radiation that occurs as either electromagnetic rays, such as X-rays and gamma rays; or particles, such as alpha and beta particles. Ionizing radiation is provided in, but not limited to, radiation therapy and is known in the art. See Hellman, Cancer, 4$^{th}$ Edition, Vol. 1, Devita et al., Eds., pp. 248-275 (1993).

The term "anti-leukemic compounds" includes, e.g., Ara-C, a pyrimidine analog, which is the 2'-α-hydroxy ribose (arabinoside) derivative of deoxycytidine. Also included is the purine analog of hypoxanthine, 6-mercaptopurine (6-MP) and fludarabine phosphate.

The term "EDG binders" as used herein refers to a class of immunosuppressants that modulates lymphocyte recirculation, such as FTY720.

The term "ribonucleotide reductase inhibitors" refers to pyrimidine or purine nucleoside analogs including, but not limited to, fludarabine and/or Ara-C; 6-thioguanine; 5-FU; cladribine; 6-mercaptopurine, especially in combination with Ara-C against ALL; and/or pentostatin. Ribonucleotide reductase inhibitors are especially hydroxyurea or 2-hydroxy-7H-isoindole-1,3-dione derivatives, such as PL-1, PL-2, PL-3, PL-4, PL-5, PL-6, PL-7 or PL-8. See Nandy et al., Ada Oncologica, Vol. 33, No. 8, pp. 953-961 (1994).

The term "S-adenosylmethionine decarboxylase inhibitors", as used herein, includes, but is not limited to, the compounds disclosed in U.S. Pat. No. 5,461,076.

ACE inhibitors include benazepril (CIBACEN), enazepril (LOTENSIN), captopril, enalapril, fosinopril, lisinopril, moexipril, quinapril, ramipril, perindopril and trandolapril.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

Some exemplary embodiments of the various aspects disclosed herein can be described by one of more of the numbered paragraphs:

1. A supramolecular combinatorial therapeutic (SCT) comprising a taxane-lipid conjugate.
2. The supramolecular combinatorial therapeutic of paragraph 1, wherein the supramolecular combinatorial therapeutic is a liposome, emulsion, micelle, or particle.
3. The supramolecular combinatorial therapeutic of paragraph 1 or 2, wherein the supramolecular combinatorial therapeutic comprises from about 1% to about 99% (w/w) of the taxane conjugate.
4. The supramolecular combinatorial therapeutic of any of paragraphs 1-3, wherein the taxane conjugate is a cabazitaxel-lipid conjugate, a paclitaxel-lipid conjugate or a docetaxel-lipid conjugate.
5. The supramolecular combinatorial therapeutic of any of paragraphs 1-4, wherein the taxane conjugate is selected from the group consisting of conjugates 1-33.
6. The supramolecular combinatorial therapeutic of any of paragraphs 1-5, wherein the supramolecular combinatorial therapeutic further comprises a lipid conjugated PI3K inhibitor.
7. The supramolecular combinatorial therapeutic of paragraph 6, wherein the supramolecular combinatorial therapeutic comprises from about 1% to about 99% (w/w) of the PI3K inhibitor conjugate.
8. The supramolecular combinatorial therapeutic of paragraph 6 or 7, wherein the supramolecular combinatorial therapeutic comprises the taxane conjugate and the PI3K inhibitor conjugate in about 10:1 to about 1:10 ratio.
9. The supramolecular combinatorial therapeutic of any of paragraphs 1-8, wherein the supramolecular combinatorial therapeutic further comprises a lipid conjugated platinum compound.
10. The supramolecular combinatorial therapeutic of paragraph 9, wherein the supramolecular combinatorial therapeutic comprises from about 1% to about 99% (w/w) of the platinum conjugate.
11. The supramolecular combinatorial therapeutic of paragraph 9 or 10, wherein the supramolecular combinatorial therapeutic comprises the taxane conjugate and the platinum conjugate in about 10:1 to about 1:10 ratio.
12. The supramolecular combinatorial therapeutic of any of paragraphs 1-11, wherein the supramolecular combinatorial therapeutic further comprises a lipid conjugated antibody.

13. The supramolecular combinatorial therapeutic of paragraph 12, wherein the antibody is a therapeutic agent or a targeting ligand.
14. The supramolecular combinatorial therapeutic of paragraphs 12 or 13, wherein the antibody is an immunomodulator comprising an anti-PD-1 antibody, an anti-PD-L1 antibody and combinations thereof.
15. The supramolecular combinatorial therapeutic of any of paragraphs 12-14, wherein the supramolecular combinatorial therapeutic comprises from about 1% to about 99% (w/w) of the antibody conjugate.
16. The supramolecular combinatorial therapeutic of any of paragraphs 12-15, wherein the supramolecular combinatorial therapeutic comprises the taxane conjugate and the antibody conjugate in about 10:1 to about 1:10 ratio.
17. The supramolecular combinatorial therapeutic of any of paragraphs 1-16, wherein the lipid is selected from the group consisting of cholesterol; 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glyceryl Tricaprylate/ Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; and γ-Linolenic acid.
18. The supramolecular combinatorial therapeutic of any of paragraphs 1-17, wherein the lipid is cholesterol, alpha-tocopherol, or a fatty acid.
19. The supramolecular combinatorial therapeutic of any of paragraphs 1-18, wherein the PI3K inhibitor conjugate is

FORMULA I

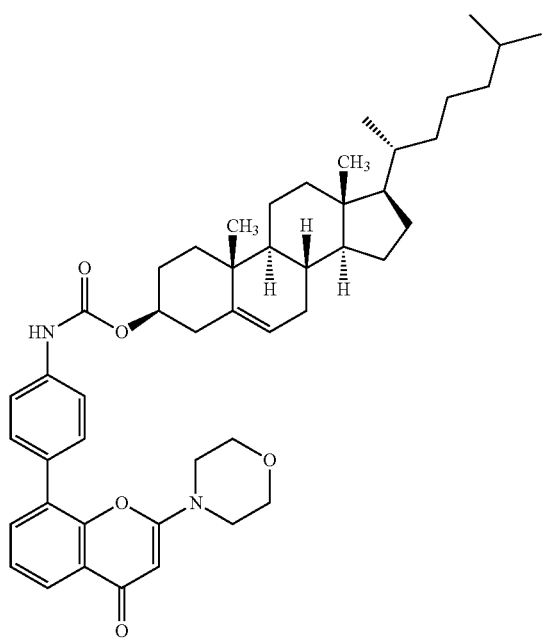

or

FORMULA II
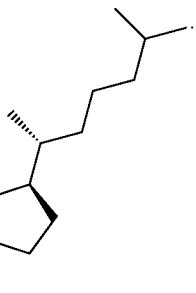
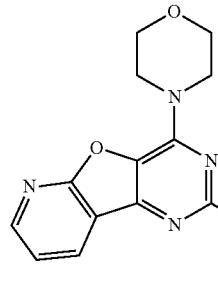
20. The supramolecular combinatorial therapeutic of any of paragraphs 1-19, wherein the platinum conjugate is
Formula IV
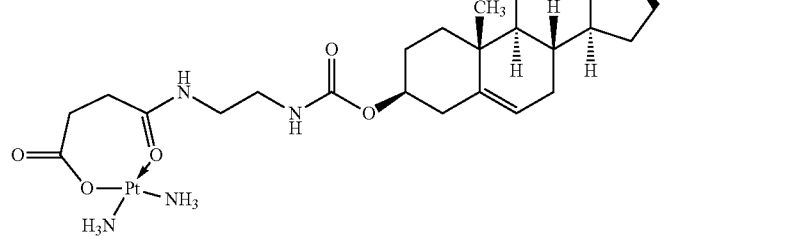
or
IO-125
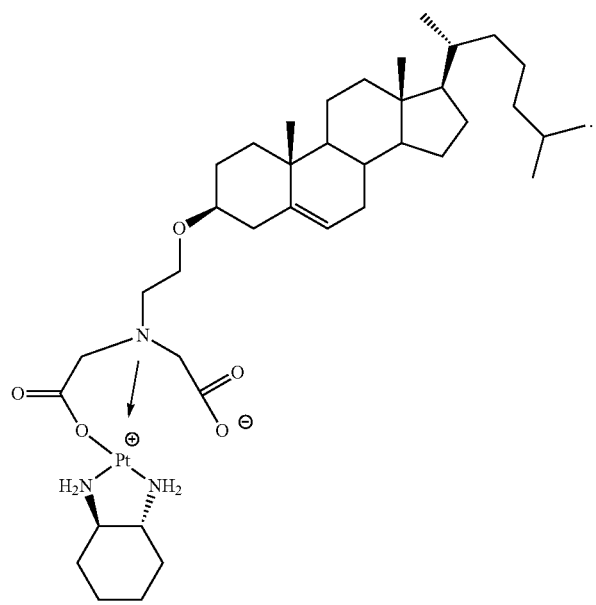
21. The supramolecular combinatorial therapeutic of any of paragraphs 1-20, wherein the supramolecular combinatorial therapeutic further comprises a first lipid in addition to the taxane conjugate.

22. The supramolecular combinatorial therapeutic of paragraph 21, wherein the first lipid is a phospholipid.
23. The supramolecular combinatorial therapeutic of paragraph 21 or 22, wherein the composition further comprises a second lipid.
24. The supramolecular combinatorial therapeutic of paragraph 23, wherein the second lipid is a phospholipid.
25. The supramolecular combinatorial therapeutic of any of paragraphs 22-24, wherein the phospholipid is selected from the group consisting of phosphatidyl cholines, phosphatidyl cholines with acyl groups having 6 to 22 carbon atoms, phosphatidyl ethanolamines, phosphatidyl inositols, phosphatidic acids, phosphatidyl serines, sphingomyelin, phosphatidyl glycerols, and any combinations thereof.
26. The supramolecular combinatorial therapeutic of paragraph 25, wherein the phospholipid is selected from the group consisting of phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyloleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof.
27. The supramolecular combinatorial therapeutic of paragraph 26, wherein the phospholipid is SOPC.
28. The supramolecular combinatorial therapeutic of any of paragraphs 24-27, wherein the first and second lipid are in about 10:1 to about 1:10 ratio.
29. The supramolecular combinatorial therapeutic of any of paragraphs 21-28, wherein the supramolecular combinatorial therapeutic comprises about 1% to about 99% of total lipid.
30. The supramolecular combinatorial therapeutic of any of paragraphs 21-29, wherein the supramolecular combinatorial therapeutic comprises the conjugate and total lipid in about 10:1 to about 1:10 ratio.
31. The supramolecular combinatorial therapeutic of any of paragraphs 1-30, wherein the supramolecular combinatorial therapeutic further comprises a polyethylene glycol (PEG).
32. The supramolecular combinatorial therapeutic of paragraph 31, wherein the PEG is conjugated with a component of the supramolecular combinatorial therapeutic.

33. The supramolecular combinatorial therapeutic of paragraph 31 or 32, wherein the PEG is conjugated to a lipid.
34. The supramolecular combinatorial therapeutic of paragraph 33, wherein the PEG conjugated lipid is selected from the group consisting of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, and any combinations thereof.
35. The supramolecular combinatorial therapeutic of paragraph 34, wherein the PEG conjugated lipid is 1,2-distearoyl-sn-glycem-3-phosphoethanolamine-N-[amino(polyethylene glycol)-2000] (DSPE-PEG2000).
36. The supramolecular combinatorial therapeutic of any of paragraphs 1-35, further comprising a targeting ligand.
37. The supramolecular combinatorial therapeutic of paragraph 36, wherein the targeting ligand is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.
38. The supramolecular combinatorial therapeutic of paragraph 37, wherein the targeting ligand binds a protein, receptor, or marker expressed on the surface of a cancer cell.
39. The supramolecular combinatorial therapeutic of any of paragraphs 36-38, wherein the targeting ligand is conjugated with a component of the composition.
40. The supramolecular combinatorial therapeutic of paragraph 39, wherein the targeting ligand is conjugated with a lipid or PEG.
41. The supramolecular combinatorial therapeutic of any of paragraphs 1-40, wherein the supramolecular combinatorial therapeutic further comprises a chemotherapeutic agent in addition to the taxane conjugate.
42. The supramolecular combinatorial therapeutic of paragraph 41, wherein the supramolecular combinatorial therapeutic comprises about 1% to about 99% (w/w) of the chemotherapeutic agent.
43. The supramolecular combinatorial therapeutic of paragraph 41 or 42, wherein the chemotherapeutic agent is selected from the group consisting of PI3K inhibitors; platinum compounds; inhibitors of topoisomerase I and II; alkylating agents; microtubule inhibitors; angiogenesis inhibitors; and any combinations thereof.
44. The supramolecular combinatorial therapeutic of any of paragraphs 41-43, wherein the chemotherapeutic agent is selected from the group consisting of PI3K inhibitors, platinum compounds, germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan-oral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof.

45. The supramolecular combinatorial therapeutic of paragraph 43 or 44, wherein the PI3K inhibitor is selected from the group consisting of PI103; P1828; LY294002; wortmannin; demethoxyviridin; IC486068; IC87114; GDC-0941; perifosine; CAL101; PX-866; IPI-145; BAY 80-6946; BEZ235; P6503; TGR1202; SF1126; INK1117; BKM120; IL147; XL765; Palomid 529; GSK1059615; ZSTK474; PWT33597; TG100-115; CAL263; GNE-447; CUDC-907; and AEZS-136, and any combinations thereof.

46. The supramolecular combinatorial therapeutic of any of paragraphs 41-45, wherein the chemotherapeutic agent is conjugated with a component of the composition.

47. The supramolecular combinatorial therapeutic of paragraph 46, wherein the chemotherapeutic agent is conjugated with a lipid or PEG.

48. The supramolecular combinatorial therapeutic of paragraph 47, wherein the chemotherapeutic agent is conjugated with cholesterol.

49. The supramolecular combinatorial therapeutic of any of paragraphs 1-48, wherein the supramolecular combinatorial therapeutic further comprises a neutral lipid, a cationic lipid, an anionic lipid, an amphiphilic lipid, a sterol, a programmable fusion lipid, or any combinations thereof.

50. The supramolecular combinatorial therapeutic of any of paragraphs 1-49, wherein the supramolecular combinatorial therapeutic comprises at least one (e.g., one, two, three, four, five, six, seven, eight, nine, ten or more different) taxane conjugate and at least one (e.g., one, two, three, four, five, six, seven, eight, nine, ten or more different) PI3K inhibitor-lipid conjugate.

51. The supramolecular combinatorial therapeutic of any of paragraphs 1-50, wherein the supramolecular combinatorial therapeutic comprises at least one (e.g., one, two, three, four, five, six, seven, eight, nine, ten or more different) taxane conjugate and at least one (e.g., one, two, three, four, five, six, seven, eight, nine, ten or more different) platinum-lipid conjugate.

52. The supramolecular combinatorial therapeutic of any of paragraphs 1-51, wherein the supramolecular combinatorial therapeutic comprises at least one (e.g., one, two, three, four, five, six, seven, eight, nine, ten or more different) taxane conjugate and at least one (e.g., one, two, three, four, five, six, seven, eight, nine, ten or more different) antibody-lipid conjugate.

53. The supramolecular combinatorial therapeutic of any of claims 1-52, wherein the supramolecular combinatorial therapeutic comprises at least one taxane conjugate, a phospholipid, and a PEG conjugated lipid.

54. The supramolecular combinatorial therapeutic of paragraph 53, wherein the composition comprises the conjugate, the phospholipid, and the PEG conjugated lipid in ratio from about 10-0.1:10-0.1:10-0.01.

55. The supramolecular combinatorial therapeutic of paragraph 53 or 54, wherein the phsopholipid is phosphatidylcholine and the PEG conjugated lipid is DSPE-PEG$_{2000}$.

56. The supramolecular combinatorial therapeutic of any of paragraphs 53-55, wherein the phospholipid is phosphatidylcholine.

57. The supramolecular combinatorial therapeutic of paragraph 56, wherein the phospatidylcholine is selected from the group consisting of SOPC, Egg PC, HSPC, and any combinations thereof.

58. The supramolecular combinatorial therapeutic of any of paragraph 1-57, wherein the supramolecular combinatorial therapeutic is a nanoparticle.

59. The supramolecular combinatorial therapeutic of paragraph 58, wherein the nanoparticle is about 5 nm to about 500 nm in diameter.

60. The supramolecular combinatorial therapeutic of paragraph 59, wherein the nanoparticle about 50 nm to about 200 nm in diameter.

61. The supramolecular combinatorial therapeutic of any of paragraphs 1-60, wherein the composition further comprises a pharmaceutically acceptable carrier.

62. A method of treating cancer, comprising, administering a supramolecular combinatorial therapeutic of any of paragraphs 1-61 to a subject in need of treatment for cancer.

63. The method of paragraph 62, wherein the cancer is selected from the group consisting of breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

64. The method of paragraph 63, further comprising co-administering one or more additional anti-cancer therapy to the subject.

65. The method of paragraph 64, wherein the additional therapy is selected from the group consisting of surgery, chemotherapy, radiation therapy, thermotherapy, immunotherapy, hormone therapy, laser therapy, anti-angiogenic therapy, and any combinations thereof.

66. The method of paragraph 65, wherein the additional therapy comprises administering a chemotherapeutic agent to the patient.

67. The method of any of paragraphs 62-66, further comprising co-administering an immunomodulator to the subject.

68. The method of paragraph 67, wherein the immunomodulator activates an immune response against cancer cells.

69. The method of paragraph 68, wherein the immunomodulator selected from the group consisting of natural killer cells, lymphokine-activated killer cells, cytotoxic T cells and dendritic cells, anti-PD-L1 antibodies, anti-PD-1 antibodies, anti-CD52 antibodies, anti-VEGF-A antibodies, anti-CD30 antibodies, anti-EGFR antibodies, anti-CD33 antibodies, anti-CD20 antibodies, anti-CTLA4 antibodies, anti-HER-2 antibodies, interferons and interleukins Additional exemplary embodiments can be described by one of more of the numbered paragraphs:

1. A method for predicting the likelihood of a cancer patient exhibiting an enhanced response to self-assembled supramolecular particles than platinates or taxanes, the method comprising assaying an expression level of one or more genes in a sample obtained from the patient; and predicting a likelihood that the patient will exhibit a positive response, wherein: increased expression level of the one or more genes selected from CAV1, CAV2, CAV3, LDLR, SMAD7, SMURF2, NEDD4, or PRKCA, relative to a reference or control, is positively correlated with a likelihood of a positive response to treatment comprising self-assembled supramolecular particles.
2. The method of paragraph 1, wherein the one or more genes are selected from the group consisting of EEA1, SRSF5, SMAD2, SNX3, PLCD1, OSBP, DNM1, DNM2, DNM3, SGK3, FAPP1, SMAD7, SMURF2, NEDD4, PRKCA, CDH-1, LDLR, CP, CD36, LYN, FLOT-1, FLOT-2, CA4, APOE, CAV1, CAV2, CAV3, LMAN2, LAT and STOM.
3. The method of paragraph 1 or 2, wherein the expression level of the one or more genes is normalized against an expression level of one or more reference genes to obtain a normalized expression level of the one or more genes.
4. The method of any of paragraphs 1-3, wherein the expression level of the one or more genes is a level of RNA transcript of the one or more genes.
5. The method of any of paragraphs 1-4, wherein the expression level of the one or more genes is a polypeptide level of the one or more genes.
6. The method of any of paragraphs 1-5, wherein the level of RNA transcript of the one or more genes is assayed using reverse transcription polymerase chain reaction (RT-PCR).
7. The method of any of paragraphs 1-6, wherein the sample is a biopsy sample.
8. The method of any of paragraphs 1-7, wherein the sample is a tumor cell.
9. The method of any of paragraphs 1-8, wherein the sample is a fixed, wax-embedded tissue sample.
10. The method of any of paragraphs 1-9, further comprising administering a supramolecular combinatorial therapeutic to the subject.

Some additional exemplary embodiments of the various aspects disclosed herein can be described by one of more of the numbered paragraphs:

1. A conjugate comprising taxane conjugated to a lipid, preferably the taxane is cabazitaxel, paclitaxel or docetaxel, more preferably the taxane is cabazitaxel.
2. The conjugate of paragraph 1, wherein the taxane is conjugated to the lipid via a linker.
3. The conjugate of paragraph 2, wherein the linker is selected from the group consisting of a direct bond or an atom such as oxygen or sulfur, a unit such as $NR^1$, C(O), C(O)O, C(O)$NR^1$, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherteroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.
4. The conjugate of paragraph 2 or 3, wherein the linker comprises at least one cleavable group.
5. The conjugate of any of paragraphs 2-4, wherein the linker comprises one or more of succinic acid, fumaric acid, propargylic acid, ethylene glycol, diethylene glycol, and natural or unnatural amino acids.
6. The conjugate of any of paragraphs 2-5, wherein the linker comprises at least one of oxalic acid, malonic acid, succinic acid, glutaric acid, succinic acid, ethylene diamine, natural or unnatural amino acid, ethylene glycol, diethylene glycol, acetic acid, propionic acid, butyric acid, valeric acid, acrylic acid, but-2-enoic acid, pent-2-enoic acid, hex-2-enoic acid, 2-propynoic acid, but-2-ynoic acid, pent-2-ynoic acid, hex-2-ynoic acid, ethylene, propylene, 1-butene, 1-pentene, 1-hexene, acetylene, propyne, but-1-yne, pent-1-yne, and any combinations thereof.
7. The conjugate of any of paragraphs 2-6, wherein the linker is selected from the group consisting of —C(O)CH$_2$CH$_2$C(O)NHCH$_2$CH$_2$NHC(O)—; —C(O)CH$_2$CH$_2$C(O)NHCH$_2$NHC(O)—; —C(O)CH$_2$OCH$_2$CH$_2$—; —C(O)CH$_2$CH$_2$OCH$_2$CH$_2$—; —C(O)CH$_2$OCH$_2$CH$_2$OCH$_2$CH$_2$—; —C(O)CH(R)NHC(O)CH$_2$—, wherein R is H, CH$_3$, CH(CH$_3$)$_2$, CH$_2$CH(CH$_3$)$_2$, C(CH$_3$)CH$_2$CH$_3$, or CH$_2$-Phenyl; —C(O)CH(R)NHC(O)CH$_2$CH$_2$—, wherein R is H, CH$_3$, CH(CH$_3$)$_2$, CH$_2$CH(CH$_3$)$_2$, C(CH$_3$)CH$_2$CH$_3$, or CH$_2$-Phenyl; —C(O)CH(R)NHC(O)(CH$_2$)$_n$C(O)—, wherein R is H, CH$_3$, CH(CH$_3$)$_2$, CH$_2$CH(CH$_3$)$_2$, C(CH$_3$)CH$_2$CH$_3$, or CH$_2$-Phenyl, and n is 1, 2, or 3; —C(O)CH(R)NHC(O)CH$_2$OCH$_2$CH$_2$—, wherein R is H, CH$_3$, CH(CH$_3$)$_2$, CH$_2$CH(CH$_3$)$_2$, C(CH$_3$)CH$_2$CH$_3$, or CH$_2$-Phenyl; —C(O)C≡C(CH$_2$)$_n$—C(O)—, wherein n is 1, 2 or 3; —C(O)C≡C(CH$_2$)$_n$—, wherein n is 0, 1, or 2; —C(O)CH═CH(CH$_2$)$_n$C(O)—, wherein n is 0, 1, 2, or 3; —C(O)CH═CH(CH$_2$)$_n$—, wherein n is 1, 2, or 3; and —C(O)CH$_2$CH$_2$C(O)NHCH$_2$C(O)—.
8. The conjugate of any of paragraphs 1-7, wherein the lipid is selected from the group consisting of cholesterol; 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; and γ-Linolenic acid.

9. The conjugate of any of paragraphs 1-8, wherein the lipid is cholesterol, alpha-tocopherol, or a fatty acid.

10. The conjugate of any of paragraphs 1-9, wherein the conjugate is selected from the group consisting of conjugates 1-15 and 21-32.

11. A composition comprising a conjugate of any of paragraphs 1-10.

12. The composition of paragraph 11, wherein the composition comprises from about 1% to about 99% (w/w) of the conjugate.

13. The composition of paragraph 11 or 12, wherein the composition further comprises a first lipid in addition to the conjugate.

14. The composition of paragraph 13, wherein the first lipid is a phospholipid.

15. The composition of paragraph 13 or 14, wherein the composition further comprises a second lipid.

16. The composition of paragraph 15, wherein the second lipid is a phospholipid.

17. The composition of any of paragraphs 14-16, wherein the phospholipid is selected from the group consisting of phosphatidyl cholines, phosphatidyl cholines with acyl groups having 6 to 22 carbon atoms, phosphatidyl ethanolamines, phosphatidyl inositols, phosphatidic acids, phosphatidyl serines, sphingomyelin, phosphatidyl glycerols, and any combinations thereof.

18. The composition of paragraph 17, wherein the phospholipid is selected from the group consisting of phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoyl-phosphatidylethanolamine (DOPE), palmitoyloleoyl-phosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof.

19. The composition of paragraph 18, wherein the phospholipid is SOPC.

20. The composition of any of paragraphs 16-18, wherein the first and second lipid are in about 10:1 to about 1:10 ratio.

21. The composition of any of paragraphs 13-20, wherein the composition comprises about 1% to about 99% of total lipid.

22. The composition of any of paragraphs 13-21, wherein the composition comprises the conjugate and total lipid in about 10:1 to about 1:10 ratio.

23. The composition of any of paragraphs 11-22, wherein the composition further comprises polyethylene glycol (PEG).

24. The composition of paragraph 23, wherein the PEG is conjugated with a component of the composition.

25. The composition of paragraph 23 or 24, wherein the PEG is conjugated a lipid.

26. The composition of paragraph 25, wherein the PEG conjugated lipid is selected from the group consisting of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, and any combinations thereof.

27. The composition of paragraph 26, wherein the PEG conjugated lipid is 1,2-distearoyl-sn-glycem-3-phosphoethanolamine-N-[amino(polyethylene glycol)-2000] (DSPE-PEG2000).

28. The composition of any of paragraphs 11-27, further comprising a targeting ligand 29. The composition of paragraph 28, wherein the targeting ligand is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.

30. The composition of paragraph 29, wherein the targeting ligand binds a protein, receptor, or marker expressed on the surface of a cancer cell.

31. The composition of paragraph 28 or 29, wherein the targeting ligand is conjugated with a component of the composition.

32. The composition of paragraph 31, wherein the targeting ligand is conjugated with a lipid or PEG.

33. The composition of any of paragraphs 11-32, wherein the composition further comprises a chemotherapeutic agent in addition to the conjugate.

34. The composition of paragraph 33, wherein the composition comprises about 1% to about 99% (w/w) of the chemotherapeutic agent.

35. The composition of paragraph 34, wherein the chemotherapeutic agent is selected from the group consisting of PI3K inhibitors; platinum compounds; inhibitors of topoisomerase I and II; alkylating agents; microtubule inhibitors; angiogenesis inhibitors; and any combinations thereof.

36. The composition of any of paragraphs 33-35, wherein the chemotherapeutic agent is selected from the group consisting of PI3K inhibitors, platinum compounds, germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof.

37. The composition of paragraph 35 or 36, wherein the PI3K inhibitor is selected from the group consisting of PI103; P1828; LY294002; wortmannin; demethoxyviridin; IC486068; IC87114; GDC-0941; perifosine; CAL101; PX-866; IPI-145; BAY 80-6946; BEZ235; P6503; TGR1202; SF1126; INK1117; BKM120; IL147; XL765; Palomid 529; GSK1059615; ZSTK474; PWT33597; TG100-115; CAL263; GNE-447; CUDC-907; and AEZS-136, and any combinations thereof.

38. The composition of any of paragraphs 33-37, wherein the chemotherapeutic agent is conjugated with a component of the composition.

39. The composition of paragraph 38, wherein the chemotherapeutic agent is conjugated with a lipid or PEG.

40. The composition of paragraph 39, wherein the chemotherapeutic agent is conjugated with cholesterol.

41. The composition of paragraph 40, wherein the lipid conjugated chemotherapeutic

FORMULA I

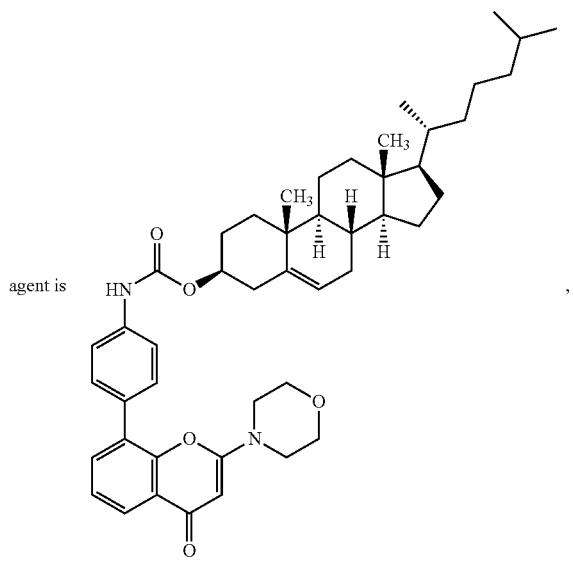

agent is

FORMULA II
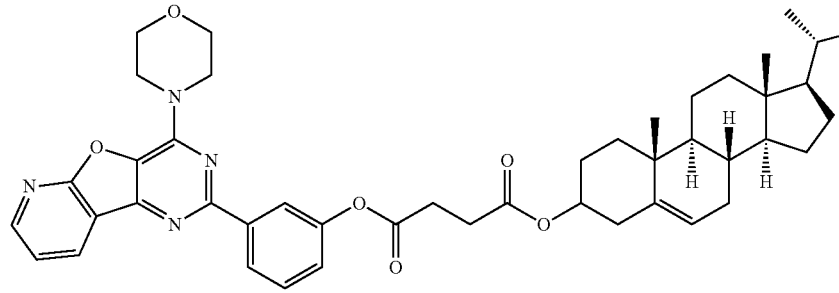
Formula IV
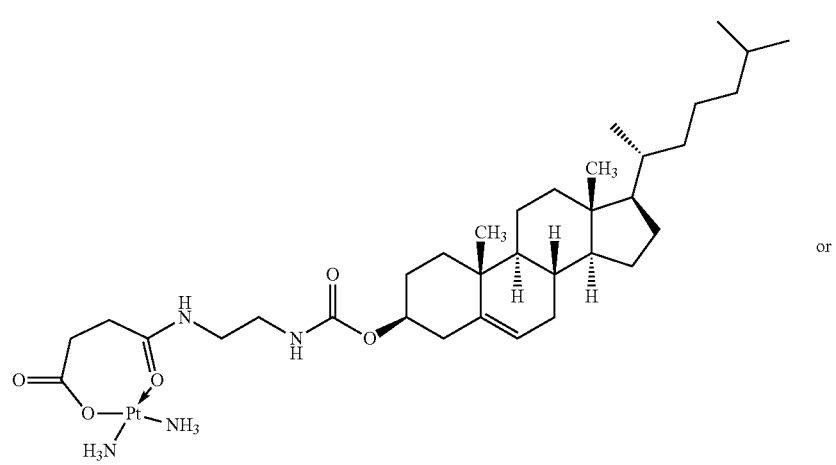
or
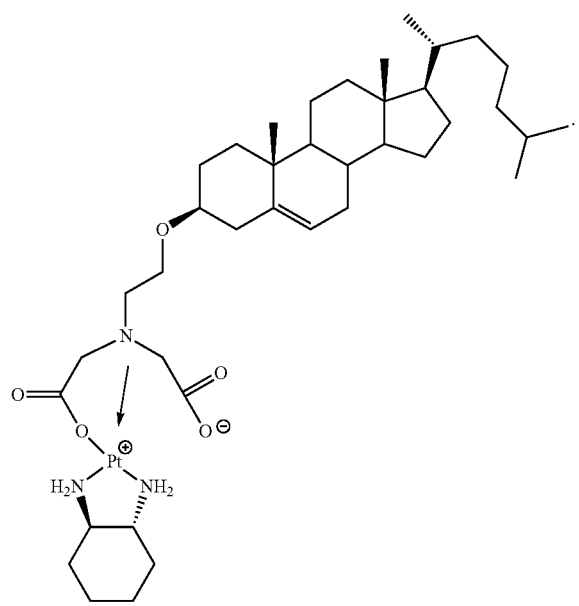
42. The composition of any of paragraphs 11-41, wherein the composition further comprises an immunomodulator comprising an anti-PD-1 antibody, an anti-PD-L1 antibody and combinations thereof.

43. The composition of paragraph 42, wherein the immunomodulator is conjugated with lipid.
44. The composition of paragraph 43, wherein the immunomodulator is conjugated with cholesterol.
45. The composition of any of paragraphs 11-44, wherein the composition further comprises a neutral lipid, a cationic lipid, an anionic lipid, an amphiphilic lipid, a sterol, a programmable fusion lipid, or any combinations thereof.
46. The composition of any of paragraphs 11-45, wherein the composition comprises the conjugate, a phospholipid, and a PEG conjugated lipid.
47. The composition of paragraph 46, wherein the composition comprises the conjugate, the phospholipid, and the PEG conjugated lipid in ratio from about 10-0.1:10-0.1:10-0.1.
48. The composition of any of paragraphs 46-47, wherein the phospholipid is phosphatidylcholine and the PEG conjugated lipid is DSPE-PEG2000.
49. The composition of any of paragraphs 46-48, wherein the phospholipid is phosphatidylcholine.
50. The composition of paragraph 49, wherein the phospatidylcholine is selected from the group consisting of SOPC, POPC, Egg PC, HSPC, and any combinations thereof.
51. The composition of any of paragraphs 11-50, wherein the composition is a liposome, emulsion, or micelle.
52. The composition of any of paragraph 11-51, wherein the composition is a nanoparticle.
53. The composition of paragraph 52, wherein the nanoparticle is about 5 nm to about 500 nm in diameter.
54. The composition of paragraph 53, wherein the nanoparticle about 50 nm to about 200 nm in diameter.
55. The composition of any of paragraphs 11-54, wherein the composition further comprises a pharmaceutically acceptable carrier.
56. A method of treating cancer, comprising, administering a composition of any of paragraphs 11-55 to a subject in need of treatment for cancer.
57. The method of paragraph 56, wherein the cancer is selected from the group consisting of breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.
58. The method of paragraph 56, further comprising co-administering one or more additional anti-cancer therapy to the subject.
59. The method of paragraph 58, wherein the additional therapy is selected from the group consisting of surgery, chemotherapy, radiation therapy, thermotherapy, immunotherapy, hormone therapy, laser therapy, anti-angiogenic therapy, and any combinations thereof.
60. The method of paragraph 59, wherein the additional therapy comprises administering a chemotherapeutic agent to the patient.
61. The method of any of paragraphs 56-60, further comprising co-administering an immunomodulator to the subject.
62. The method of paragraph 61, wherein the immunomodulator activates an immune response against cancer cells.
63. The method of paragraph 62, wherein the immunomodulator selected from the group consisting of natural killer cells, lymphokine-activated killer cells, cytotoxic T cells and dendritic cells, anti-PD-L1 antibodies, anti-PD-1 antibodies, anti-CD52 antibodies, anti-VEGF-A antibodies, anti-CD30 antibodies, anti-EGFR antibodies, anti-CD33 antibodies, anti-CD20 antibodies, anti-CTLA4 antibodies, anti-HER-2 antibodies, interferons and interleukins The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

In taxane-lipid conjugate 1 the drug cabazitaxel is conjugated to cholesterol through a linker comprise of succinic acid and ethylene diamine. Cholesterol and one end of ethylene diamine are covalently bonded through a carbamate linkage where as another end is coupled to succinic acid through amide linkage. Succinic acid and C-2' hydroxyl group of cabazitaxel is coupled through an ester bond.

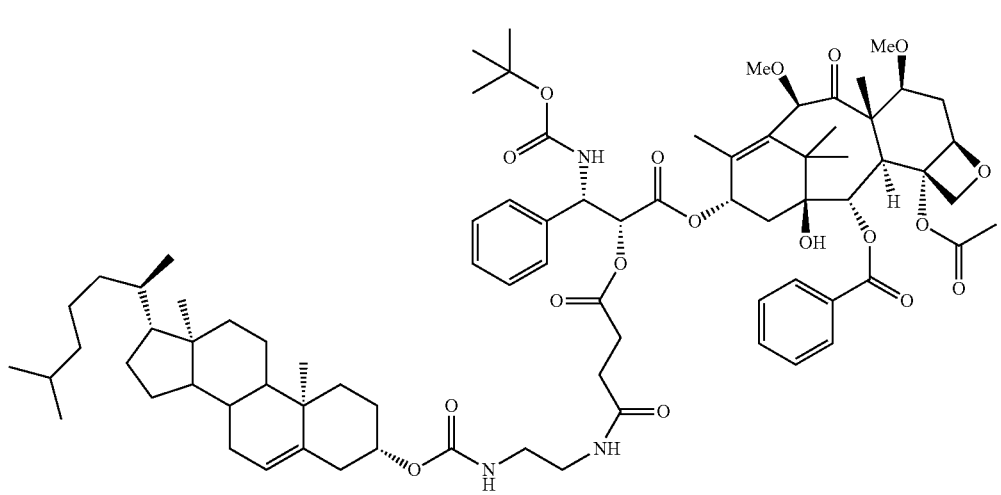

In taxane-lipid conjugate 2 the drug cabazitaxel is conjugated to cholesterol through a linker comprise of succinic acid and natural or unnatural amino acid. The acid group of amino acid is connected to cholesterol through an ester bond where as the amine group is connected to succinic acid through amide bond. Cabazitaxel C-2' hydroxyl group is connected to succinic acid via an ester bond.

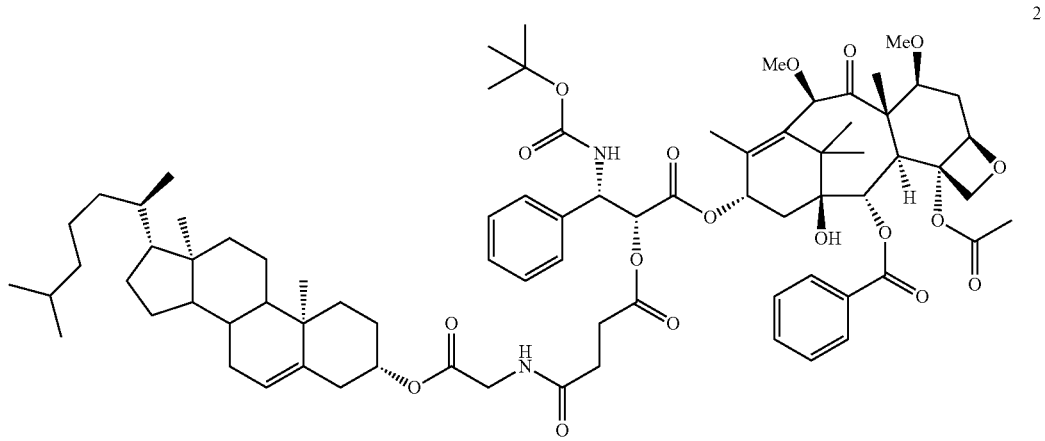 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](OC(=O)CCC(=O)NCC(=O)O[C@H]3CC[C@@]4(C)C(=CCC5C4CC[C@@]4(C)C5CC[C@@H]4[C@H](C)CCCC(C)C)C3)[C@@H](NC(=O)OC(C)(C)C)c3ccccc3)C(C)=C1C2(C)C]

In taxane-lipid conjugate 3 the drug cabazitaxel is conjugated to alpha tocopherol through a linker comprise of succinic acid and natural or unnatural amino acid. The acid group of amino acid is connected to alpha tocopherol through an ester bond where as the amine group is connected to succinic acid through amide bond. Cabazitaxel C-2' hydroxyl group is connected to succinic acid via an ester bond.

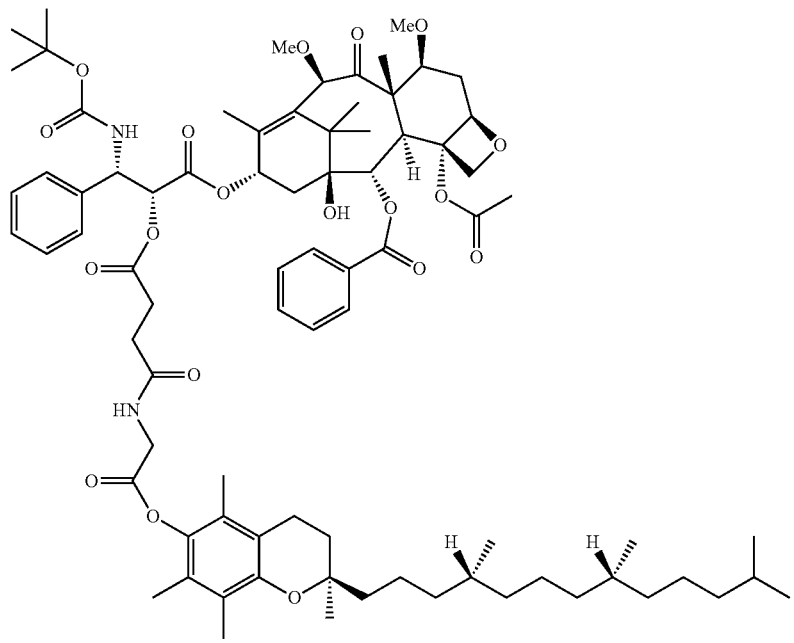

3

In taxane-lipid conjugate 4 the drug cabazitaxel is conjugated to cholesterol through a linker comprise of ethylene glycol and acetic acid. One end of ethylene glycol is connected to cholesterol via an ether bond and another hydroxyl group is connected to an acid group via a methylene spacer. The acid group is connected to C-2' hydroxyl group of cabazitaxel is coupled through an ester bond.

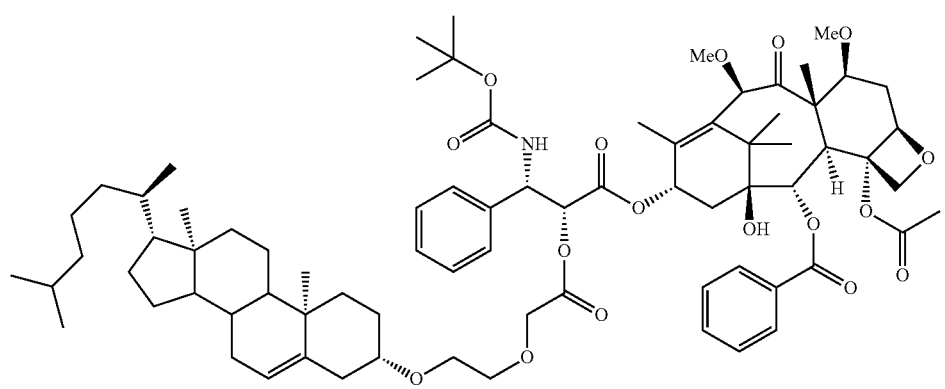

4

In taxane-lipid conjugate 5 the drug cabazitaxel is conjugated to cholesterol through a linker comprise of ethylene glycol and acrylic acid. One end of ethylene glycol is connected to cholesterol via an ether bond and another hydroxyl group is connected to an acid group via two methylene unit. The acid group is connected to C-2' hydroxyl group of cabazitaxel is coupled through an ester bond.

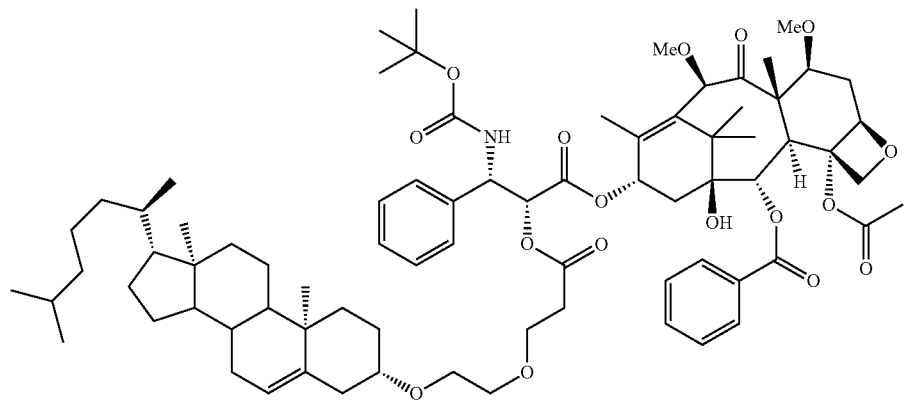

5

In taxane-lipid conjugate 6 the drug cabazitaxel is conjugated to cholesterol through a linker comprise of diethylene glycol and acetic acid. One end of diethylene glycol is connected to cholesterol via an ether bond and another hydroxyl group is connected to an acid group via a methylene spacer. The acid group is connected to C-2' hydroxyl group of cabazitaxel is coupled through an ester bond.

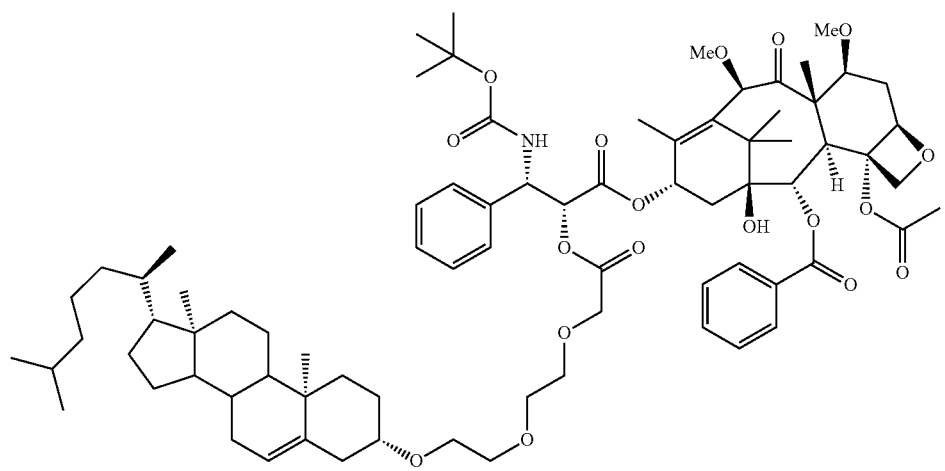

6

In taxane-lipid conjugate 7 the drug cabazitaxel is conjugated to cholesterol through a linker comprise of hydrophobic amino acid and glycolic acid. Hydroxyl group of glycolic acid is connected with cholesterol via an ether bond and the acid end is connected via an amide bond with amine group of amino acid. The C-2' hydroxyl group of cabazitaxel is connected to the acid group of amino acid through an ester bond.

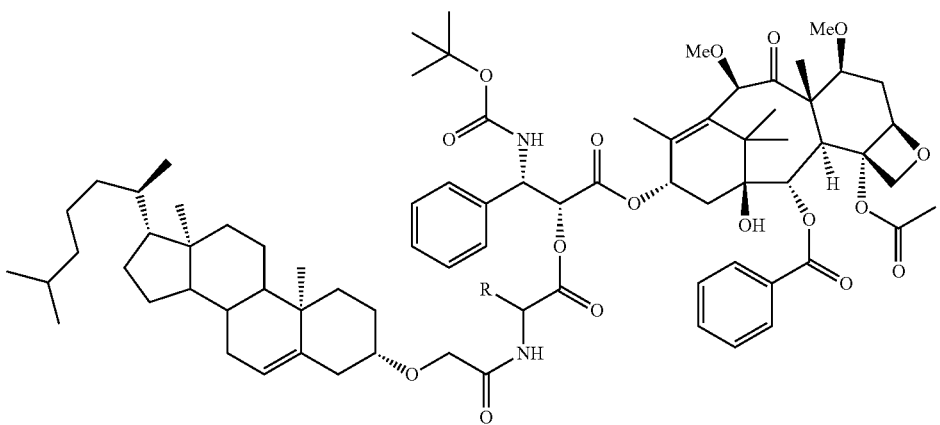

7

R = H, CH3, CH(CH3)2, CH2CH(CH3)2, C(CH3)CH2CH3, CH2Ph

Additional taxane-lipid conjugates:
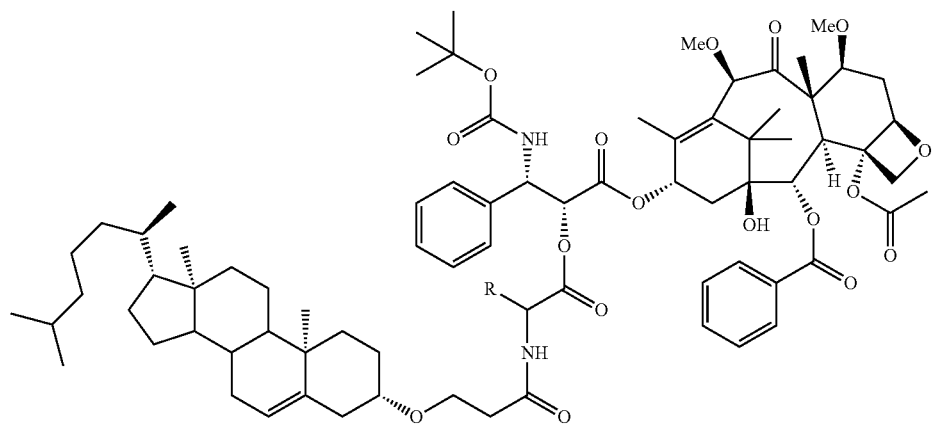
8
R = H, CH3, CH(CH3)2, CH2CH(CH3)2, C(CH3)CH2CH3, CH2Ph
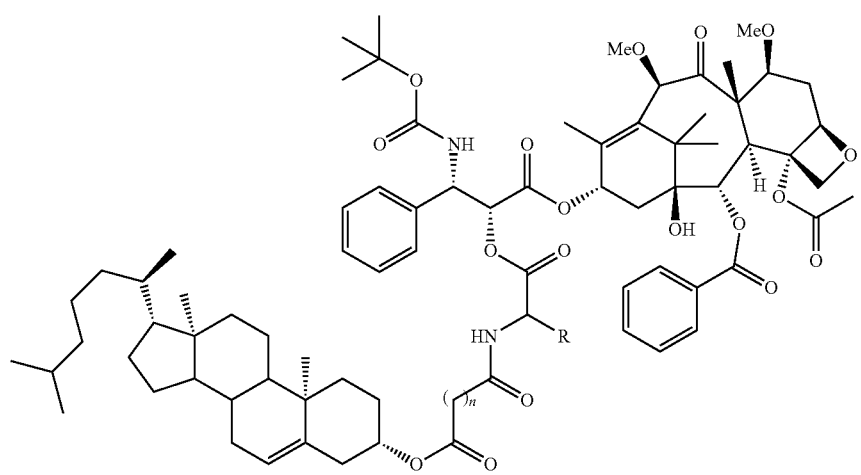
9
R = H, CH3, CH(CH3)2, CH2CH(CH3)2, C(CH3)CH2CH3, CH2Ph
n = 1 to 3
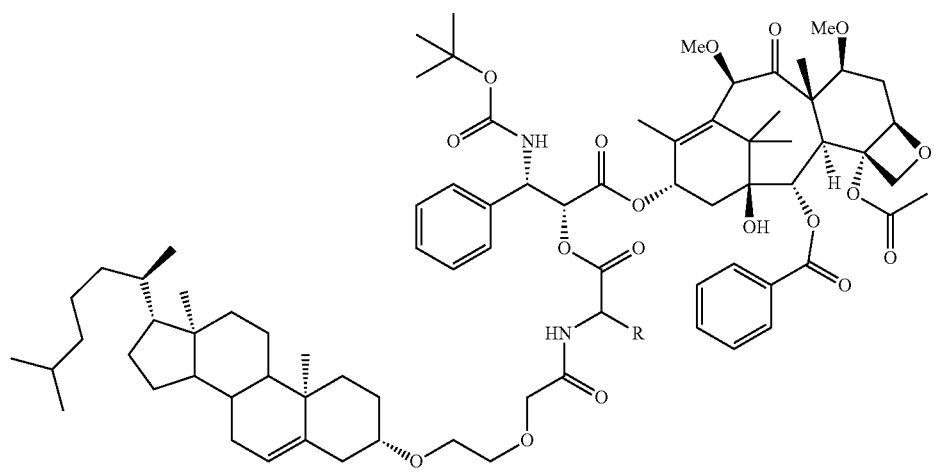
10
R = H, CH3, CH(CH3)2, CH2CH(CH3)2, C(CH3)CH2CH3, CH2Ph -continued
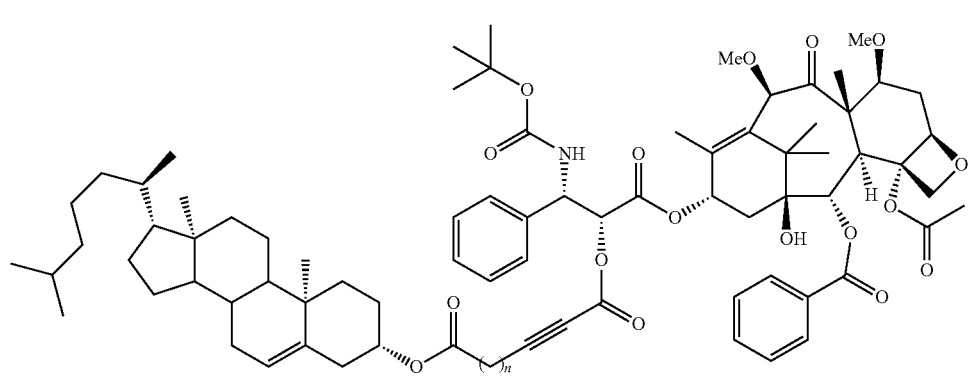
n = 1, 2, 3
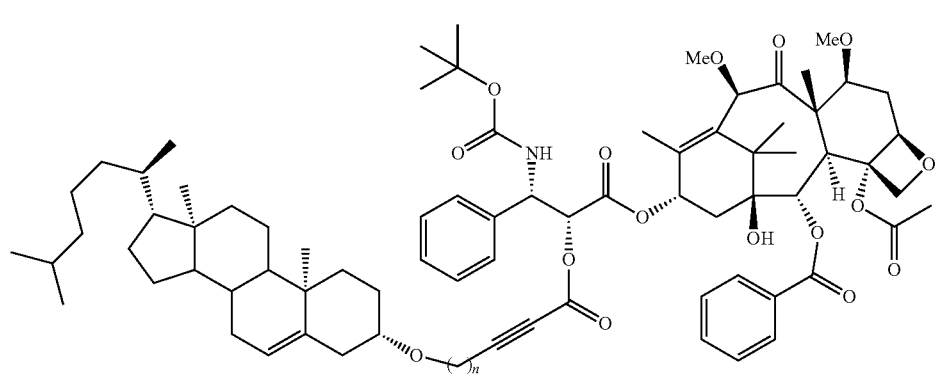
n = 0, 1, 2
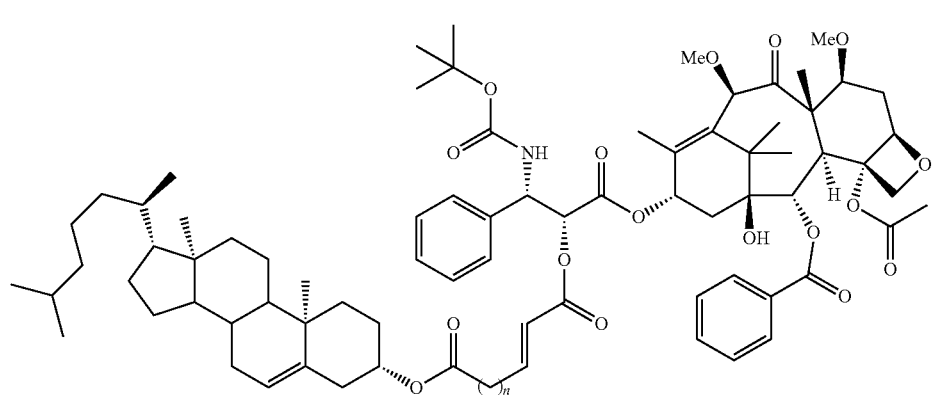
n = 1, 2, 3

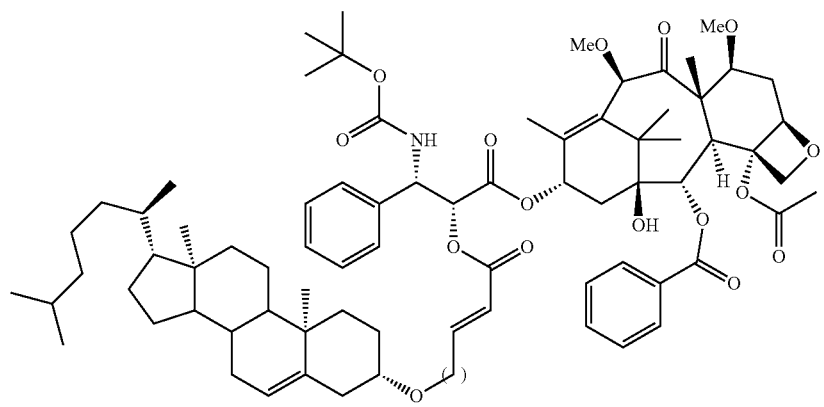
14
n = 0, 1, 2
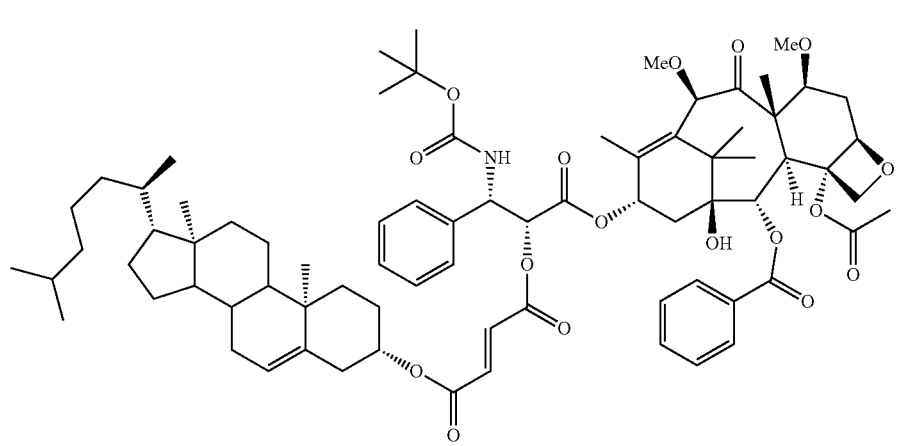
15
Paclitaxel-lipid conjugates (16 and 17)
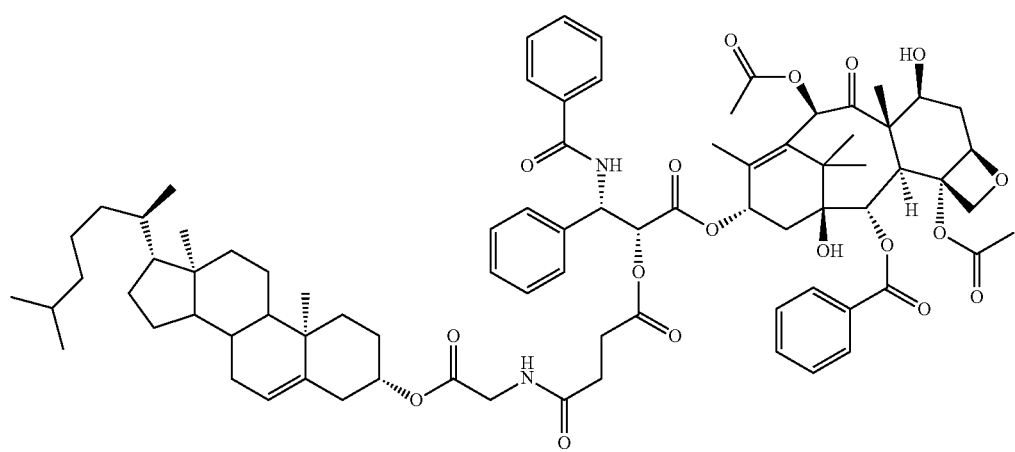
16

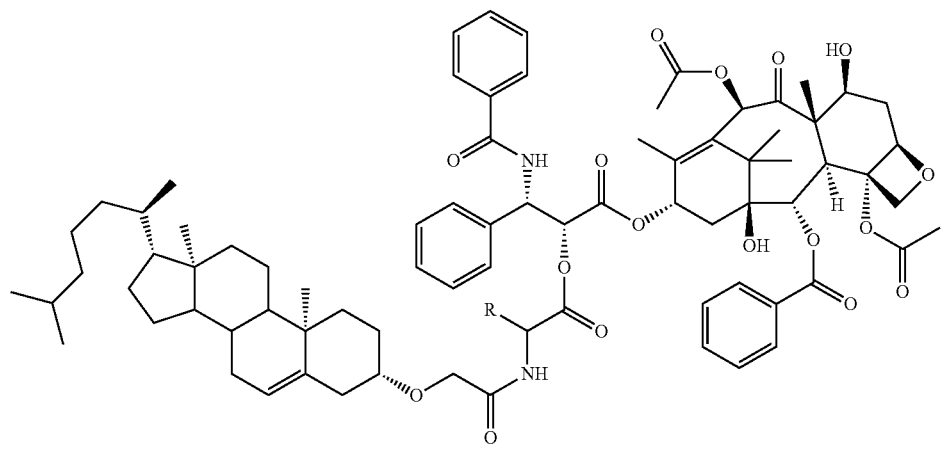
R = H, CH3, CH(CH3)2, CH2CH(CH3)2, C(CH3)CH2CH3, CH2Ph
Docetaxel-lipid conjugates (18-20 and 33) and cabazitaxel-lipid conjugates (21-32)
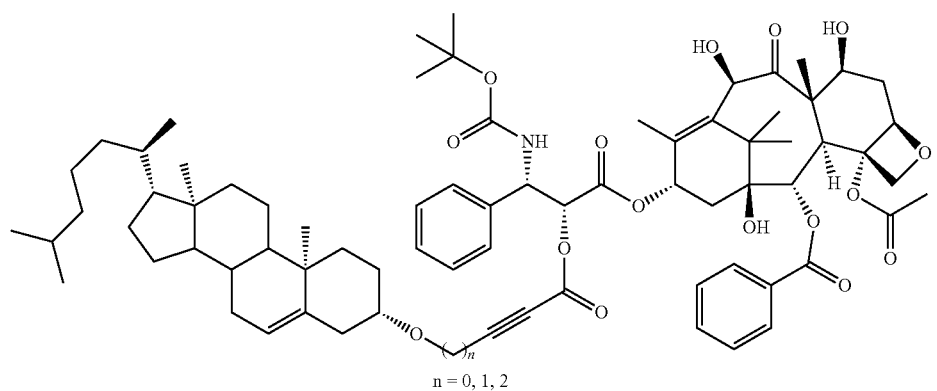
n = 0, 1, 2
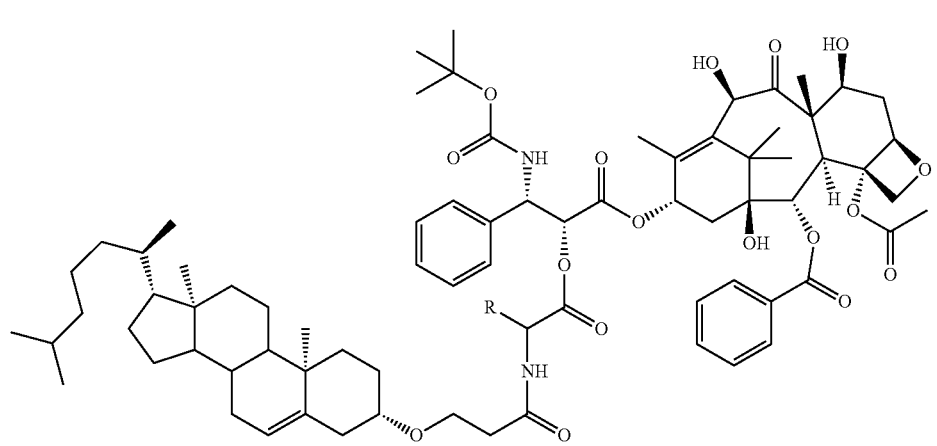
R = H, CH3, CH(CH3)2, CH2CH(CH3)2, C(CH3)CH2CH3, CH2Ph

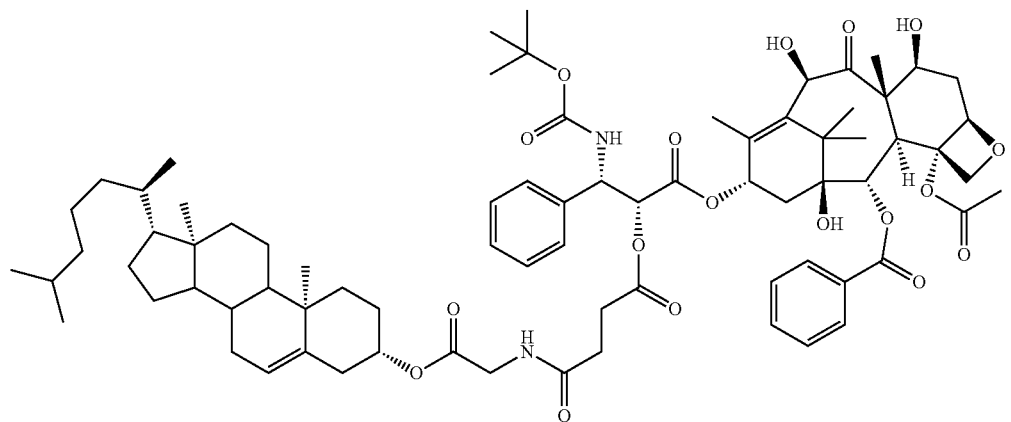
20
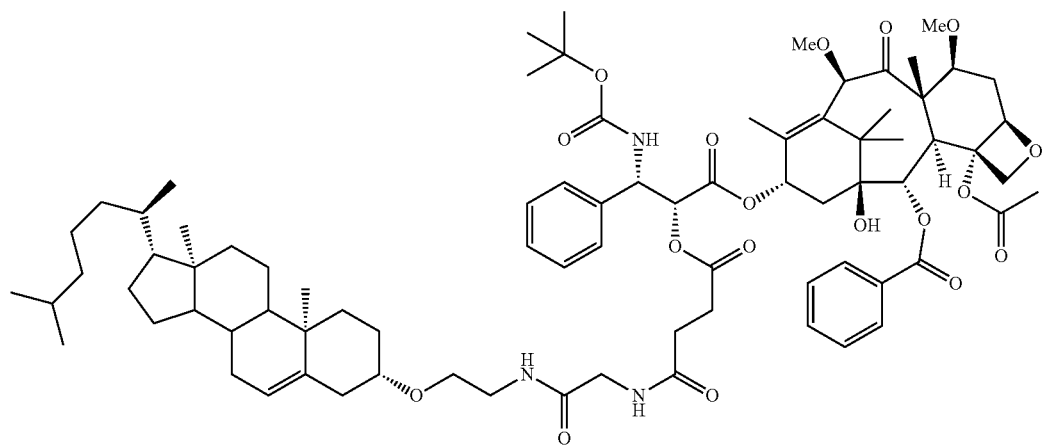
21
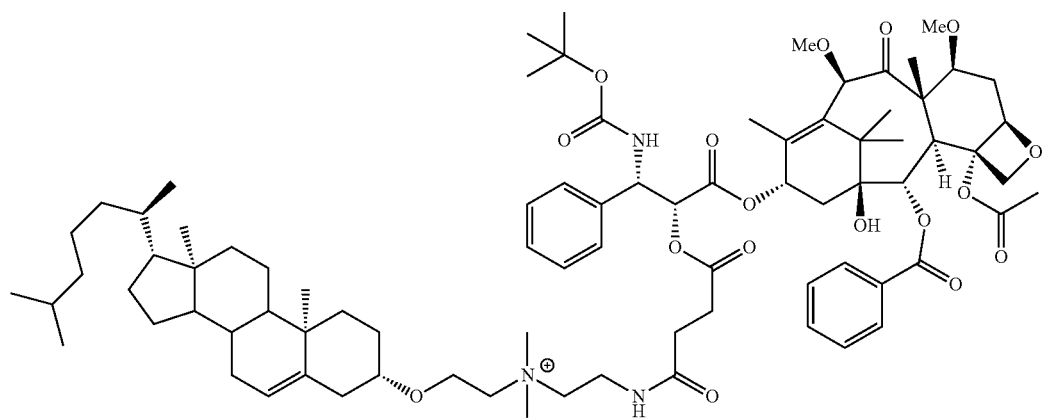
22

-continued
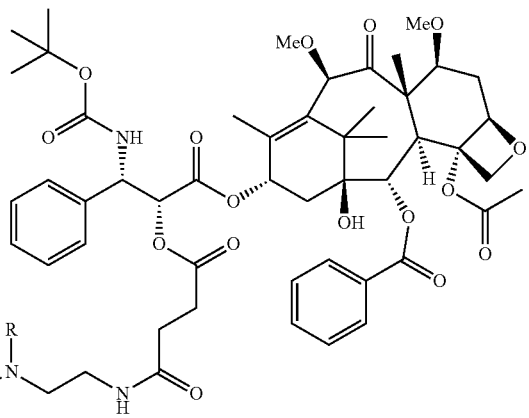
23
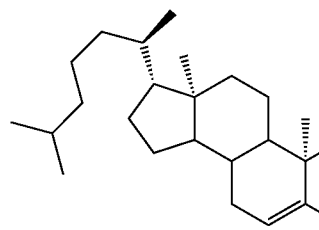
R = H, Me, CH2COOH
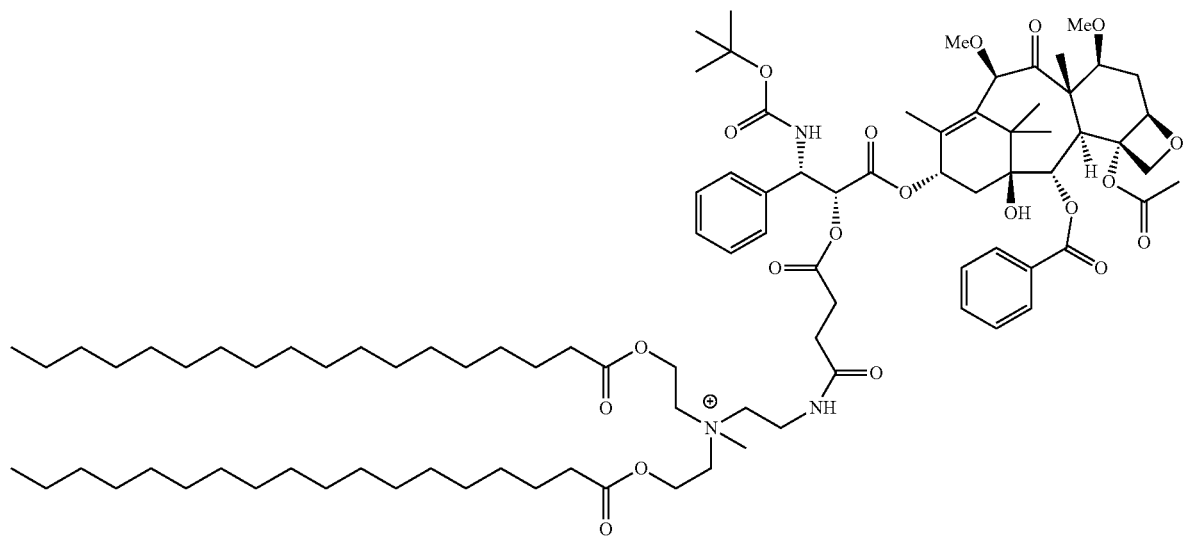
24
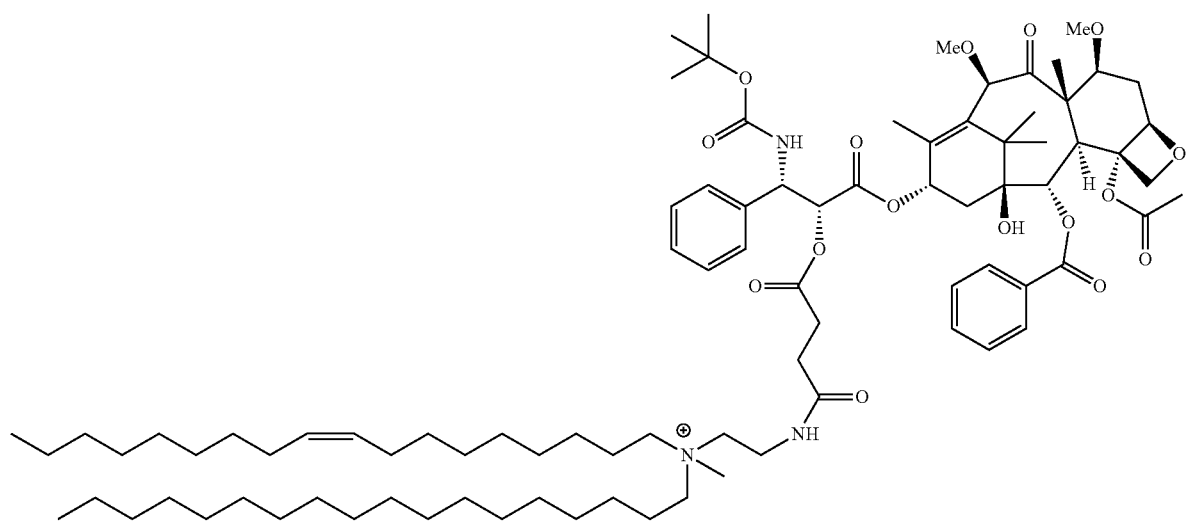
25

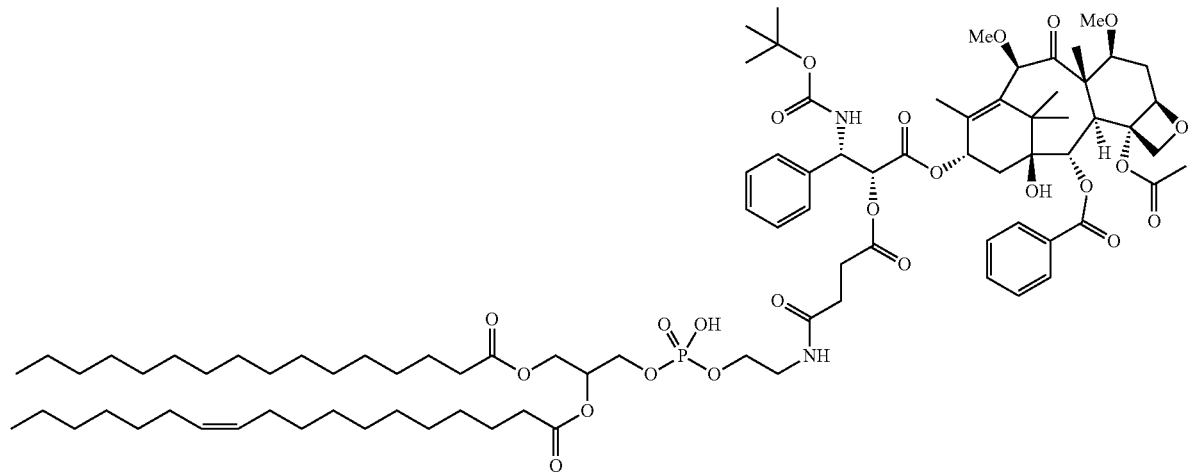
26
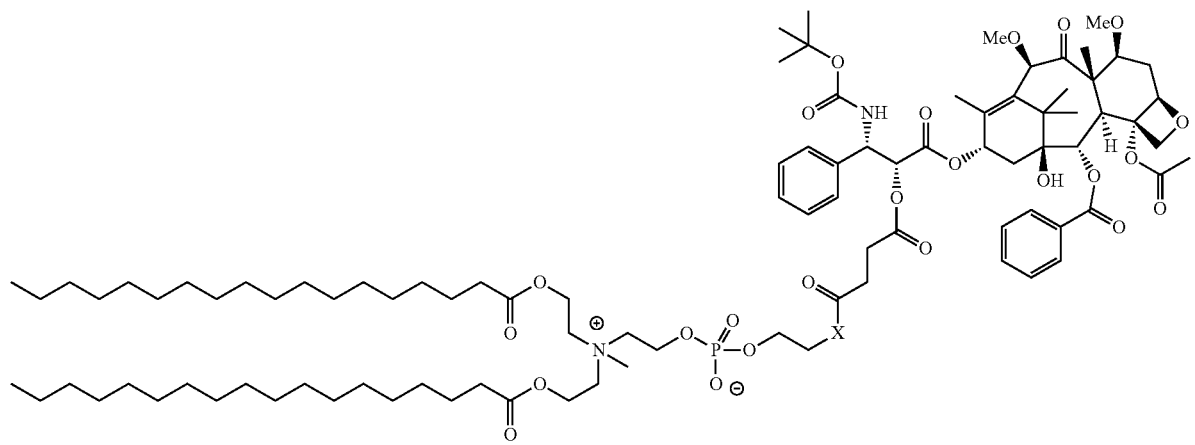
27
X = N, O
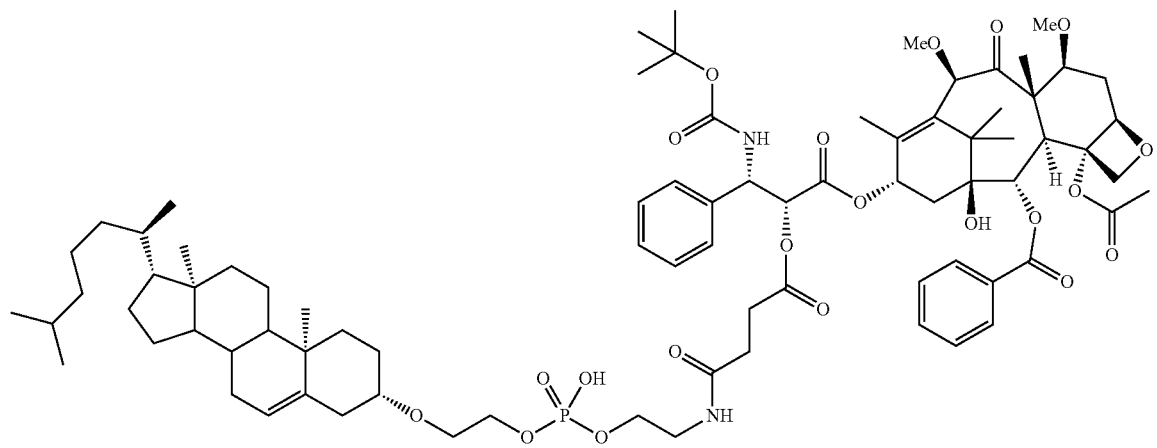
28

-continued
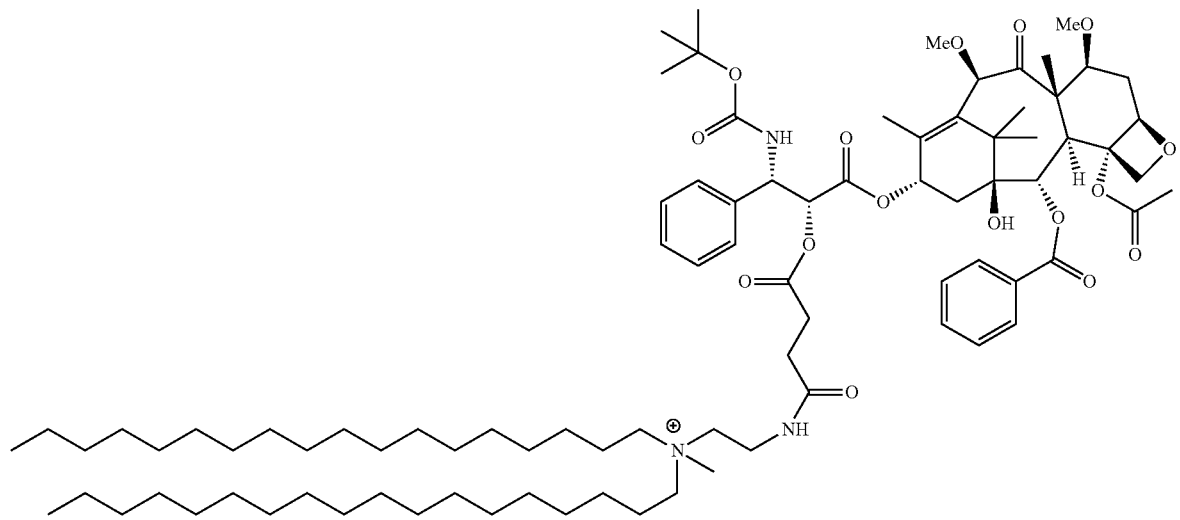
29
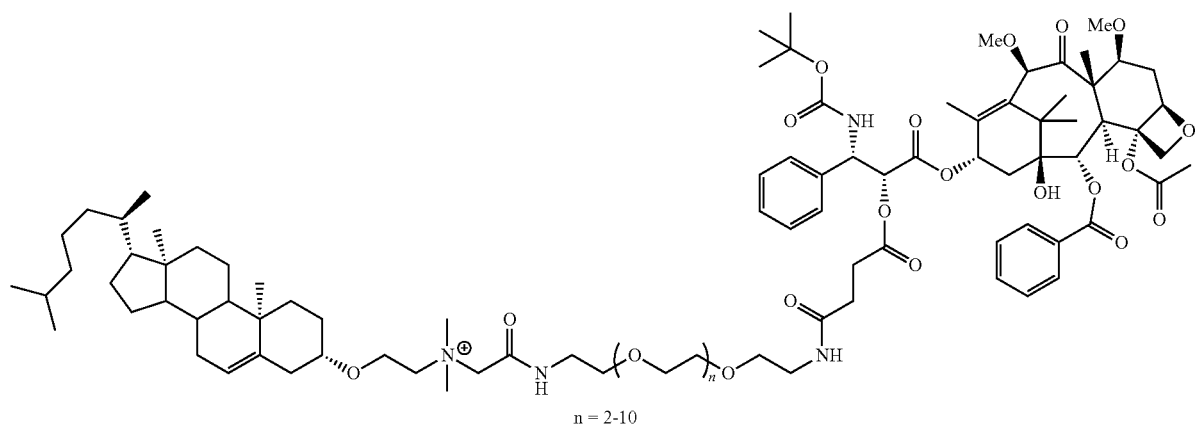
30
n = 2-10
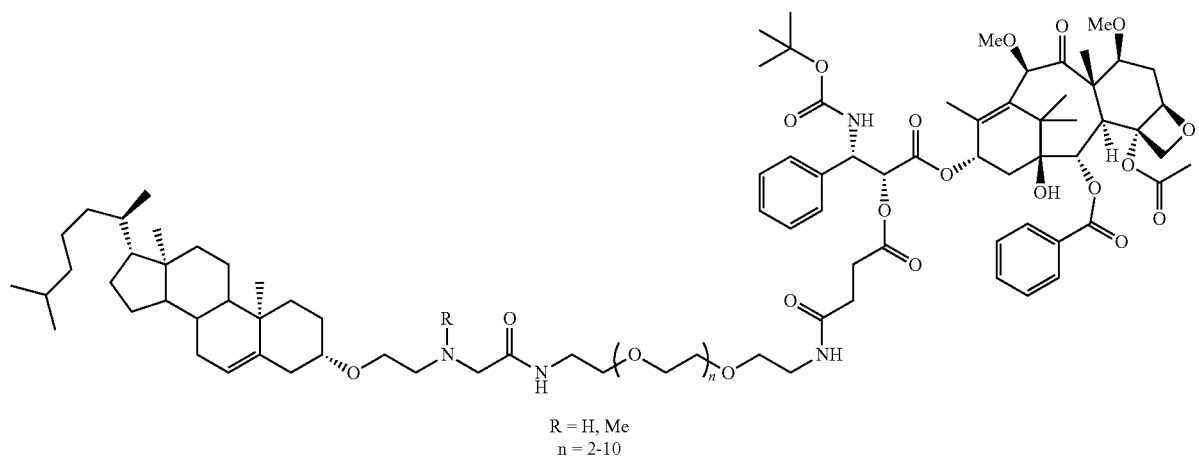
31
R = H, Me
n = 2-10

-continued
32
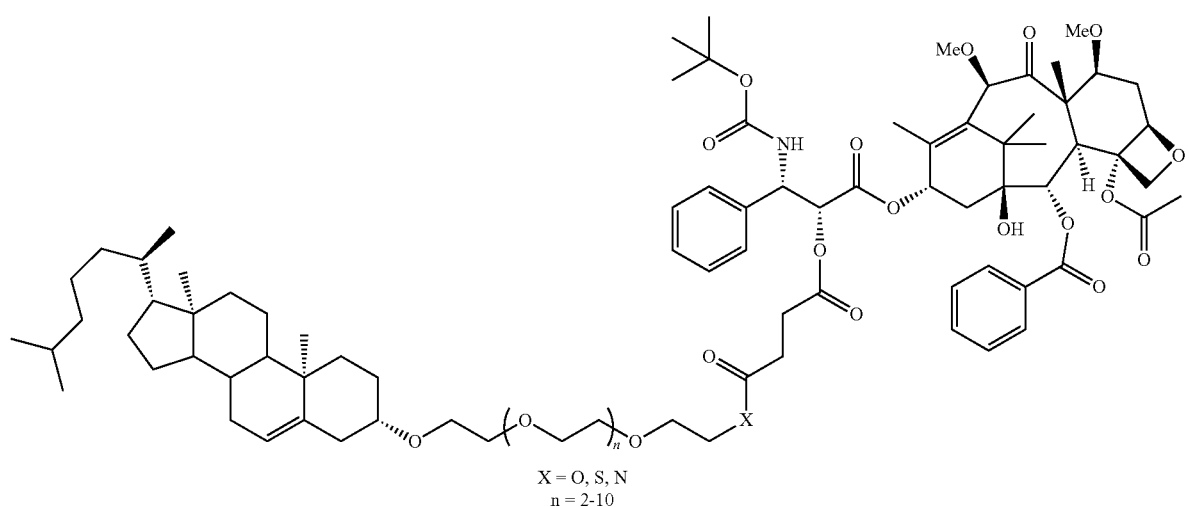
X = O, S, N
n = 2-10
33
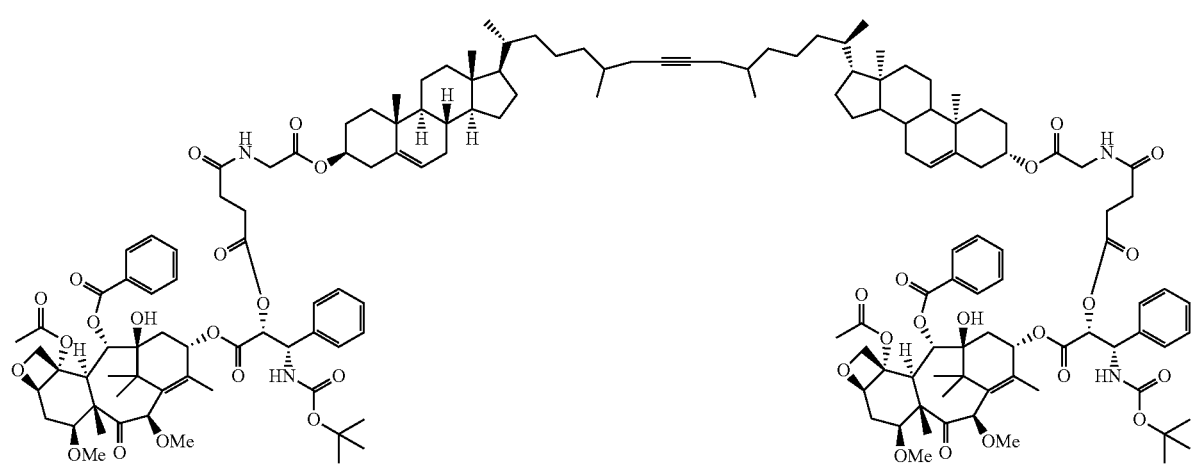
34
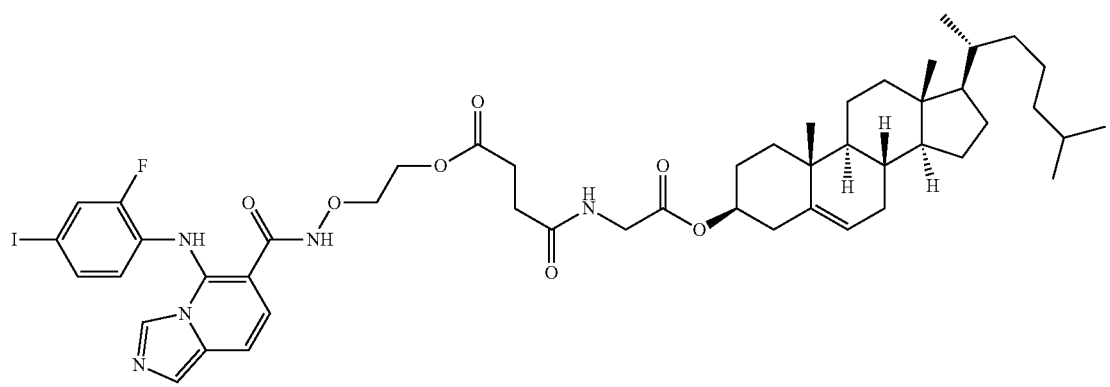

Example 2: Synthesis of Cholesterol Cabazitaxel Conjugate 1
Scheme 1:
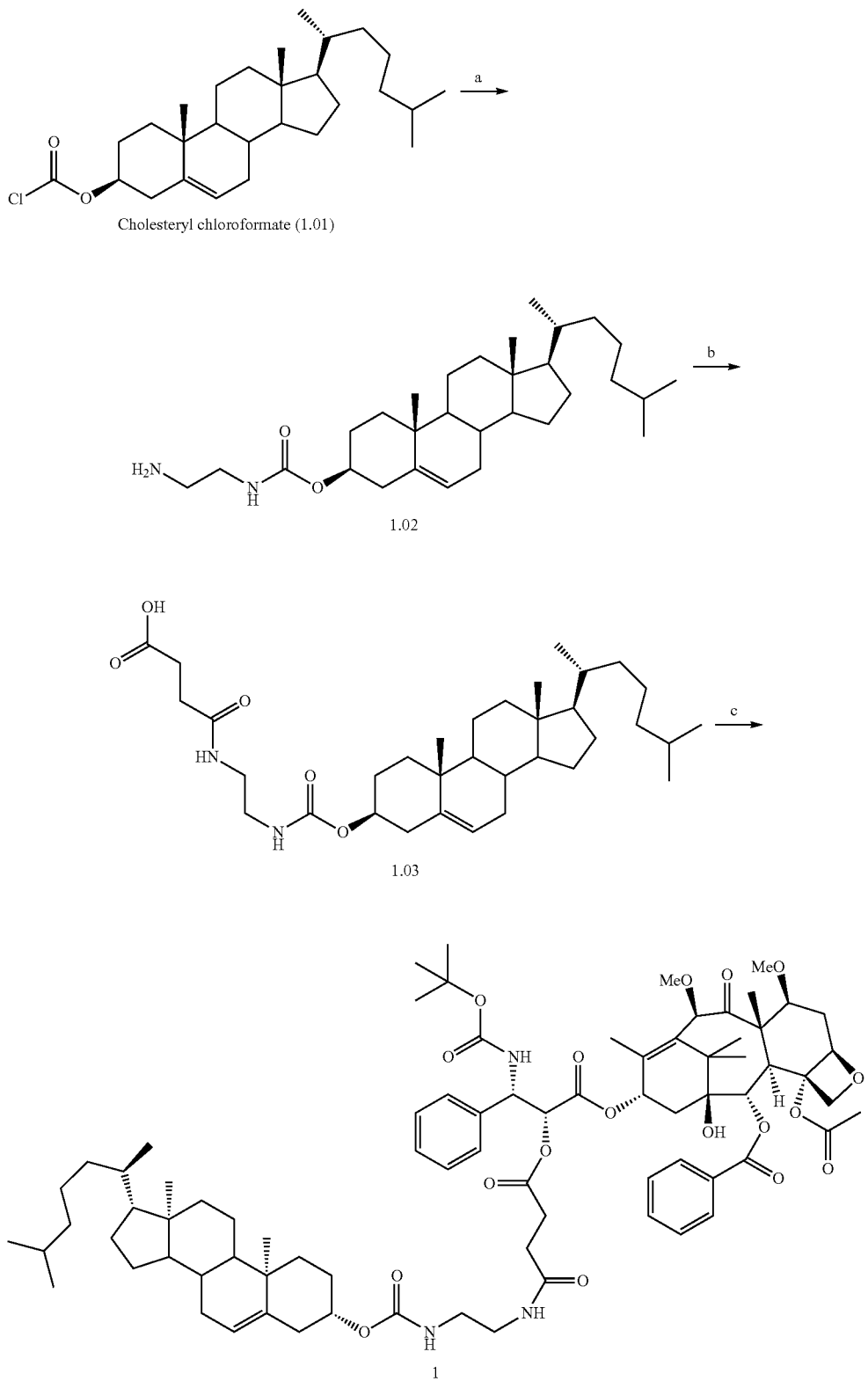
Reagents and conditions: (a) Ethylene diamine, CH2Cl2, 0 oC to r.t, 12 h (b) Succinic anhydride, Pyridine, CH2Cl2, r.t, 12 h (c) DIPC, DMAP, CH2Cl2, 0 oC to r.t, 12 h Step a:

To an ice cooled solution of ethylenediamine (22.2 mL) in dichliromethane (40 mL) was added a solution of cholesteryl chloroformate 1.01 (5 g, 11.13 mmol) in dichliromethane (50 mL) drop wise over a period of 45 min and stirred at the same temperature for 1 h. The ice bath was removed and the reaction mixture was stirred at room temperature for additional 20 h. After completion (checked by TLC) the reaction mixture was quenched with water, extracted with dichloromethane (4×50 mL), the organic layer was dried over anhydrous $Na_2SO_4$ and concentrate under reduced pressure. The residue was purified by silica gel chromatography utilizing methanol-chloroform as mobile phase to obtain intermediate 1.02 in 80% yield. $^1H$ NMR of 1.02 (500 MHz, $CDCl_3$) δ: 5.30 (s, 1H), 5.05 (s, 1H), 4.42 (s, 1H), 3.18 (s, 2H), 2.79 (s, 2H), 2.35-2.05 (m, 4H), 2.0-1.85 (m, 2H), 1.85-1.7 (m, 3H), 1.67-0.78 (m, 33H of cholesterol back bone), 0.70 (bs, 3H). $^{13}C$ NMR of 1.02 (125 MHz, $CDCl_3$) δ: 156.48, 139.84, 122.46, 77.23, 76.98, 76.73, 74.41, 56.71, 56.20, 50.04, 43.02, 42.32, 41.51, 39.76, 39.51, 38.56, 37.01, 36.56, 36.19, 35.78, 31.89, 28.20, 28.17, 27.98, 24.27, 23.85, 22.80, 22.76, 22.54, 22.52, 21.05, 19.31, 18.71, 11.84. IR of 1.02 (KBr) v: 1363.9, 1338.8, 2945.3, 2891.3, 2868.2, 2850.8, 1716.7, 1697.4, 1546.9, 1535.3, 1460.1, 1369.5, 1247.9, 1018.4 $cm^{-1}$ ESIMS m/z=472 $[M+Na]^+$ for $[C_{30}H_{52}N_2O_2Na]$. Melting Point: 163° C.

Step b:

To an ice cooled solution of intermediate 1.02 (1.0 g, 2.12 mmol) in dry dichliromethane (20 mL) was added pyridine (3.41 mL, 42.3 mmol) and stirred for 20 minutes under nitrogen atmosphere. Succinic anhydride (1.06 g, 10.6 mmol) was added to the reaction mixture and stirred for another 12 h at room temperature. After completion the reaction mixture was diluted with chloroform (50 mL), washed with 0.1N HCl (3×100 mL) and brine (1×100 mL) successively. The organic layer was dried over anhydrous sodium sulfate, concentrated under reduced pressure and the residue was purified by silicagel chromatography to afford intermediate 1.03 in good yield (1.06 g, 87%). $^1H$ NMR of 1.03 (500 MHz, $CDCl_3$) δ: 6.79 (s, 1H), 6.23 (s, 1H), 5.39 (s, 1H), 5.17 (s, 1H), 4.50 (bs, 1H), 3.38-3.23 (m, 4H), 2.72 (bs, 2H), 2.56 (bs, 2H), 2.41-2.25 (m, 2H), 2.08-1.94 (m, 2H), 1.94-1.80 (m, 3H), 1.67-0.78 (m, 33H), 0.70 (bs, 3H). $^{13}C$ NMR of 1.03 (125 MHz, $CDCl_3$) δ: 173.63, 166.59, 157.03, 139.55, 122.30, 74.49, 56.50, 55.93, 49.84, 49.03, 48.87, 48.71, 42.11, 39.53, 39.31, 38.31, 36.77, 36.36, 35.98, 35.60, 31.69, 31.66, 30.38, 29.06, 28.02, 27.91, 27.80, 24.07, 23.61, 22.56, 22.30, 20.83, 19.07, 18.47, 11.62. IR of 1.03 (KBr) v: 3313.7, 3267.4, 3107.3, 3080.3, 2953.0, 2935.6, 2906.7, 2889.4, 2866.2, 2850.8, 1707.0, 1649.1, 1550.8, 1533.4, 1467.8, 1415.8, 1338.6, 1246.0, 1193.9 1149.6, 1103.3, 1031.9 $cm^{-1}$ ESIMS m/z=595.4 $[M+Na]^+$ for $[C_{35}H_{56}N_2O_5Na]^+$. Melting Point: (160-170)° C.

Step c:

To a 10 mL single neck round bottom flask acid intermediate 1.03 (68 mg, 0.1196 mmol) was taken in anhydrous $CH_2Cl_2$ (3 mL) under nitrogen atmosphere at 0° C. To this cooled solution DIPC (18 µL, 0.1196 mmol) followed by DMAP (14.6 mg, 0.1196 mmol) and stirred at same temperature for 1 h. To this activated acid solution cabazitaxel (50 mg, 0.1196 mmol) was added and stirred for another 3 h at room temperature and TLC was checked. After completion the reaction mixture was quenched with water, extracted with CH2Cl2, dried over anhydrous sodium sulphate, concentrated under reduced pressure and purified by silica gel chromatography to obtain new taxane 1 in 92% yield. $^1H$ NMR of 1 (500 MHz, $CDCl_3$) δ: 8.05 (d, J=7.6 Hz, 1H), 7.56 (t, J=7.2 Hz, 1H), 7.45 (t, J=7.6 Hz, 2H), 7.38-7.17 (m, 5H), 6.34 (s, 1H), 6.14 (bs, 1H), 5.66-5.57 (bs, 1H), 5.57 (d, J=6.5 Hz, 1H), 5.41 (bs, 1H), 5.34 (s, 1H), 5.25 (s, 1H), 5.16 (s, 1H), 4.93 (d, J=9.2 Hz, 1H), 4.75 (s, 1H), 4.42 (m, 1H), 4.24 (d, J=8.2 Hz, 1H), 4.10 (d, J=8.3 Hz, 1H), 3.88-3.68 (m, 3H), 3.37 (s, 3H), 3.35-3.14 (m, 5H), 3.23 (s, 3H), 2.75-2.57 (m, 4H), 2.48-2.10 (m, 9H), 2.00-0.73 (m, 57H), 0.64 (s, 3H); $^{13}C$ NMR of 1 (100 MHz, $CDCl_3$) δ: 205.04, 171.82, 171.48, 169.72, 168.43, 166.97, 155.26, 139.65, 139.54, 134.88, 133.58, 130.15, 129.24, 128.87, 128.59, 128.29, 126.56, 122.60, 84.14, 82.44, 81.45, 80.61, 80.36, 78.82, 76.40, 74.69, 72.07, 57.06, 56.76, 56.64, 56.08, 49.97, 47.26, 43.27, 42.38, 42.26, 40.63, 40.52, 39.67, 39.47, 38.49, 36.92, 36.52, 36.13, 35.75, 34.80, 31.96, 31.86, 31.81, 30.92, 29.40, 28.14, 27.98, 26.63, 24.25, 23.78, 23.36, 22.79, 22.74, 22.53, 20.99, 19.29, 18.67, 14.42, 11.82, 10.35. IR of 1 (KBr) v: 3342.7, 2965.6, 2959.9, 2939.6, 2905.8, 2869.2, 2853.8, 2825.8, 1714.7, 1660.78, 1643.4, 1529.6, 1493.9, 1466.9, 1453.4, 1367.5, 1266.3, 1247.0, 1168.9, 1103.3, 1071.5, 1060.8, 1027.1, 998.2 $cm^{-1}$. ESIMS m/z=1412.6 $[M+Na]^+$ for $[C_{79}H_{111}N_3O_{18}Na]^+$. Melting Point: 143° C. Specific rotation $[\alpha]_D^{25}$=−14 (C=0.1, Methanol).

Example 3: Synthesis of Cholesterol Cabazitaxel Conjugate 2

Step a:

To a 250 mL single neck round bottom flask BocHNCH2COOH (2 g, 11.417 mmol), cholesterol 2.01 (4.414 g, 11.417 mmol) and DMAP (697 mg, 5.708 mmol) were taken in anhydrous dichloromethane (75 mL) under nitrogen atmosphere and stirred at 0° C. for 20 minutes. To this cooled solution DCC (2.591 g, 12.558 mmol) was added and stirred for another 24 h at room temperature and TLC was checked. After completion the reaction mixture was quenched with water, extracted with CHCl3, dried over anhydrous sodium sulphate, concentrated and purified by silica gel chromatography to obtain intermediate 2.02 in 60% yield. $^1H$ NMR of 2.02 (400 MHz, $CDCl_3$) δ: 5.36 (d, J=4.3 Hz, 1H), 4.98 (s, 1H), 4.72-4.59 (m, 1H), 3.86 (d, J=5.3 Hz, 2H), 2.36-0.65 (m, 52H of cholesterol back bone). $^{13}C$ NMR of 2.02 (125 MHz, $CDCl_3$) δ: 169.72, 155.67, 139.35, 122.90, 79.86, 75.15, 56.68, 56.14, 50.01, 42.66, 42.30, 39.71, 39.51, 38.01, 36.91, 36.55, 36.18, 35.77, 31.88, 31.84, 28.31, 28.20, 27.99, 27.69, 24.26, 23.82, 22.79, 22.54, 21.02, 19.26, 18.70, 11.84. IR of 2.02 (KBr) v: 3384.1, 2938.7, 2868.7, 1754.2, 1726.7, 1696.4, 1677.9, 1538.3, 1519.4, 1467.3, 1424.3, 1366.9, 1283.9, 1270.1, 1202.3, 1171.9, 1055.6, 1028.8, 1007.4 $cm^{-1}$ ESIMS m/z=566.2 $[M+Na]^+$ for $[C_{34}H_{57}NO_4Na]^+$ and 1109.5 $[2M+Na]^+$ for $2[C_{34}H_{57}NO_4]Na^+$. Melting Point: 84° C.

Scheme 2:
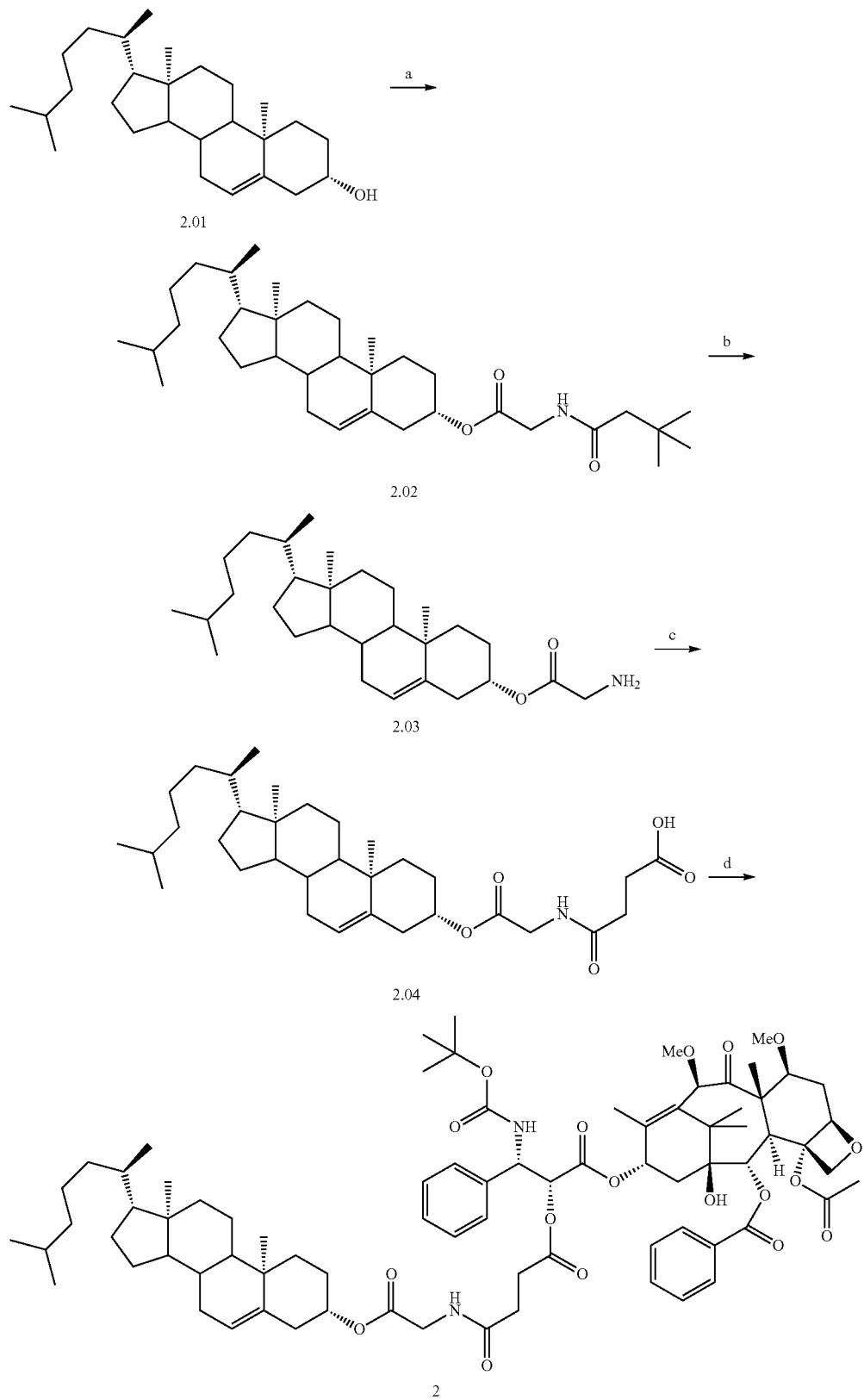
Reagents and conditions: (a) BocHNCH2COOH, DCC, DMAP, CH2Cl2, 0 oC to r.t, 12 h (b) TFA, CH2Cl2, 0 oC to r.t, 3 h (c) Succinic anhydride, Pyridine, 0 oC to r.t, 12 h (d) Cabazitaxel, DIPC, DMAP, CH2Cl2, 4 h Step b:

To a 25 mL single neck round bottom flask intermediate 2.02 (1 g crude, 1.838 mmol) was taken in anhydrous $CH_2Cl_2$ (5 mL) under nitrogen atmosphere at 0° C. To this reaction mixture TFA (2 mL) was added slowly over a period of 5 minute and stirred at room temperature for 3 h and TLC was checked. After completion the solvent was removed under reduced pressure and the crudeamine compound 2.03 was utilized for the next reaction without further purification.

Step c:

The crude amine compound 2.03 obtained from the previous reaction was diluted with dichloromethane (20 mL) and cooled to 0° C. To this ice cooled solution DIPEA (3 mL, 17.12 mmol) was added slowly followed by succinic anhydride (856 mg, 8.56 mmol) and stirred at room temperature for 12 h. After completion the reaction mixture was quenched with water (10 mL), washed with 1% HCl solution, extracted with $CH_2Cl_2$ (3×10 mL), dried over anhydrous $Na_2SO_4$ and purified by silica gel to obtain pure acid intermediate 2.04 in 88% yield. $^1H$ NMR of 2.04 (500 MHz, $CDCl_3$) δ: 6.47 (t, J=5 Hz, 1H), 5.35 (d, J=4.8 Hz, 1H), 4.65 (m, 1H), 3.99 (d, J=5.1 Hz, 2H), 2.68 (t, J=6.6 Hz, 2H), 2.56 (t, J=6.7 Hz, 2H), 2.37-0.57 (m, 43H of cholesterol back bone). $^{13}C$ NMR of 2.04 (125 MHz, $CDCl_3$) δ: 176.67, 172.28, 169.49, 139.18, 122.99, 75.57, 56.61, 56.07, 49.91, 42.24, 41.68, 39.64, 39.45, 37.89, 36.82, 36.49, 36.12, 35.76, 31.84, 31.75, 30.29, 29.66, 29.30, 28.19, 27.97, 27.59, 24.23, 23.80, 22.80, 22.53, 20.97, 19.24, 18.67, 11.81. IR of 2.04 (KBr) v: 3311.1, 2935.7, 2902.8, 2850.8, 1751.4, 1748.5, 1745.5, 1637.6, 1544.9, 1203.6 $cm^{-1}$. MALDI-TOF MS m/z=566.29 $[M+Na]^+$ for $[C_{33}H_{53}NO_5Na]^+$ and 582.27 $[M+K]^+$ for $[C_{33}H_{53}NO_5K]^+$. Melting point: (170-180)° C.

Step d:

To a 10 mL single neck round bottom flask acid intermediate 2.04 (137 mg, 0.2392 mmol) was taken in anhydrous $CH_2Cl_2$ (10 mL) under nitrogen atmosphere at 0° C. To this cooled solution DMAP (29 mg, 0.2392 mmol) followed by DIPC (37 μL, 0.2392 mmol) was added and stirred at same temperature for 1 h. To this activated acid solution cabazitaxel (100 mg, 0.1196 mmol) was added and stirred for another 4 h at room temperature and TLC was checked. After completion the reaction mixture was quenched with water, extracted with CHCl3, dried over anhydrous sodium sulphate, concentrated and purified by silica gel chromatography to obtain conjugate 2 which was further precipitated in acetone-Hexane to obtain pure product in 76% yield. $^1H$ NMR of 2 (400 MHz, $CDCl_3$) δ: 8.10 (d, J=7.6 Hz, 2H), 7.61 (t, J=7.3 Hz, 1H), 7.50 (t, J=7.6 Hz, 2H), 7.39 (t, J=7.5 Hz, 2H), 7.31 (d, J=7.5 Hz, 3H), 6.19 (bs, 2H), 5.62 (m, 2H), 5.44 (bs, 1H), 5.38 (d, J=4.1 Hz, 1H), 5.30 (s, 1H), 4.98 (d, J=9.3 Hz, 1H), 4.81 (s, 1H), 4.72-4.61 (m, 1H), 4.29 (d, J=8.0 Hz, 1H), 4.15 (d, J=8.3 Hz, 1H), 3.99 (m, 2H), 3.92-3.77 (m, 5H), 3.42 (s, 3H), 3.29 (s, 3H), 2.85-2.63 (m, 3H), 2.58-2.50 (m, 2H), 2.45-2.30 (m, 5H), 2.29-0.77 (m, 60H), 0.67 (s, 3H). $^{13}C$ NMR of 2 (100 MHz, $CDCl_3$) δ: 204.98, 171.64, 170.95, 169.67, 168.43, 166.98, 155.24, 139.55, 139.23, 137.28, 134.93, 133.56, 130.16, 129.29, 128.86, 128.59, 128.26, 126.56, 123.05, 84.17, 82.48, 81.49, 80.63, 80.40, 78.84, 76.42, 75.58, 74.74, 72.07, 57.12, 57.06, 56.78, 56.67, 56.10, 54.23, 50.04, 47.31, 43.28, 42.28, 41.67, 39.69, 39.48, 37.97, 36.90, 36.55, 36.14, 35.75, 34.86, 31.98, 31.87, 31.80, 30.69, 29.36, 28.17, 27.99, 27.68, 26.64, 24.24, 23.79, 22.79, 22.74, 22.54, 21.01, 19.27, 18.69, 14.45, 11.83, 10.35. IR of IO-502_01 (KBr) v: 3341.8, 2967.6, 2959.9, 2938.6, 2905.8, 2870.2, 2825.8, 1724.4, 1673.5, 166.5, 1661.7, 1615.4, 1573.9, 1563.3, 1523.8, 1519.0, 1497.7, 1494.9, 1464.0, 1455.3, 1440.8, 1384.9, 1326.1, 1316.4, 1267.2, 1247.0, 1224.8, 1194.9, 1169.8, 1130.3, 1103.3, 1071.5, 1060.8, 1027.1, 1018.4, 997.2, 949.0, 920.0 $cm^{-1}$. ESIMS m/z=1383.6 $[M+Na]^+$ for $[C_{78}H_{108}N_2O_{18}Na]^+$. Melting point: 141° C. Specific rotation $[\alpha]_D^{25}$=−16 (C=0.1, Methanol).

Example 4: Synthesis of Cholesterol Cabazitaxel Conjugate 6

Scheme 3:

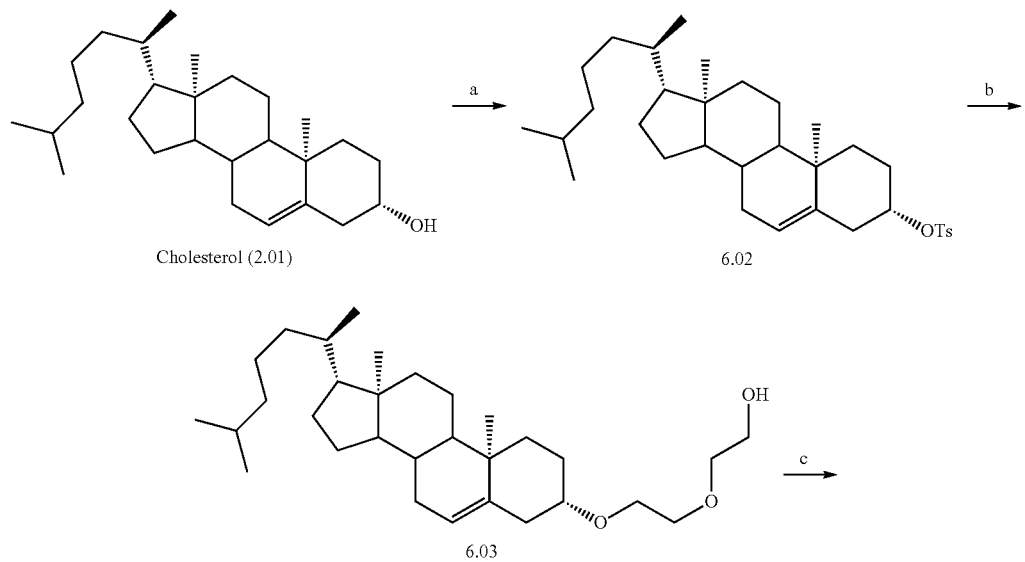

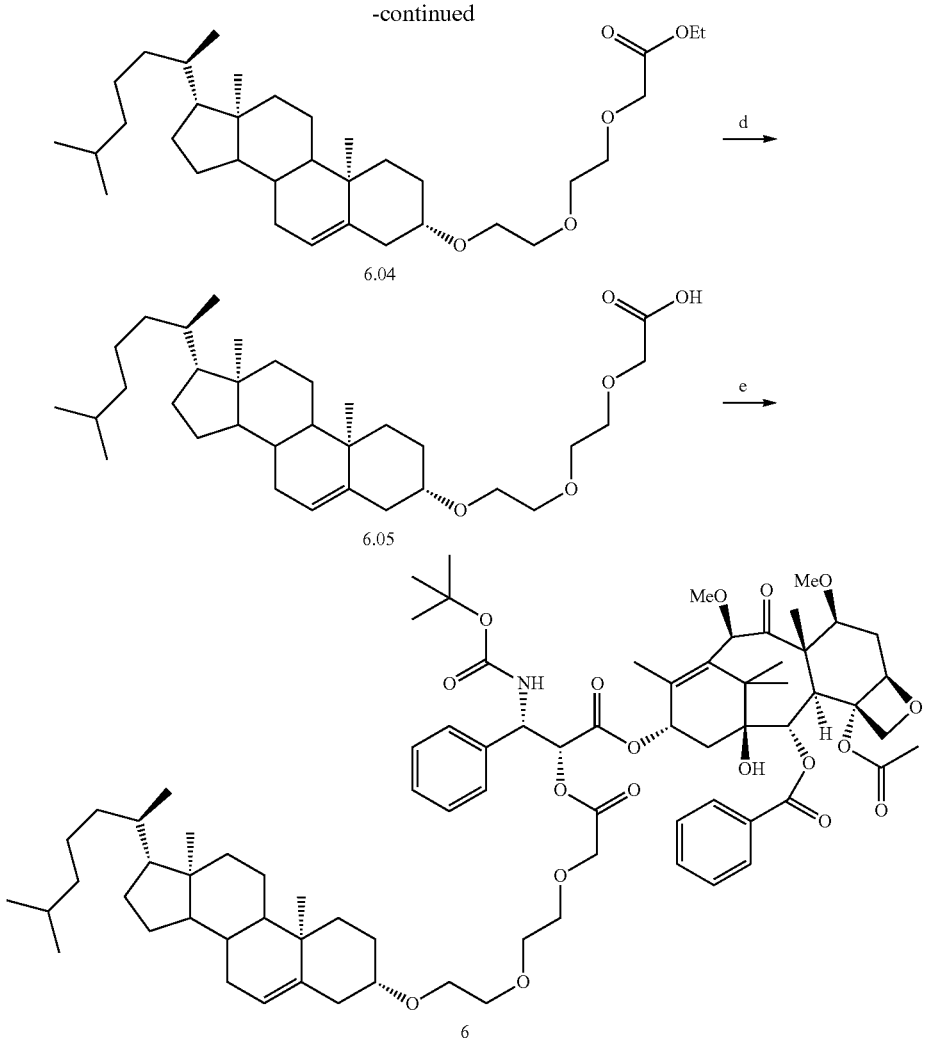

Reagents and conditions: (a) pTSCl, Pyridine, CH2Cl2, 0 oC, 4 h (b) Diethylene glycol, Dioxane, 80 oC, 4 h (c) NaH, THF, ethyl bromoacetate, 0 oC to r.t, 12 h (d) LiOH, THF/H2O (3:1), 0 oC to r.t, 3 h (e) Cabazitaxel, DIPC, DMAP, CH2Cl2, 4 h Step b:

To the solution of intermediate 6.02 (crude 6 g, 0.011 mol) in dioxane (30 mL) was added diethylene glycol (20 mL) and allowed to reflux for 6 h. After completion the reaction mixture was quenched with water (20 mL) and extracted with ethyl acetate. The organic layer was washed with water (3×50 mL) and brine (20 mL) successively and dried over anhydrous $Na_2SO_4$. The organic layer was concentrated under reduced pressure and purified by silica gel chromatography utilizing methanol-chloroform as mobile phase to obtain intermediate 6.03 as viscous liquid (52% over two steps). $^1$H NMR of 6.03 (500 MHz, $CDCl_3$) δ: 5.34-5.31 (m, 1H), 3.73-3.69 (m, 2H), 3.67-3.58 (m, 6H), 3.18 (tt, J=11.3, 4.5 H, 1H), 2.42-0.61 (m, 43H, Cholesterol backbone); $^{13}$CNMR of 6.03 (125 MHz, $CDCl_3$) δ: 140.69, 121.73, 79.62, 72.50, 70.72, 67.38, 61.81, 56.73, 56.11, 50.13, 42.29, 39.74, 39.48, 38.91, 37.15, 36.83, 36.15, 35.76, 31.91, 31.84, 28.26, 28.21, 27.99, 24.26, 23.79, 22.80, 22.54, 21.03, 19.35, 18.69, 11.83; ESIMS m/z=497.1 [M+Na]$^+$ for [$C_{31}H_{54}O_3Na$].

Step c:

To a 100 mL single neck round bottom flask NaH (594 mg, 14.84 mmol) was taken in THF (10 mL) under nitrogen atmosphere. The reaction was cooled to 0° C. under ice bath and a solution of intermediate 6.03 (2.35 g, 4.95 mmol) in THF (15 mL) was added slowly. The resulting solution was stirred for 1 h and ethyl bromoacetate was added slowly and stirred for 6 h at room temperature and TLC was checked. After completion the reaction mixture was cooled to 0° C., quenched with water and extracted with ethyl acetate (3×15 mL). The organic layer was washed with water and dried over anhydrous $Na_2SO_4$, concentrated and the residue was purified by silica gel chromatography to obtain intermediate 6.04 in 46% yield. $^1$H NMR of 6.04 (500 MHz, $CDCl_3$) δ: 5.34-5.29 (m, 1H), 4.19 (q, J=7.1 Hz, 2H), 4.14 (s, 2H), 3.73-3.66 (m, 4H), 3.62 (s, 4H), 3.16 (tt, J=11.3, 4.4 H, 1H), 2.41-0.58 (m, 46H, Cholesterol backbone); $^{13}$CNMR of 6.04 (125 MHz, $CDCl_3$) δ: 170.49, 140.93, 121.53, 79.48, 70.87, 70.84, 70.66, 68.72, 67.23, 60.78, 56.74, 56.11, 50.14, 42.28, 39.74, 39.48, 39.01, 37.20, 36.83, 36.15, 35.76, 31.91, 31.85, 28.31, 28.21, 27.98, 24.26, 23.79, 22.80, 22.53, 21.03, 19.35, 18.68, 14.19, 11.82. ESIMS m/z=583.2 [M+Na] for [$C_{35}H_{60}O_5Na$].

Step d:

To a 100 mL single neck round bottom flask ester intermediate 6.04 (1.272 g, 2.27 mmol) was taken in 20 mL of THF/H$_2$O (3:1) and cooled to 0° C. under ice bath. To this ice cooled solution LiOH (136 mg, 5.67 mmol) was added and was stirred at rt for 4 h and TLC was checked. After completion the reaction mixture was acidified by Na2HSO4, extracted with ethyl acetate. The organic layer was dried over anhydrous Na$_2$SO$_4$ and concentrated under vacuum and column performed to obtain pure acid intermediate 6.05 in 50% yield. $^1$H NMR of acid 6.05 (500 MHz, CDCl$_3$) δ: 5.31 (dd, J=13.6, 10.7 Hz, 1H), 4.15 (s, 2H), 3.77-3.59 (m, 8H), 3.17 (tt, J=11.3, 4.4 Hz, 1H), 2.45-0.85 (m, 41 H, from cholesterol back bone), 070 (s, 3H); $^{13}$C NMR of acid 6.05 (125 MHz, CDCl$_3$) δ: 172.25, 140.82, 121.70, 79.68, 71.49, 71.04, 70.13, 68.87, 67.06, 56.80, 56.19, 50.20, 42.35, 39.81, 39.54, 38.97, 37.22, 36.88, 36.21, 35.80, 31.96, 31.91, 28.28, 28.25, 28.03, 24.31, 23.85, 22.82, 22.57, 21.09, 19.39, 18.74, 11.87. ESIMS m/z=555.366 [M+Na]$^+$ for [C$_{33}$H$_{56}$O$_3$Na].

Step e:

To a 25 mL single neck round bottom flask acid 6.05 (25.46 mg, 0.047 mmol) was taken in anhydrous CH$_2$Cl$_2$ (5 mL) under nitrogen atmosphere at 0° C. To this cooled solution DIPC (7 µL, 0.0478 mmol) followed by DMAP (5.84 mg, 0.0478 mmol) and stirred at same temperature for 2 h. To this activated acid solution cabazitaxel (20 mg, 0.0239 mmol) was added and stirred for another 3 h at room temperature and TLC was checked. After completion the reaction mixture was quenched with water, extracted with CHCl3, dried over anhydrous sodium sulphate, concentrated and purified by silica gel chromatography to obtain conjugate 6 in 92% yield. $^1$H NMR of 6 (400 MHz, CDCl$_3$) δ: 8.09 (d, J=7.8 Hz, 2H), 7.58 (t, J=7.3 Hz, 1H), 7.47 (t, J=7.6 Hz, 2H), 7.37 (t, J=7.6 Hz, 2H), 7.33-7.26 (m, 3H), 6.24 (t, J=8.9 Hz, 1H), 5.73 (bs, 1H), 5.63 (d, J=7.0 Hz, 1H), 5.47 (bs, 1H), 5.35 (d, J=2.6 Hz, 1H), 5.29 (d, J=5.1 Hz, 1H), 4.97 (d, J=9.1 Hz, 1H), 4.80 (s, 1H), 4.33-4.24 (m, 1H), 4.22 (s, 1H), 4.18-4.09 (m, 2H), 3.92-3.79 (m, 2H), 3.79-3.54 (m, 8H), 3.41 (s, 3H), 3.28 (s, 3H), 3.17-3.05 (m, 1H), 2.74-2.62 (m, 1H), 2.42 (s, 3H), 2.37-0.73 (m, 66H from cholesterol back bone), 0.64 (s, 3H); $^{13}$CNMR of 6 (100 MHz, CDCl$_3$) δ: 204.97, 169.84, 169.66, 168.00, 167.00, 155.30, 140.86, 139.50, 137.22, 134.99, 133.54, 130.16, 129.27, 128.89, 128.61, 128.21, 126.52, 121.58, 84.17, 82.50, 81.58, 80.66, 80.29, 79.51, 78.82, 77.32, 76.46, 74.69, 72.28, 70.88, 70.62, 68.16, 67.16, 57.07, 56.81, 56.75, 56.13, 54.11, 50.16, 47.33, 43.33, 42.29, 39.75, 39.49, 38.98, 37.19, 36.83, 36.16, 35.75, 34.95, 32.01, 31.92, 31.86, 28.29, 28.19, 28.15, 27.98, 26.63, 24.26, 23.79, 22.78, 22.53, 21.03, 20.99, 19.34, 18.69, 14.41, 11.82, 10.35. Melting Point of 6: 138-142° C. ESIMS m/z=1372.5 [M+Na]$^+$ for [C$_{78}$H$_{111}$NO$_{18}$Na]$^+$ Specific rotation [∝]$_D^{25}$=−15 (C=0.1, Methanol).

Example 5: Synthesis of Cholesterol Cabazitaxel Conjugate 7

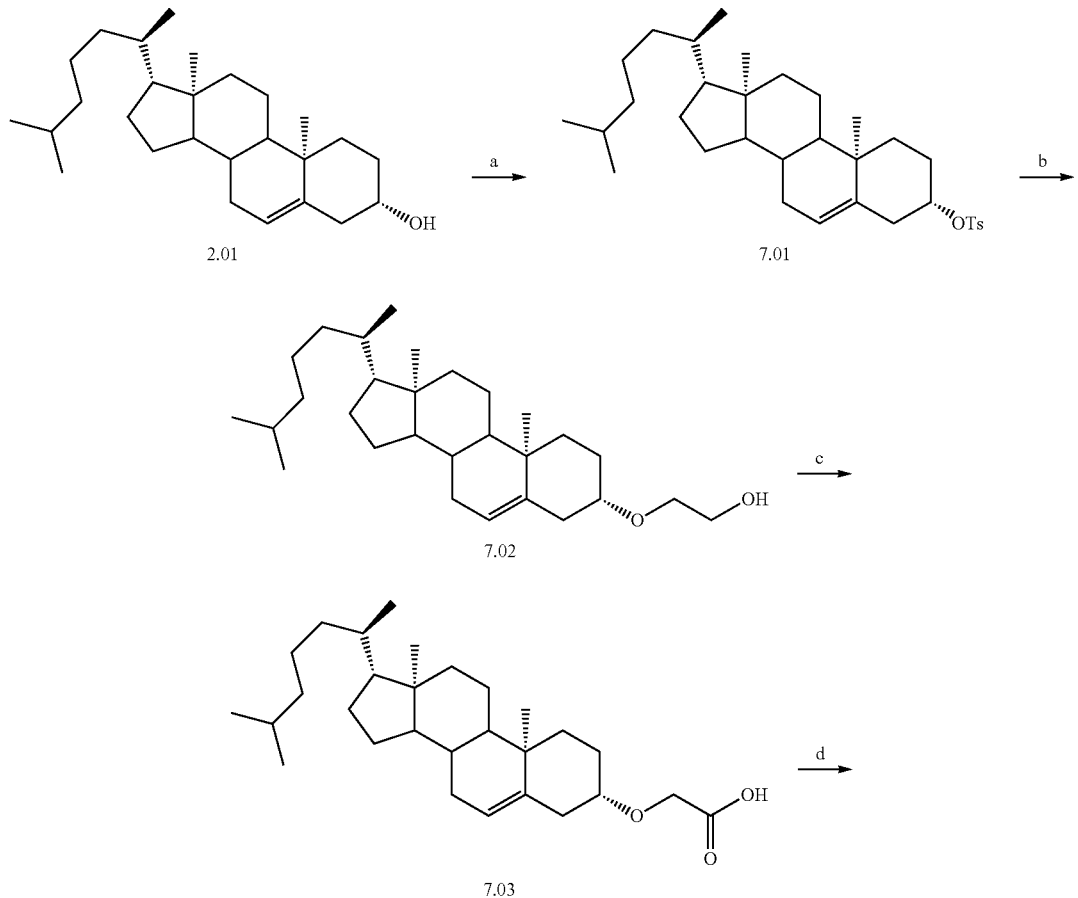

Scheme 4:

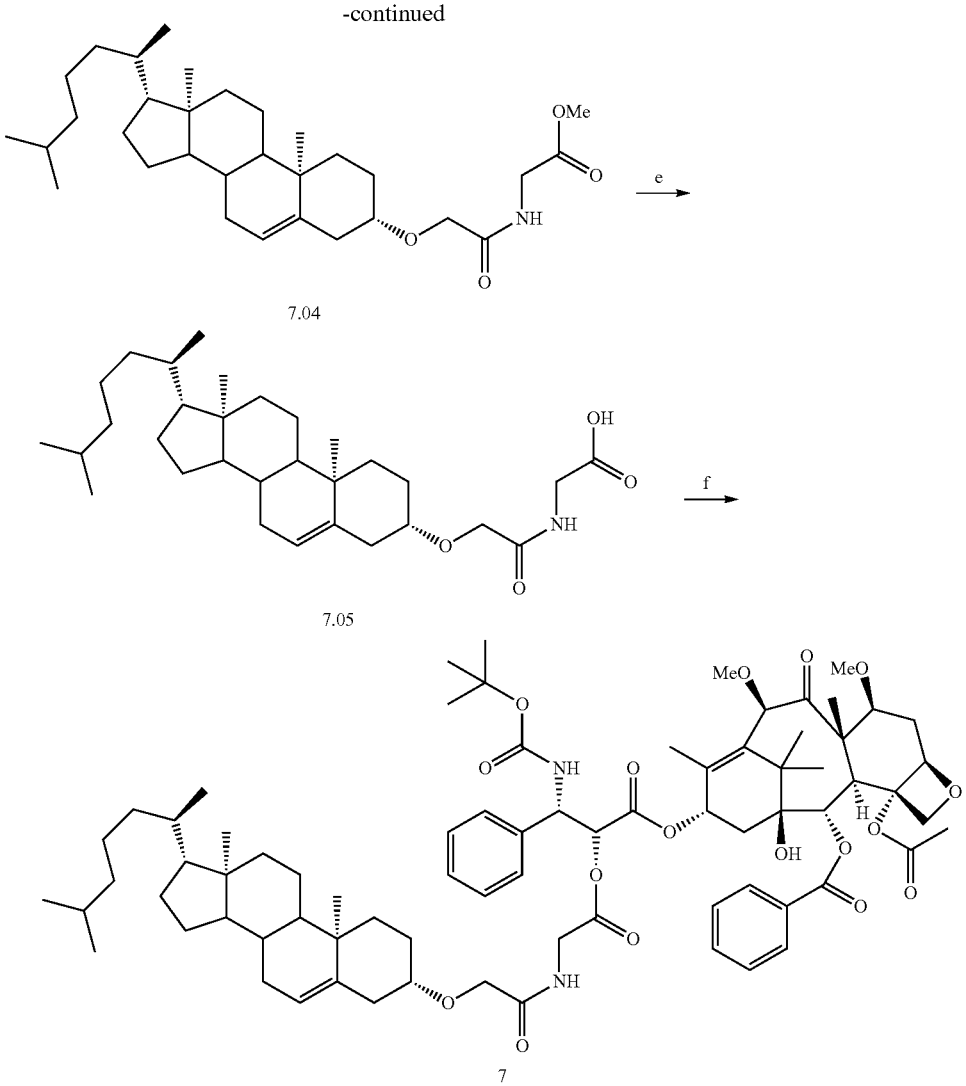

Reagents and conditions: (a) TsCl, Pyridine, 0° C., 4 h (b) Ethylene glycol, Dioxane, 80° C., 6 h (c) CrO3•H2SO4•H2O, Acetone-THF r.t, 1 h (d) EDCI, HOBT, CH2Cl2, 0° C. to r.t, 12 h (e) LiOH, THF/H2O r.t, 3 h (f) Cabazitaxel, DIPC, DMAP, CH2Cl2, 0° C. to r.t, 5 h Step a:

To an ice cooled solution of cholesterol 2.01 (10 g, 0.026 mol) in dichloromethane (45 mL) was added pyridine (15 mL) and stirred for 15 minutes. To this solution p-toluene sulphonyl chloride (9.8 g, 0.052 mol) was added and stirred for 6 h at 0° C. and TLC was checked. After completion the reaction mixture was diluted with $CHCl_3$ (20 mL) and washed with 1N HCl (3×50 mL) and brine (20 mL) successively. The organic layer was dried over anhydrous $Na_2SO_4$ and concentrated under vacuum to afford intermediate 7.01 and directly move for the next reaction without further purification.

Step b:

To the solution of crude intermediate 7.01 (10 g, 0.018 mol) in dioxane (45 mL) was added ethylene glycol (15 mL) and refluxed for 4 h. The TLC was checked. After completion the reaction mixture was extracted with ethyl acetate and washed with water (3×50 mL) and brine (20 mL) successively. The organic layer was dried over anhydrous $Na_2SO_4$, concentrated under vacuum and column purified to afford intermediate 7.02 in 55% yield over two steps. $^1$H NMR of 7.02 (400 MHz, $CDCl_3$) δ: 5.33 (d, J=4 Hz, 1H), 3.70 (t, J=4 Hz, 2H), 3.57 (t, J=4 Hz, 2H), 3.23-3.12 (m, 1H), 2.42-0.56 (m, 44H cholesterol back bone); $^{13}$C NMR of 7.02 (125 MHz, $CDCl_3$) δ: 140.71, 121.73, 79.45, 68.95, 62.07, 56.77, 56.17, 50.18, 42.32, 39.78, 39.51, 39.10, 37.17, 36.85, 36.18, 35.77, 31.93, 31.56, 28.41, 28.21, 27.99, 24.27, 23.82, 22.79, 22.54, 21.06, 19.35, 18.70, 11.84. IR of 7.02 (KBr) v: 3452.2, 2932.9, 2862.7, 1632.5, 1466.2, 1365.8, 1275.5, 1110.6, 1062.8 $cm^{-1}$. ESIMS m/z=453.1 $[M+Na]^+$ for $[C_{29}H_{50}O_2Na]^+$ and 883.4 $[2M+Na]^+$ for $2[C_{29}H_{50}O_2]Na^+$ Melting Point of 7.02: 91° C.

Step c:

To solution of intermediate 7.02 (1 g, 2.322 mmol) in acetone-THF mixture (30+5 mL) was added chromic acid (4 mL) dropwise under vigorous stirring at room temperature for 1 h and TLC was checked. After completion the reaction mixture was filtered through a thin pad of silica gel, washed with acetone, dried on Na2SO4 and concentrated under reduced pressure and diluted with water (10 mL) and extracted with EtOAc (2×10 mL). The organic layer was dried over anhydrous $Na_2SO_4$, concentrated and column purified to afford intermediate 7.03 in 83% yield. $^1$H NMR of 7.03 (500 MHz, CDCl$_3$) δ: 5.42-5.36 (m, 1H), 4.18 (s, 2H), 3.38-3.29 (m, 1H), 2.43-0.65 (m, 43H, from cholesterol back bone). $^{13}$C NMR of 7.03 (125 MHz, CDCl$_3$) δ: 173.95, 139.98, 122.33, 80.33, 65.14, 56.69, 56.10, 50.06, 42.27, 39.70, 39.48, 38.62, 36.95, 36.73, 36.14, 35.75, 31.88, 31.81, 29.67, 28.19, 28.03, 27.98, 24.25, 23.79, 22.80, 22.53, 21.02, 19.30, 18.68, 11.82. ESIMS m/z=443.3 [M−1]$^+$ for [C$_{29}$H$_{48}$O$_3$].

Step d:

To a 50 mL single neck round bottom flask acid intermediate 7.03 (500 mg, 1.124 mmol) was taken in anhydrous CH$_2$Cl$_2$ (15 mL) under nitrogen atmosphere at 0° C. To this cooled solution EDCI (430 mg, 2.248 mmol) followed by HOBT (303 mg, 2.248 mmol) and stirred at same temperature for 1 h. To this activated acid solution DIPEA (0.8 mL, 4.497) followed by glycine methyl ester (282 mg, 2.248 mmol) was added and stirred for another 5 h at room temperature and TLC was checked. After completion the reaction mixture was quenched with water, extracted with CHCl3, dried over anhydrous sodium sulphate, concentrated and purified by silica gel chromatography to obtain intermediate 7.04 in 92% yield. $^1$H NMR of 7.04 (500 MHz, CDCl$_3$) δ: 7.11 (s, 1H), 5.34 (s, 1H), 4.07 (s, 2H), 4.01 (s, 1H), 3.75 (s, 3H), 3.27-3.17 (m, 1H), 2.40-0.57 (m, 43H, Cholesterol backbone). $^{13}$C NMR of 7.04 (125 MHz, CDCl$_3$) δ: 170.66, 170.10, 140.05, 122.27, 80.29, 67.40, 56.69, 56.10, 52.38, 50.07, 42.29, 40.51, 39.71, 39.49, 38.87, 36.97, 36.76, 36.15, 35.76, 31.89, 31.83, 28.26, 28.21, 27.99, 24.26, 23.79, 22.80, 22.54, 21.04, 19.34, 18.69, 11.83. ESIMS m/z=538.1 [M+Na]$^+$ for [C$_{33}$H$_{57}$NO$_4$Na] and 1053.3 [2M+Na]$^+$ for 2[C$_{33}$H$_{57}$NO$_4$]Na.

Step e:

To a 50 mL single neck round bottom flask ester compound 7.04 (560 mg, 1.086 mmol) was taken in THF/water (12 mL, 3:1) and cooled to 0° C. To this ice cooled solution LiOH (136 mg, 3.258 mmol) was added and stirred at room temperature for 3 h and TLC was checked. After completion the reaction mixture was acidified with saturated NaHSO$_4$ up to P$^H$ 3 and extracted with Ethyl acetate (3×10 mL). The combined organic layer was dried over anhydrous Na$_2$SO$_4$ and column purified to obtain pure acid 7.05 in good yield (390 mg, 65%). $^1$H NMR of 7.05 (500 MHz, CDCl$_3$) δ: 7.20 (s, 1H), 5.34 (s, 1H), 4.10 (s, 1H), 4.03 (s, 1H), 3.29-3.17 (m, 1H), 2.39-0.61 (m, 43H, from cholesterol back bone). $^{13}$C NMR of 7.05 (125 MHz, CDCl$_3$+5 μL CD3OD) δ: 170.89, 170.82, 170.06, 139.97, 122.25, 80.28, 67.28, 56.64, 56.05, 50.02, 42.24, 40.47, 40.37, 39.66, 39.44, 38.80, 36.91, 36.71, 36.10, 35.72, 31.84, 31.78, 28.19, 28.16, 27.95, 24.21, 23.74, 22.75, 22.49, 20.99, 19.28, 18.64, 11.78. IR of 7.05 (KBr) ν: 3388.9, 2900.9, 2868.1, 2850.8, 2632.8, 1724.4, 1710.8, 1629.8, 1544.9, 1438.9, 1350.2, 1240.2, 1226.7, 1116.8 cm$^{-1}$ ESIMS m/z=500.3 [M]$^+$ for [C$_{31}$H$_{51}$NO$_4$].

Step f:

To a 10 mL single neck round bottom flaskacid intermediate 7.05 (23.9 mg, 0.0478 mmol) was taken in anhydrous CH$_2$Cl$_2$ (2 mL) under nitrogen atmosphere at 0° C. To this cooled solution DIPC (7 μL, 0.0478 mmol) followed by DMAP (5.84 mg, 0.0478 mmol) and stirred at same temperature for 1 h. To this activated acid solution cabazitaxel (20 mg, 0.0239 mmol) was added and stirred for another 3 h at room temperature and TLC was checked. After completion the reaction mixture was quenched with water, extracted with CHCl3, dried over anhydrous sodium sulphate, concentrated and purified by silica gel chromatography to obtain new taxane 7 in 75% yield. $^1$H NMR of 7 (400 MHz, CDCl$_3$) δ: 8.11 (d, J=7.8 Hz, 2H), 7.61 (t, J=7.5 Hz, 1H), 7.50 (t, J=7.7 Hz, 2H), 7.40 (t, J=7.4 Hz, 2H), 7.33 (d, J=7 Hz, 1H), 7.28 (d, J=7.4 Hz, 2H), 7.05 (t, J=5.5 Hz, 1H), 6.25 (t, J=7 Hz, 1H), 5.64 (d, J=7.0 Hz, 1H), 5.48 (bs, 1H), 5.35 (s, 3H), 4.99 (d, J=9.4 Hz, 1H), 4.82 (s, 1H), 4.31 (d, J=8.4 Hz, 1H), 4.21-4.10 (m, 3H), 4.00 (s, 2H), 4.03-3.93 (m, 1H), 3.89 (dd, J=10.6, 6.5 Hz, 1H), 3.83 (t, J=9.2 Hz, 2H), 3.44 (s, 3H), 3.30 (s, 3H), 3.30-3.17 (m, 1H), 2.70 (m, 1H), 2.47-0.74 (m, 66H), 0.68 (d, J=8.8 Hz, 2H). $^{13}$CNMR of 7 (100 MHz, CDCl$_3$) δ: 205.02, 170.73, 169.76, 169.01, 167.94, 167.12, 155.17, 140.08, 139.44, 135.18, 133.67, 130.25, 129.32, 129.11, 128.72, 128.48, 126.40, 122.43, 84.24, 82.59, 81.68, 80.75, 80.67, 80.38, 78.95, 75.22, 74.81, 72.45, 67.40, 57.25, 57.16, 56.91, 56.78, 56.21, 50.16, 47.42, 43.43, 42.38, 40.39, 39.79, 39.58, 38.97, 37.04, 36.85, 36.24, 35.84, 35.01, 32.10, 31.99, 31.93, 28.29, 28.21, 28.08, 26.75, 24.35, 23.89, 23.05, 22.88, 22.63, 22.41, 21.13, 21.08, 19.43, 18.78, 14.52, 11.92, 10.45. IR of 7 (KBr) ν: 1723.5, 1677.2, 1617.4, 1573.0, 1568.2, 1464.0, 1384.9, 1365.6, 1265.4, 1247.0, 1104.3 cm$^{-1}$ Melting Point of 7: 155-160° C. ESIMS m/z=1341.6 [M+Na]$^+$ for C76H106N2O17Na. Specific rotation [∝]$_D^{25}$=−27 (C=0.1, Methanol).

Example 6: Synthesis of Cholesterol Taxane Conjugate 8

Step a:

To a 250 mL single neck round bottom flask cholesterol (10 g, 25.862 mmol) was taken in THF (60 mL) under nitrogen atmosphere at 0° C. Sodium hydride (2.068 g, 51.724 mmol) was added by pinch to the reaction mixture over a period of 10 minutes. The resulting solution was stirred for 20 minutes and methyl acrylate (11.6 mL, 129.31 mmol) in THF (20 mL) was added slowly and stirred for 2 h at 0° C. and TLC was checked. After completion the reaction mixture was cooled to 0° C. and quenched with water and extracted with ethyl acetate, dried over anhydrous Na2SO4, concentrated and column purified by silica gel chromatography to obtain product 8.01 in 20% yield.

Step b:

To a 50 mL single neck round bottom flask ester intermediate 8.01 (1 g, 4.231 mmol) was taken in THF/water (12 mL, 3:1) and cooled to 0° C. To this ice cooled solution LiOH (355 mg 8.462 mmol) was added and stirred at room temperature for 2 h and TLC was checked. After completion the reaction mixture was acidified with saturated NaHSO$_4$ up to P$^H$ 3 and extracted with Ethyl acetate (3×10 mL). The combined organic layer was dried over anhydrous Na$_2$SO$_4$ and column purified to obtain pure compound 8.02 in good yield (80%). $^1$H NMR of 8.02 (400 MHz, CDCl$_3$) δ: 5.36-5.29 (m, 1H), 3.74 (t, J=8 Hz, 2H), 3.23-3.13 (m, 1H), 2.60 (td, J=8 Hz, J=4 Hz, 2H), 2.39-0.56 (m, 43H, Cholesterol back bone). $^{13}$CNMR of 8.02 (100 MHz, CDCl$_3$) δ: 176.80, 140.71, 121.88, 79.66, 63.11, 56.84, 56.24, 50.24, 42.39, 39.85, 39.59, 38.98, 37.23, 36.91, 36.27, 35.86, 35.30, 32.01, 31.95, 28.31, 28.08, 24.36, 23.91, 22.89, 22.64, 21.14, 19.44, 18.79, 11.93. IR of 8.02 (KBr) ν: 3784.1, 2939.7, 1713.8, 1600.0, 1444.3, 1230.7, 1107.5 cm$^{-1}$ ESIMS m/z=481 [M+Na]$^+$ for [C$_{30}$H$_{50}$O$_3$Na]$^+$.

Scheme 5:
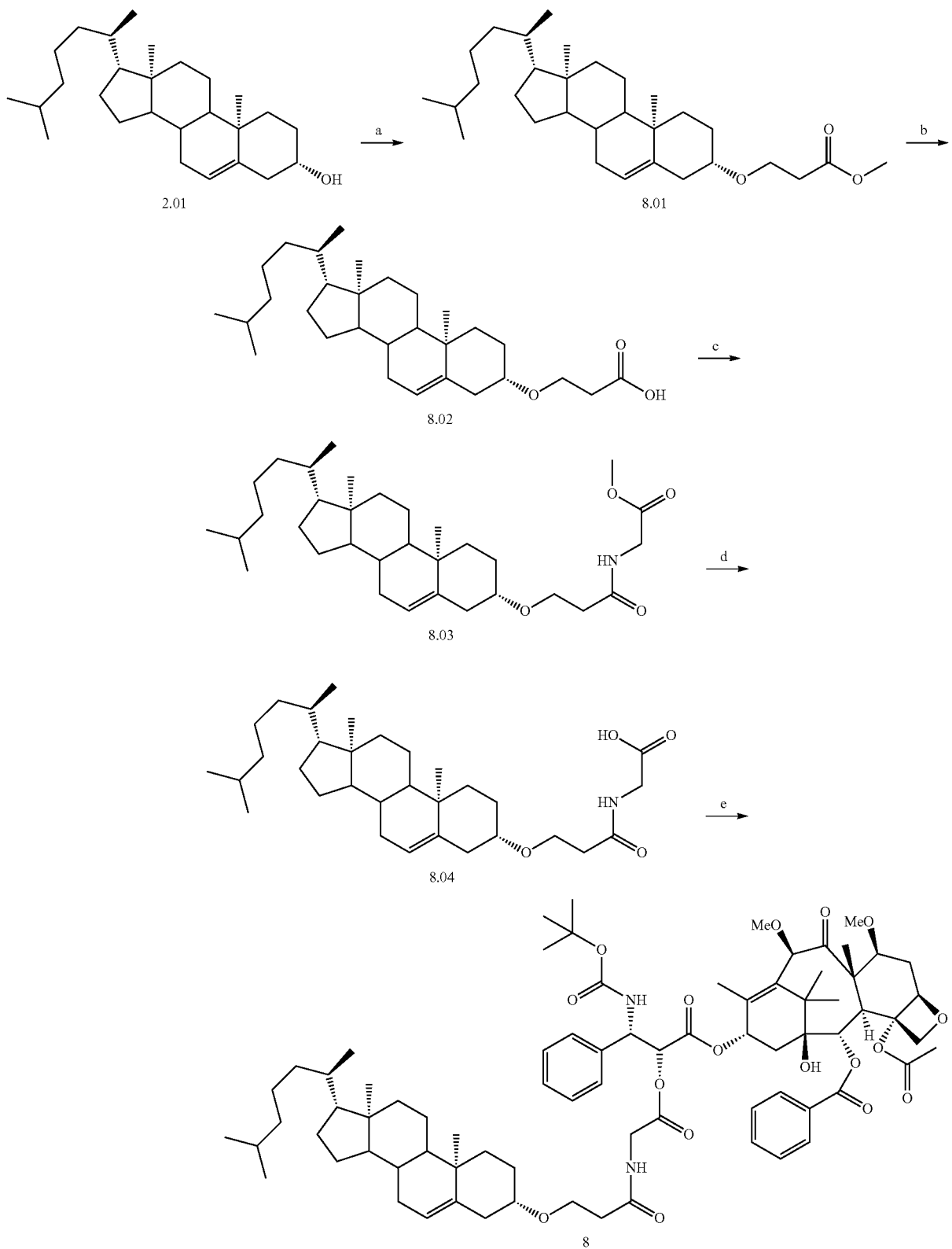
Reagents and conditions: (a) NaH, THF, Methyl acrylate, 0° C., 2 h (b) LiOH, THF/H2O r.t, 3 h (3) EDCI, HOBT, CH2Cl2, 0° C. to r.t, 12 h, (d) LiOH, THF/H2O r.t, 3 h (e) Cabazitaxel, DIPC, DMAP, CH2Cl2, r.t, 12 h Step c:

To a 100 mL single neck round bottom flask acid intermediate 8.02 (1 g, 2.179 mmol) was taken in anhydrous dichloromethane (15 mL) under nitrogen atmosphere at 0° C. To this cooled solution DIPC (0.67 ml, 4.359 mmol) followed by DMAP (133 mg, 1.089 mmol) were added and stirred at same temperature for 0.5 h. To this activated acid solution DIPEA (1.5 mL. 8.716 mmol) followed by glycine methyl ester (547 mg, 4.359 mmol) was added and stirred for another 6 h at room temperature and TLC was checked. After completion the reaction mixture was quenched with water, extracted with CHCl3 (2×10 mL), dried over anhydrous sodium sulphate, concentrated and purified by silica gel chromatography to obtain intermediate 8.03 as gummy solid (92% yield). $^1$H NMR of 8.03 (400 MHz, CDCl$_3$) δ: 7.02 (bs, 1H), 5.31-5.25 (m, 1H), 3.99 (d, J=5 Hz, 2H), 3.69 (s, 3H), 3.71-3.62 (m, 2H), 3.21-3.10 (m, 1H), 2.49 (t, J=5.6 Hz, 2H), 2.37-0.55 (m, 43H, Cholesterol back bone). $^{13}$CNMR of 8.03 (100 MHz, CDCl$_3$) δ: 172.05, 170.41, 140.60, 121.96, 79.56, 63.72, 56.82, 56.22, 52.34, 50.22, 42.39, 42.30, 41.31, 39.83, 39.58, 38.95, 37.21, 36.99, 36.93, 36.25, 35.85, 32.00, 31.95, 28.33, 28.30, 28.08, 24.35, 23.89, 23.51, 22.88, 22.62, 21.13, 19.42, 18.78, 11.92. IR of 8.03 (KBr) ν: 3787.1, 3338.9, 2934.0, 1742.6, 1643.4, 1451.7, 1208.4, 1104.9 cm$^{-1}$ ESIMS m/z=552 [M+Na]$^+$ for [C$_{33}$H$_{55}$NO$_4$Na]$^+$.

Step d:

To a 50 mL single neck round bottom flask ester intermediate 8.03 (1 g, 1.887 mmol) was taken in THF/water (21 mL, 3:1) and cooled to 0° C. To this ice cooled solution LiOH (230 mg, 5.662 mmol) was added and stirred at room temperature for 3 h and TLC was checked. After completion the reaction mixture was acidified with saturated NaHSO$_4$ up to P$^H$ 3 and extracted with Ethyl acetate (3×10 mL). The combined organic layer was dried over anhydrous Na$_2$SO$_4$ and column purified to obtain pure compound 8.04 as white solid (800 mg, 82%). $^1$H NMR of 8.04 (400 MHz, CDCl$_3$) δ: 5.32 (d, J=4.8 Hz, 1H), 4.03 (d, J=4.8 Hz, 2H), 3.72 (dd, J=12.4, 7.9 Hz, 2H), 3.25-3.14 (m, 1H), 2.51 (t, J=5.5 Hz, 2H), 2.37-0.55 (m, 43H, Cholesterol back bone). $^{13}$CNMR of 8.04 (100 MHz, CDCl$_3$) δ: 172.76, 172.49, 140.54, 121.98, 79.67, 63.68, 56.82, 56.24, 50.22, 42.71, 42.39, 41.67, 39.84, 39.59, 38.89, 37.20, 36.90, 36.77, 36.26, 35.86, 32.00, 31.95, 28.30, 28.26, 28.08, 24.36, 23.91, 23.28, 22.89, 22.63, 21.14, 19.43, 18.79, 11.94. IR of 8.04 (KBr) ν: 3366.9, 3309.0, 2954.1, 2907.8, 2868.3, 2849.9, 1933.7, 1718.6, 1601.9, 1536.4, 1465.9, 1443.7, 1365.6, 1331.9, 1280.8, 1224.8, 1202.7, 1104.3 cm$^{-1}$. Melting Point: 146° C. ESIMS m/z=538.2 [M+Na]$^+$ for [C$_{32}$H$_{53}$NO$_4$Na]$^+$ and 1053.6 [2M+Na]$^+$ for 2[C$_{32}$H$_{53}$NO$_4$]Na$^+$.

Step e:

To a 10 mL single neck round bottom flask acid intermediate 8.04 (184 mg, 0.3588 mmol) was taken in anhydrous CH$_2$Cl$_2$ (10 mL) under nitrogen atmosphere at 0° C. To this cooled solution DIPC (111 μL, 0.7176 mmol) followed by DMAP (58.4 mg, 0.4758 mmol) and stirred at same temperature for 0.5 h. To this activated acid solution cabazitaxel (200 mg, 0.2392 mmol) was added and stirred for another 5 h at room temperature and TLC was checked. After completion the reaction mixture was quenched with water, extracted with CHCl3, dried over anhydrous sodium sulphate, concentrated and purified by silica gel chromatography to obtain new taxane 8 as white solid which was further precipitated in acetone-hexane to obtain pure product in 91% yield. $^1$H NMR of 8 (400 MHz, CDCl$_3$) δ: 8.09 (d, J=7.6 Hz, 4H), 7.58 (t, J=7.4 Hz, 2H), 7.47 (t, J=7.6 Hz, 4H), 7.38 (t, J=7.4 Hz, 4H), 7.29 (dd, J=16.6, 7.4 Hz, 6H), 7.05 (t, J=5.0 Hz, 2H), 6.23 (t, J=8.8 Hz, 2H), 5.62 (d, J=7.0 Hz, 2H), 5.50-5.29 (m, 8H), 4.97 (d, J=8.8 Hz, 2H), 4.78 (s, 2H), 4.29 (d, J=8.4 Hz, 2H), 4.18-4.08 (m, 6H), 3.91-3.78 (m, 4H), 3.73-3.61 (m, 4H), 3.41 (s, 6H), 3.28 (s, 6H), 3.17 (dt, J=15.6, 5.6 Hz, 2H), 2.74-2.62 (m, 2H), 2.61 (s, 1H), 2.46 (t, J=5.5 Hz, 4H), 2.43-0.75 (m, 153H), 0.64 (d, J=6.7 Hz, 6H). $^{13}$CNMR of 8 (100 MHz, CDCl$_3$) δ: 204.95, 172.02, 169.70, 169.25, 167.87, 167.02, 155.12, 140.43, 139.34, 136.96, 135.12, 133.57, 130.16, 129.25, 129.00, 128.63, 128.37, 126.35, 121.93, 84.14, 82.51, 81.59, 80.71, 80.54, 79.50, 78.82, 77.20, 76.45, 75.08, 74.73, 72.27, 63.51, 57.17, 57.05, 56.80, 56.69, 56.12, 54.02, 53.77, 50.12, 47.32, 43.34, 42.28, 41.04, 39.72, 39.48, 38.82, 37.12, 36.82, 36.76, 36.15, 35.74, 34.95, 32.01, 31.91, 31.86, 31.71, 29.24, 28.21, 28.18, 28.13, 27.99, 26.67, 24.27, 23.79, 22.80, 22.54, 21.06, 21.01, 19.39, 18.70, 14.31, 11.82, 10.36, −0.03. IR of 8 (KBr) ν: 3334.6, 2934.2, 1716.9, 1520.0, 1454.5, 1367.8, 1264.3, 1245.7, 1172.5, 1102.6, 1068.5 cm$^{-1}$. Melting Point: 143° C. ESIMS m/z=1355.2 [M+Na]$^+$ for [C$_{77}$H$_{108}$N$_2$O$_{17}$Na]$^+$. Specific rotation [∝]$_D^{25}$=−26 (C=0.1, Methanol).

Example 7: Synthesis of Cholesterol Taxane Conjugate 14

Step a:

To an ice cooled solution of cholesterol (10 g, 0.026 mol) in CH$_2$Cl$_2$ (45 mL) was added pyridine (15 mL) and stirred for 15 minutes. To this solution p-toluene sulphonyl chloride (9.8 g, 0.052 mol) was added and stirred for 6 h at 0° C. and TLC was checked. After completion the reaction mixture was diluted with CHCl$_3$ (20 mL) and washed with 1N HCl (3×50 mL) and brine (20 mL) successively. The organic layer was dried over anhydrous Na$_2$SO$_4$ and concentrated under vacuum to afford intermediate 14.01 and directly move for the next reaction without further purification.

Step b:

To the solution of crude intermediate 14.01 (0.026 mol) in dioxane (45 mL) was added ethylene glycol (15 mL) and refluxed for 4 h. The TLC was checked. After completion the reaction mixture was extracted with ethyl acetate and washed with water (3×50 mL) and brine (20 mL) successively. The organic layer was dried over anhydrous Na$_2$SO$_4$ and concentrated under vacuum and column purified to afford intermediate 14.02 as white solid (55% yield over two steps). $^1$H NMR of 14.02 (400 MHz, CDCl$_3$) δ: 5.33 (d, J=4 Hz, 1H), 3.70 (t, J=4 Hz, 2H), 3.57 (t, J=4 Hz, 2H), 3.23-3.12 (m, 1H), 2.42-0.56 (m, 44H cholesterol back bone); $^{13}$C NMR of 14.02 (125 MHz, CDCl$_3$) δ: 140.71, 121.73, 79.45, 68.95, 62.07, 56.77, 56.17, 50.18, 42.32, 39.78, 39.51, 39.10, 37.17, 36.85, 36.18, 35.77, 31.93, 31.89, 31.56, 28.41, 28.21, 27.99, 24.27, 23.82, 22.79, 22.54, 21.06, 19.35, 18.70, 14.08, 11.84. IR of 14.02 (KBr) ν: 3452.2, 2932.9, 2862.7, 1632.5, 1466.2, 1365.8, 1275.5, 1110.6, 1062.8, cm$^{-1}$. ESIMS m/z=453.1 [M+Na]$^+$ for [C$_{29}$H$_{50}$O$_2$Na]$^+$. Melting Point of 14.02: 91° C.

Scheme 6:
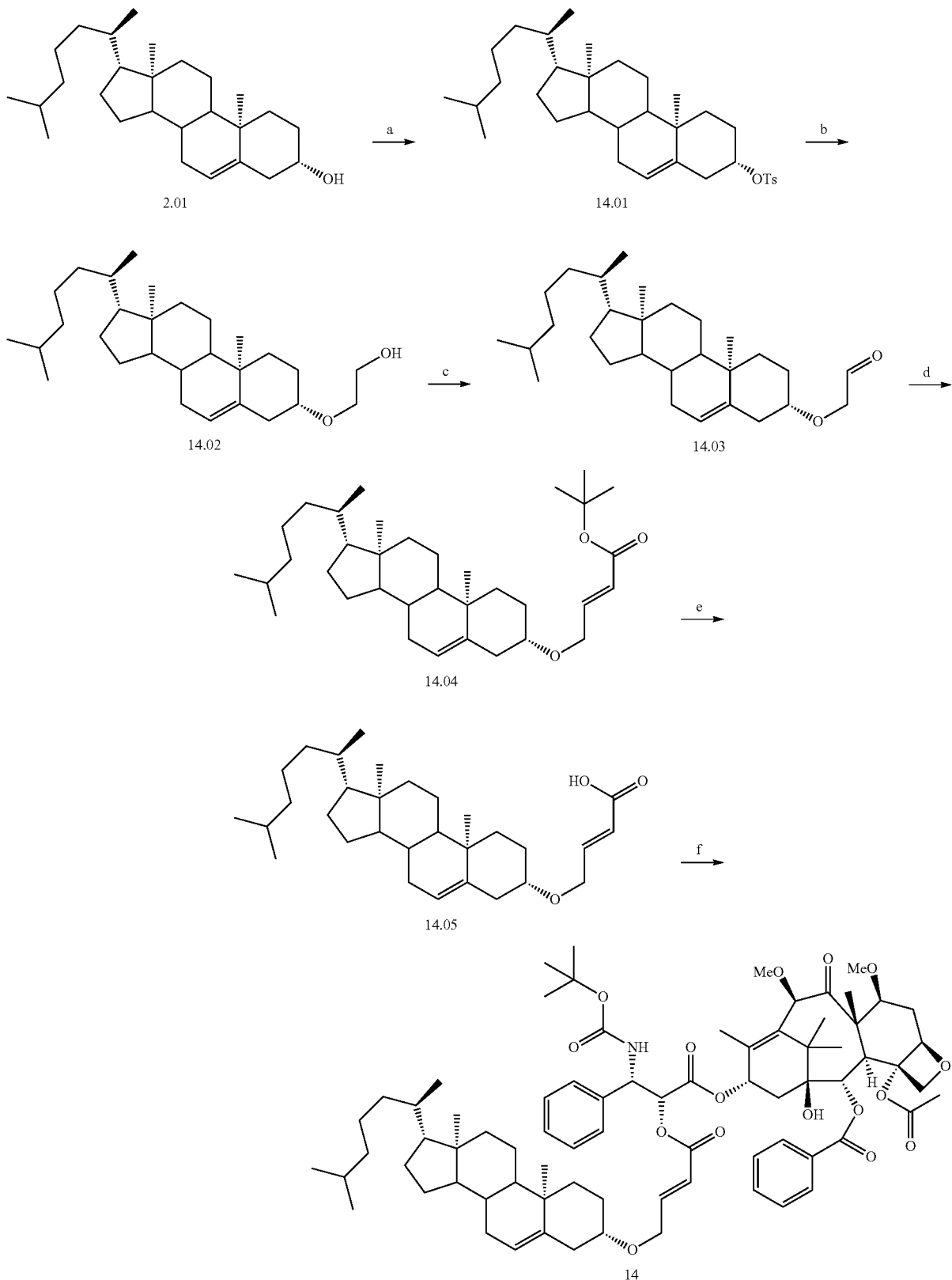
Reagents and conditions: (a) TsCl, Pyridine, 0° C., 4 h (b) Ethylene glycol, Dioxane, 80° C., 6 h (c) IBX, DMSO—THF r.t, 3 h
(d) Ph3P=CHCOOBu$^t$, toluene, 80° C., 4 h (e) TFA, CH2Cl2, r.t, 2.5 h (f) DIPC, DMAP, CH2Cl2, 0° C. to r.t, 5 h Step c:

To a 50 ml round bottom flask calculated amount of IBX (650 mg, 2.322 mmol) was taken in DMSO (1.5 ml) under nitrogen and allowed to stir for 15 minutes at room temperature. Alcohol intermediate 14.02 (500 mg, 1.160 mmol) in dry THF (10 ml) was added to the reaction mixture and allowed to stir for another 1.5 hour at room temperature and TLC was checked. After Completion the reaction mixture was quenched with excess diethyl ether and filtered through a thin pad of celite. Combined organic layer was concentrated under vacuum and purified by column chromatography to obtain aldehyde intermediate 14.03 in 78% yield. As the aldehyde intermediate 14.03 is less stable over storage, was utilized for next reaction without further characterization.

Step d:

To 50 ml single neck round bottom flask Wittig salt (1 g, 2.733 mmol) was taken in Toluene (7 ml) and heated at 80° C. To this solution aldehyde intermediate 14.03 (390 mg, 0.911 mmol) in toluene (5 mL) was added and allowed to stir for overnight at same temperature and TLC was checked. After completion, the reaction was quenched with Hexane to precipitate out unreacted Wittig reagent and Filtered off through a thin pad of celite and washed with hexane (15 mL). Combined Organic Layer was concentrated under vacuum and purified by column chromatography to obtain ester intermediate 14.04 in good yield (85%). $^1$H NMR of 14.04 (400 MHz, CDCl$_3$) δ: 6.84 (dt, J=16, 4.4 Hz, 1H), 5.97 (dd, J=16, 1.5 Hz, 1H), 5.33 (d, J=4.4 Hz, 1H), 4.18-4.09 (m, 2H), 3.24-3.13 (m, 1H), 2.40-0.76 (m, 49H Cholesterol back bone), 0.66 (s, 3H). $^{13}$C NMR of 14.04 (100 MHz, CDCl$_3$) δ: 165.72, 143.80, 140.69, 122.96, 121.79, 80.28, 79.18, 66.61, 56.77, 56.15, 50.18, 42.32, 39.77, 39.51, 39.01, 37.15, 36.86, 36.19, 35.77, 31.93, 31.88, 28.33, 28.22, 28.12, 28.00, 24.28, 23.82, 22.80, 22.55, 21.06, 19.36, 18.71, 11.85. IR of 14.04 (KBr) v: 2934.4, 1714.7, 1448.9, 1303.4, 1278.3, 1250.3, 1153.4, 1124.5, 990.2, 959.4 cm$^{-1}$. ESIMS m/z=549 [M+Na]$^+$ for [C$_{35}$H$_{58}$O$_3$Na]$^+$. Melting Point of 14.04: 108° C.

Step e:

To 50 ml single neck round bottom flask ester intermediate 14.04 (380 mg, 0.722 mmol) was taken in dry DCM (3 ml) and cooled to ° C. To this solution TFA (1 mL) was added, stirred for 2.5 hour at room temperature and TLC was checked. After Completion the reaction mixture was concentrated under vacuum to remove TFA (using NaOH trap on rota vapour). Solid residue was purified by silica gel chromatography to obtain acid intermediate 14.05 in good yield. $^1$H NMR of 14.05 (400 MHz, CDCl$_3$) δ: 7.07 (dt, J=15.8, 3.9 Hz, 1H), 6.14-6.03 (m, 2H), 5.37-5.28 (m, 1H), 4.22-4.17 (m, 2H), 3.19 (dt, J=15.4, 5.4 Hz, 1H), 2.42-0.73 (m, 42H Cholesterol back bone), 0.64 (s, 3H). $^{13}$C NMR of 14.05 (100 MHz, CDCl$_3$) δ: 171.50, 148.06, 140.53, 121.90, 120.09, 79.46, 66.47, 56.76, 56.16, 50.17, 42.31, 39.77, 39.51, 38.98, 37.13, 36.85, 36.18, 35.77, 31.92, 31.87, 28.32, 28.22, 28.00, 24.27, 23.82, 22.80, 22.55, 21.06, 19.35, 18.71, 11.85. IR of 14.05 (KBr) v: 2935.4, 1694.1, 1448.9, 1302.0, 1194.4, 959.4 cm$^{-1}$ ESIMS m/z=469.2 [M-1]$^+$ for [C$_{31}$H$_{50}$O$_3$]$^+$. Melting Point of 14.05: 180° C.

Step f:

To a 25 mL single neck round bottom flask acid 14.05 (112 mg, 0.2393 mmol) was taken in anhydrous CH$_2$Cl$_2$ (10 mL) under nitrogen atmosphere at 0° C. To this cooled solution DMAP (14 mg, 0.1196 mmol) followed by DIPC (37 μL, 0.2393 mmol) was added and stirred at same temperature for 1 hour. To this activated acid solution cabazitaxel (100 mg, 0.1196 mmol) was added and stirred for another 4 hour at room temperature and TLC was checked. After completion the reaction mixture was quenched with water, extracted with CHCl$_3$, dried over anhydrous sodium sulphate, concentrated and purified by silica gel chromatography to obtain new taxane 14 as white solid which was further precipitated in aceton-Hexane to obtain pure product in 68% yield. $^1$H NMR of 14 (400 MHz, CDCl$_3$) δ: 8.08 (d, J=7.2 Hz, 2H), 7.59 (t, J=7.5 Hz, 1H), 7.48 (t, J=7.6 Hz, 2H), 7.40-7.33 (m, 2H), 7.32-7.25 (m, 2H), 7.02 (d, J=15.8 Hz, 1H), 6.32 (t, J=8 Hz, 1H), 6.14 (d, J=15.8 Hz, 1H), 5.62 (d, J=7 Hz, 1H), 5.44 (bs, 1H), 5.39-5.29 (m, 3H), 4.97 (d, J=9.5 Hz, 1H), 4.81 (s, 1H), 4.29 (d, J=8.4 Hz, 1H), 4.21-4.11 (m, 1H), 3.88 (dd, J=10.5 Hz, 6.4 Hz, 1H), 3.83 (d, J=6.9 Hz, 1H), 3.40 (s, 3H), 3.28 (s, 3H), 3.24-3.13 (m, 1H), 2.74-2.62 (m, 1H), 2.41 (s, 3H), 2.37-0.74 (m, 66H, cholesterol back bone), 0.66 (s, 3H). $^{13}$CNMR of 14 (125 MHz, CDCl$_3$) δ: 204.97, 169.68, 168.32, 167.01, 165.30, 155.19, 147.97, 140.45, 139.68, 137.38, 134.87, 133.55, 130.15, 129.30, 128.87, 128.61, 128.18, 126.41, 121.99, 118.84, 84.18, 82.50, 81.54, 80.65, 80.43, 79.52, 78.88, 76.44, 74.77, 74.36, 71.99, 66.47, 57.07, 56.81, 56.74, 56.14, 50.16, 47.35, 43.30, 42.31, 42.22, 39.75, 39.49, 38.96, 37.10, 36.84, 36.17, 35.76, 34.94, 32.00, 31.92, 31.86, 31.56, 28.31, 28.20, 28.14, 27.99, 26.63, 24.26, 23.80, 23.47, 22.79, 22.75, 22.53, 21.06, 20.99, 19.35, 18.70, 14.44, 14.09, 11.84, 10.36. IR of 14 (KBr) v: 3809.5, 3518.2, 2924.3, 1728.7, 1608.4, 1474.1, 1267.1, 1172.0 cm$^{-1}$. ESIMS m/z of 14=1310.3 [M+Na]$^+$ for [C$_{76}$H$_{105}$NO$_{16}$Na]$^+$. Melting Point of 14: 142° C. Specific rotation [α]$_D^{25}$=-8 (C=0.1, Methanol).

Example 8: Synthesis of Cholesterol Taxane Conjugate 16

Step a: To a 250 mL single neck round bottom flask BocHNCH2COOH (2 g, 11.417 mmol), cholesterol 2.01 (4.414 g, 11.417 mmol) and DMAP (697 mg, 5.708 mmol) were taken in anhydrous dichloromethane (75 mL) under nitrogen atmosphere and stirred at 0° C. for 20 minutes. To this cooled solution DCC (2.591 g, 12.558 mmol) was added and stirred for another 24 h at room temperature and TLC was checked. After completion the reaction mixture was quenched with water, extracted with CHCl3, dried over anhydrous sodium sulphate, concentrated and purified by silica gel chromatography to obtain intermediate 2.02 in 60% yield. $^1$H NMR of 2.02 (400 MHz, CDCl$_3$) δ: 5.36 (d, J=4.3 Hz, 1H), 4.98 (s, 1H), 4.72-4.59 (m, 1H), 3.86 (d, J=5.3 Hz, 2H), 2.36-0.65 (m, 52H of cholesterol back bone). $^{13}$C NMR of 2.02 (125 MHz, CDCl$_3$) δ: 169.72, 155.67, 139.35, 122.90, 79.86, 75.15, 56.68, 56.14, 50.01, 42.66, 42.30, 39.71, 39.51, 38.01, 36.91, 36.55, 36.18, 35.77, 31.88, 31.84, 28.31, 28.20, 27.99, 27.69, 24.26, 23.82, 22.79, 22.54, 21.02, 19.26, 18.70, 11.84. IR of 2.02 (KBr) v: 3384.1, 2938.7, 2868.7, 1754.2, 1726.7, 1696.4, 1677.9, 1538.3, 1519.4, 1467.3, 1424.3, 1366.9, 1283.9, 1270.1, 1202.3, 1171.9, 1055.6, 1028.8, 1007.4 cm$^{-1}$. ESIMS m/z=566.2 [M+Na]$^+$ for [C$_{34}$H$_{57}$NO$_4$Na]$^+$ and 1109.5 [2M+Na]$^+$ for 2[C$_{34}$H$_{57}$NO$_4$]Na$^+$. Melting Point: 84° C.

Scheme 7:
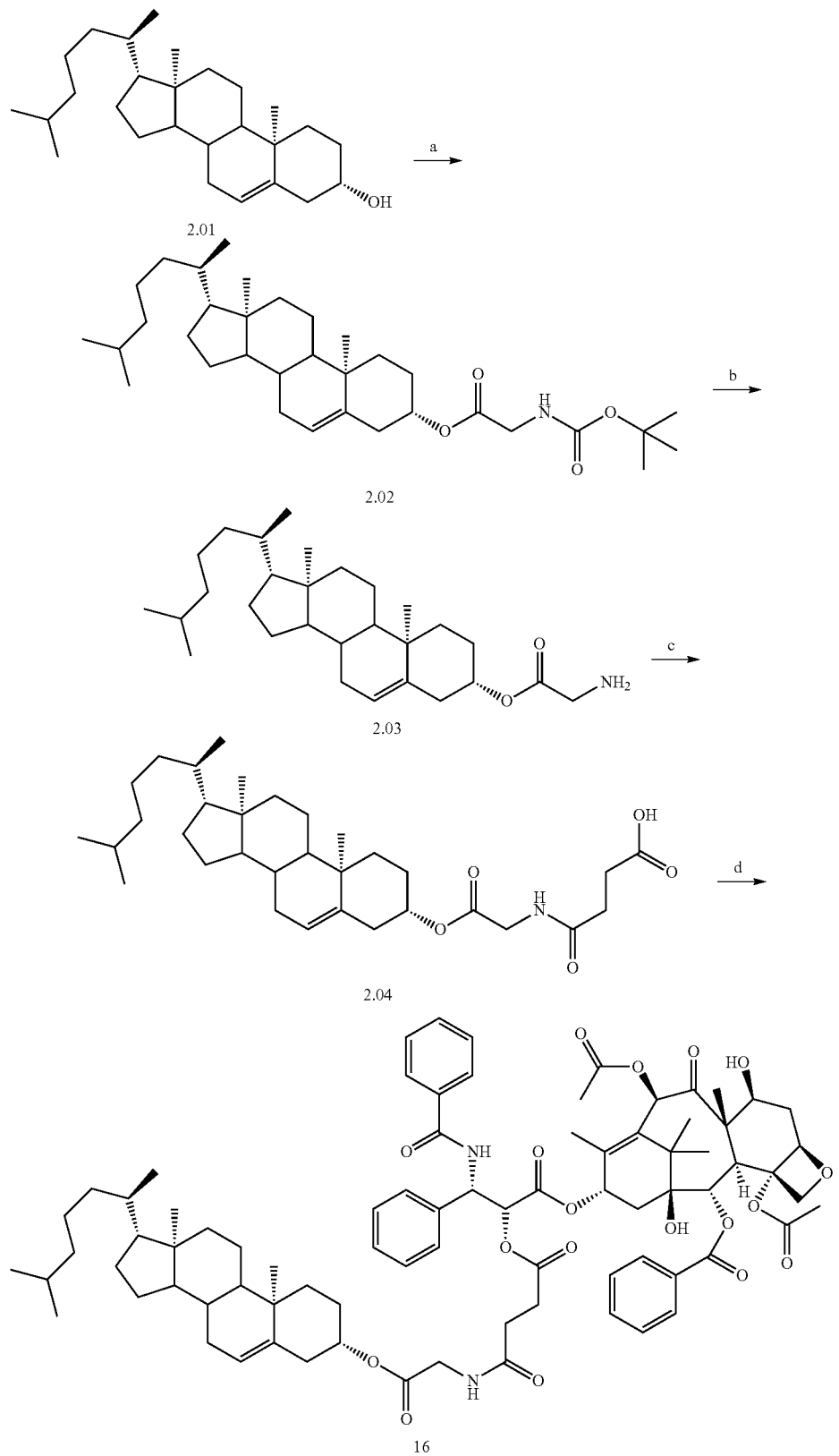
Reagents and conditions: (a) BocHNCH2COOH, DCC, DMAP, CH2Cl2, 0° C. to r.t, 12 h (b) TFA, CH2Cl2, 0° C. to r.t, 3 h, (c) Succinic anhydride, Pyridine, 0° C. to r.t, 12 h (d) Paclitaxel, DIPC, DMAP, CH2Cl2, 4 h Step b:

To a 25 mL single neck round bottom flask intermediate 2.02 (1 g crude, 1.838 mmol) was taken in anhydrous CH$_2$Cl$_2$ (5 mL) under nitrogen atmosphere at 0° C. To this reaction mixture TFA (2 mL) was added slowly over a period of 5 minute and stirred at room temperature for 3 h and TLC was checked. After completion the solvent was removed under reduced pressure and the crudeamine compound 2.03 was utilized for the next reaction without further purification.

Step c:

The crude amine intermediate 2.03 obtained from the previous reaction was diluted with dichloromethane (20 mL) and cooled to 0° C. To this ice cooled solution DIPEA (3 mL, 17.12 mmol) was added slowly followed by succinic anhydride (856 mg, 8.56 mmol) and stirred at room temperature for 12 h. After completion the reaction mixture was quenched with water (10 mL), washed with 1% HCl solution, extracted with CH$_2$Cl$_2$ (3×10 mL), dried over anhydrous Na$_2$SO$_4$ and purified by silica gel to obtain pure acid intermediate 2.04 in 88% yield. $^1$H NMR of 2.04 (500 MHz, CDCl$_3$) δ: 6.47 (t, J=5 Hz, 1H), 5.35 (d, J=4.8 Hz, 1H), 4.65 (m, 1H), 3.99 (d, J=5.1 Hz, 2H), 2.68 (t, J=6.6 Hz, 2H), 2.56 (t, J=6.7 Hz, 2H), 2.37-0.57 (m, 43H of cholesterol back bone). $^{13}$C NMR of 2.04 (125 MHz, CDCl$_3$) δ: 176.67, 172.28, 169.49, 139.18, 122.99, 75.57, 56.61, 56.07, 49.91, 42.24, 41.68, 39.64, 39.45, 37.89, 36.82, 36.49, 36.12, 35.76, 31.84, 31.75, 30.29, 29.66, 29.30, 28.19, 27.97, 27.59, 24.23, 23.80, 22.80, 22.53, 20.97, 19.24, 18.67, 11.81. IR of 2.04 (KBr) v: 3311.1, 2935.7, 2902.8, 2850.8, 1751.4, 1748.5, 1745.5, 1637.6, 1544.9, 1203.6 cm$^{-1}$. MALDI-TOF MS m/z=566.29 [M+Na]$^+$ for [C$_{33}$H$_{53}$NO$_5$Na] and 582.27 [M+K]$^+$ for [C$_{33}$H$_{53}$NO$_5$K]. Melting point: (170-180)° C.

Step d:

To a 10 mL single neck round bottom flask acid 2.04 (286 mg, 0.5269 mmol) was taken in anhydrous CH$_2$Cl$_2$ (10 mL) under nitrogen atmosphere at 0° C. To this cooled solution DMAP (85 mg, 0.7026 mmol) followed by DIPC (109 µL, 0.7026 mmol) was added and stirred at same temperature for 1 h. To this activated acid solution paclitaxel (300 mg, 0.3513 mmol) was added and stirred for another 4 h at room temperature and TLC was checked. After completion the reaction mixture was quenched with water, extracted with CHCl3, dried over anhydrous sodium sulphate, concentrated and purified by silica gel chromatography (ethyl acetate-hexane was used as mobile phase) to obtain new taxane 16 as solid. $^1$H NMR of 16 (500 MHz, CDCl$_3$) δ: 8.13-8.08 (m, 2H), 7.79-7.73 (m, 2H), 7.59 (t, J=7.4 Hz, 1H), 7.53-7.25 (m, 10H), 6.26 (s, 1H), 6.17 (t, J=8.7 Hz, 1H), 6.08 (bs, 1H), 5.89 (dd, J=8.7, 4.1 Hz, 1H), 5.64 (d, J=7.1 Hz, 1H), 5.44 (d, J=4.1 Hz, 1H), 5.35 (d, J=4.9 Hz, 1H), 4.94 (d, J=7.9 Hz, 1H), 4.62-4.55 (m, 1H), 4.41 (dd, J=10.9, 6.7 Hz, 1H), 4.28 (d, J=8.5 Hz, 1H), 4.16 (d, J=8.4 Hz, 1H), 3.85 (qd, J=18.4, 5.1 Hz, 2H), 3.77 (d, J=7.0 Hz, 1H), 2.75 (t, J=7.0 Hz, 2H), 2.58-2.46 (m, 3H), 2.38 (s, 3H), 2.20 (s, 3H), 1.89 (s, 3H), 1.65 (s, 3H), 1.20 (s, 3H), 1.10 (s, 3H), 2.34-0.63 (m, 35H aliphatic proton from paclitaxol and cholesterol back bone). $^{13}$C NMR of 16 (125 MHz, CDCl$_3$) δ: 203.81, 171.66, 171.19, 171.01, 169.81, 169.38, 168.11, 167.26, 166.97, 142.79, 139.22, 137.06, 133.74, 133.65, 132.72, 131.87, 130.20, 129.22, 129.00, 128.68, 128.59, 128.45, 127.28, 126.75, 123.04, 84.42, 81.00, 79.09, 76.39, 75.58, 75.08, 74.36, 72.07, 71.77, 58.46, 56.66, 56.11, 53.13, 49.99, 45.56, 43.12, 42.29, 41.59, 39.68, 39.48, 37.96, 36.83, 36.54, 36.15, 35.75, 35.50, 35.44, 31.88, 31.81, 30.62, 29.34, 28.18, 27.98, 27.63, 26.77, 24.25, 23.79, 22.78, 22.62, 22.53, 22.08, 21.00, 20.79, 19.25, 18.69, 14.79, 11.83, 9.57. ESIMS m/z=1403.1 [M+Na]$^+$ for [C$_{80}$H$_{102}$N$_2$O$_{18}$Na]$^+$. CHN analysis (Obtained percentage): C=69.45, H=7.74, N=2.21 (calculated percentage: C=69.64, H=7.45, N=2.03).

Example 9: Synthesis of Novel MEK Inhibitor 34

Scheme 8:

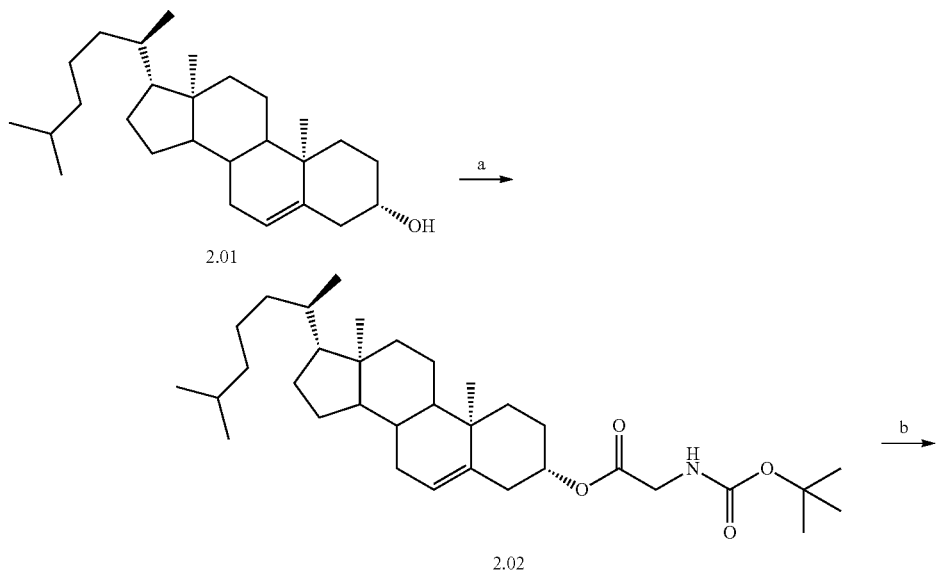

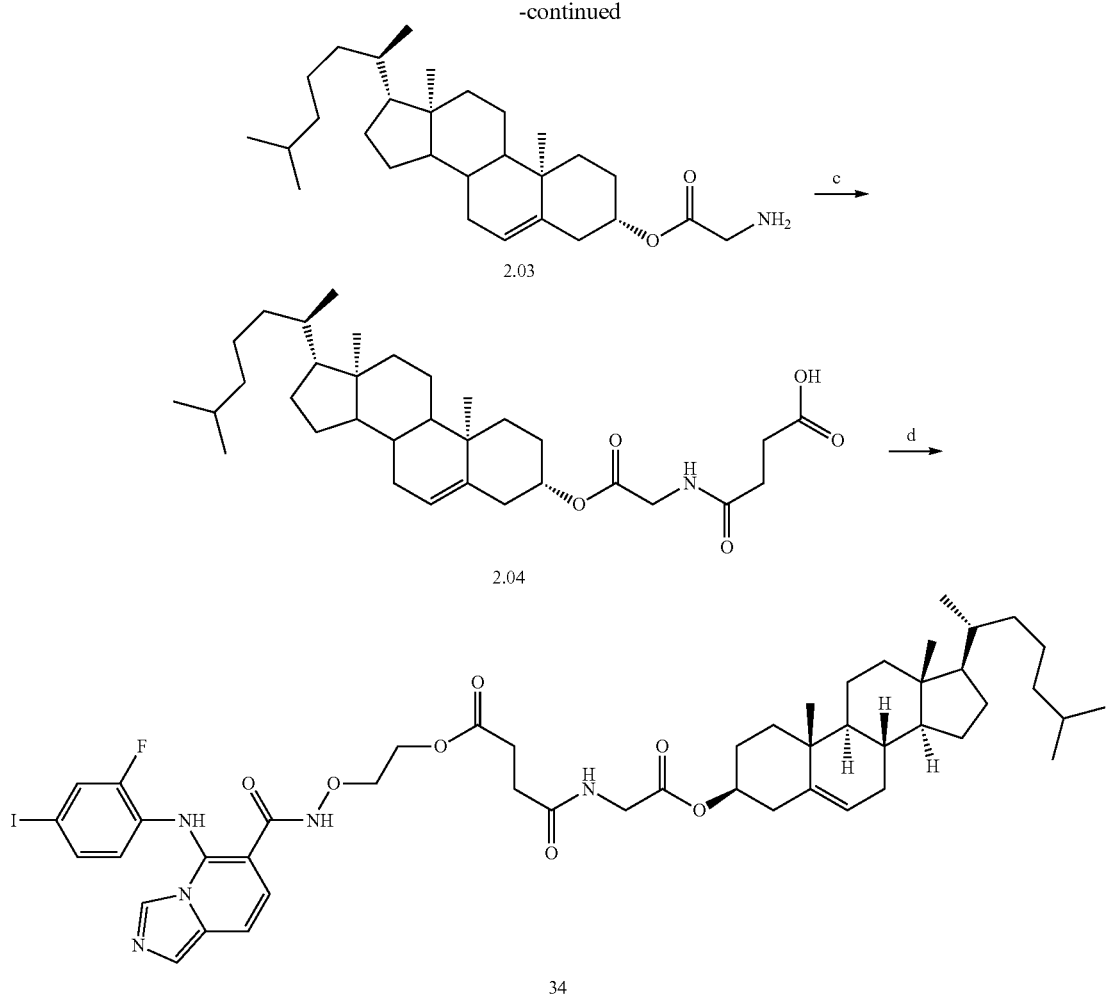

Reagents and conditions: (a) BocHNCH2COOH, DCC, DMAP, CH2Cl2, 0° C. to r.t, 12 h (b) TFA, CH2Cl2, 0° C. to r.t, 3 h, (c) Succinic anhydride, Pyridine, 0° C. to r.t, 12 h (d) GDC 0623, DIPC, DMAP, CH2Cl2, 4 h Step a:

To a 250 mL single neck round bottom flask BocHNCH2COOH (2 g, 11.417 mmol), cholesterol 2.01 (4.414 g, 11.417 mmol) and DMAP (697 mg, 5.708 mmol) were taken in anhydrous dichloromethane (75 mL) under nitrogen atmosphere and stirred at 0° C. for 20 minutes. To this cooled solution DCC (2.591 g, 12.558 mmol) was added and stirred for another 24 h at room temperature and TLC was checked. After completion the reaction mixture was quenched with water, extracted with CHCl3, dried over anhydrous sodium sulphate, concentrated and purified by silica gel chromatography to obtain intermediate 2.02 in 60% yield. $^1$H NMR of 2.02 (400 MHz, CDCl$_3$) δ: 5.36 (d, J=4.3 Hz, 1H), 4.98 (s, 1H), 4.72-4.59 (m, 1H), 3.86 (d, J=5.3 Hz, 2H), 2.36-0.65 (m, 52H of cholesterol back bone). $^{13}$C NMR of 2.02 (125 MHz, CDCl$_3$) δ: 169.72, 155.67, 139.35, 122.90, 79.86, 75.15, 56.68, 56.14, 50.01, 42.66, 42.30, 39.71, 39.51, 38.01, 36.91, 36.55, 36.18, 35.77, 31.88, 31.84, 28.31, 28.20, 27.99, 27.69, 24.26, 23.82, 22.79, 22.54, 21.02, 19.26, 18.70, 11.84. IR of 2.02 (KBr) v: 3384.1, 2938.7, 2868.7, 1754.2, 1726.7, 1696.4, 1677.9, 1538.3, 1519.4, 1467.3, 1424.3, 1366.9, 1283.9, 1270.1, 1202.3, 1171.9, 1055.6, 1028.8, 1007.4 cm$^{-1}$ ESIMS m/z=566.2 [M+Na]$^+$ for [C$_{34}$H$_{57}$NO$_4$Na]$^+$ and 1109.5 [2M+Na]$^+$ for 2[C$_{34}$H$_{57}$NO$_4$]Na$^+$. Melting Point: 84° C.

Step b:

To a 25 mL single neck round bottom flask intermediate 2.02 (1 g crude, 1.838 mmol) was taken in anhydrous CH$_2$Cl$_2$ (5 mL) under nitrogen atmosphere at 0° C. To this reaction mixture TFA (2 mL) was added slowly over a period of 5 minute and stirred at room temperature for 3 h and TLC was checked. After completion the solvent was removed under reduced pressure and the crudeamine compound 2.03 was utilized for the next reaction without further purification.

Step c:

The crude amine compound 2.03 obtained from the previous reaction was diluted with dichloromethane (20 mL) and cooled to 0° C. To this ice cooled solution DIPEA (3 mL, 17.12 mmol) was added slowly followed by succinic anhydride (856 mg, 8.56 mmol) and stirred at room temperature for 12 h. After completion the reaction mixture was quenched with water (10 mL), washed with 1% HCl solution, extracted with CH$_2$Cl$_2$ (3×10 mL), dried over anhydrous Na$_2$SO$_4$ and purified by silica gel to obtain pure acid intermediate 2.04 in 88% yield. $^1$H NMR of 2.04 (500 MHz, CDCl$_3$) δ: 6.47 (t, J=5 Hz, 1H), 5.35 (d, J=4.8 Hz, 1H), 4.65

(m, 1H), 3.99 (d, J=5.1 Hz, 2H), 2.68 (t, J=6.6 Hz, 2H), 2.56 (t, J=6.7 Hz, 2H), 2.37-0.57 (m, 43H of cholesterol back bone). $^{13}$C NMR of 2.04 (125 MHz, CDCl$_3$) δ: 176.67, 172.28, 169.49, 139.18, 122.99, 75.57, 56.61, 56.07, 49.91, 42.24, 41.68, 39.64, 39.45, 37.89, 36.82, 36.49, 36.12, 35.76, 31.84, 31.75, 30.29, 29.66, 29.30, 28.19, 27.97, 27.59, 24.23, 23.80, 22.80, 22.53, 20.97, 19.24, 18.67, 11.81. IR of 2.04 (KBr) v: 3311.1, 2935.7, 2902.8, 2850.8, 1751.4, 1748.5, 1745.5, 1637.6, 1544.9, 1203.6 cm$^{-1}$. MALDI-TOF MS m/z=566.29 [M+Na]$^+$ for [C$_{33}$H$_{53}$NO$_5$Na] and 582.27 [M+K]$^+$ for [C$_{33}$H$_{53}$NO$_5$K]. Melting point: (170-180)° C.

Step d:

To a 25 mL single neck round bottom flask acid intermediate 2.04 (137 mg, 0.2392 mmol) is taken in anhydrous CH$_2$Cl$_2$ (10 mL) under nitrogen atmosphere at 0° C. To this cooled solution DMAP (29 mg, 0.2392 mmol) followed by DIPC (37 μL, 0.2392 mmol) is added and stirred at same temperature for 1 h. GDC 0623 (100 mg, 0.1196 mmol) is added to the activated acid solution and stirred for another 4 h at room temperature and TLC is checked. After completion the reaction mixture is quenched with water, extracted with CHCl3, dried over anhydrous sodium sulphate, concentrated and purified by silica gel chromatography to obtain novel MEK inhibitor 33.

Example 10: Synthesis of Novel Taxane 28

Step a:

To a flame dried two necked round bottom flask phosphorus oxychloride (1.3 mL, 13.930 mmol) is taken in anhydrous THF (50 mL) at 0° C. Cholesteryl alcohol 7.02 (5 g, 11.609 mmol) and triethylamine (1.78 mL, 24.18 mmol) in THF (100 mL) is dropped slowly to the reaction mixture while vigorous stirring. Triethylammonium chloride is slowly precipitated from the reaction mixture. The reaction is continued under the protection of argon for further 5 hours and the intermediate 28.01 is used directly for the next step without any treatment.

Step b:

Triethylamine (3.88 mL, 34.825 mmol) and ethanolamine (0.834 mL. 13.93 mmol) in THF (50 mL) is added to the above reaction mixture slowly while vigorous stirring at 0° C. Triethylammonium chloride is slowly precipitated from the solution and the reaction is continued under the protection of nitrogen for further 5 hours. After completion triethylammonium chloride is removed by suction filtration and the solvent is evaporated to obtain intermediate 28.02 as white gum which is used directly for the next step without further purification.

Scheme 9:

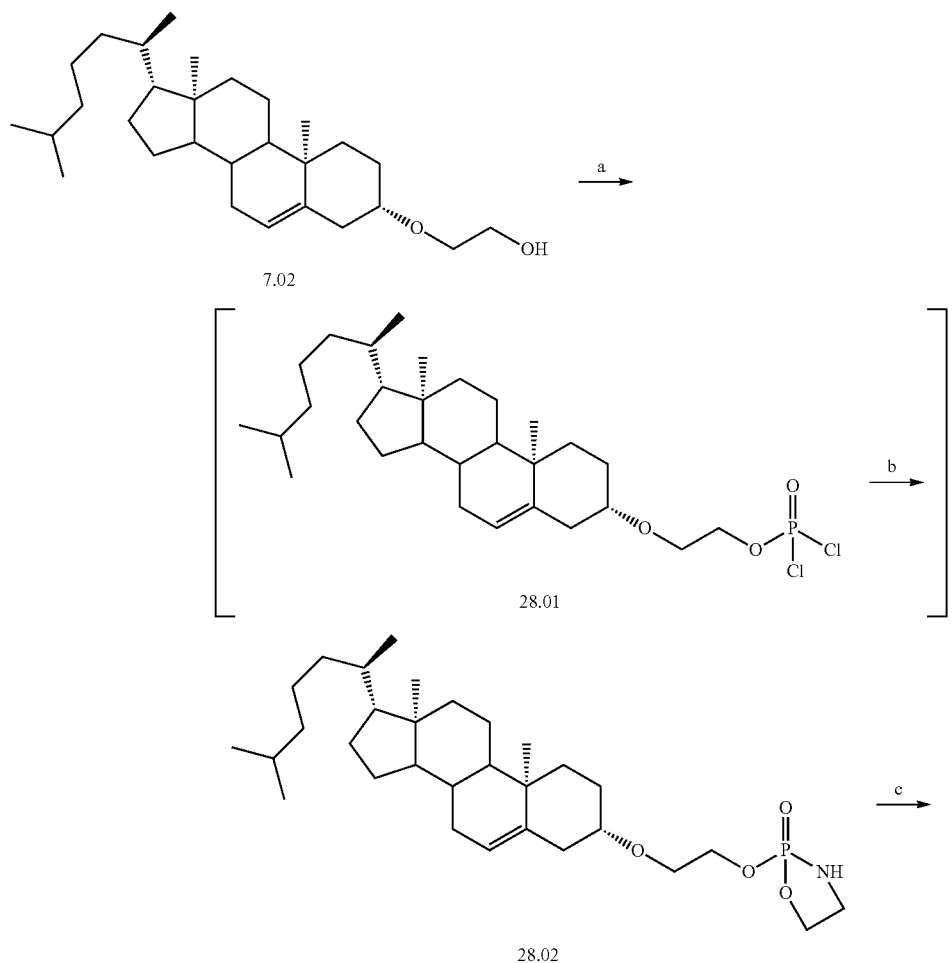

-continued

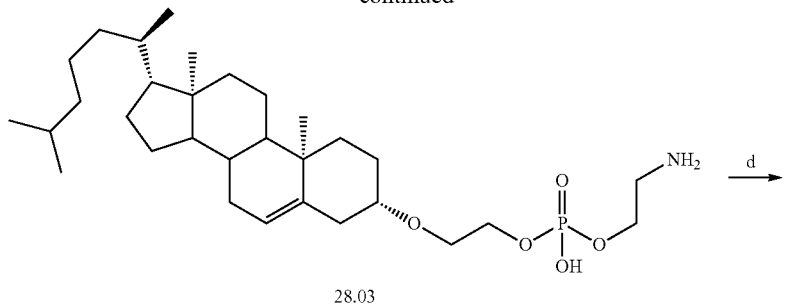
28.03

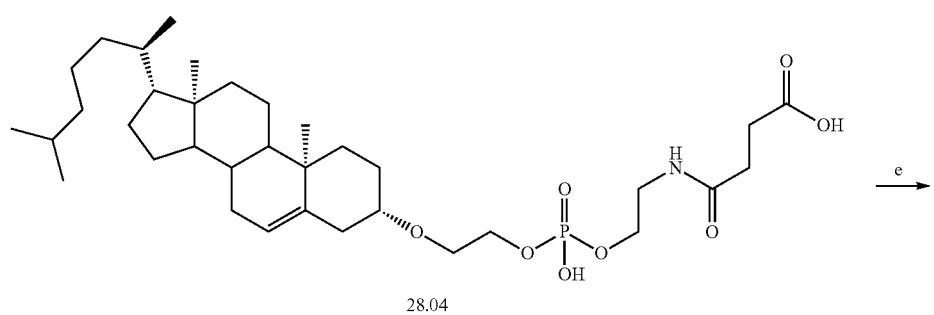
28.04

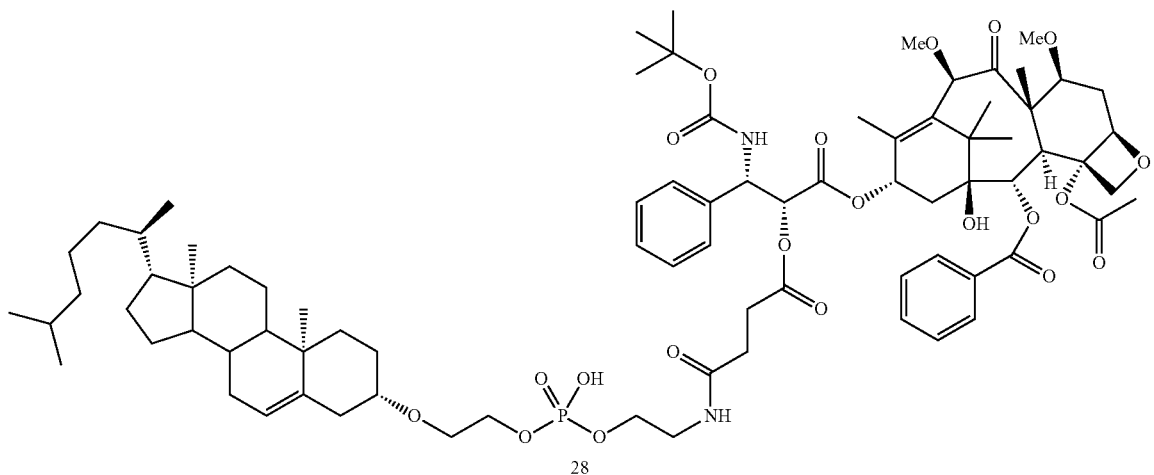
28

Reagents and conditions: (a) POCl3, Et3N, CH2Cl2, 0° C., 5 h (b) ethanolamine, Et3N, CH2Cl2, 0° C., 5h (c) AcOH, H2O, THF, 0° C., 5h (d) Succinic anhydraide, Pyridine, CH2Cl2, r.t, 12 h (e) Cabazitaxel, DIPC, DMAP, CH2Cl2, 0° C. to r.t, 5 h Step c:

The intermediate 28.02 is dissolved in THF (50 mL) at room temperature. Acetic acid-water solution (15 g acetic acidin 40 mL water) is added in one portion and heated at 70° C. for 5 h under the protection of nitrogen atmosphere. Then the mixture is condensed by azeotropic distillation with ethanol and the ring-openproduct 28.03 is precipitated out by dripping the solution slowly into acetone under vigorous stirring. The precipitation is collected by suction filtration, dried under high vacuum and used directly for the next step.

Step d:

The white gummy intermediate 28.03 is taken in dichloromethane (50 mL) and pyridine (10 mL) is added to the reaction mixture at room temperature. To this solution succinic hydride (5.5 g, 55.6 mmol) is added in one portion and stirred at room temperature for 12 h under the protection of nitrogen. After completion the reaction is diluted with CHCl3 (20 mL) and washed with HCl solution (1 N, 250 mL) and concentrated under reduced pressure. The slurry is precipitated in acetone to obtain intermediate 28.04 (1.5 g, 19.7% over four steps starting from 28.01).

Step e:

To a 25 mL single neck round bottom flask acid intermediate 28.04 (152 mg, 0.2392 mmol) is taken in anhydrous dichloromethane (5 mL) under nitrogen atmosphere at 0° C. To this cooled solution DIPC (37 µL, 0.2392 mmol) followed by DMAP (29 mg, 0.2392 mmol) is added and stirred at same temperature for 1 h. To this activated acid solution cabazitaxel (100 mg, 0.1196 mmol) is added and stirred for another 5 h at room temperature and TLC is checked. After completion the reaction mixture is diluted with chloroform (10 mL) and washed with 0.1N HCl (10 mL) solution. The organic layer is evaporated under reduced pressure and the residue is purified on silica to obtain new taxane 28.

Example 11: Synthesis of Novel Taxane 29

Step a:

To a 100 mL single neck round bottom flask octadecyl bromide 29.01 (31.122 g, 93.632 mmol) and mono NBoc ethylenediamine 29.02 (5 g, 31.211 mmol) is taken in acetonitrile (100 mL) and refluxed in presence of anhydrous K2CO3 (17.253 g, 124.844 mmol) for 24 h under nitrogen atmosphere. After completion the reaction mixture is concentrated under reduced pressure and diluted with ethyl acetate (100 mL). The organic layer is washed with water (100 mL), dried over anhydrous sodium sulphate and concentrated. The residue is purified on silica gel to afford intermediate 29.03.

Step b:

To a 250 mL single neck round bottom flask intermediate 29.03 (5 g, 82.685 mmol) and methyl iodide (7.72 mL, 124.028 mmol) is taken in acetone (100 mL) and refluxed for 24 h under nitrogen atmosphere. After completion the reaction mixture is concentrated under reduced pressure and the solid residue is washed with hexane (10 mL×2) to obtain intermediate 29.04 as white powder.

Scheme 10:

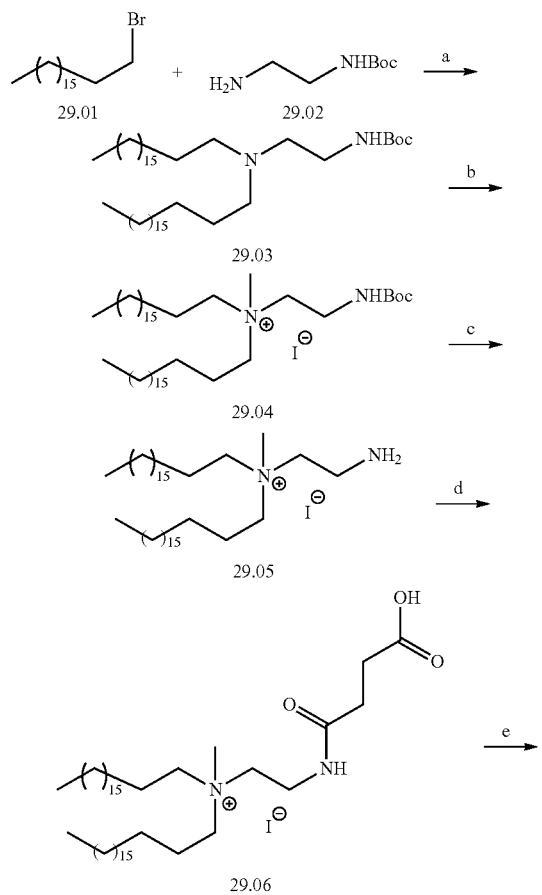

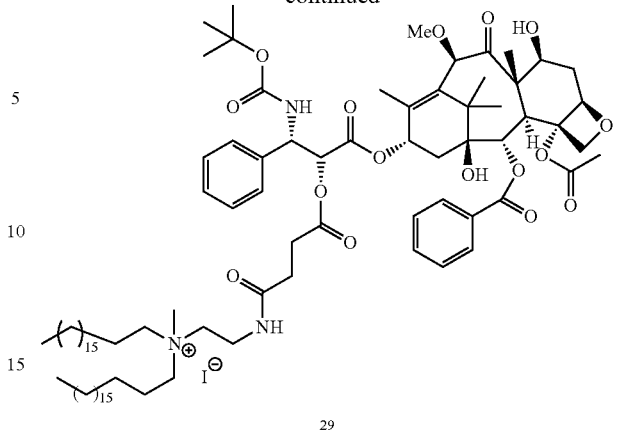

Reagents and conditions: (a) K2CO3, CH3CN, reflux, 24 h
(b) CH3I, (CH3)2CO, reflux, 24 h, (c) TFA, CH2Cl2, 0° C., 4 h
(d) Succinic anhydride, Pyridine, 0° C. to r.t, 12 h
(e) DIPC, DMAP, CH2Cl2, Cabazitaxel, 0° C. to r.t, 5 h Step c:

To a 100 mL single neck round bottom flask intermediate 29.04 (2 g, 2.477 mmol) is taken in anhydrous dichloromethane (12 mL) at 0° C. under nitrogen atmosphere. To this solution TFA (3 mL) is added and stirred at same temperature for 4 h and TLC is checked. After completion the reaction mixture is concentrated under reduced pressure and the solid residue of 29.05 is utilized for next reaction without further purification.

Step d:

The crude amine intermediate 29.05 obtained from the previous reaction is diluted with dichloromethane (20 mL) and cooled to 0° C. To this ice cooled solution DIPEA (2.21 mL, 12.385 mmol) is added slowly followed by succinic anhydride (495 mg, 4.954 mmol) and stirred at room temperature for 12 h. After completion the reaction mixture is quenched with water (10 mL), washed with 1% HCl solution, extracted with CH2Cl2 (3×10 mL), dried over anhydrous Na2SO4 and purified by silica gel to obtain pure acid intermediate 29.06.

Step e:

To a 25 mL single neck round bottom flask acid intermediate 29.06 (193 mg, 0.2392 mmol) is taken in anhydrous dichloromethane (5 mL) under nitrogen atmosphere at 0° C. To this cooled solution DIPC (37 µL, 0.2392 mmol) followed by DMAP (29 mg, 0.2392 mmol) is added and stirred at same temperature for 1 h. To this activated acid solution cabazitaxel (100 mg, 0.1196 mmol) is added and stirred for another 5 h at room temperature and TLC is checked. After completion the reaction mixture is diluted with chloroform (10 mL) and washed with 0.1N HCl (10 mL) solution. The organic layer is evaporated under reduced pressure and the residue is purified on silica to obtain new taxane 29.

Example 12: Synthesis of Lipid Functionalized Gemcitabine

Gemcitabine, an anticancer agent which acts against wide range of tumors, is known to be administered in very high dose (1000 mg/m$^2$) due to its very short plasma half life. Gemcitabine itself is water soluble. Functionalization of this molecule by hydrophobic lipids through linkers would be given amphiphilic nature to this molecule. Formulation of these compounds to produce supramolecular assembly could provide a protection against its short plasma half life and also could contribute to an enhanced permeation and retention (EPR) effect. Here we describe N (Scheme 11) and O (Scheme 12) terminal functionalization of gemcitabine by lipids with different linkers to yield a series of amphiphiles (compounds 35 to 41). Formation of supramolecular assembly (formulation) from these molecules has also been described in the other section of this application.

Scheme 11.

Representative example of N terminal functionalized Gemcitabine

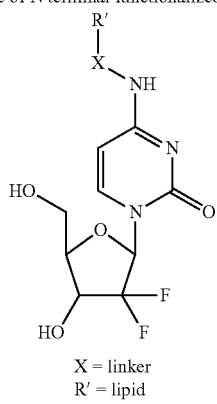

X = linker
R' = lipid

Examples of N terminal functionalization of zemcitabines with different linkers

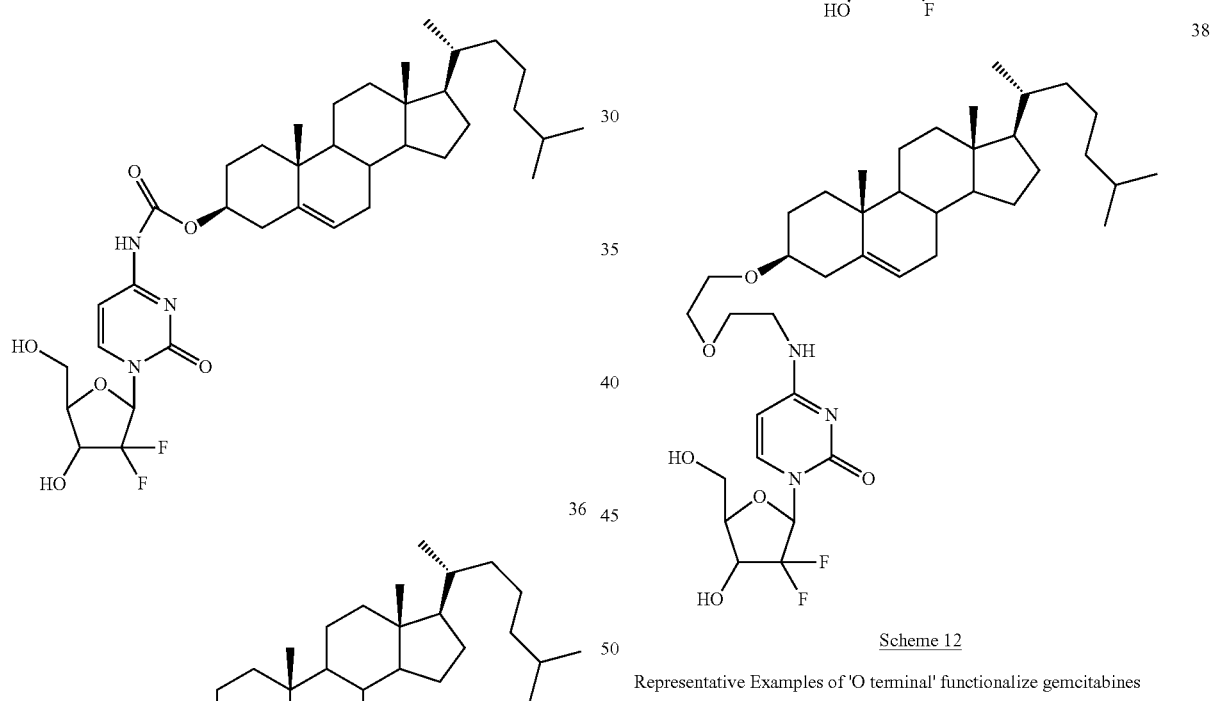

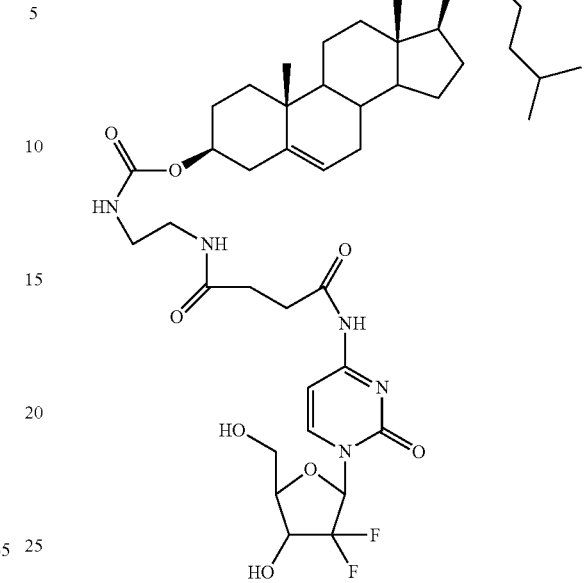

Scheme 12

Representative Examples of 'O terminal' functionalize gemcitabines

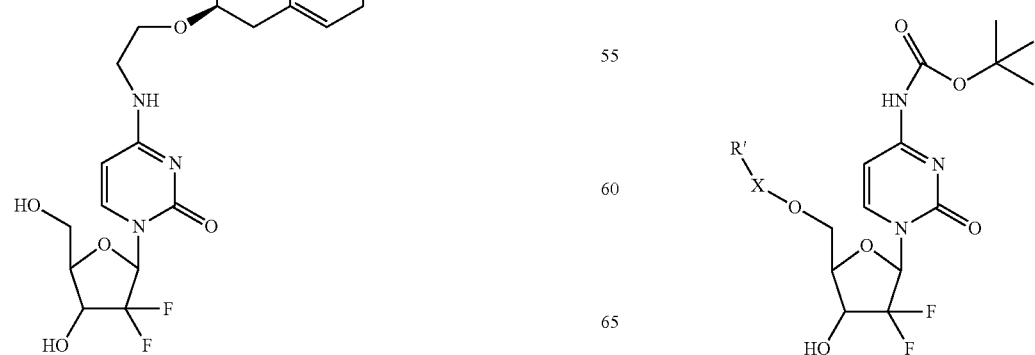

Example 3  R' = lipids
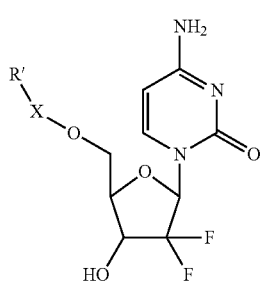
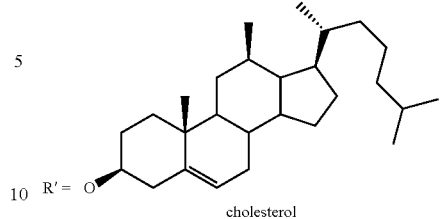
Example 4
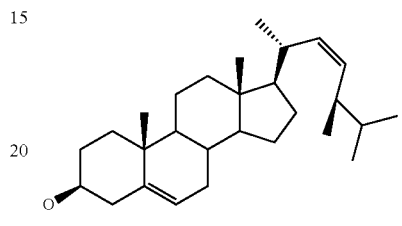
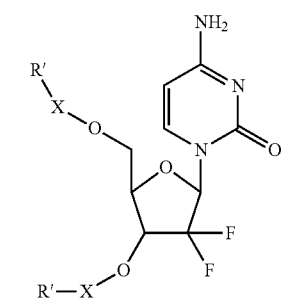
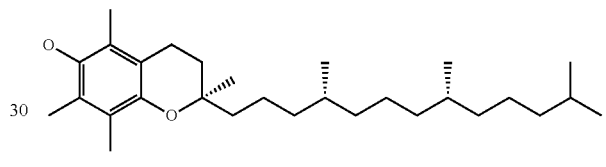
Example 5
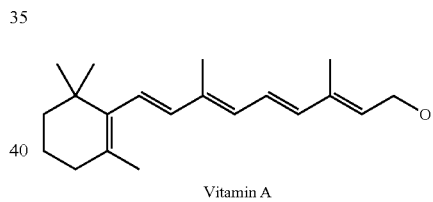
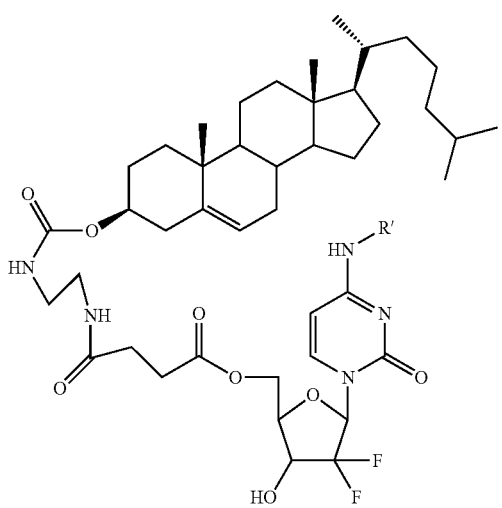
39a, R' = H
39b, R' = BOC
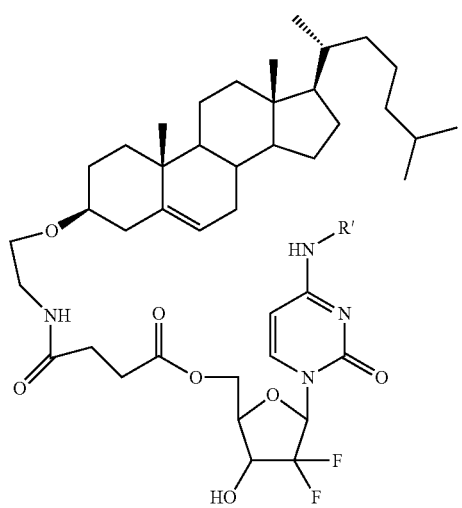
40a, R' = H
40b, R' = BOC -continued
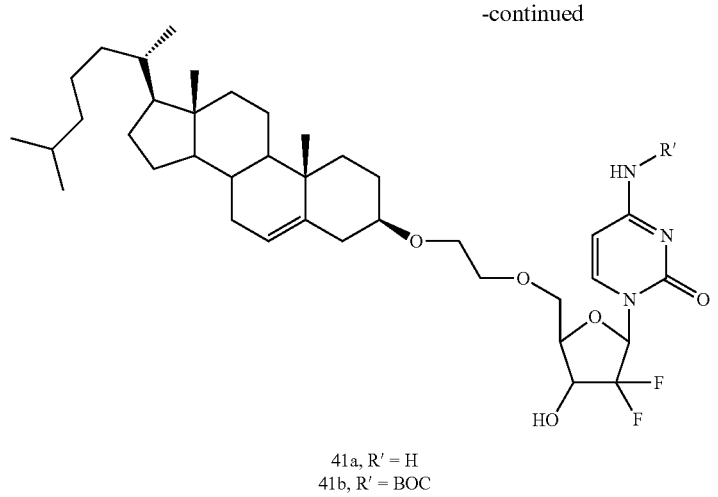
41a, R' = H
41b, R' = BOC
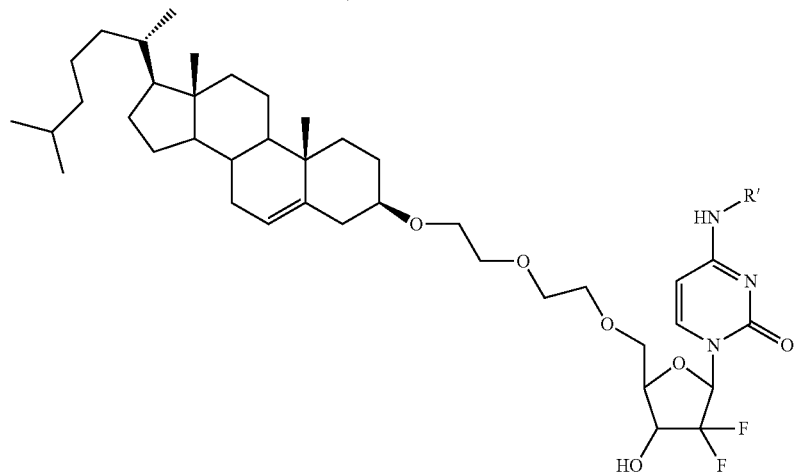
R' = H or BOC
Synthetic Schemes for Lipid Functionalized Gemcitabine Compounds 35, 37, 39 and 41
Scheme 13:
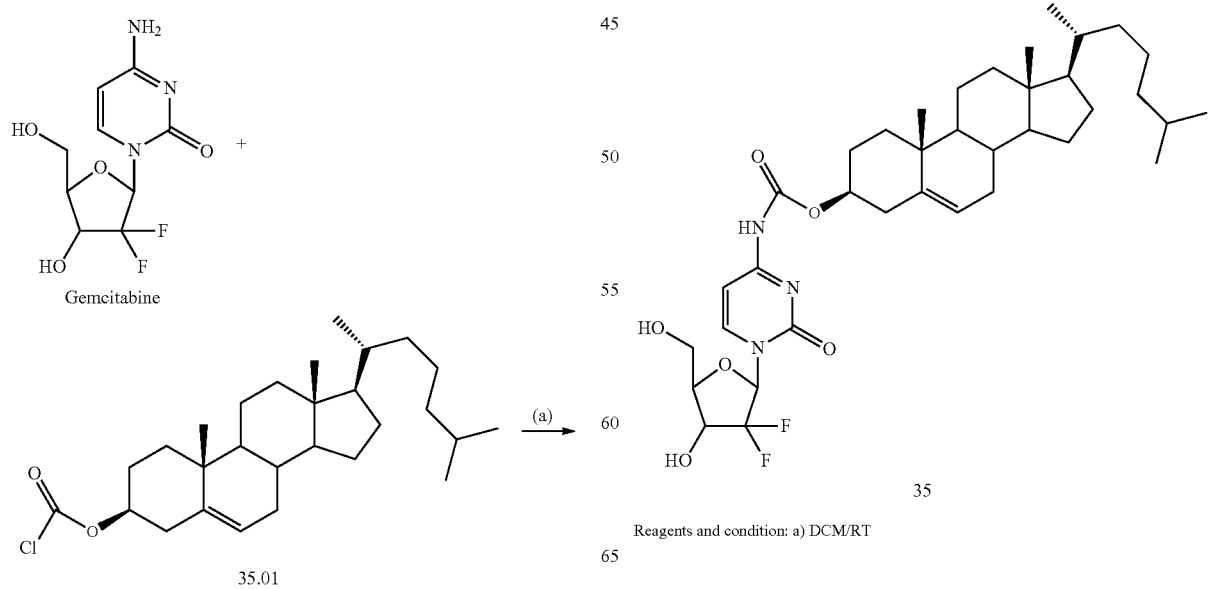
Reagents and condition: a) DCM/RT Scheme 14:
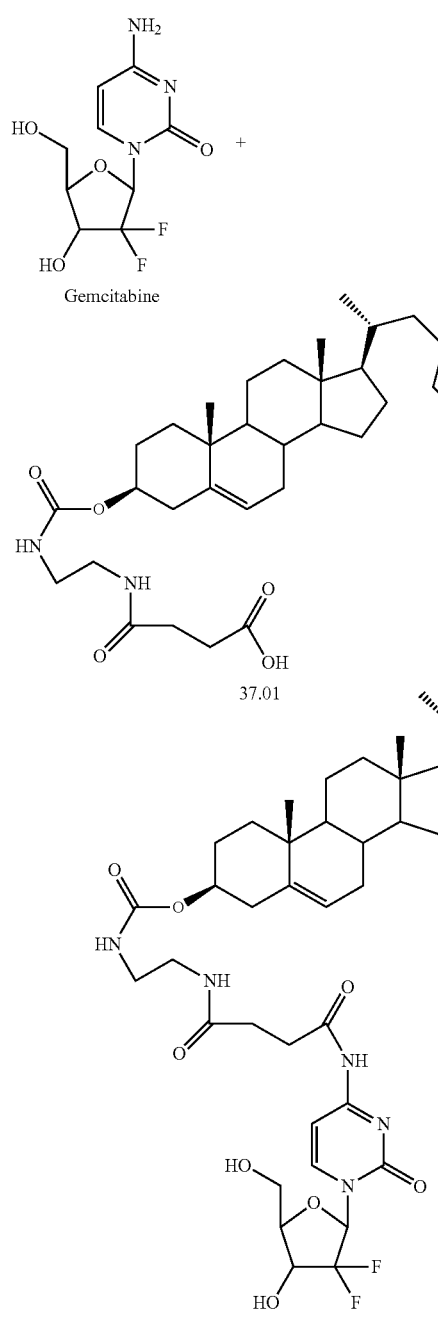
37
Reagents and condition: a) Triethylamine/DMAP/DCM/RT
Scheme 15:
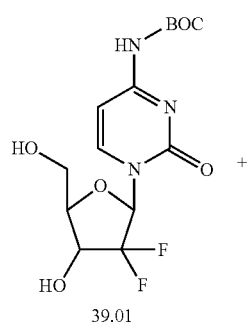
39.01
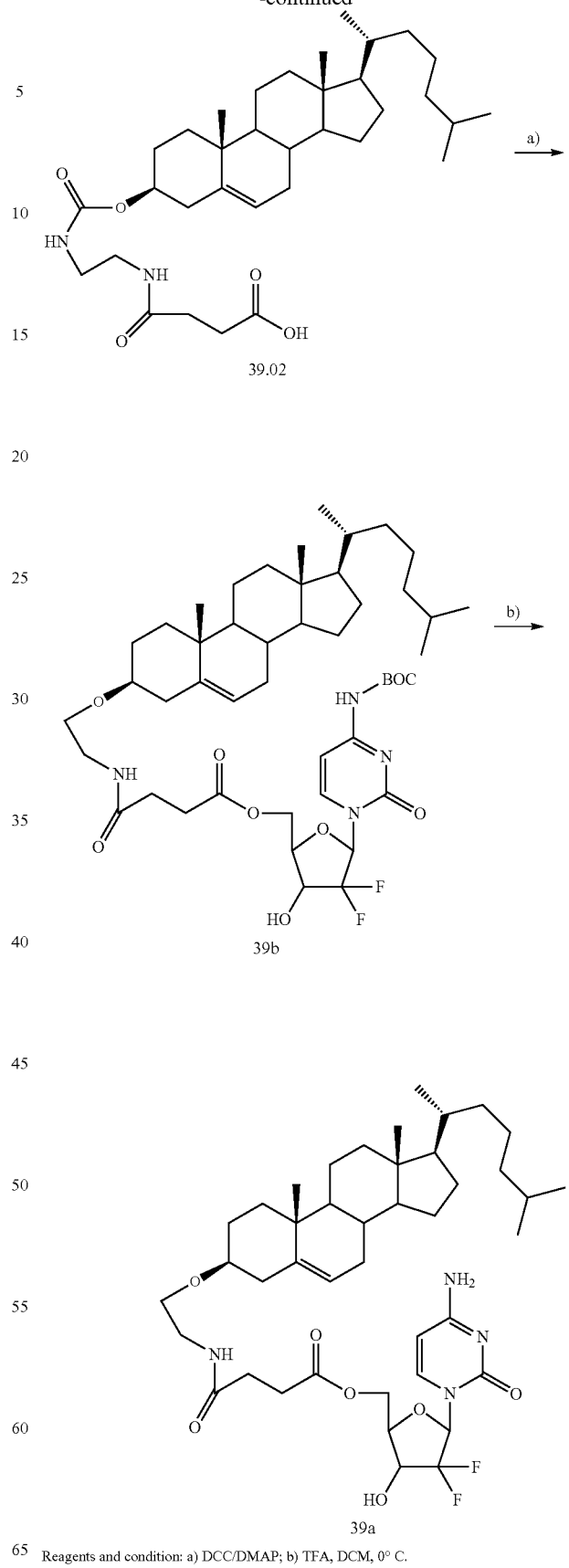
Reagents and condition: a) DCC/DMAP; b) TFA, DCM, 0° C.

Scheme 16:

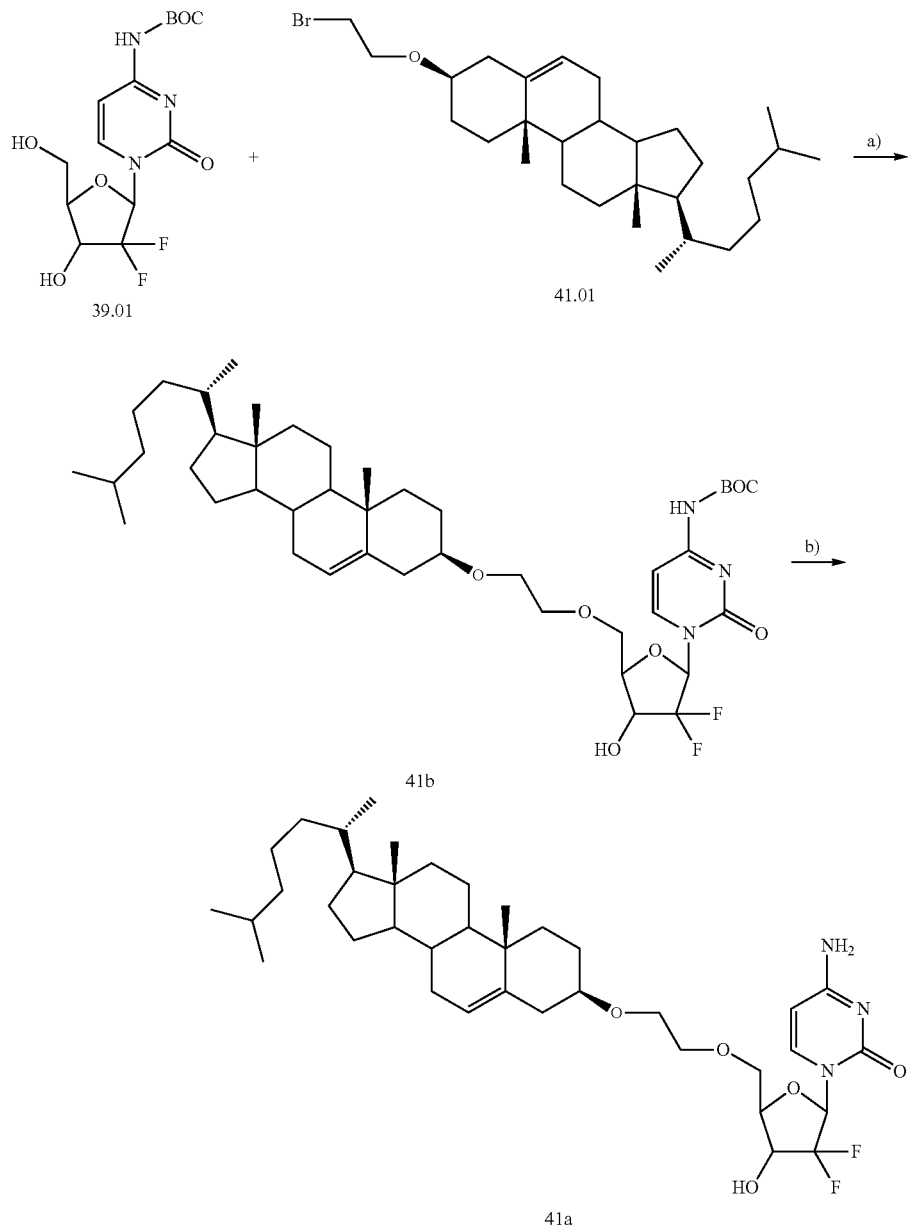

Reagents and condition: a) NaH/THF, Reflux; b) TFA, DCM, 0° C.

Example 13: Alternate Synthesis of Cholesterol Taxane Conjugate 7

Step a:

To a 100 mL single neck R.B cholesterol 2.01 (2 g, 5.172 mmol) was taken in anhydrous THF (20 mL) under nitrogen atmosphere at 0° C. NaH (2.859 mg, 20.690 mmol) was added to the reaction mixture by pinch over a period of 5 minutes. The resulting solution was stirred for 20 minutes and ethyl bromo acetate (1.191 mL, 10.354 mmol) was added slowly and stirred for another 4 h at room temperature and TLC was checked. After completion the reaction mixture was quenched with water and the compound was extracted with ethyl acetate (2×20 mL). The combined organic layer was dried over anhydrous sodium sulphate, concentrated and purified by silica gel chromatography to obtain intermediate 7.01 in 10% yield.

Step b:

To a 100 mL single neck round bottom flask ester intermediate 7.01 (200 mg, 0.432 mmol) was taken in 8 mL of THF/$H_2O$ (3:1) and cooled to 0° C. under ice bath. To this ice cooled solution LiOH (35 mg, 0.846 mmol) was added and was stirred at rt for 4 h and TLC was checked. After completion the reaction mixture was acidified by Na2HSO4, extracted with ethyl acetate. The organic layer was dried over anhydrous $Na_2SO_4$ and concentrated under vacuum and column performed to obtain pure acid intermediate 7.02 in 60% yield.

Scheme 4:
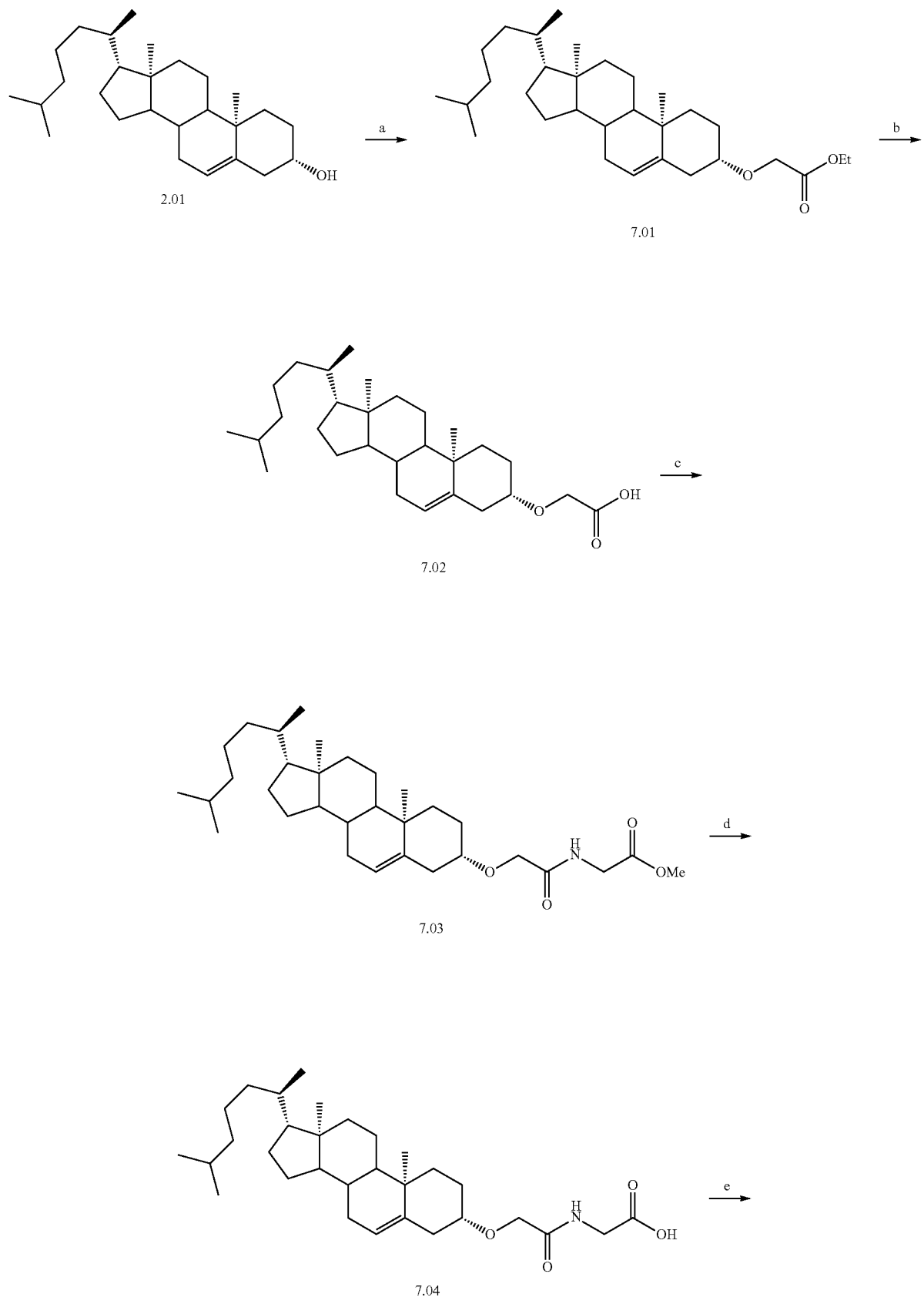

-continued

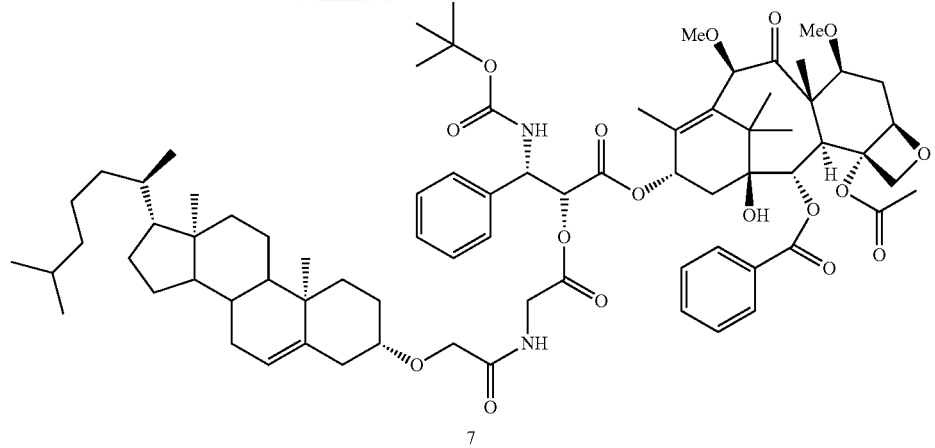

Reagents and conditions: (a) NaH, THF, Ethyl bromoacetate, 0° C. to r.t, 4 h (b) LiOH, THF/H2O (3:1), 0° C. to r.t, 3h
c) EDCI, HOBT, DIPEA, CH2Cl2, 0° C. to r.t, 12 h (d) LiOH, THF/H2O (3:1), 0° C. to r.t, 3 h (e) DIPC, DMAP, CH2Cl2, 3 h Step c:

To a 25 mL single neck round bottom flask acid 7.02 (100 mg, 0.2248 mmol) was taken in anhydrous $CH_2Cl_2$ (5 mL) under nitrogen atmosphere at 0° C. To this cooled solution EDCI (86.2 mg, 0.4497 mmol) followed by HOBT (60 mg, 0.4497 mmol) and stirred at same temperature for 1 h. To this activated acid solution DIPEA (0.15 mL, 0.8995) followed by glycine methyl ester (56 mg, 0.4497 mmol) was added and stirred for another 3 h at room temperature and TLC was checked. After completion the reaction mixture was quenched with water, extracted with CHCl3, dried over anhydrous sodium sulphate, concentrated and purified by silica gel chromatography to obtain coupling product 7.03 in 82% yield.

Step d:

To a 50 mL single neck round bottom flask ester intermediate 7.03 (96 mg, 0.186 mmol) was taken in THF/water (4 mL, 3:1) and cooled to 0° C. To this ice cooled solution LiOH (23.4 mg, 0.558 mmol) was added and stirred at room temperature for 2 h and TLC was checked. After completion the reaction mixture was acidified with saturated $NaHSO_4$ up to $P^H$ 3 and extracted with Ethyl acetate (3×10 mL). The combined organic layer was dried over anhydrous $Na_2SO_4$ and column purified to obtain pure compound 7.04 80% yield.

Step e:

To a 10 mL single neck round bottom flask acid intermediate 7.04 (23.9 mg, 0.0478 mmol) was taken in anhydrous $CH_2Cl_2$ (2 mL) under nitrogen atmosphere at 0° C. To this cooled solution DIPC (7 microliter, 0.0478 mmol) followed by DMAP (5.84 mg, 0.0478 mmol) and stirred at same temperature for 1 h. To this activated acid solution cabazitaxel (20 mg, 0.0239 mmol) was added and stirred for another 3 h at room temperature and TLC was checked. After completion the reaction mixture was quenched with water, extracted with CHCl3, dried over anhydrous sodium sulphate, concentrated and purified by silica gel chromatography to obtain conjugate 7 in 79% yield. $^1H$ NMR of 7 (400 MHz, CDCl3) δ 8.11 (d, J=7.8 Hz, 2H), 7.61 (t, J=7.5 Hz, 1H), 7.50 (t, J=7.7 Hz, 2H), 7.40 (t, J=7.4 Hz, 2H), 7.33 (d, J=7 Hz, 1H), 7.28 (d, J=7.4 Hz, 2H), 7.05 (t, J=5.5 Hz, 1H), 6.25 (t, J=7 Hz, 1H), 5.64 (d, J=7.0 Hz, 1H), 5.48 (bs, 1H), 5.35 (s, 3H), 4.99 (d, J=9.4 Hz, 1H), 4.82 (s, 1H), 4.31 (d, J=8.4 Hz, 1H), 4.21-4.10 (m, 3H), 4.00 (s, 2H), 4.03-3.93 (m, 1H), 3.89 (dd, J=10.6, 6.5 Hz, 1H), 3.83 (t, J=9.2 Hz, 2H), 3.44 (s, 3H), 3.30 (s, 3H), 3.30-3.17 (m, 1H), 2.70 (m, 1H), 2.47-0.74 (m, 66H), 0.68 (d, J=8.8 Hz, 2H). ESIMS m/z=1341.6 $[M+Na]^+$ for C76H106N2O17

Example 14: Synthesis of Cholesterol Taxane Conjugate 14

Step a:

To an ice cooled solution of cholesterol 2.01 (5 g, 0.013 mol) in $CH_2Cl_2$ (20 mL) is added pyridine (5 mL) and stirred for 15 minutes. To this solution paratoluene sulphonyl chloride (4.9 g, 0.026 mol) is added and stirred for another 4 h at 0° C. and TLC is checked. After completion the reaction mixture is diluted with $CHCl_3$ (20 mL), washed with 1N HCl (3×50 mL) and brine (20 mL) successively. The organic layer was dried anhydrous $Na_2SO_4$ and concentrated under vacuum to afford intermediate 6.02 which is utilized for the next reaction without further purification.

Scheme:

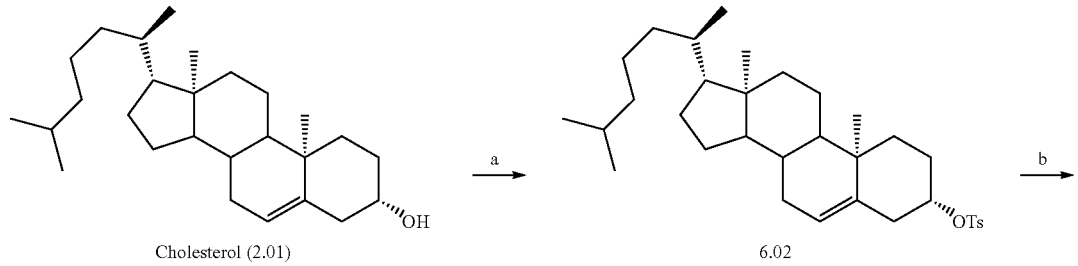

-continued

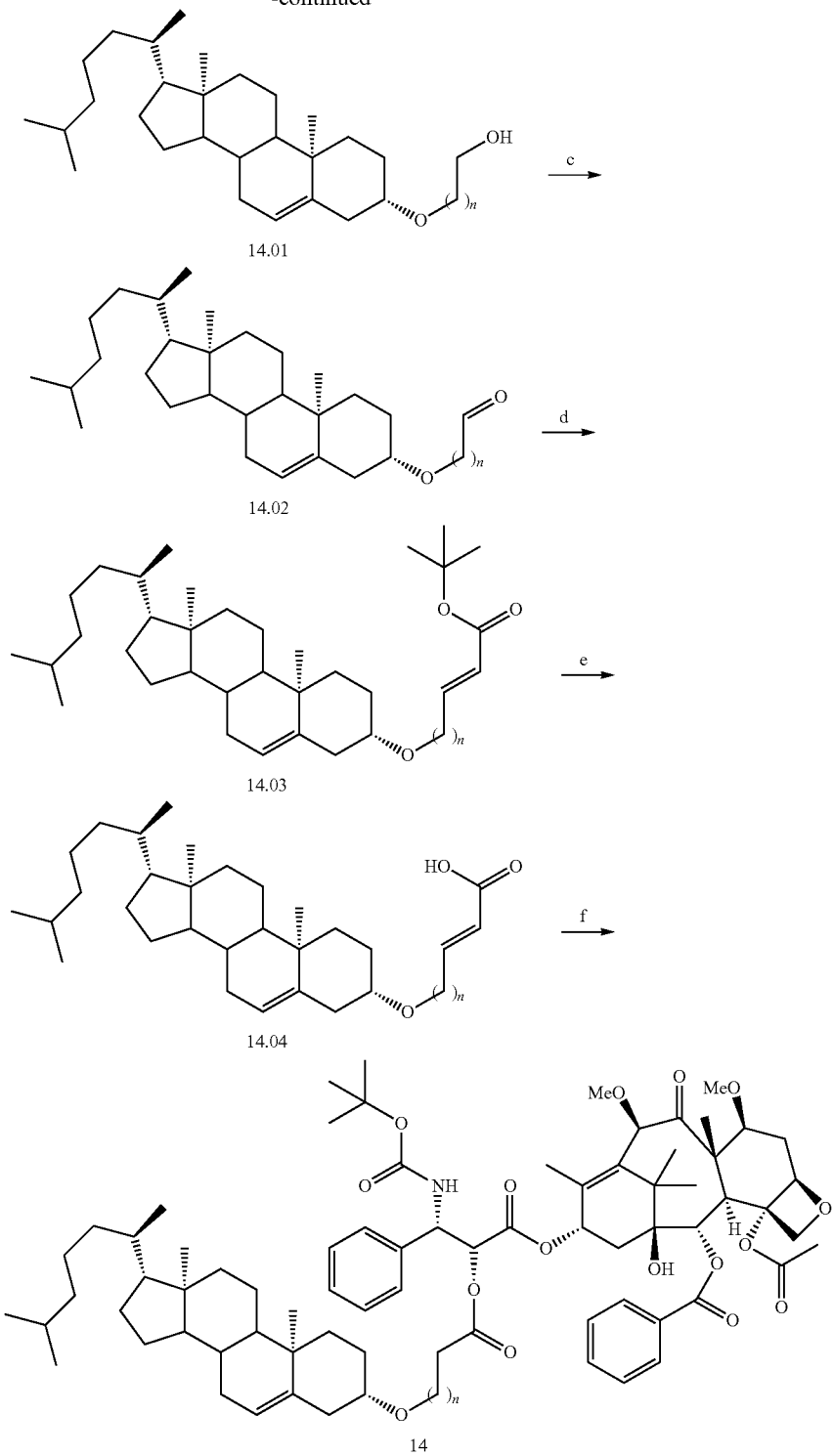

Reagents and conditions: (a) TsCl, Pyridine, 0° C., 4 h (b) Ethylene glycol, Dioxane, 80° C., 6 h (c) IBX,DMSO—THF r.t, 3 h
(d) Ylide, toluene, 80° C., 4 h (e) TFA, CH2Cl2, r.t, 2.5 h (f) DIPC, DMAP, CH2Cl2, 0° C. to r.t, 5 h
n = 0, 1, 2, 3, 4 . . .

Step b:

To a solution of intermediate 6.02 (crude 6 g, 0.011 mol) in dioxane (30 mL) is added ethylene glycol (20 mL) and allowed to reflux for 12 h. After completion dioxane is removed under vacuum and quenched with water (20 mL). The compound is extracted in ethyl acetate and washed with water (3×50 mL) and brine (20 mL) successively. The combined organic layer is dried over anhydrous $Na_2SO_4$ and concentrated under reduced pressure. The residue is purified on silica gel utilizing methanol-chloroform as mobile phase to obtain intermediate 14.01.

Step c:

To 50 mL single neck round bottom flask IBX (1.301 g, 4.647 mmol) is taken in anhydrous dimethy sulphoxide (3 mL) and stirred for 30 minutes to get a clear solution. To this solution alcohol intermediate 14.01 (1 g, 2.323 mmol) is added in anhydrous THF (10 mL) over a period of 10 minutes. The resulting solution is stirred for another 3 h at room temperature and TLC is checked. After completion the reaction mixture is diluted with diethyl ether and the white solid is filtered through a thin pad of celite and washed with water (2×15 mL). The organic layer is dried over anhydrous Na2SO4, concentrated under vacuum and purified by silica gel chromatography to obtain aldehyde intermediate 14.02.

Step d:

To 50 mL single neck round bottom flask phosphonium ylide Ph3P=CH2COOBu$^t$ (1.404 g, 3.732 mmol) is taken in toluene (20 mL) and heated to 40° C. To this solution aldehyde intermediate 14.02 (800 mg, 1.866 mmol) in toluene (2 mL) is added. The oil bath temperature is raised to 80° C. and stirred for 2 h and TLC is checked. After completion the organic solvent is removed under reduced pressure and the residue is purified by silica gel chromatography to obtain intermediate 14.03.

Step e:

To a 25 mL single neck round bottom flask intermediate 14.03 (500 mg, 0.949 mmol) is taken in anhydrous $CH_2Cl_2$ (5 mL) under nitrogen atmosphere at 0° C. To this reaction mixture TFA (2 mL) is added slowly over a period of 5 minute and stirred at room temperature for 3 h and TLC is checked. After completion the solvent is removed under reduced pressure and washed with hexane (5 mL). The residue is purified by silica gel chromatography to obtain acid intermediate 14.04.

Step f:

To a 25 mL single neck round bottom flask flask acid intermediate 14.04 (112 mg, 0.2392 mmol) is taken in anhydrous $CH_2Cl_2$ (7 mL) under nitrogen atmosphere at 0° C. To this cooled solution DIPC (37 μL, 0.2392 mmol) followed by DMAP (29 mg, 0.2392 mmol) is added and stirred at same temperature for 2 h. To this activated acid solution cabazitaxel (100 mg, 0.1196 mmol) is added and stirred for another 3 h at room temperature and TLC is checked. After completion the reaction mixture is quenched with water, extracted with CHCl3, dried over anhydrous sodium sulphate, concentrated and purified by silica gel chromatography to obtain conjugate 14.

Example 15: Supramolecular Combinatorial Therapeutics

Supramolecular nanostructures were formulated using different mole ratios of phospholipids (such as POPC, SOPC, Egg PC or HSPC), taxane supramolecules and PEGylated-phospholipids (such as DSPE-PEG).

POPC, New taxane 2 and DSPE-PEG, taken in 34:16:50 mol % ratio, were dissolved in Chloroform. All lipid solutions were mixed homogeneously in round bottom flask and organic solvent was evaporated by rotary evaporator and the lipid film was kept under high vacuum for 3-4 hr. The thin film was, then, hydrated (by adding 5% Lactose solution to it) for 1.0 h at 70° C. in hot water bath. Next, hydrated liposomes were sequentially extruded through 400 nm and 200 nm pore size membrane held by filter support for 11 times at 70° C. using Avanti extruder supported over hot plate. UV measurement reveals % encapsulation efficiency of this formulation to be 14 mol % of taxane supramolecule. The resulting solution was lyophilized and stored at −20° C. The weight cut-off (the final weight ratio of total lipid to taxane supramolecule) of this system was determined to be ~8.66:1.

Variation in combinations of different lipids demonstrates that aforementioned supra-molecular formulation requires an optimum amount of rigidity and fluidity of the lipid bilayer. This led to the use of POPC/SOPC (as both of them contain only one double bond in one chain and other chain is 16-Carbon long in POPC and 18-Carbon long in SOPC) which is supposed to provide a little more rigidity to the bilayer compared to DOPC (having of two double bonds in two tails). It has also been proven that higher mol % of HSPC (both the 18-tails are saturated) is not suitable for this supra-molecular formulation. DSPE-PEG has a dichotomous role in this supra-molecular self-assembly: balancing the required initial weight for a higher mol % loading of API as well as preventing the precipitation of API from the bilayer.

This supramolecule was lyophilized (5% Lactose solution was used as cryo-protectant) over 16-20 hrs. The white solid powder formed thereafter was reconstituted by adding required volume of water. DLS study of this reconstituted supramolecular formulation reveals similar size, PDI, surface potential of supramolecules as it was before lyophilization.

To clarify the characteristics of the present invention, some examples of its implementation are described with different mol % of DSPE-PEG and variable mol % of taxane supramolecule.

Example 15.1

POPC, New taxane 2 and DSPE-PEG, taken in 34:16:50 mol % ratio, were dissolved in Chloroform. All lipid solutions were mixed homogeneously in round bottom flask and organic solvent was evaporated by rotary evaporator and the lipid film was kept under high vacuum for 3-4 hr. The thin film was, then, hydrated (by adding 5% Lactose solution to it) for 1.0 h at 70° C. in hot water bath. Next, hydrated liposomes were sequentially extruded through 400 nm and 200 nm pore size membrane held by filter support for 11 times at 70° C. using Avanti extruder supported over hot plate. UV measurement reveals % encapsulation efficiency of this formulation to be 14 mol % of taxane supramolecule. The resulting solution was lyophilized and stored at −20° C. The weight cut-off (the final weight ratio of total lipid to taxane supramolecule) of this system was determined to be ~8.66:1.

The solution was lyophilized (5% Lactose solution was used as cryo-protectant) over 16-20 hrs and the white solid powder formed thereafter was reconstituted by adding required volume of water. DLS study of this reconstituted supramolecular formulation reveals similar size, PDI, surface potential of supramolecules as it was before lyophilization.

Example 15.2

POPC, New taxane 2 and DSPE-PEG, taken in 30:20:50 mol % ratio, were dissolved in Chloroform. All lipid solutions were mixed homogeneously in round bottom flask and organic solvent was evaporated by rotary evaporator and the lipid film was kept under high vacuum for 3-4 hr. The thin film was, then, hydrated (by adding 5% Lactose solution to it) for 1.0 h at 70° C. in hot water bath. Next, hydrated liposomes were sequentially extruded through 400 nm and 200 nm pore size membrane held by filter support for 11 times at 70° C. using Avanti extruder supported over hot plate. UV measurement reveals % encapsulation efficiency of this formulation to be 14 mol % of taxane supramolecule. The resulting solution was lyophilized and stored at −20° C. The weight cut-off (the final weight ratio of total lipid to taxane supramolecule) of this system was determined to be ~8.5:1.

The solution was lyophilized (5% Lactose solution was used as cryo-protectant) over 16-20 hrs and the white solid powder formed thereafter was reconstituted by adding required volume of water. DLS study of this reconstituted supramolecular formulation reveals similar size, PDI, surface potential of supramolecules as it was before lyophilization.

Example 15.3

POPC, New taxane 2 and DSPE-PEG, taken in 40:10:50 mol % ratio, were dissolved in Chloroform. All lipid solutions were mixed homogeneously in round bottom flask and organic solvent was evaporated by rotary evaporator and the lipid film was kept under high vacuum for 3-4 hr. The thin film was, then, hydrated (by adding 5% Lactose solution to it) for 1.0 h at 70° C. in hot water bath. Next, hydrated liposomes were sequentially extruded through 400 nm and 200 nm pore size membrane held by filter support for 11 times at 70° C. using Avanti extruder supported over hot plate. UV measurement reveals % encapsulation efficiency of this formulation to be 9.7 mol % of taxane supramolecule. The final weight ratio of total lipid to taxane supramolecule of this system was determined to be ~12.9:1.

Example 15.4

POPC, HSPC, New taxane 2 and DSPE-PEG, taken in 55:34:10:1 mol % ratio, were dissolved in Chloroform. All lipid solutions were mixed homogeneously in round bottom flask and organic solvent was evaporated by rotary evaporator and the lipid film was kept under high vacuum for 3-4 hr. The thin film was, then, hydrated for 1.0 h at 60° C. in hot water bath. Next, hydrated liposomes were sequentially extruded through 400 nm and 200 nm pore size membrane held by filter support for 11 times at 70° C. using Avanti extruder supported over hot plate. UV measurement reveals % encapsulation efficiency of this formulation to be 5.7 mol % of taxane supramolecule. The final weight ratio of total lipid to taxane supramolecule of this system was determined to be ~9.1:1.

Example 15.5

POPC, HSPC, New taxane 2 and DSPE-PEG, taken in 55:34:10:1 mol % ratio, were dissolved in Chloroform. All lipid solutions were mixed homogeneously in round bottom flask and organic solvent was evaporated by rotary evaporator and the lipid film was kept under high vacuum for 3-4 hr. The thin film was, then, hydrated (by adding 5% Lactose solution to it) for 1.0 h at 60° C. in hot water bath. Next, hydrated liposomes were sequentially extruded through 400 nm and 200 nm pore size membrane held by filter support for 11 times at 70° C. using Avanti extruder supported over hot plate. UV measurement reveals % encapsulation efficiency of this formulation to be 5.7 mol % of taxane supramolecule. The resulting solution was lyophilized and stored at −20° C. The final weight ratio of total lipid to taxane supramolecule of this system was determined to be ~9.1:1.

The solution was lyophilized (5% Lactose solution was used as cryo-protectant) over 16-20 hrs and the white solid powder formed thereafter was reconstituted by adding required volume of water. DLS study of this reconstituted supramolecular formulation reveals similar size, PDI, surface potential of supramolecules as it was before lyophilization.

Bioassays

Cell Culture:

Mammalian cells were grown in specific culture media, supplemented with 10% fetal bovine serum (FBS) and antibiotics in a humidified environment containing 5% $CO_2$ at 37° C.

Cell Viability Assay:

The effects of supramolecular taxane conjugates on the viability of cancer cells were measured using MTT assay ([6,7,8]). Cells in 100 μl culture-media were plated in 96-well plates (3000-5000 cells/well) and allowed to adhere overnight in a humidified environment containing 5% $CO_2$ at 37° C. Fresh media (100 μL) containing different concentrations of compounds were added to cells and incubated for 48, 72 and 96 hrs. Following incubation, cell viability was determined using the MTT assay. Similar assay was performed on normal human epithelial cells seeded in 100 μl media in 96-well plate (5000-10,000 cells per well), under identical incubation time and dosage of compounds, used for cancer cells to determine the effect of this targeted therapy on normal cells. The cell viability was plotted as dose-response curves using curve fitting.

Figure 2:
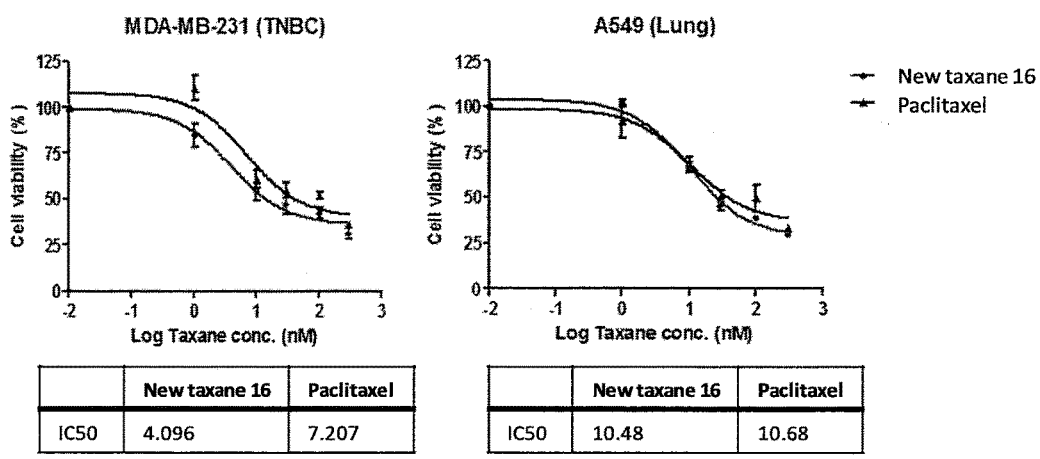
FIG. 2 shows in vitro characterization of supramolecular new taxane 16 according to an embodiment of the disclosure.
Figure 3:
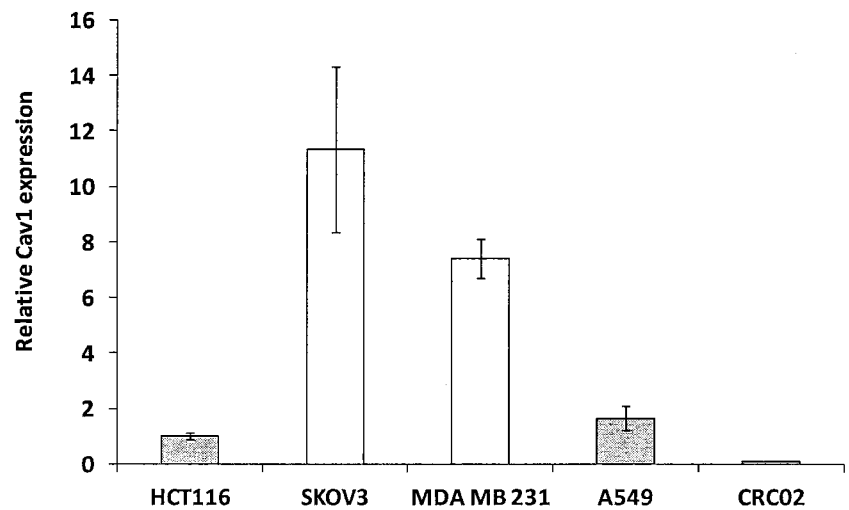
FIG. 3 shows expression of CAV1 mRNA by qPCR in responsive (unshaded) and non-responsive (shaded) cell-lines.
Figure 4:
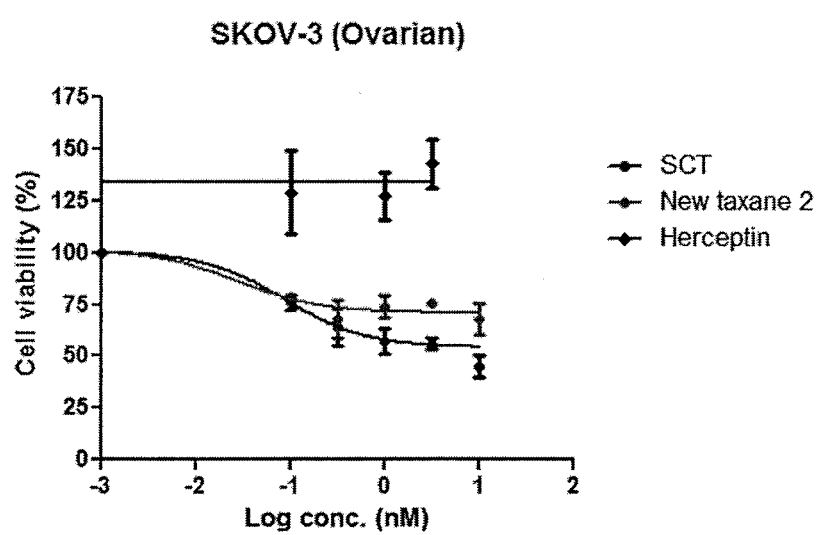
FIG. 4 shows in vitro characterization of a supramolecular combinatorial therapeutic (SCT) molecule, according to an embodiment of the disclosure, where the supramolecular new taxane is attached to an antibody which binds a protein, receptor, or marker expressed on the surface of a cancer cell.

The effects of compounds (New taxane 2 and 16) were evaluated in vitro in comparison with standard taxanes in breast cancer (MDA-MB-231), ovarian cancer (SKOV-3), lung cancer (A549), prostate cancer (DU-145), and colorectal cancer (HCT-116) cell lines. The supramolecular taxane conjugates showed comparable efficacy to standard taxanes in all cell lines (See FIGS. 1, 2 and 4).

Example 16: Supramolecular Combinatorial Therapeutics Including Immunotherapeutics Cell Culture:

Mammalian cells were grown in specific culture media, supplemented with 10% fetal bovine serum (FBS) and antibiotics in a humidified environment containing 5% CO2 at 37° C.

Combinatorial Therapy:

Therapeutic effects of supramolecules and PD-L1 or PD-1 were examined in melanoma, breast or lung carcinoma models. Mice (4-6 per group) were inoculated subcutaneously with cells (melanoma (B16F10): $3\times10^5$ cells; breast (4T1): $5\times10^5$ cells; lung (LLC): $5\times1^05$ cells). In tumor bearing mice, once the average tumor volume reaches between 60-90 $mm^3$, drug therapy consisted of the following administration: saline (for control group), platinum drug (5 mg/kg); platinum drug (5 mg/kg) plus anti-PD-1 or PD-L1 antibodies (2 mg/kg); platinum drug (10 mg/kg); platinum drug (10 mg/kg) plus anti-PD-1 or PD-L1 antibodies (2 mg/kg); anti-PD-1 or PD-L1 antibodies (2 mg/kg); platinum-supramolecules (5 mg/kg); platinum-supramolecules (5 mg/kg) plus anti-PD-1 or PD-L1 antibodies (2 mg/kg); platinum-supramolecules (10 mg/kg); platinum-supramolecules (10 mg/kg) plus anti-PD-1 or PD-L1 antibodies (2 mg/kg); taxane (5 mg/kg); taxane (5 mg/kg) plus anti-PD-1 or PD-L1 antibodies (2 mg/kg); taxane (10 mg/kg); taxane (10 mg/kg) plus anti-PD-1 or PD-L1 antibodies (2 mg/kg); taxane-supramolecules (5 mg/kg); taxane-supramolecules (5 mg/kg) plus anti-PD-1 or PD-L1 antibodies (2 mg/kg);

taxane-supramolecules (10 mg/kg); taxane-supramolecules (10 mg/kg) plus anti-PD-1 or PD-L1 antibodies (2 mg/kg).

The compounds were administered via tail vein, with platinum/taxane compounds being administered at q2d dosing and anti-PD-1 or PD-L1 antibodies being dosed on subsequent days with the same dosing regimen. Tumor volumes and body weights were recorded every alternate day for 2 weeks. Tumor volumes were determined in individual mouse by measuring two opposing diameters and represented as mm$^3$. The animals were sacrificed when the average tumor volume exceeded 2000 mm$^3$. The tumors were harvested immediately following sacrifice and stored in 10% formalin or flash frozen for further analysis.

Example 17: Supramolecular Combinatorial Therapeutics Including Immunotherapeutics Combinatorial Therapy:

Therapeutic effects of platinum supramolecules and PD-L1 were examined in TNBC models. Mice (6 per group) were inoculated subcutaneously with TNBC cells (4×10$^5$ cells). In tumor bearing mice, once the average tumor volume reaches between 60-80 mm$^3$, drug therapy consisted of the following administration: saline (for control group), Carboplatin (5 mg/kg); anti-PD-L1 antibodies (2 mg/kg); IO-125 (5 mg/kg); IO-125 (5 mg/kg) plus anti-PD-L1 antibodies (2 mg/kg).

The compounds were administered via tail vein, with platinum compounds being administered at q2d dosing and anti-PD-L1 antibodies being dosed on subsequent days with the same dosing regimen. Tumor volumes and body weights were recorded every alternate day for 1 week. Tumor volumes were determined in individual mouse by measuring two opposing diameters and represented as mm$^3$. The tumors were harvested immediately following sacrifice and stored in 10% formalin or flash frozen for further analysis.

Figure 5:
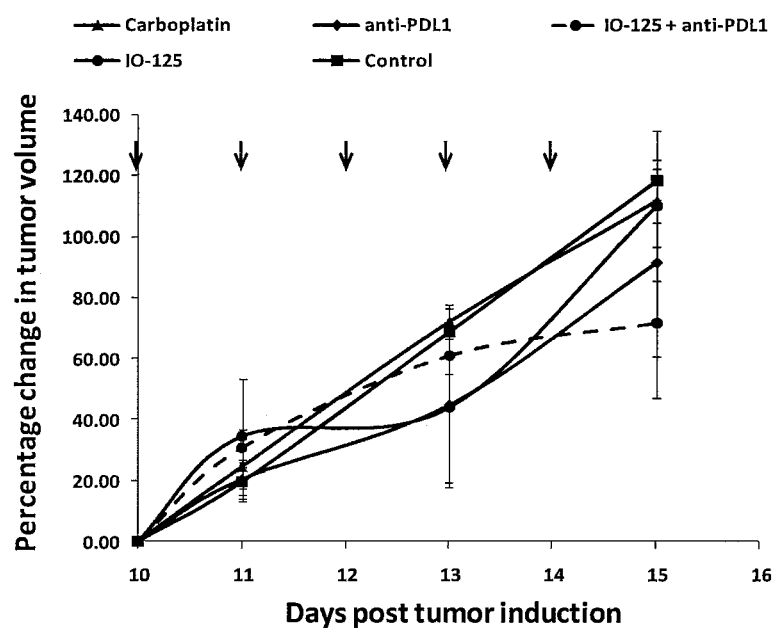
FIG. 5 shows therapeutic effects of IO-125 and anti-PD-L1 against 4T1 (TNBC) tumors.

FIG. 5 shows the therapeutic effects of IO-125 and anti-PD-L1 against 4T1 (TNBC) tumors. Tumor-bearing mice received platinum drugs (grey arrows) or immunization with anti-PD-L1 (orange arrows). By day 5 following administration, tumor sizes were reduced by 35% when a combination of IO-125 and anti-PD-L1 was used to treat TNBC. The tumor volume was calculated by using the formula, (L×W×W)/2, where the longest diameter measured was considered 'L' and the shortest diameter was 'W'.

REFERENCES (1a) Hennenfent, K. L.; Govindan, R. Novel formulations of taxanes: a review. Old wine in a new bottle?, Ann. Oncol. 2006, 17, 734-749
(1b) Fetterly, G. J.; Straubinger, R. M. Pharmacokinetics of paclitaxel-containing liposomes in rats, AAPS PharmSci 2003, 5, 1-11
(1c) Sparreboom, A.; Scripture, C. D.; Trieu, V.; Williams, P. J.; De, T; Yang, A.; Beals, B.; Figg, M. Hawkins, W. D.; Desai, N. Comparative preclinical and clinical pharmacokinetics of a cremophor free, nanoparticle albumin-bound paclitaxel (ABI-007) and paclitaxel formulated in cremophor (Taxol). Clin. Cancer Res. 2005, 11, 4136-4143
(1d) Sparreboom, A.; van Zuylen, L.; Brouwer, E.; Loos, W. J.; de Bruijn, P.; Gelderblom, H.; Pillay, M; Nooter, K.; Stoter, G.; Verweij, J. Cremophor EL-mediated alteration of paclitaxel distribution in human blood: Clinical pharmacokinetic implications. Cancer Res. 1999, 59, 1454-1457

(2) Yared, J. A; Tkaczuk, K. H; Update on taxane development: new analogs and formulations Drug Design, Development and Therapy 2012: 6 371-384.
(3a) Ansell, S. M; Johnstone, S; Tardi, P; Mayer, L; Taxane delivery system. U.S. patent Ser. No. 12/741, 954 2007.
(3b) Bradley, M. O; Shashoua, V. E; Swindell, C. S; Webb, S. N; Compositions comprising conjugates of cis-docosahexanoic acid and taxotere. U.S. Pat. No. 008,866 1997.
(4) Mayer, L. D; Prud'homme R. K; Allen C. J; Saad W. S. Pub. No. WO/2006/014626.
(5) Stevens, P. J.; Sekido, M.; Lee, R. J. A folate receptor-targeted lipid nanoparticle formulation for a lipophilic paclitaxel prodrug. Pharm. Res. 2004, 21, 2153-2157.
(6) Bissery, M. C., Bouchard, H., Riou, J. F. Preclinical evaluation of TXD258, a new taxoid. Proc Am Assoc Cancer Res (AACR) 2000, 41: Abst 1364.
(7) Mita, A. C., Denis, L. J., Rowinsky, E. K. et al. Phase I and pharmacokinetic study of XRP6258 (RPR 116258A), a novel taxane, administered as a 1-hour infusion every 3 weeks in patients with advanced solid tumors. Clin Cancer Res 2009, 15(2): 723-30.
(8) Aller, A. W. In vitro activity of TXD258 in chemotherapeutic resistant tumor xenografts. Proc Am Assoc Cancer Res (AACR) 2000, 41: Abst 1923.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A supramolecular combinatorial therapeutic (SCT) comprising a taxane-lipid conjugate, wherein the taxane-lipid conjugate is a cabazitaxel-lipid conjugate; and wherein the cabazitaxel-lipid conjugate is selected from the group consisting of conjugates 1-15 and 21-32

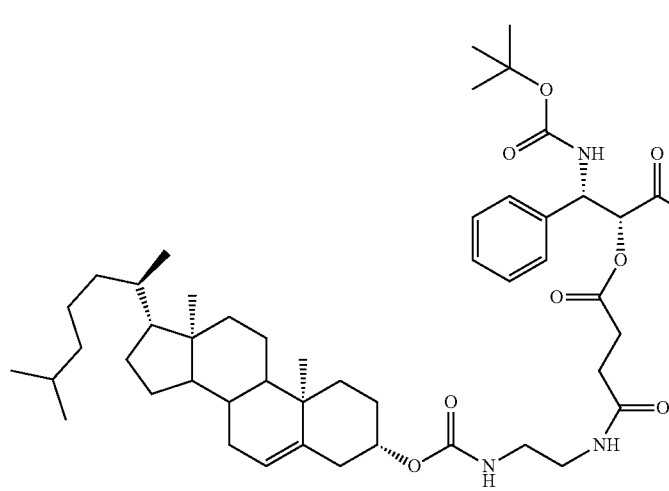
1
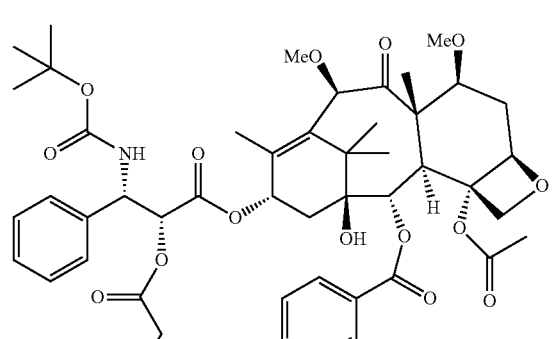
2
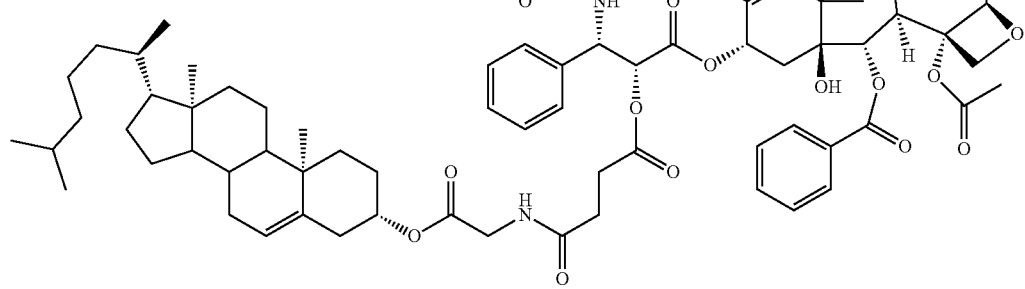
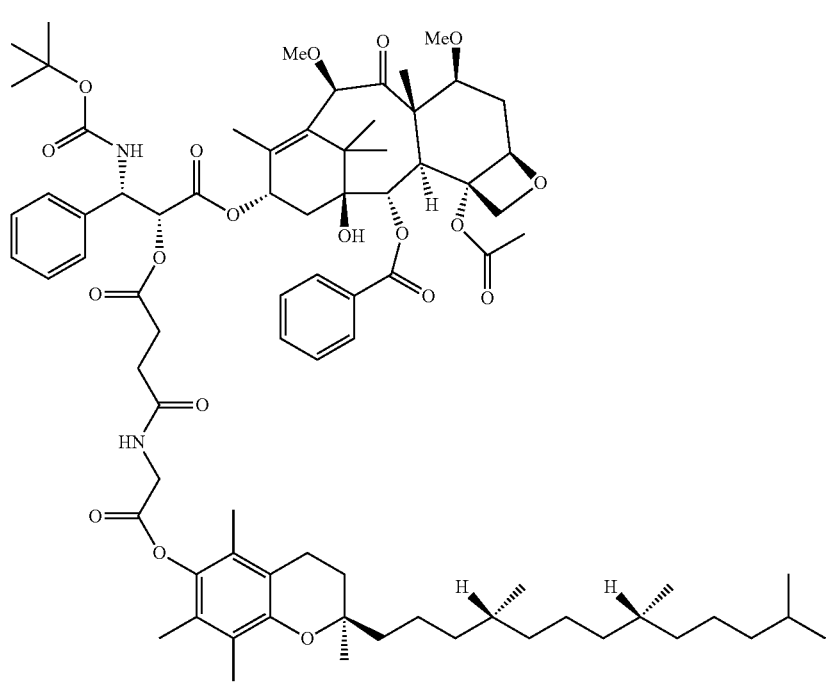
3

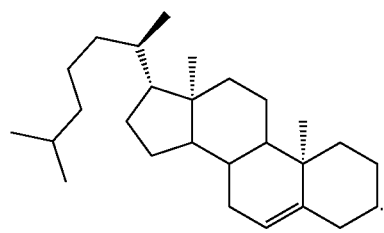
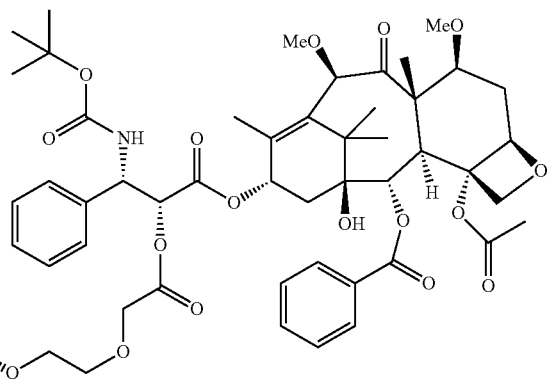
4
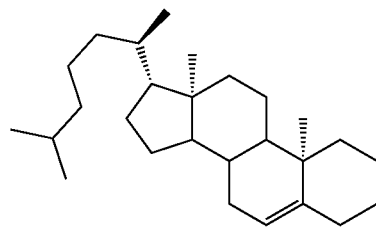
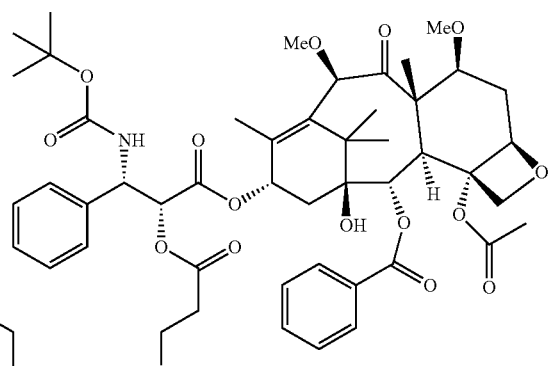
5
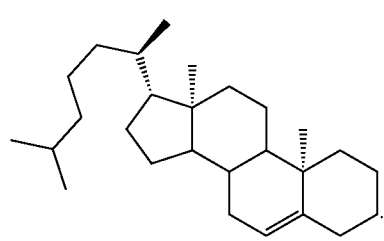
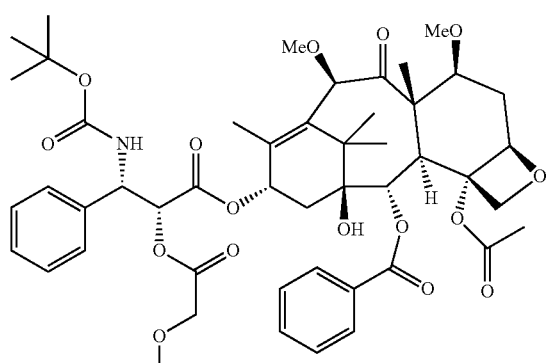
6

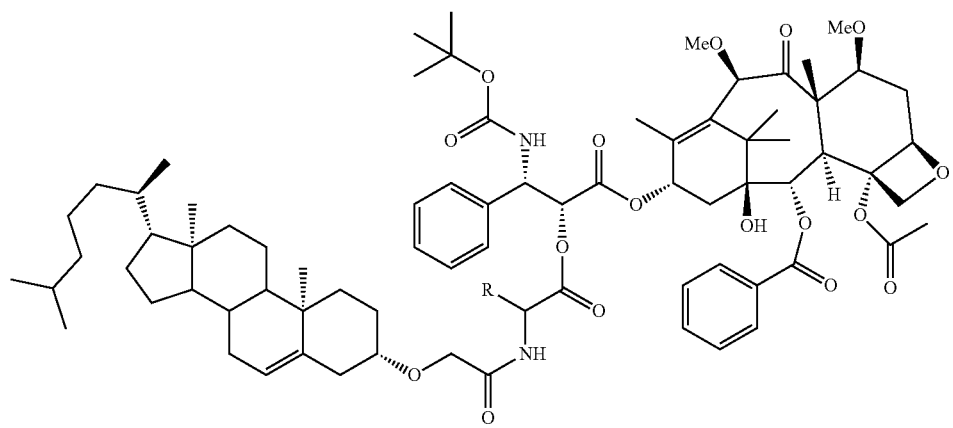
7
R = H, CH3, CH(CH3)2, CH2CH(CH3)2, C(CH3)CH2CH3, CH2Ph
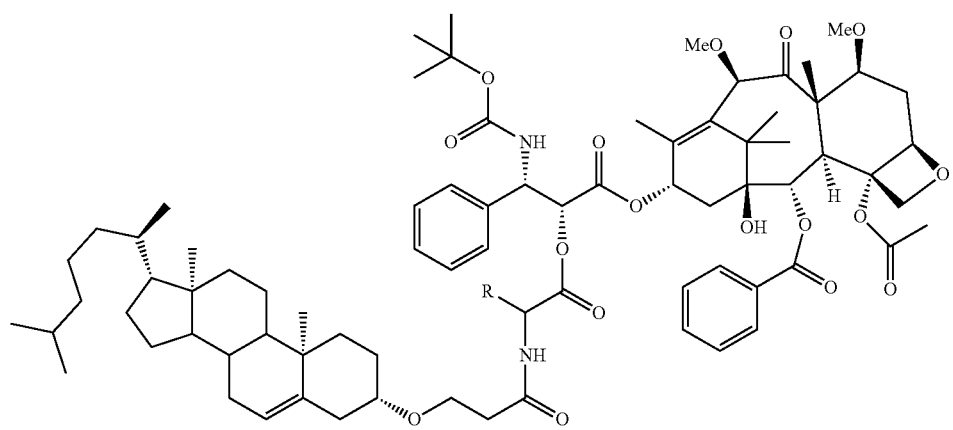
8
R = H, CH3, CH(CH3)2, CH2CH(CH3)2, C(CH3)CH2CH3, CH2Ph
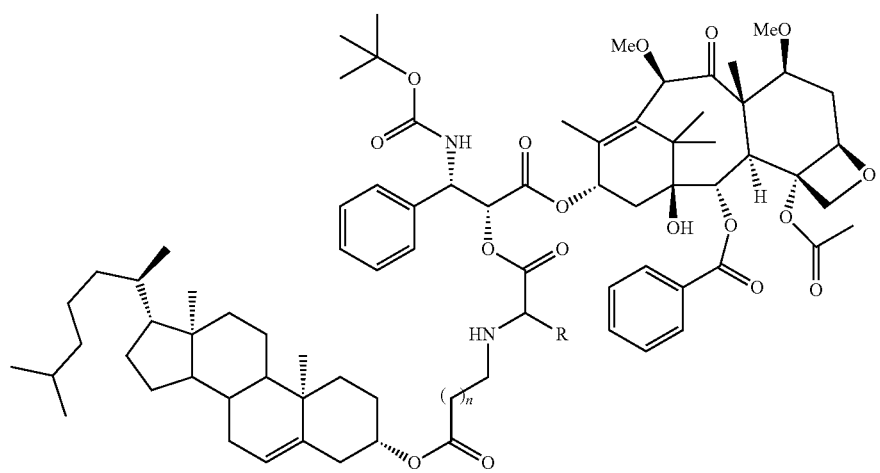
9
*n* = 1 to 3
R = H, CH3, CH(CH3)2, CH2CH(CH3)2, C(CH3)CH2CH3, CH2Ph

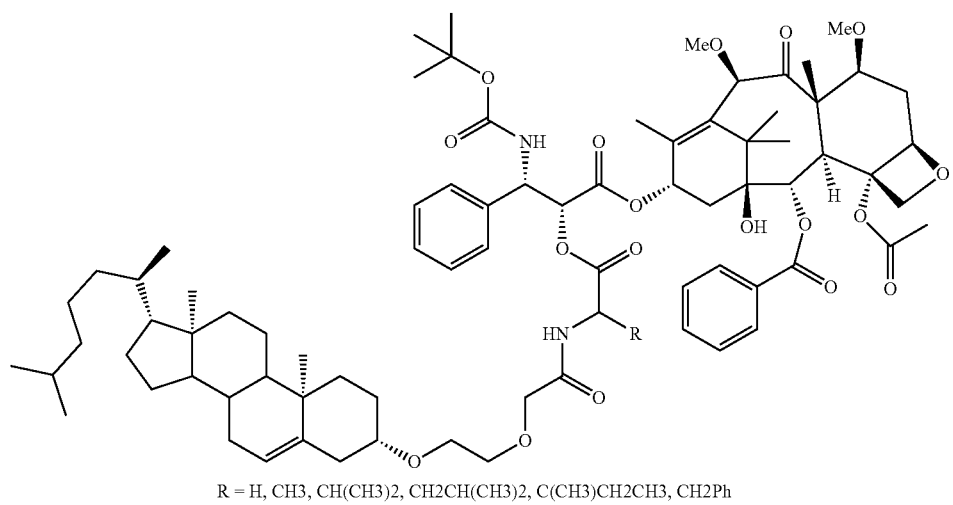
10
R = H, CH3, CH(CH3)2, CH2CH(CH3)2, C(CH3)CH2CH3, CH2Ph
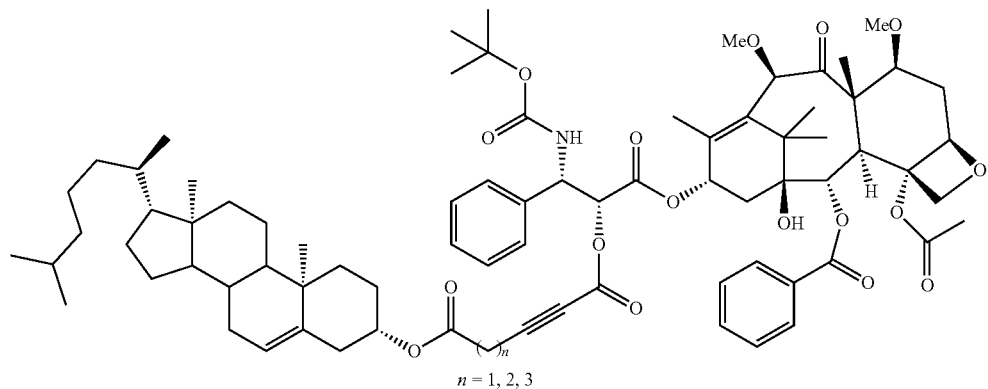
11
n = 1, 2, 3
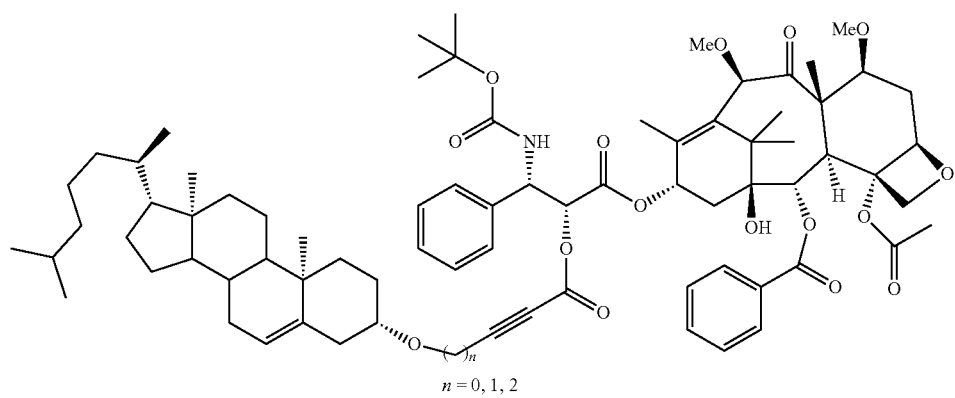
12
n = 0, 1, 2

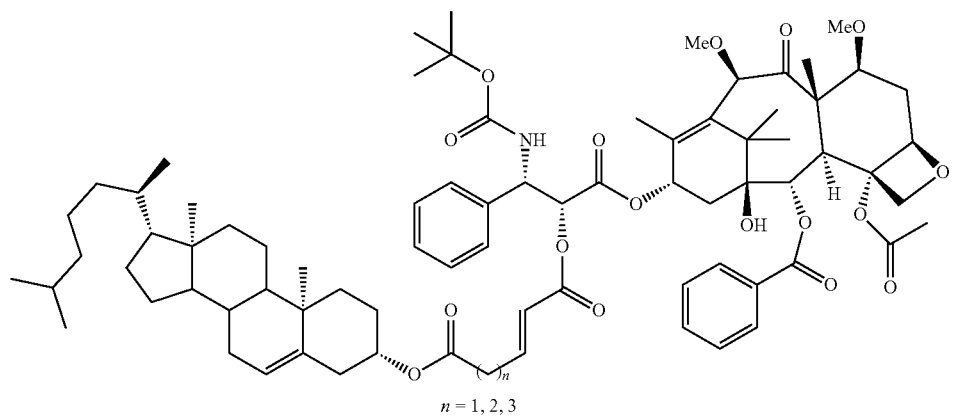
13
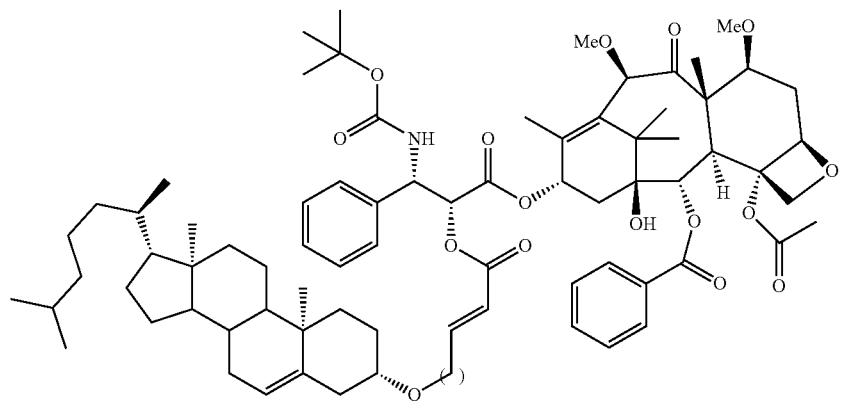
n = 0, 1, 2
14
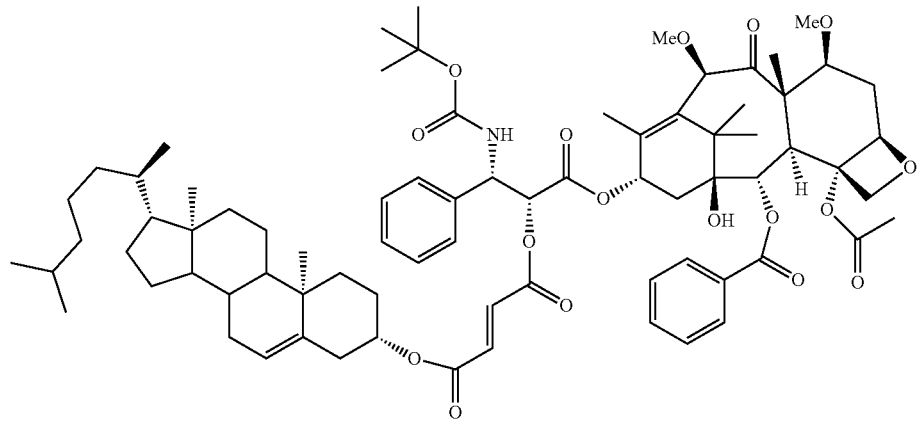
15

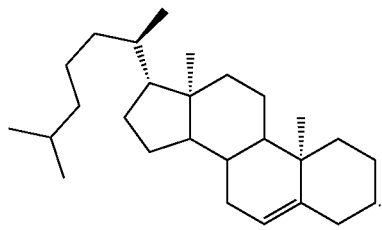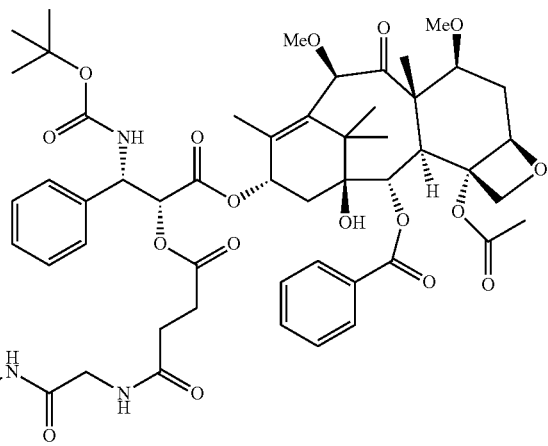
21
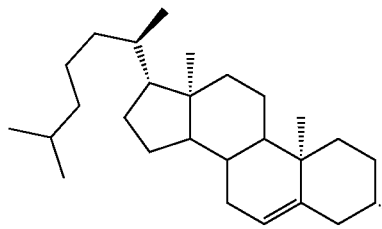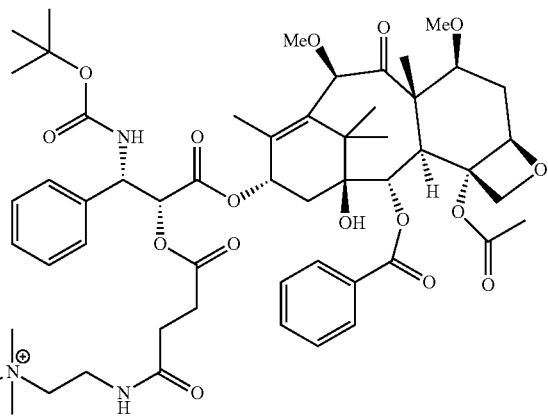
22
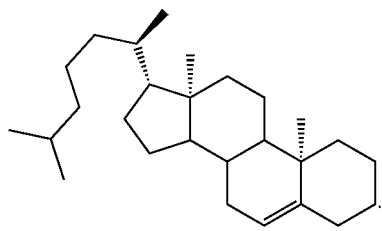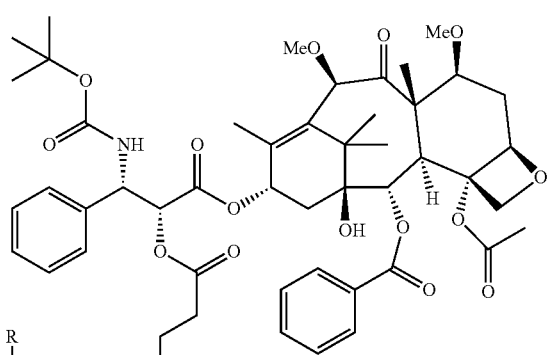
23
R = H, Me, CH2COOH -continued
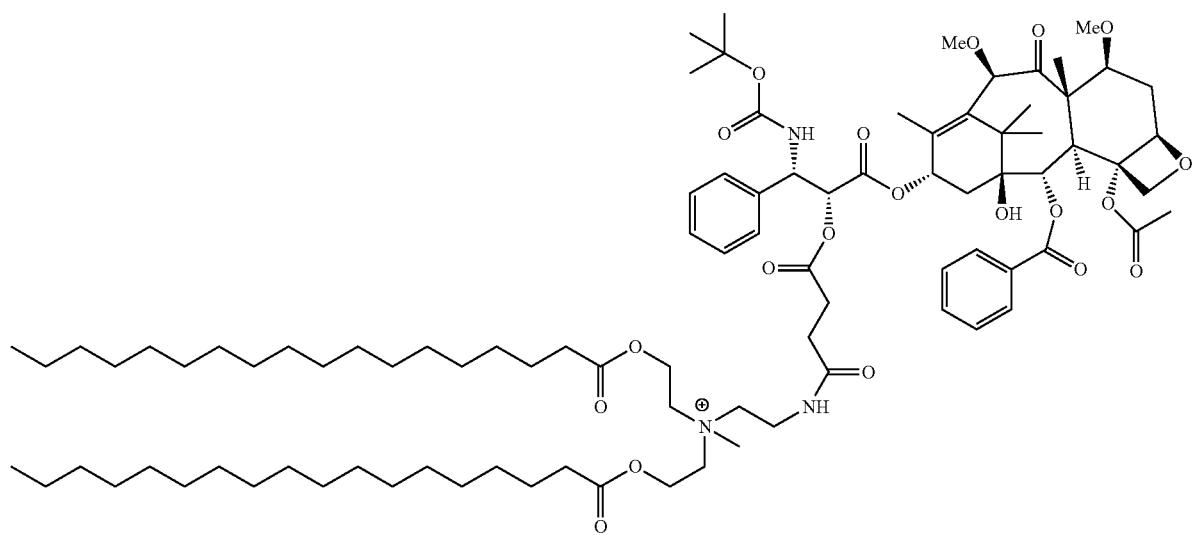
24
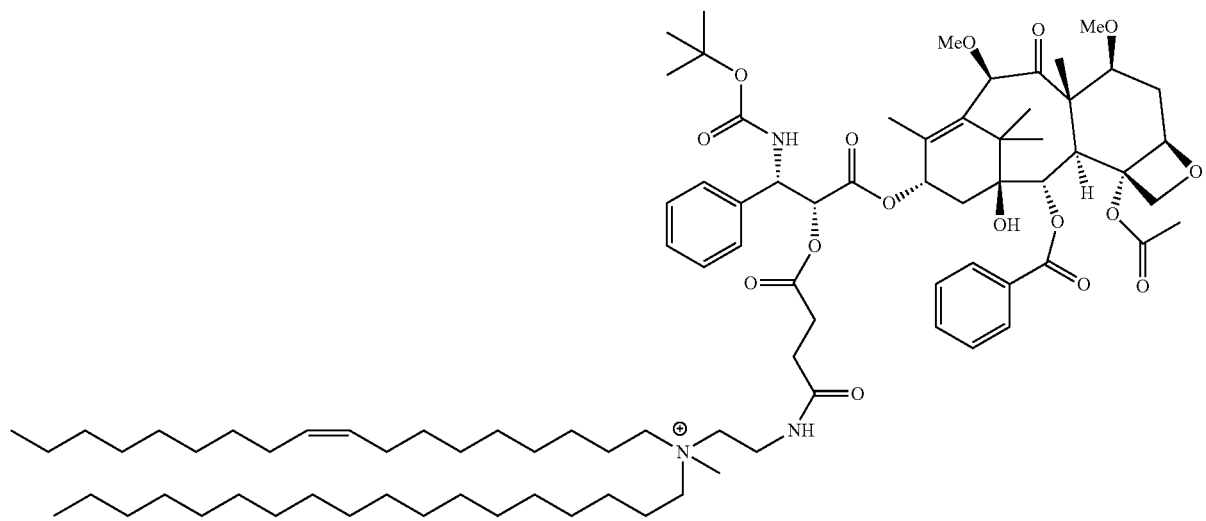
25
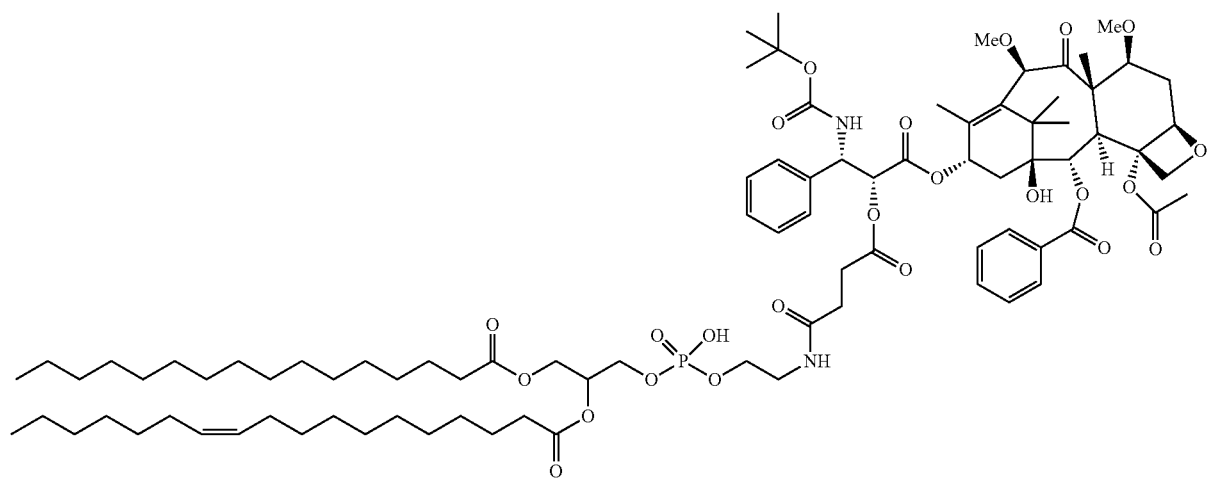
26

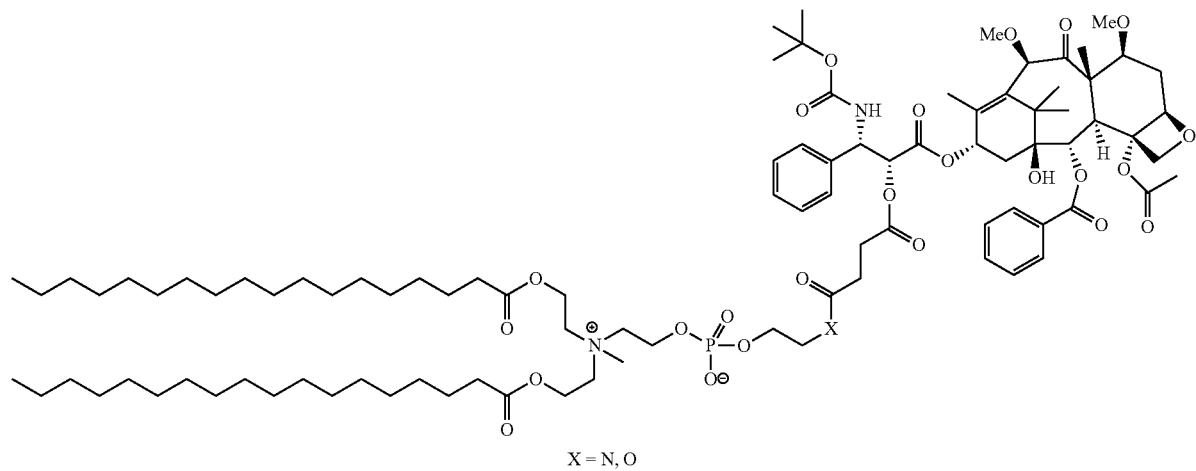
27
X = N, O
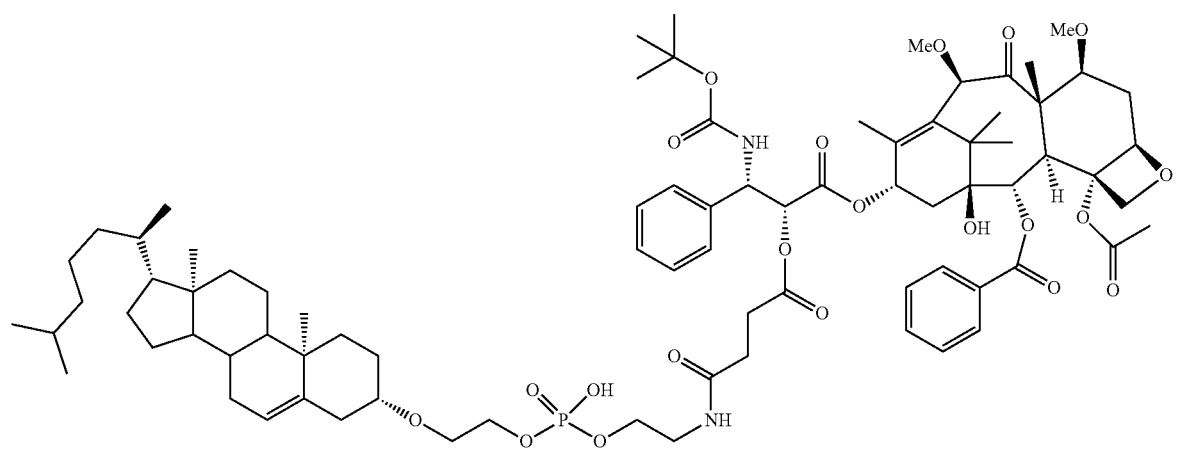
28
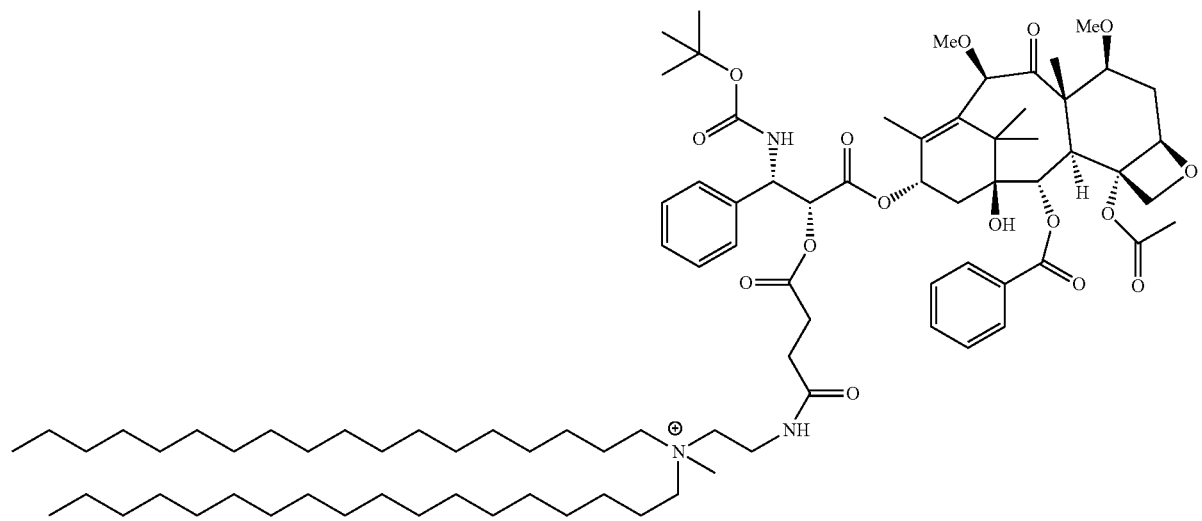
29

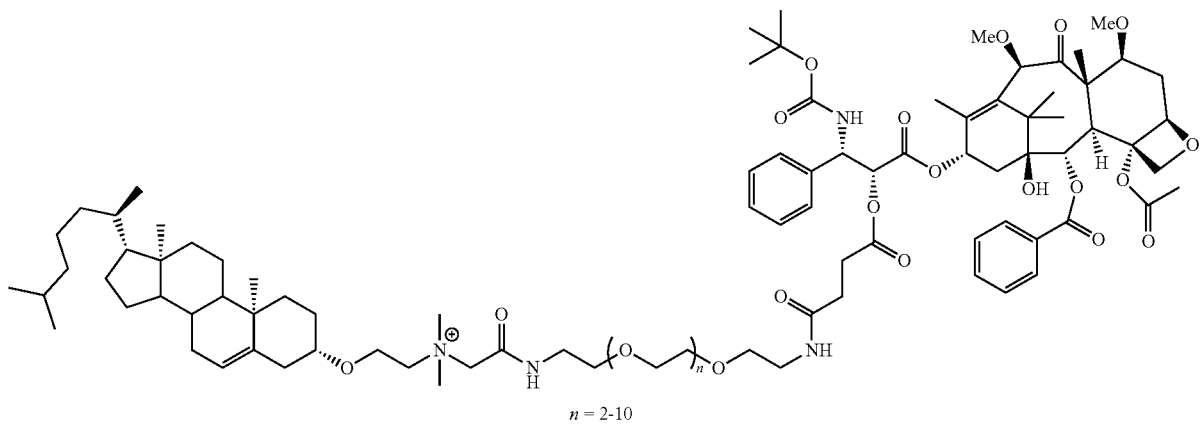

30

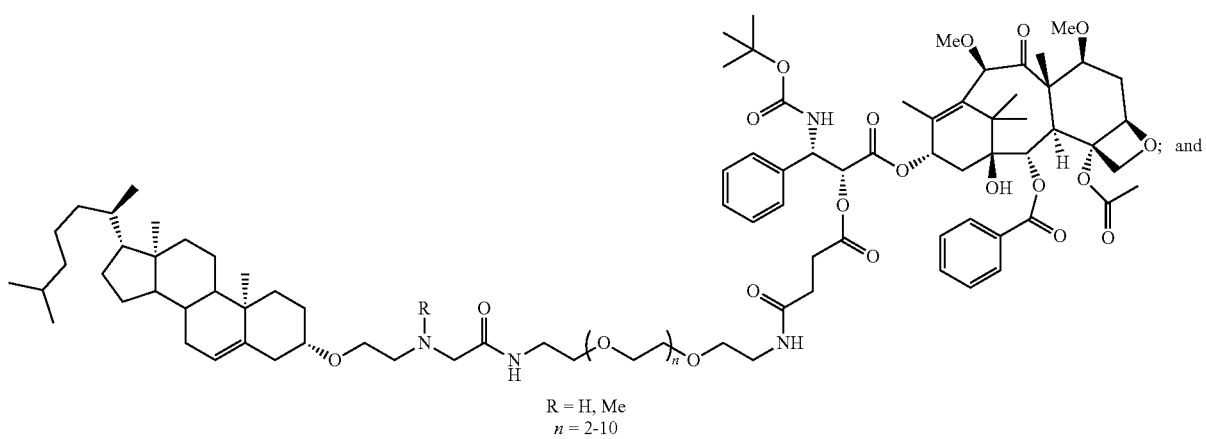

31

R = H, Me
n = 2-10

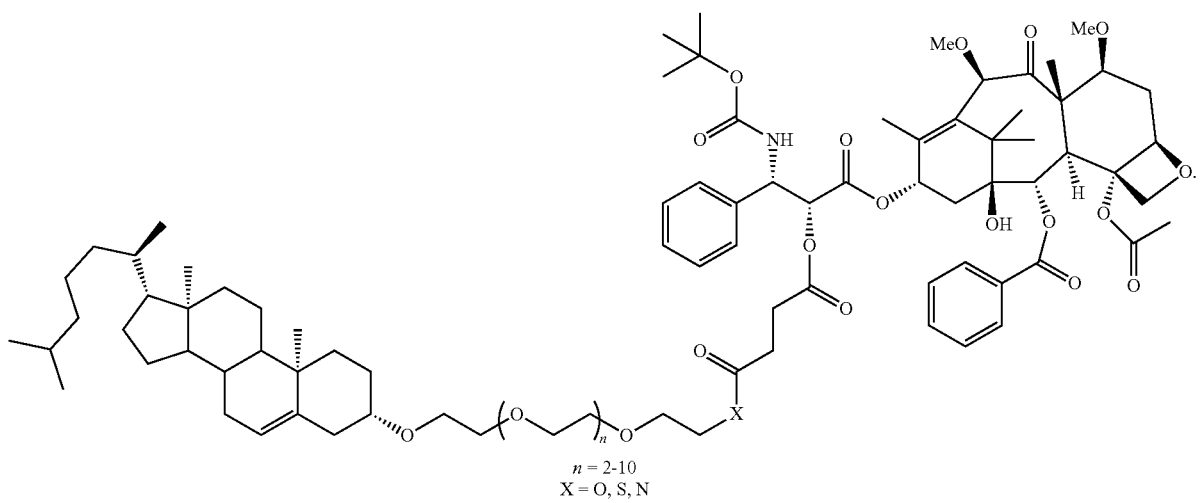

32 n = 2-10
X = O, S, N

2. The supramolecular combinatorial therapeutic of claim 1, wherein the supramolecular combinatorial therapeutic is a liposome, emulsion, micelle, or particle; the supramolecular combinatorial therapeutic comprises from about 1% to about 99% (w/w) of the taxane conjugate.

3. The supramolecular combinatorial therapeutic of claim 1, wherein the supramolecular combinatorial therapeutic further comprises a lipid conjugated PI3K inhibitor, a lipid conjugated platinum compound, a lipid conjugated antibody, a neutral lipid, a cationic lipid, an anionic lipid, an amphiphilic lipid, a sterol, a programmable fusion lipid and combinations thereof or a pharmaceutically acceptable carrier; wherein the antibody is a therapeutic agent or a targeting ligand or is an immunomodulatory comprising an anti-PD-1 antibody, an anti-PD-L1 antibody and combinations thereof; wherein the lipid is cholesterol, 1,3-Propanediol Dicaprylate/Dicaprate, 10-undecenoic acid, 1-dotriacontanol, 1-heptaconsanol, 1-nonacosanol, 2-ethyl hexanol, Androstanes, Arachidic acid, Arachidonic acid, arachidyl alcohol, Benenic acid, behenyl alcohol, Capmul MCM C10, Capric acid, capric alcohol, capryl alcohol, Caprylic acid, Caprylic/Capric Acid Ester of Saturated Fatty Alcohol C12-C18, Caprylic/Capric Triglyceride, Cermide phosphorylcholine (Sphingomyelin, SPH), Ceramide phosphorylethanolamine (Sphingomyelin, Cer-PE), Ceramide phosphorylglycerol, Ceroplastic acid, Cerotic acid, ceryl alcohol, Cetearyl alcohol, Ceteth-10, cetyl alcohol, Cholanes, Cholestanes, cholesterol, cis-11-eicosenoic acid, cis-11-octadecenoic acid, cis-13-docosenoic acid, cluytyl alcohol, Dihomo-γ-linolenic, Docohexaenoic acid, egg lecithin, Eicosapentaenoic acid, Eicosenoic acid, Elaidic acid, elaidolinolenyl alcohol, elaidolinoleyl alcohol, elaidyl alcohol, Erucic acid, erucyl alcohol, Estranes, Ethylene glycol distearate (EGDS), Geddic acid, geddyl alcohol, glycerol distearate (type I) EP (Precirol ATO 5), Glycerol Tricaprylate/Caprate, Glycerol Tricaprylate/Caprate (CAPTEX® 355 EP/NF), glyceryl monocaprylate (Capmul MCM C8 EP), Glyceryl Triacetate, Glyceryl Tricaprylate, Glyceryl Tricaprylate/Caprate/Laurate, Glyceryl Tricaprylate/Tricaprate, glyceryl tripalmitate (Tripalmitin), Henatriacontylic acid, Heneicosyl alcohol, Heneicosyl acid, Heptacosylic acid, Heptadecanoic acid, Heptadecyl alcohol, Hexatriacontylic acid, isostearic acid, isostearyl alcohol, Lacceroic acid, Lauric acid, Lauryl alcohol, Lignoceric acid, Lignoceryl alcohol, Linoelaidic acid, Linoleic acid, Linolenyl alcohol, linoleyl alcohol, Margaric acid, Mead, Melissic acid, melissyl alcohol, Montanic acid, montanyl alcohol, myricyl alcohol, Myrisitic acid, Myristoleic acid, Myristyl alcohol, neodecanoic acid, neohaptanoic acid, neononanoic acid, Nevronic, Nonacosylic acid, Nonadecyl alcohol, Nonadecylic acid, Oleic acid, oleyl alcohol, Palmitic acid, Palmitoleic acid, palmitoleyl alcohol, Pelargonic acid, Pelargonic alcohol, Pentacosylic acid, Pentadecyl alcohol, Pentadecylic acid, Phosphatidic acid (phosphatidate, PA), Phosphatidylcholine (lecithin, PC), Phosphatidylethanolamine (cephalin, PE) Phosphatidylinositol (PI), Phosphatidylinositol bisphosphate (PEP2) Phosphatidylinositol phosphate (PIP), Phosphatidylinositol triphosphate (PIP3), Phosphatidylserine (PS), Polyglycerol-6-disearate, Pregananes, Propylene Glycol Dicaprate, Propylene Glycol Dicaprylocaprate, Propylene Glycol Dicaprylocaprate, Psyllic acid, recinoleaic acid, recinoleyl alcohol, Sapienic acid, soy lecithin, Stearic acid, Stearidonic, stearyl alcohol, Tricosylic acid, Tridecyl alcohol, Tridecyclic acid, Triolein, Undecyl alcohol, undecylenic acid, Undecylic acid, Vaccenic acid, α-Linolenic acid, γ-Linolenic acid, alpha-tocopherol, or a fatty acid; wherein the PI3K inhibitor conjugate is

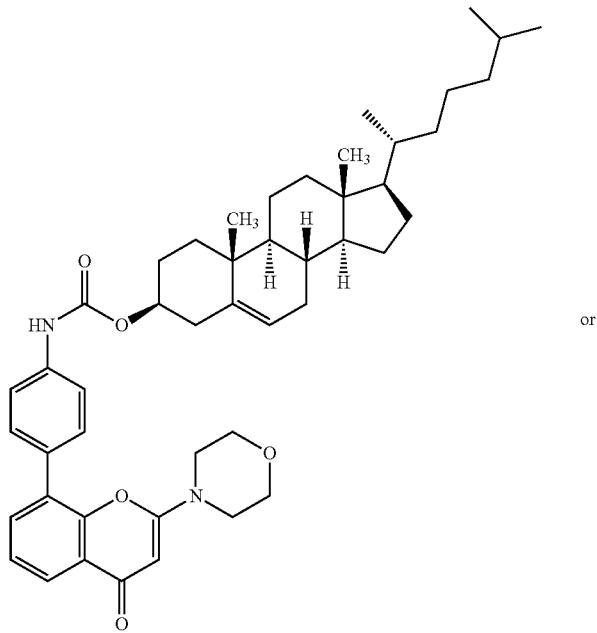

wherein the supramolecular combinatorial therapeutic comprises from about 1% to about 99% (w/w) of the PI3K inhibitor conjugate or the platinum conjugate or the conjugated antibody; and wherein the supramolecular combinatorial therapeutic comprises the taxane conjugate and the PI3K inhibitor conjugate or taxane conjugate and the platinum conjugate, or the taxane conjugate and the antibody conjugate in about 10:1 to about 1:10 molar ratio.

4. The supramolecular combinatorial therapeutic of claim 1, wherein the supramolecular combinatorial therapeutic further comprises at least one additional lipid, a polyethylene glycol (PEG), targeting ligand or a chemotherapeutic agent; wherein the at least one additional lipid is a phospholipid; wherein each phospholipid is selected from the group consisting of phosphatidyl cholines, phosphatidyl cholines with acyl groups having 6 to 22 carbon atoms, phosphatidyl ethanolamines, phosphatidyl inositols, phosphatidic acids, phosphatidyl serines, phosphatidyl glycerols, phosphatidylglycerol, lecithin, β,γ-dipalmitoyl-α-lecithin, sphingomyelin, phosphatidylserine, phosphatidic acid, N-(2, 3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoylphosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), di stearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-di stearoyl-sn-glycerol-3-phosphoethanolamine (DSPE), and any combinations thereof; wherein the first and second lipid, or the conjugate and total lipid are in about 10:1 to about 1:10 molar ratio; wherein the supramolecular combinatorial therapeutic comprises about 1% to about 99% (w/w) of total lipid; wherein the PEG is conjugated with a component of the supramolecular combinatorial therapeutic, or the PEG is conjugated to a lipid; wherein the PEG conjugated lipid is selected from the group consisting of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, 1,2-distearoyl-sn-glycerol-3-phosphoethanolamine-N-[amino(polyethylene glycol)-2000] (DSPE-PEG2000) and any combinations thereof; wherein the targeting ligand is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof; wherein the targeting ligand binds a protein, receptor, or marker expressed on the surface of a cancer cell; the targeting ligand or the chemotherapeutic agent is conjugated with a component of the composition; wherein the component is a lipid or PEG or cholesterol; wherein the supramolecular combinatorial therapeutic comprises about 1% to about 99% (w/w) of the chemotherapeutic agent; wherein the chemotherapeutic agent is selected from the group consisting of PI3K inhibitors, platinum compounds, inhibitors of topoisomerase I and II, alkylating agents, microtubule inhibitors, angiogenesis inhibitors, germicitibine, Aldesleukin, Alemtuzumab, alitretinoin, allopurinol, altretamine, amifostine, anastrozole, arsenic trioxide, Asparaginase, BCG Live, bexarotene capsules, bexarotene gel, bleomycin, busulfan intravenous, busulfanoral, calusterone, capecitabine, platinate, carmustine, carmustine with Polifeprosan Implant, celecoxib, chlorambucil, cladribine, cyclophosphamide, cytarabine, cytarabine liposomal, dacarbazine, dactinomycin, actinomycin D, Darbepoetin alfa, daunorubicin liposomal, daunorubicin, daunomycin, Denileukin diftitox, dexrazoxane, docetaxel, doxorubicin, doxorubicin liposomal, Dromostanolone propionate, Elliott's B Solution, epirubicin, Epoetin alfa estramustine, etoposide phosphate, etoposide (VP-16), exemestane, Filgrastim, floxuridine (intraarterial), fludarabine, fluorouracil (5-FU), fulvestrant, gemtuzumab ozogamicin, goserelin acetate, hydroxyurea, Ibritumomab Tiuxetan, idarubicin, ifosfamide, imatinib mesylate, Interferon alfa-2a, Interferon alfa-2b, irinotecan, letrozole, leucovorin, levamisole, lomustine (CCNU), mechlorethamine (nitrogenmustard), megestrol acetate, melphalan (L-PAM), mercaptopurine (6-MP), mesna, methotrexate, methoxsalen, mitomycin C, mitotane, mitoxantrone, nandrolone phenpropionate, Nofetumomab, LOddC, Oprelvekin, pamidronate, pegademase, Pegaspargase, Pegfilgrastim, pentostatin, pipobroman, plicamycin, mithramycin, porfimer sodium, procarbazine, quinacrine, Rasburicase, Rituximab, Sargramostim, streptozocin, talbuvidine (LDT), talc, tamoxifen, temozolomide, teniposide (VM-26), testolactone, thioguanine (6-TG), thiotepa, topotecan, toremifene, Tositumomab, Trastuzumab, tretinoin (ATRA), Uracil Mustard, valrubicin, valtorcitabine (monoval LDC), vinblastine, vinorelbine, zoledronate and any combinations thereof; and wherein the PI3K inhibitor is selected from the group consisting of PI103, P1828, LY294002, wortmannin, demethoxyviridin, IC486068, IC87114, GDC-0941, perifosine, CAL101, PX-866, IPI-145, BAY 80-6946, BEZ235, P6503, TGR1202, SF1126, INK1117, BKM120, IL147, XL765, Palomid 529, GSK1059615, ZSTK474, PWT33597, TG100-115, CAL263, GNE-447, CUDC-907, and AEZS-136, and any combinations thereof.

5. The supramolecular combinatorial therapeutic of claim 1, wherein the supramolecular combinatorial therapeutic comprises at least one taxane lipid conjugate in combination with a conjugate selected from the group consisting of the PI3K inhibitor-lipid conjugate, the platinum-lipid conjugate and the antibody-lipid conjugate; a PEG conjugated lipid; and a phospholipid;

wherein the taxane-lipid conjugate, the phospholipid, and the PEG conjugated lipid is in a molar ratio from about 10-0.1:10-0.1:10-0.01; wherein the phospholipid is phosphatidylcholine and the PEG conjugated lipid is DSPE-PEG$_{2000}$; and wherein the phosphatidylcholine is selected from the group consisting of SOPC, POPC, Egg PC, HSPC, and any combinations thereof.

6. The supramolecular combinatorial therapeutic of claim 1, wherein the supramolecular combinatorial therapeutic is in the form of a composition or a nanoparticle; wherein said composition comprises supramolecular combinatorial therapeutic and a pharmaceutically acceptable carrier;

wherein said nanoparticle comprises supramolecular combinatorial therapeutic and a co-lipid, and wherein the nanoparticle is about 5 nm to about 500 nm in diameter.

7. A method of treating cancer, comprising administering a supramolecular combinatorial therapeutic of claim 1, optionally along with co-administering one or more additional anti-cancer therapy, chemotherapeutic agent or immunomodulatory to a subject in need of treatment for cancer, thereby treating the cancer.

8. The method of claim 7, wherein the cancer is selected from the group consisting of breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer; wherein the additional therapy is selected from the group consisting of surgery, chemotherapy, radiation therapy, thermotherapy, immunotherapy, hormone therapy, laser therapy, anti-angiogenic therapy, and any combinations thereof; and wherein the immunomodulator selected from the group consisting of natural killer cells, lymphokine-activated killer cells, cytotoxic T cells and dendritic cells, anti-PD-L1 antibodies, anti-PD-1 antibodies, anti-CD52 antibodies, anti-VEGF-A antibodies, anti-CD30 antibodies, anti-EGFR antibodies, anti-CD33 antibodies, anti-CD20 antibodies, anti-CTLA4 antibodies, anti-HER-2 antibodies, interferons and interleukins.

9. A composition comprising a conjugate of claim 1 and a pharmaceutically acceptable carrier.

10. The composition of claim 1, wherein the composition comprises from about 1% to about 99% (w/w) of the conjugate, a first lipid, and a second lipid, optionally along with a pharmaceutically acceptable carrier; wherein the first lipid and second lipid are phospholipids, wherein the phospholipids are selected from the group consisting of phosphatidyl cholines, phosphatidyl cholines with acyl groups having 6 to 22 carbon atoms, phosphatidyl ethanolamines, phosphatidyl inositols, phosphatidic acids, phosphatidyl serines, sphingomyelin, phosphatidyl glycerols, lecithin, β,γ-dipalmitoyl-α-lecithin, phosphatidylserine, phosphatidic acid, N-(2,3-di(9-(Z)-octadecenyloxy))-prop-1-yl-N,N,N-trimethylammonium chloride, lysolecithin, lysophosphatidylethanolamine, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phsophatidylcholine, di-palmitoyl-pohsophatidylethanolamine, di-stearoyl-phosphatidylethanolamine, di-myrstoyl-phosphatidylserine, di-oleyl-phosphatidylcholine, dimyristoyl phosphatidyl choline (DPMC), dioleoylphosphatidylethanolamine (DOPE), palmitoyloleoylphosphatidylcholine (POPC), egg phosphatidylcholine (EPC), disearoylphosphatidylcholine (DSPC), dioleoylphosphatidylcholine (DOPC), diplamitoylphosphatidylcholine (DPPC), dioleoylphosphatidylglycerol (DOPG), dipalmitoylphosphatidylglycerol (DPPG), phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-disearoyl-sn-glycerol-3-phosphatidylethanolamine (DSPE), and any combination thereof; wherein the first and second lipid are in about 10:1 to about 1:10 ratio; wherein the composition comprises about 1% to about 99% of total lipid; and wherein the composition comprises the conjugate and total lipid in about 10:1 to about 1:10 ratio.

11. The composition of claim 10, wherein the composition further comprises polyethylene glycol (PEG), a targeting ligand, a chemotherapeutic agent, an immunodulator, a neutral lipid, a cationic lipid, an anionic lipid, an amphiphilic lipid, a sterol, a programmable fusion lipid, or any combinations thereof; wherein the PEG is conjugated with a component of the composition, wherein the component is a lipid; wherein the PEG conjugated lipid is selected from the group consisting of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, 1,2-distearoyl-sn-glycerol-3-phosphoethanolamine-N-[amino(polyethylene glycol)-2000] (DSPE-PEG2000) and any combinations thereof; wherein the targeting ligand is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, or markers expressed on the surface of a cancer cell and analogs and derivatives thereof; wherein the targeting ligand, chemotherapeutic agent or the immunomodulator is conjugated with a component of the composition; wherein the component is a lipid or PEG or cholesterol; wherein the chemotherapeutic agent is present in about 1% to 99% (w/w); the chemotherapeutic agent is selected from the group consisting of PI3K inhibitors, platinum compounds, inhibitors of topoisomerase I and II, alkylating agents, microtubule inhibitors, angiogenesis inhibitors, gemcitibine, Aldesleukin, Alemtuzumab, alitretinoin, allopurinol, altretamine, amifostine, anastrozole, arsenic trioxide, Asparaginase, BCG Live, bexarotene capsules, bexarotene gel, bleomycin, bisulfan intravenous, busulfanoral, calusterone, capecitabine, platinate, carmustine, carmustine with Polifeprosan Implant, celecoxib, chlorambucil, cladribine, cyclophosphamide, cytarabine, cytarabine liposomal, dacarbazine, dactinomycin, actinomycin D, Darbepoetin alfa, daunorubicin, doxorubicin liposomal, Dromostanolone propionate, Elliott's B Solution, epirubicin, Epoetin alfa estramustine, etoposide phosphate, etoposide (VP-16), exemestane, Filgrastim, floxuridine (intraarterial), fludarabine, fluorouracil (5-FU), fulvestrant, gemtuzumab ozogamicin, goserelin acetate, hydroxyurea, Ibritumomab Tiuxetan, idarubicin, ifosfamide, imatinib mesylate, Interferon alfa-2a, Interferon alfa-2b, irinotecan, letrozole, leucovorin, levamisole, lomustine (CCNU), mechlorethamine (nitrogenmustard), megestrol acetate, melphalan (L-PAM), mercaptopurine (6-MP), mesna, methotrexate, methoxsalen, mitomycin C, mitotane, mitoxantrone, nandrolone phenpropionate, Nofetumomab, LOddC, Oprelvekin, pamidronate, pegademase, Pegasparagase, Pegfilgrastim, pentostatin, pipobroman, plicamycin, mithramycin, porfimer sodium, procarbazine, quinacrine, Rasburicase, Rituximab, Sargramostim, streptozocin, talbuvidine (LDT), talc, tamoxifen, temozolomide, teniposide (VM-26), testolactone, thioguanine (6-TG), thiotepa, topotecan, toremifene, Tostumomab, Trastuzumab, tretinoin (ATRA), Uracil Mustard, valrubicin, valtorcitabine (monoval LDC), vinblastine, vinorelbine, zoledronate, and any combinations thereof; wherein the PI3K inhibitor is selected from the group consisting of PI103, PI828, LY294002, wortmannin, demethoxyviridin, IC486068, IC87114, GDC-0941, perfoxine, CAL101, PX-866, IPI-145, BAY 80-6946, BEZ235, P6503, TGR1202, SF1126, INK1117, BKM120, IL147, XL765, Palomid 529, GSK1059615, ZSTK474, PWT33597, TG100-115, CAL263, GNW-447, CUDC-907, and AEZS-136, and any combinations thereof; wherein the lipid conjugated chemotherapeutic agent FORMULA I
is 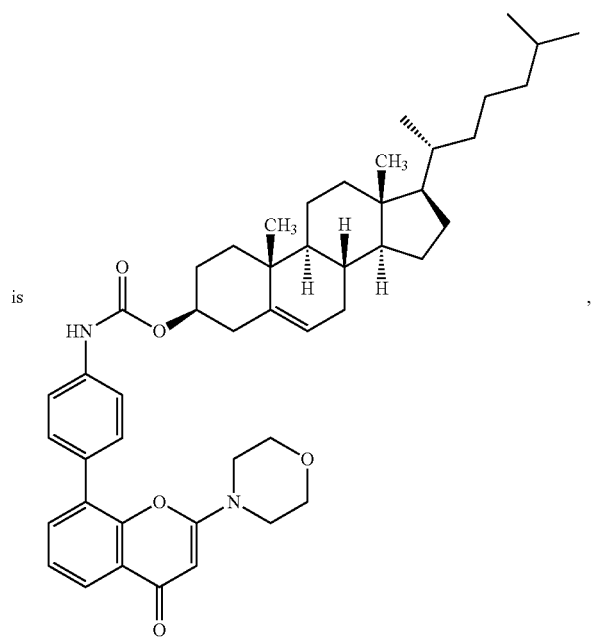,
FORMULA II
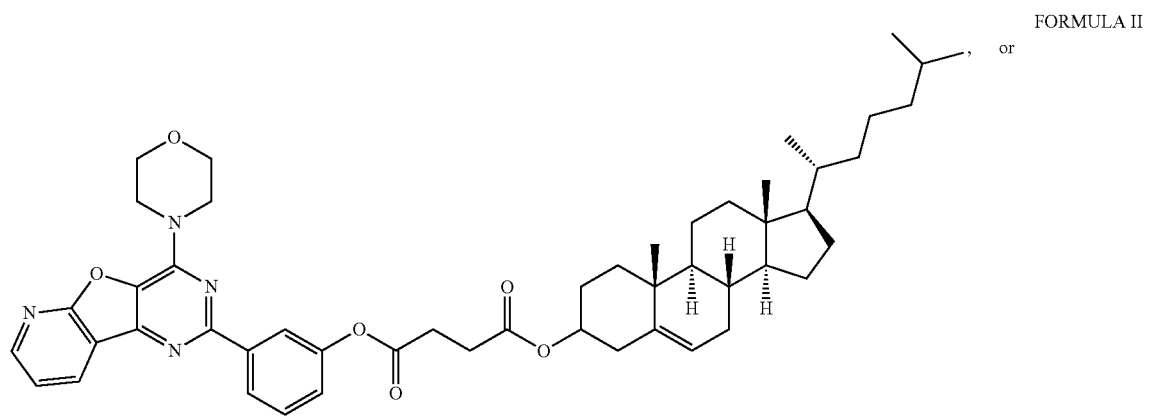, or
Formula IV
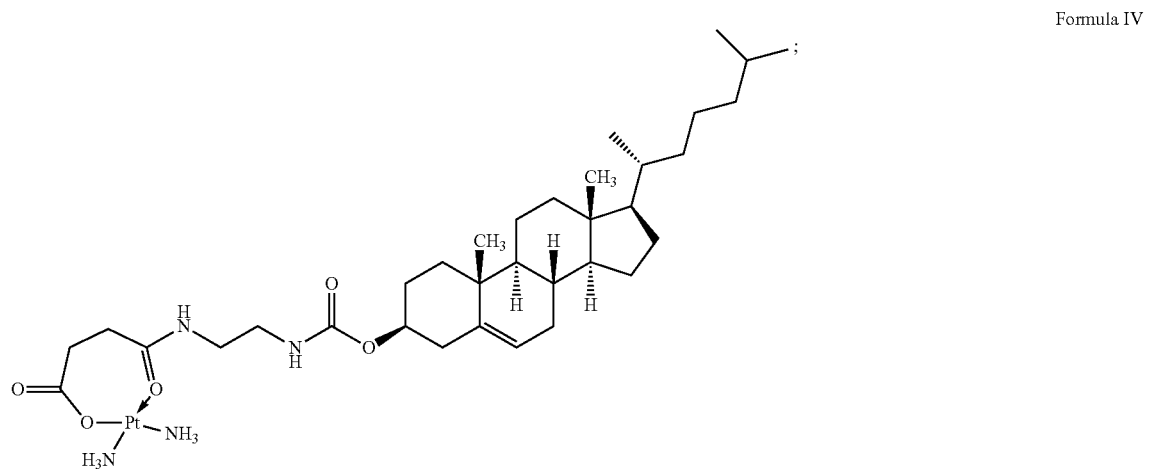;

wherein the composition further comprises an immunomodulator comprising and anti-PD-1 antibody, an anti-PD-L1 antibody or combination thereof; wherein the composition comprises the conjugate, a phospholipid, and a PEG conjugated lipid; wherein the conjugate, the phospholipid, and the PEG conjugated lipid are present in a ratio from about 10-0.1:10-0.1:10-0.1; wherein the phospholipid is phosphatidycholine and the PEG conjugated lipid is DSPE-PEG2000; wherein the composition is a liposome, emulsion, micelle or a nanoparticle; and wherein the nanoparticle is about 5 nm to about 500 nm in diameter.

12. A method of treating cancer, comprising administering a composition of claim 10, and optionally co-administering one or more of an additional anti-cancer therapy, and an immunomodulator to a subject in need of treatment for cancer, thereby treating the cancer.

13. The method of claim 12, wherein the cancer is selected from the group consisting of breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer; wherein the additional therapy is selected from the group consisting of surgery, chemotherapy, radiation therapy, thermotherapy, immunotherapy, hormone therapy, laser therapy, anti-angiogenic therapy, and any combinations thereof; wherein the additional therapy comprises administering a chemotherapeutic agent to the patient; wherein the additional therapy comprises administering a chemotherapeutic agent to the patient; wherein the immunomodulator activates an immune response against cancer cells; and wherein the immunomodulator is selected from the group consisting of natural killer cells, lymphokine-activated killer cells, cytotoxic T cells and dendritic cells, anti-PD-L1 antibodies, anti-PD-1 antibodies, anti-CD52 antibodies, anti-VEGF-A antibodies, anti-CD30 antibodies, anti-EGFR antibodies, anti-CD33 antibodies, anti-CD20 antibodies, anti-CTLA4 antibodies, anti-HER-2 antibodies, interferons and interleukins.

14. A supramolecular combinatorial therapeutic (SCT) comprising a taxane-lipid conjugate, wherein the taxane-lipid conjugate is a paclitaxel-lipid conjugate or a docetaxel-lipid conjugate; and wherein the paclitaxel-lipid conjugate is selected from the group consisting of conjugate 16 and conjugate 17

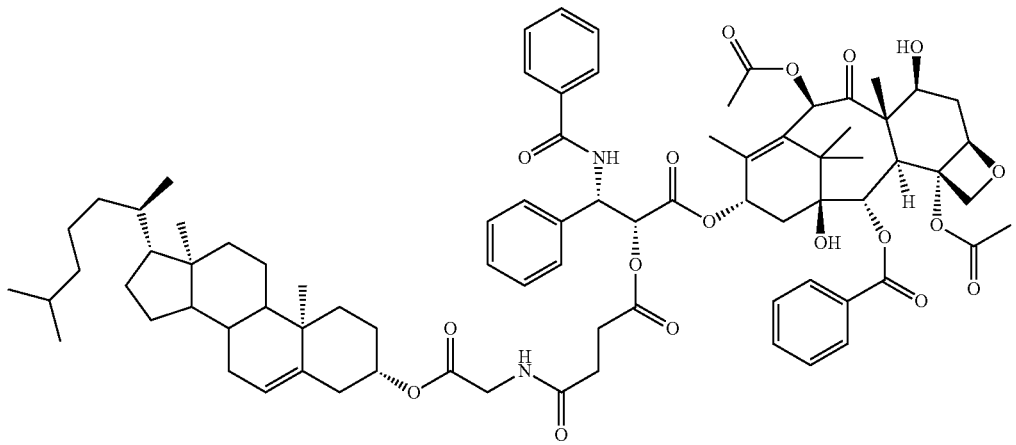

16

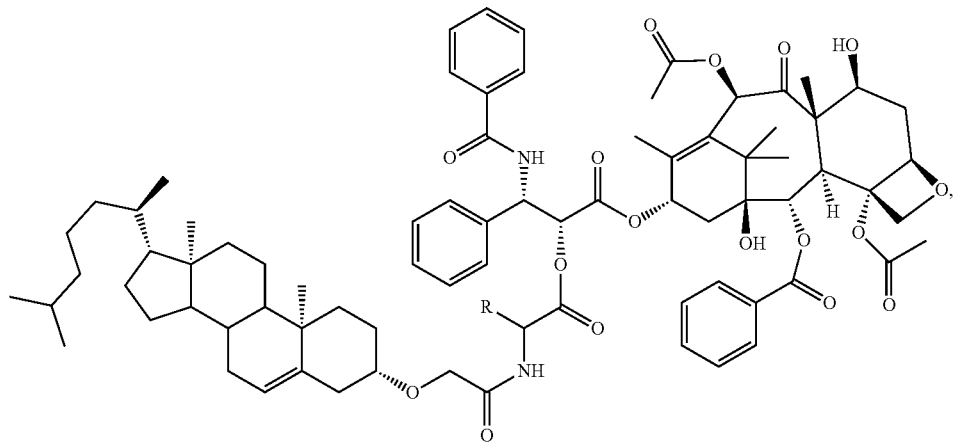

17

R = H, CH3, CH(CH3)2, CH2CH(CH3)2, C(CH3)CH2CH3, CH2Ph wherein the docetaxel-lipid conjugate is selected from the group consisting of conjugates 18-20 and conjugate 33
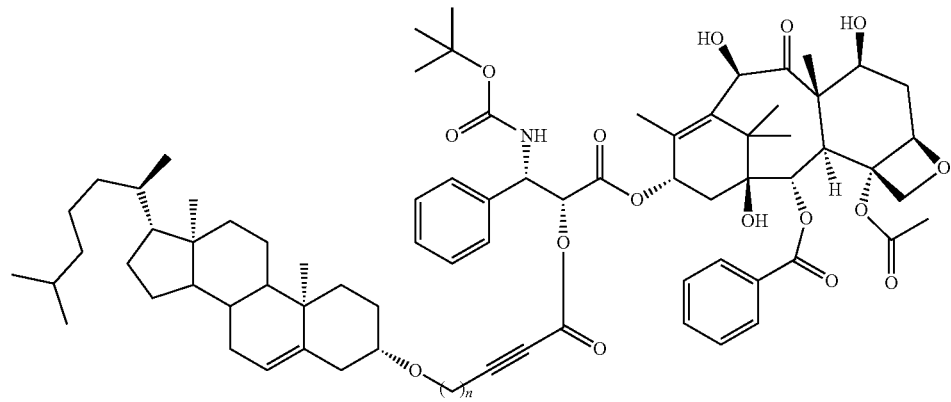
18
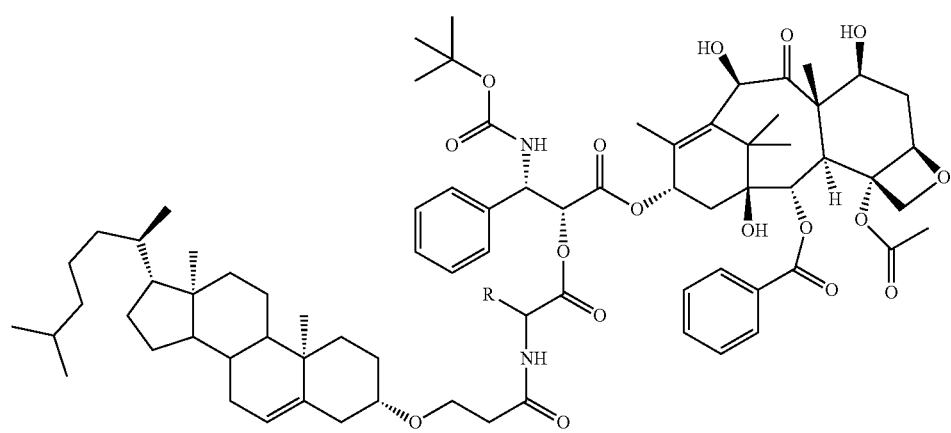
19
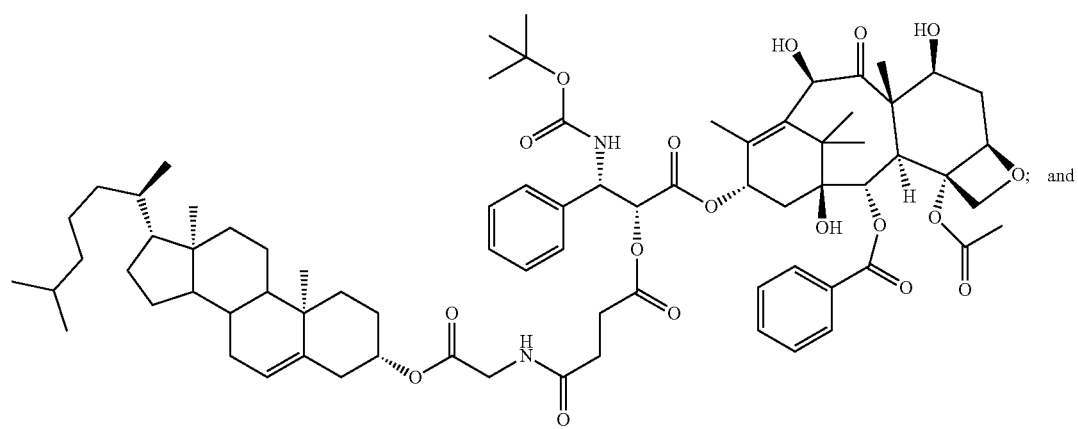
20
; and

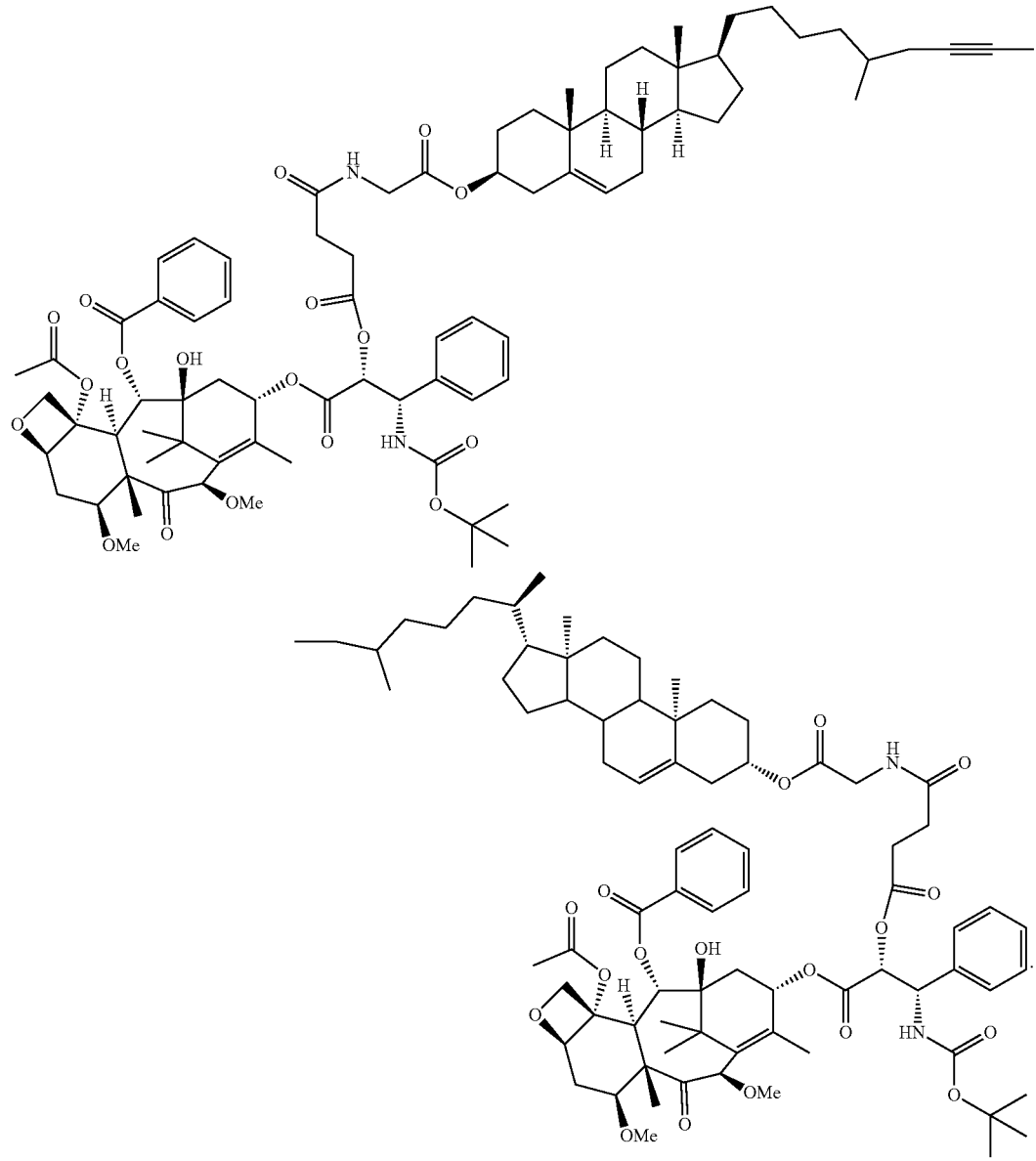
n = 0, 1, 2
R = H, CH3, CH(CH3)2, CH2CH(CH3)2, C(CH3)CH2CH3, CH2Ph
\* \* \* \* \*